US008071575B2

(12) United States Patent
Pierce, Jr. et al.

(10) Patent No.: US 8,071,575 B2
(45) Date of Patent: Dec. 6, 2011

(54) METHODS AND COMPOUNDS FOR THE TARGETED DELIVERY OF AGENTS TO BONE FOR INTERACTION THEREWITH

(75) Inventors: William M. Pierce, Jr., Louisville, KY (US); K. Grant Taylor, Louisville, KY (US); Leonard C. Waite, Corydon, IN (US)

(73) Assignee: University of Louisville Research Foundation, Louisville, KY (US)

( * ) Notice: Subject to any disclaimer, the term of this patent is extended or adjusted under 35 U.S.C. 154(b) by 556 days.

(21) Appl. No.: 12/036,057

(22) Filed: Feb. 22, 2008

(65) Prior Publication Data

US 2009/0118164 A1 May 7, 2009

Related U.S. Application Data

(60) Provisional application No. 60/891,299, filed on Feb. 23, 2007, provisional application No. 60/893,375, filed on Mar. 7, 2007.

(51) Int. Cl.
*A61K 31/04* (2006.01)
*A61K 31/085* (2006.01)
*A61K 31/35* (2006.01)
*A61K 31/352* (2006.01)
*A61K 31/166* (2006.01)
*C07C 233/64* (2006.01)
*C07D 309/00* (2006.01)
*C07J 41/00* (2006.01)

(52) U.S. Cl. ........ 514/169; 514/171; 514/456; 514/459; 514/616; 514/619; 514/622; 552/623; 552/624; 552/626; 552/220; 549/405; 549/407; 564/153; 564/156; 564/157; 564/158

(58) Field of Classification Search .................. None
See application file for complete search history.

(56) References Cited

U.S. PATENT DOCUMENTS

| 5,641,762 | A | 6/1997 | Pierce et al. | |
|---|---|---|---|---|
| 6,218,519 | B1 | 4/2001 | Kenten et al. | |
| 6,326,366 | B1 | 12/2001 | Potter et al. | |
| 6,503,896 | B1 | 1/2003 | Tanabe et al. | |
| 7,196,220 | B2 | 3/2007 | Pierce et al. | |
| 2004/0097500 | A1 | 5/2004 | Liao et al. | |
| 2004/0110793 | A1 | 6/2004 | Lloyd et al. | |
| 2004/0241173 | A1 | 12/2004 | Wilson et al. | |
| 2005/0143366 | A1* | 6/2005 | Pierce et al. | 514/182 |
| 2007/0161710 | A1 | 7/2007 | Pierce et al. | |
| 2008/0221070 | A1* | 9/2008 | Pierce et al. | 514/100 |

FOREIGN PATENT DOCUMENTS

| WO | 2000066613 | 11/2000 |
|---|---|---|
| WO | 2004043336 | 5/2004 |
| WO | 2004043693 | 5/2004 |
| WO | 2005065315 | 7/2005 |

OTHER PUBLICATIONS

Silverman (The Organic Chemistry of Drug Design and Drug Action, 1992, pp. 15-20.*

Pierce, et al.; International Search Report and Written Opinion issued on PCT Application No. PCT/US2008/054790, May 2008.
Pierce, et al.; International Search Report and Written Opinion issued on PCT Application No. PCT/US2008/056100, Jun. 2008.
U.S. Appl. No. 12/036,057 to Pierce, et al., for "Bone Targeting Compounds for Delivering Agents to the Bone for Interaction Therewith", Feb. 2008.
U.S. Appl. No. 12/043,904 to Pierce, et al., for "Bone Targeting Compounds for Delivering Agents to the Bone for Interaction Therewith", Mar. 2008.
International Patent Application No. PCT/US2008/054790 to Pierce, et al., for "Bone Targeting Compounds for Delivering Agents to the Bone for Interaction Therewith", May 2008.
International Patent Application No. PCT/US08/56100 to Pierce, et al., for "Bone Targeting Compounds for Delivering Agents to the Bone for Interaction Therewith", Jun. 2008.
Bilezikian JP; Osteonedrosis of the Jaw—Do Bisphosphonates Pose a Risk N Engl J Med, (2006); pp. 2278-2281; vol. 355.
Cranney A, Adachi JD; Benefit-risk assessment of raloxifene in postmenopausal osteoporosis; Drug Saf (2005); pp. 721-730; vol. 28(8).
Delmas PD, et al.; The Use of Biochemical Markers of Bone Turnover in Osteoporosis; Osteoporosis Int. (2000); pp. S2-17; suppl 6.
Garrett IR, Chen D, Gutierrez G, Rossini G, Zhao M, Escobedo A, Kim KB, Hu S, Crews CM, and Mundy GR; Selective inhibitors of the osteoblast proteasome stimulate bone formation in vivo and in vitro; J Clin Invest, (2003), pp. 1771-1782, vol. 111(11).
Ishida H; Preventive effects of the plant isoflavones, daidzin and genistin, on bone loss in ovariectomized rats fed a calcium-deficient diet; Biol Pharm Bull. Jan. 1998:21; pp. 62-66; vol. (1).
Keenan MJ, Hegsted M, Jones KL, Delany JP, Kime JC, Melancon LE, Tulley RT, Hong KD. Comparison of bone density measurement techniques: DXA and Archimedes' principle; J Bone Miner Res (1997); pp. 1903-1907; vol. 12(11).
Marshall JK ; The gastrointestinal tolerability and safety of oral bisphosphonates; Expert Opin Drug Saf; (2002); pp. 71-78; vol. 1.
Mundy GR, Garrett R, Harris SE, Chan J, Chen D, Rossini G, Boyce B, Zhao M, and Gutierrez G; Stimulation of bone formation in vitro and in rodents by statins. Science (1999); pp. 1946-1949; vol. 286 (5446).
Pierce; Bone-targeted carbonic anhydrase inhibitors: effect of a proinhibitor on bone resorption in vitro; Proceedings of the Society for Experimental Biology and Medicine [0037-9727] (1987) vol. 186 iss:1 pp. 96-102.
Riggs BL, and Parfitt AM; Drugs Used to Treat Osteoporosis: The Critical Need for a Uniform Nomenclature Based on Their Action on Bone Remodeling, J. Bone and Mineral Res. (2005); p. 177-184; vol. 20(2).
Rossouw JE, et al.; Risks and benefits of estrogen plus progestin in healthy postmenopausal women: principal results From the Women's Health Initiative randomized controlled trial. JAMA (2002); pp. 321-333; vol. 288(3).
Seibel MJ.; Biochemical Markers of Bone Turnover: biochemistry and variability; Clin Biochem Rev. (2005); pp. 97-122; vol. 26(4).
Vahle JL, et al.; Skeletal changes in rats given daily subcutaneous injections of recombinant human parathyroid hormone (1-34) for 2 years and relevance to human safety; Toxicol Pathol (2002); pp. 312-321; vol. 30(3).

* cited by examiner

*Primary Examiner* — Rosalynd Keys

(74) *Attorney, Agent, or Firm* — Stites & Harbison PLLC; Mandy Wilson Decker

(57) ABSTRACT

Bone targeted compounds and methods are provided. Compounds can include a Bone Targeting Portion ($R_T$), having an affinity for bone; a Bone Active Portion ($R_A$) for interacting with and affecting bone; and a Linking Portion ($R_L$) connecting the Bone Targeting Portion and the Bone Active Portion.

50 Claims, 26 Drawing Sheets

(A)-Cell Proliferation data for day 5 and day 6

(B)- Cell proliferation data for each day

METHODS AND COMPOUNDS FOR THE TARGETED DELIVERY OF AGENTS TO BONE FOR INTERACTION THEREWITH

RELATED APPLICATIONS

This application claims priority from U.S. Provisional Application Ser. No. 60/891,299 filed Feb. 23, 2007, and U.S. Provisional Application Ser. No. 60/893,375 filed Mar. 7, 2007, the entire disclosures of which are incorporated herein by this reference.

TECHNICAL FIELD

The presently-disclosed subject matter relates to prevention and treatment of bone disorders and conditions, and, more particularly, to the targeted delivery of prophylactic and therapeutic agents to bone.

BACKGROUND

Bone is a dynamic tissue, consisting of cells in a protein matrix, upon which is superimposed a crystalline structure of various calcium salts. Because bone is the primary structural support system for the body of an animal, bone disorders can create substantial problems. Bone disorders include, for example, fractures, suboptimal mechanical competence, suboptimal bone blood perfusion, suboptimal bone healing ability, cancerous transformation (primary and bone metastasis), and infection.

Bone disorders can occur in a variety of manners. For example, bone disorders can result from excessive forces being exerted onto the bone, primary bone conditions, and secondary bone conditions associated with other conditions. Bone conditions include, for example, metabolic bone diseases (MBDs). MBDs are conditions characterized by weakening of bones, which weakening is associated with suboptimal mechanical competence and an increased likelihood of fracturing. Osteoporosis is an example of a MBD. Osteoporosis is characterized by bone degeneration caused by a relative excess of bone resorption. Clinical osteoporosis is found in approximately 25% of postmenopausal women, and subclinical osteoporosis, which is responsible for untold numbers of bone fractures, is far more widespread. Other examples of MBDs include, but are not limited to: Paget's disease, characterized by an abnormal growth of bone such that the bone is larger and weaker than normal bone; and osteogenesis imperfecta, characterized by bones that are abnormally brittle.

In addition to serving as a rigid support for the body of an animal, bone is an organ that responds to various agents. To the extent that bone has the ability to interact with and respond to certain agents, disorders associated with bone conditions can be prevented, diagnosed, or treated using appropriate agents having the ability to interact with and affect a desired response in bone. For example, with regard to osteoporosis, there are certain agents, which are thought to interact with bone and are currently available for the treatment or prevention of the condition. Such agents include: bisphosphonates (e.g., alendronate, risedronate); calcitonin; selective estrogen receptor modulators (SERMs) (e.g., raloxifene); selective androgen receptor modulators (SARMs); growth factors; cytokines; agents used for estrogen or hormone replacement therapy (ET4HRT); and parathyroid hormone (PTH) (e.g., teriparatide).

There are a variety of disadvantages associated with treatment using these known agents. For example, although PTH has some anabolic activity, biphosphonates, calcitonin, SERMs, and ET/RHT are primarily anti-catabolic, operating to limit bone resportion. In this regard, the anti-catabolic compounds only treat osteoporosis in so much as they attempt to keep bone density from further decreasing. There are also various side effects associated with such agents; for example, bisphosphonate treatment is associated with gastrointestinal and esophageal erosion, and has been implicated in osteonecrosis of the jaw; SERM treatment has been associated with deep vein thrombosis and hot flashes; ET4HRT has been implicated in increased risk of breast cancer and cardiovascular disease; and PTH therapy has been suggested to potentially increase risk of osteosarcoma (osteogenic sarcoma), a type of cancer that develops in bone, is characterized by formation of a bone matrix having decreased strength relative to normal non-malignant bone matrix, and which can metastasize to other bones and other organs. See e.g., Bilezikian J P (2006) *N Engl J Med* 355:2278-2281; Cranney A, Adachi J D (2005) *Drug Saf* 28:721-730; Marshall J K (2002) *Expert Opin Drug Saf* 1:71-78; Rossouw J E, et al., Writing Group for the Women's Health Initiative Investigators (2002) Risks and benefits of estrogen plus progestin in healthy postmenopausal women: principal results From the Women's Health Initiative randomized controlled trial. *JAMA* 288:321-333; Vahle J L, et al. (2002) *Toxicol Pathol* 30:312-321, which are incorporated herein by this reference. There are also various drawbacks associated with the delivery of such known agents to an animal, for example, bisphosphonates demonstrate poor oral bioavailability, calcitonin is not orally deliverable, and PTH must be injected. Additionally, some known agents have a limited capacity to affect bone because they lack a specific affinity for bone. That is to say that, when some of the known agents are delivered to an animal, they are not specifically directed to the bone. In this regard, when some of the known agents are delivered to an animal, they are delivered to non-specific locations in the body of the animal, such that they fail to interact with the bone or require a large dose to affect a response in bone. Also in this regard, when such agents are delivered to an animal, they can be directed to undesirable locations in the body of the animal, resulting in undesirable side effects.

Accordingly, there remains a need in the art for compounds, systems, and methods for treating bone disorders and conditions that satisfactorily address some or all of the above-identified disadvantages.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently-disclosed subject matter includes compounds, or pharmaceutically acceptable compositions thereof, having an affinity for bone, or "bone targeted compounds." The presently-disclosed subject matter includes bone targeted compounds and methods useful for treating conditions of interest, e.g., conditions affecting bone. The presently-disclosed subject matter further includes methods for delivering an agent of interest to bone.

The bone targeted compounds of the presently-disclosed subject matter can in some embodiments generally include three units. The three units of the compounds are: a Bone Targeting Portion ($R_T$), having an affinity for bone; a Linking Portion ($R_L$) that is capable of connecting the Bone Targeting Portion to a third unit; and the third unit ($R_A$). As such, the compounds of the presently-disclosed subject matter can be represented by the following formula:

Formula 1

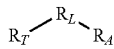

The third unit ($R_A$) can be a Bone Active Portion, a protecting group, or hydrogen or hydroxyl. In embodiments where $R_A$ is a Bone Active Portion, the Bone Active Portion interacts with and affects the bone. The Bone Active Portion can be derived from a Bone Active Agent, which can be selected for its efficacy in treating a condition of interest. In embodiments where $R_A$ is a protecting group, the protecting group can assist with maintaining the stability of the compound, for example, by keeping an adjacent group on the linking portion from reacting with other portions of the compound, e.g., cyclizing. Compounds including a protecting group can be stably stored until it becomes desirable to associate the compound with a Bone Active Portion derived from a Bone Active Agent of interest. In this regard, the compounds including a protecting group are useful for preparing compounds for treating conditions associated with bone. In some embodiments, $R_A$ is hydrogen or hydroxyl, depending on the embodiment of the Linking Portion, $R_L$, being used, as will be described below. The presently-disclosed subject matter includes salts derived from compounds where $R_A$ is hydrogen or hydroxyl, which salts can be stably stored until it becomes desirable to associate the compound with a Bone Active Portion. In this regard, the compounds in which $R_A$ is hydrogen or hydroxyl are useful for preparing compounds for treating conditions associated with bone.

In some embodiments, the compound of the presently-disclosed subject matter can be represented by the formula:

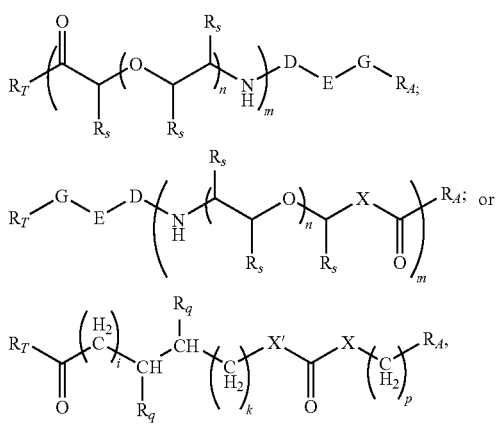

where $R_T$ is

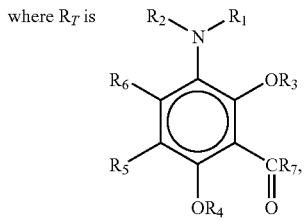

and where $R_T$ is connected to the compound at $R_1$, $R_2$, or $R_4$.

In some embodiments, $R_1$ can be hydrogen, lower alkyl, alkyl, aryl lower alkyl, aryl, or a covalent bond when $R_T$ is connected to the compound at $R_1$. $R_2$ can be hydrogen, lower alkyl, alkyl, aryl lower alkyl, aryl, or a covalent bond when $R_T$ is connected to the compound at $R_2$. $R_3$ can be hydrogen, lower alkyl, alkyl, aryl lower alkyl, aryl, or carbonyl-containing. $R_4$ can be hydrogen, lower alkyl, alkyl, aryl lower alkyl, aryl, carbonyl-containing, or a covalent bond when $R_T$ is connected to the compound at $R_4$. $R_5$ and $R_6$ can be independently hydrogen, lower alkyl, or alkyl, or $R_5$ and $R_6$, taken together with the carbon atoms to which they are bonded, can form a ring containing about 6 to about 14 ring carbon atoms and up to a total of about 18 carbon atoms, which formed ring can be monocyclic, bicyclic, or tricyclic, wherein the ring can optionally have substituents, including heteroatoms. $R_7$ can be hydroxy, lower alkoxy, or $NR_8R_9$; and $R_8$ and $R_9$ can be independently hydrogen, or lower alkyl. In some embodiments of the compounds, i can be 0-3, k can be 0-3, p can be 0-4, and each $R_q$ is independently hydrogen or hydroxyl. In some embodiments, X can be O, NH, S, or a covalent bond, and X' can be O, NH, S, or a covalent bond. In some embodiments of the compounds, m can be 1-3, n can be 1-4, and when m>1, each n is independently 1-4; each $R^S$ can independently be hydrogen, hydroxy, lower alkyl, or lower alkyl with heteroatoms; D and G can be independently a covalent bond, carbonyl, epoxy, or anhydride; and E can be a covalent bond, $(CT_2)_r$, where T is hydrogen, hydroxy, or lower alkyl, and where r is 0-8, or $(C)_r$, where r is 2-8, and where the carbons are unsaturated or partially saturated with hydrogen. $R_A$ can be hydrogen, hydroxyl, a protecting group, or a Bone Active Portion.

In some embodiments, $R_5$ and $R_6$ are hydrogen. In some embodiments, $R_7$ is $NR_8R_9$. In some embodiments, $R_8$ and $R_9$ are both hydrogen. In some embodiments, $R_3$ is hydrogen.

In some embodiments, $R_T$ is

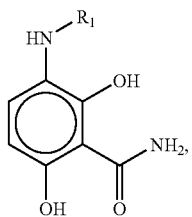

and $R_T$ is connected to the compound at $R_1$. In some embodiments, $R_T$ is

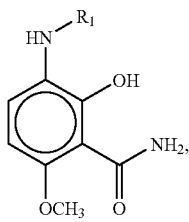

and $R_T$ is connected to the compound at $R_1$. In some embodiments, $R_T$ is

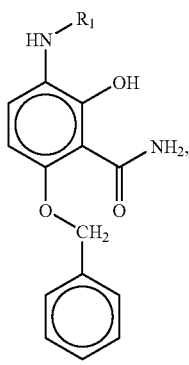

and $R_T$ is connected to the compound at $R_1$.

In some embodiments, the compounds of the presently-disclosed subject matter can be represented by the formula

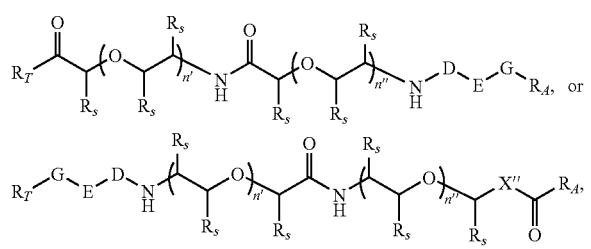

where n' and n" are independently 1-4, and X" is O, NH, S, or a covalent bond.

In some embodiments, the compounds of the presently-disclosed subject matter can be represented by the formula

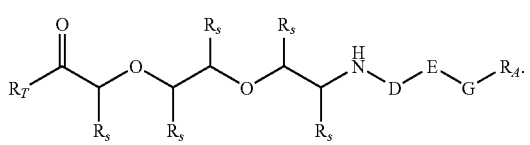

In some embodiments, the compounds of the presently-disclosed subject matter can be represented by the formula

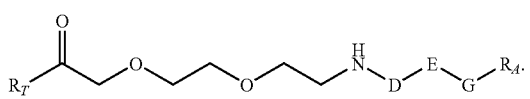

In some embodiments, the compounds of the presently-disclosed subject matter can be represented by the formula

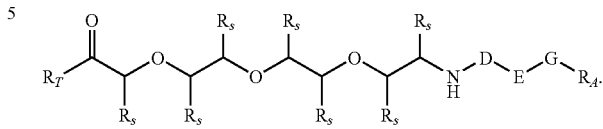

In some embodiments, the compounds of the presently-disclosed subject matter can be represented by the formula

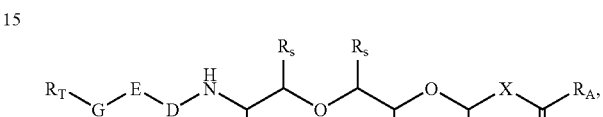

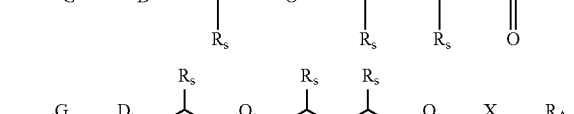

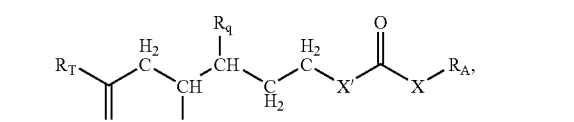

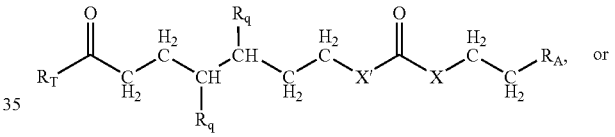

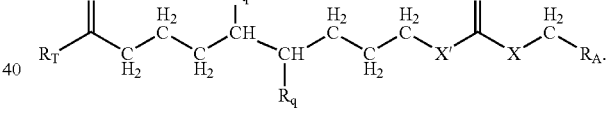

In some embodiments, the compounds of the presently-disclosed subject matter can be represented by the formula

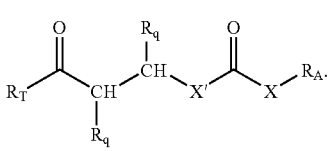

In some embodiments, the compounds of the presently-disclosed subject matter can be represented by the formula

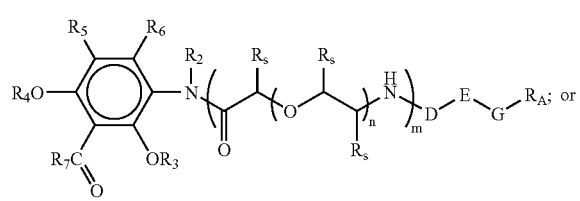

-continued

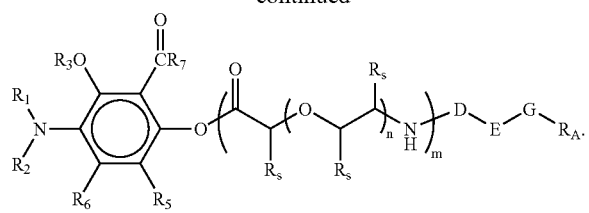

In some embodiments, $R_A$ is hydrogen. In some embodiments, $R_A$ is a protecting group. In some embodiments, $R_A$ is a bone active portion derived from a bone active agent selected from the bone active agents set forth in Tables A-D. In some embodiments, $R_A$ is a bone active portion derived from a steroid. In some embodiments, $R_A$ is a bone active portion derived from an estrogenic agent. In some embodiments, $R_A$ is a bone active portion derived from a steroidal estrogenic agent. In some embodiments, the steroidal estrogenic agent is estradiol. In some embodiments, the compound can be represented by the formula

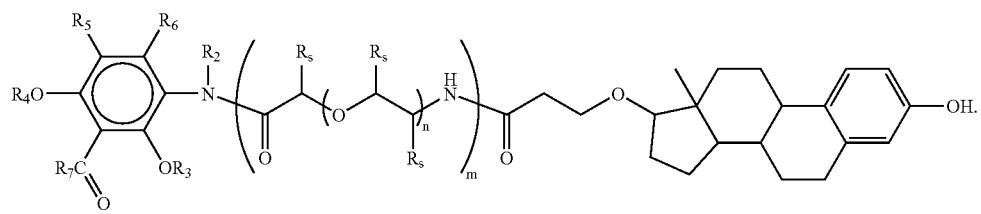

In some embodiments, the compound can be represented by the formula

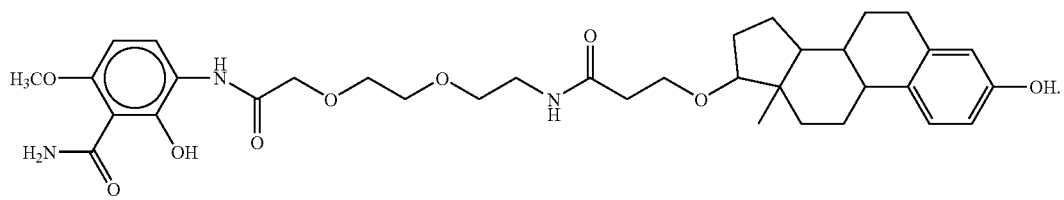

In some embodiments, the compound can be represented by the formula

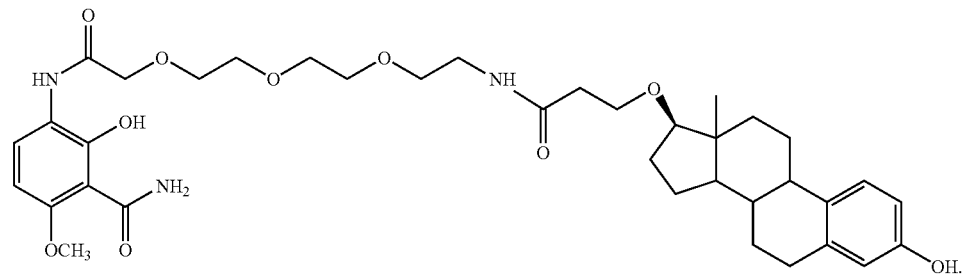

In some embodiments, the compound can be represented by the formula

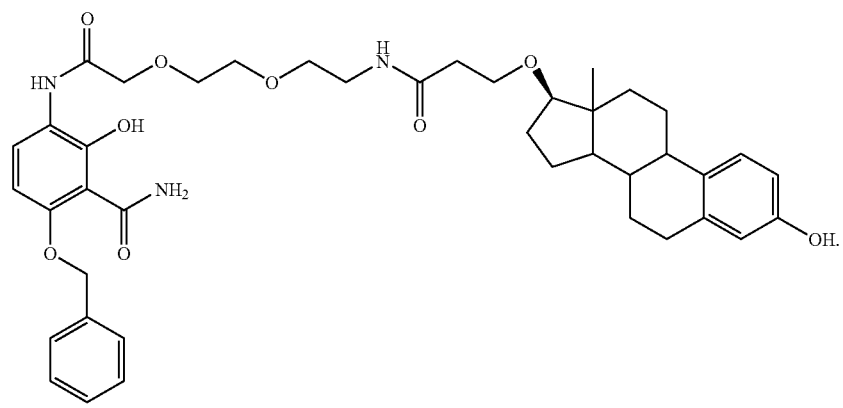

In some embodiments, the compound can be represented by the formula

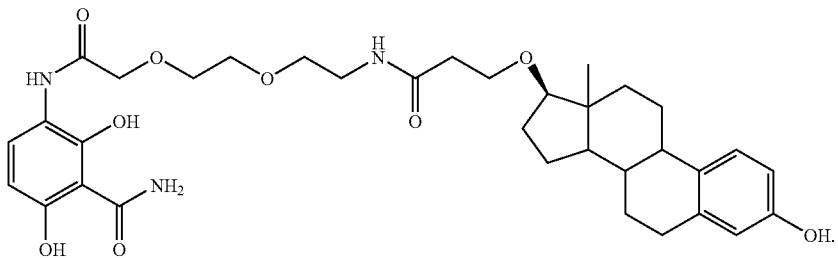

In some embodiments, $R_A$ is a bone active portion derived from a non-steroidal estrogenic agent. In some embodiments, the non-steroidal estrogenic agent is genistein. In some embodiments, the compound can be represented by the formula

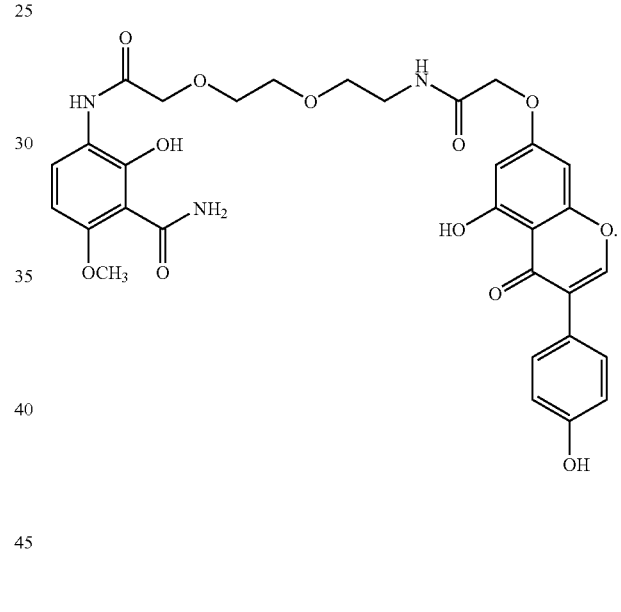

In some embodiments, the compound can be represented by the formula

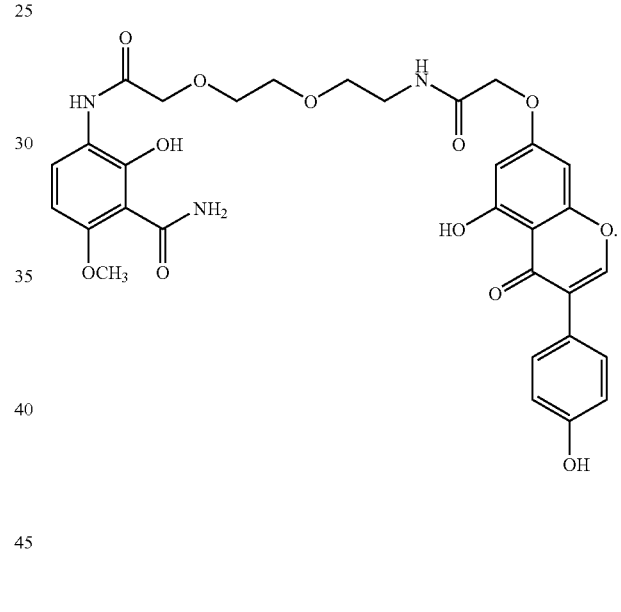

In some embodiments, $R_A$ is a bone active portion derived from a nitric oxide agent. In some embodiments, the nitric oxide agent is alkoxy-$(NO_2)_2$. In some embodiments, the compound can be represented by the formula

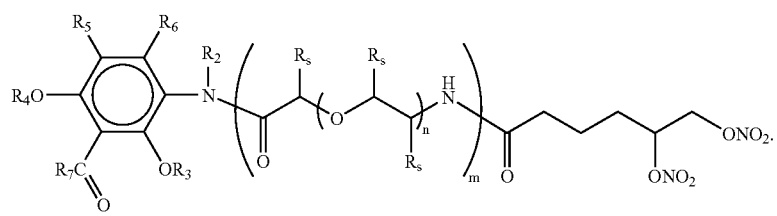

In some embodiments, the compound can be represented by the formula

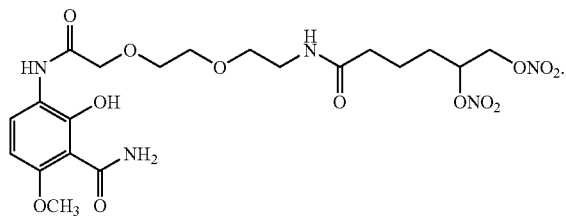

In some embodiments, $R_A$ is a bone active portion derived from an androgen. In some embodiments, androgen is testosterone. In some embodiments, the androgen is DHEA. In some embodiments, the compound can be represented by the formula

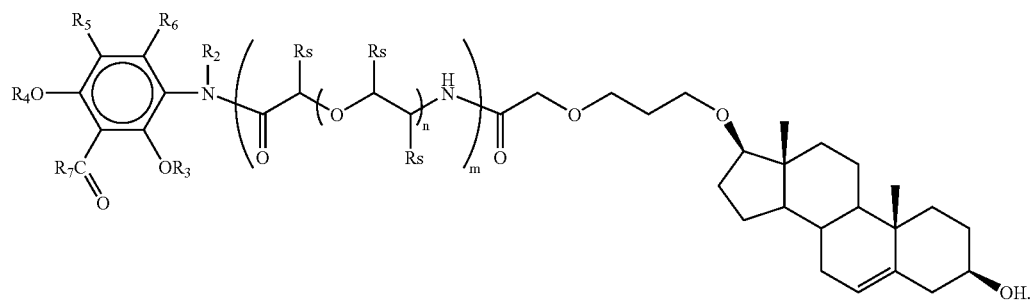

In some embodiments, the compound can be represented by the formula

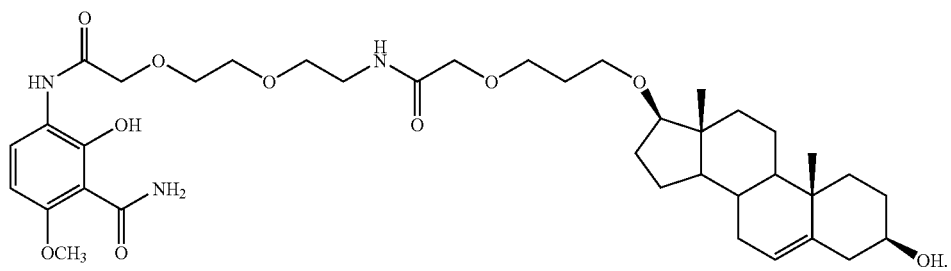

In some embodiments, $R_A$ is a bone active portion derived from a carbonic anhydrase inhibitor. In some embodiments, $R_A$ is a bone active portion derived from a 2-amino-1,3,4-thiadiazole-5-sulfonamide. In some embodiments, $R_A$ is a bone active portion derived from an anti-cancer agent. In some embodiments, the anti-cancer agent is doxorubicin. In some embodiments, the compound can be represented by the formula

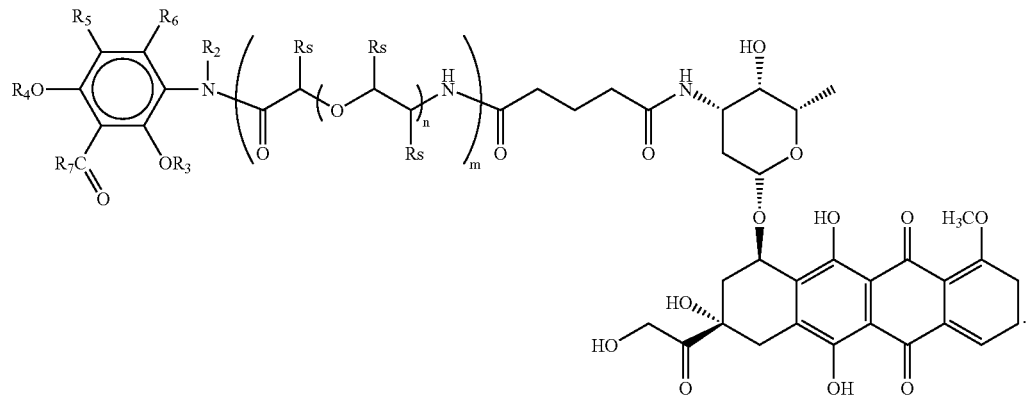

In some embodiments, the compound can be represented by the formula
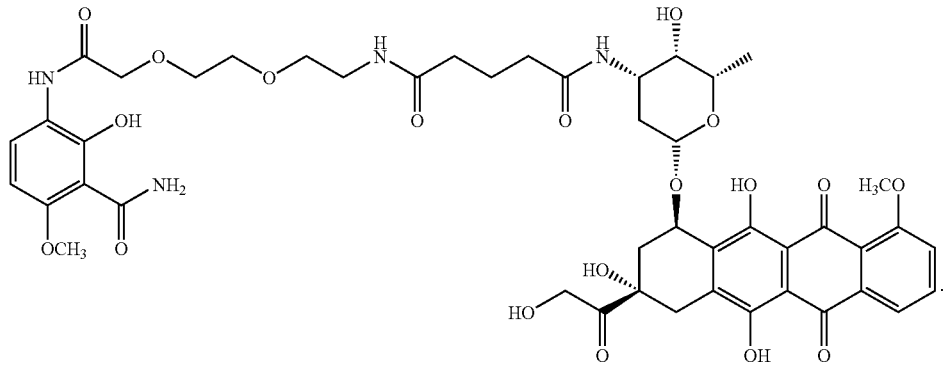
In some embodiments, $R_A$ is a bone active portion derived from an antimicrobial agent. In some embodiments, the antimicrobial agent is vancomycin. In some embodiments, the compound can be represented by the formula
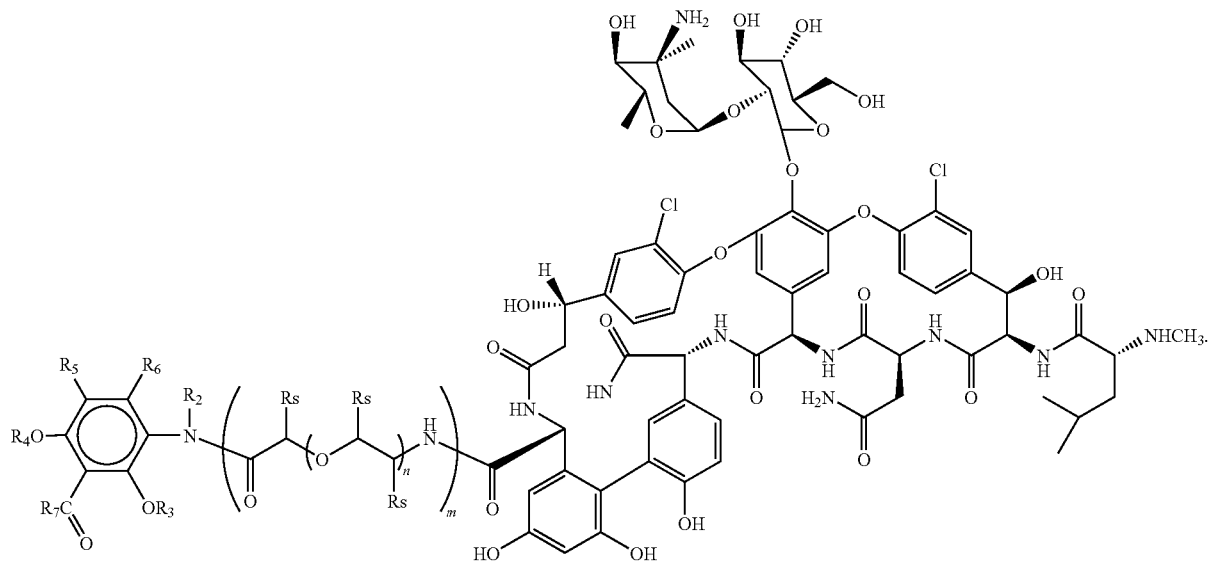
In some embodiments, the compound can be represented by the formula

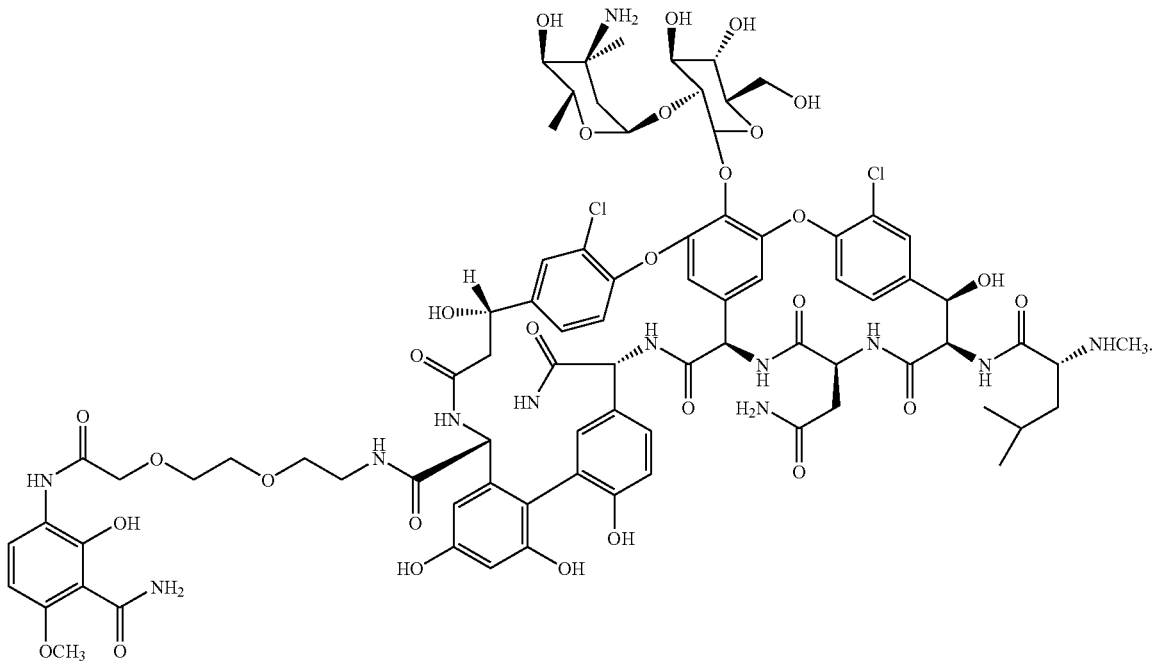

In some embodiments, the compounds of the presently-disclosed subject matter can be represented by the formula

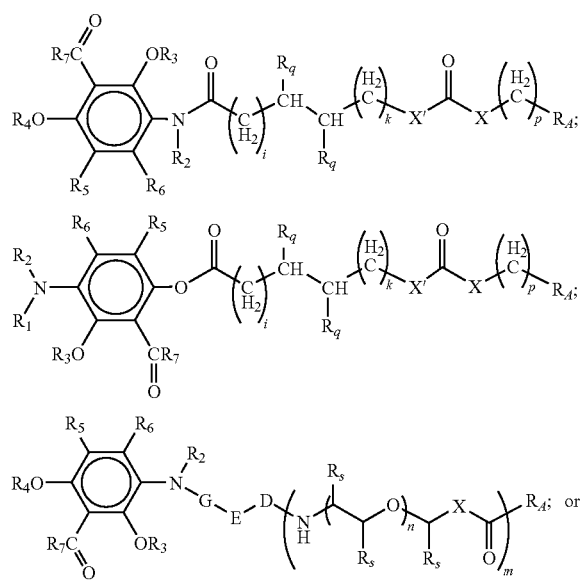

-continued

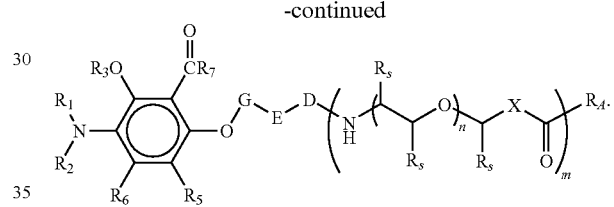

In some embodiments, $R_A$ is hydroxyl. In some embodiments, $R_A$ is a protecting group. In some embodiments, $R_A$ is a bone active portion derived from a bone active agent selected from the bone active agents set forth in Tables A-D. In some embodiments, $R_A$ is a bone active portion derived from a steroid. In some embodiments, $R_A$ is a bone active portion derived from an estrogenic agent. In some embodiments, $R_A$ is a bone active portion derived from a steroidal estrogenic agent. In some embodiments, the steroidal estrogenic agent is estradiol. In some embodiments, $R_A$ is a bone active portion derived from a non-steroidal estrogenic agent. In some embodiments, the non-steroidal estrogenic agent is genistein. In some embodiments, $R_A$ is a bone active portion derived from a nitric oxide agent. In some embodiments, the nitric oxide agent is alkoxy-$(NO_2)_2$. In some embodiments, $R_A$ is a bone active portion derived from an androgen. In some embodiments, the androgen is DHEA. In some embodiments, the androgen is Testosterone. In some embodiments, the compound can be represented by the formula

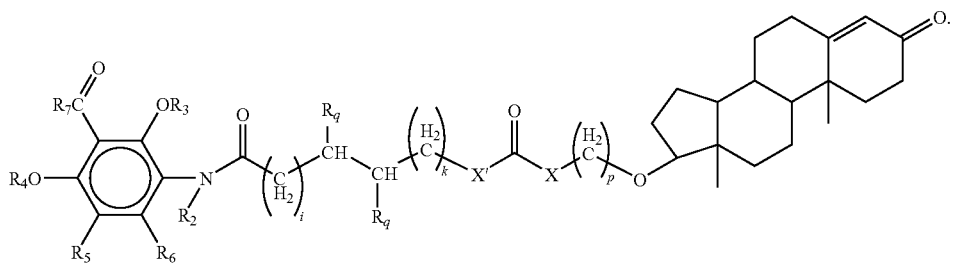

In some embodiments, the compound can be represented by the formula

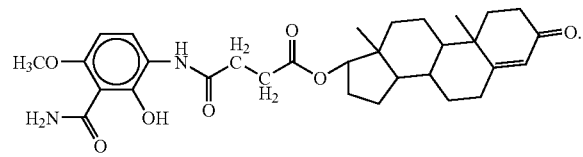

In some embodiments, $R_A$ is a bone active portion derived from a carbonic anhydrase inhibitor. In some embodiments, $R_A$ is a bone active portion derived from 2-amino-1,3,4-thiadiazole-5-sulfonamide. In some embodiments, the compound can be represented by the formula

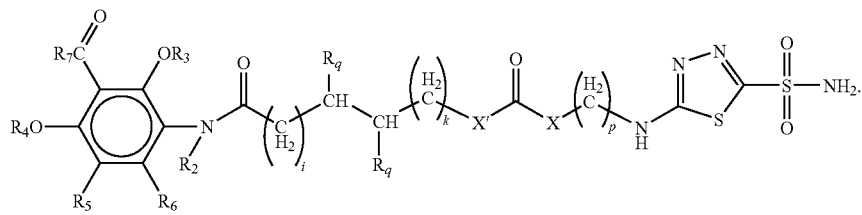

In some embodiments, the compound can be represented by the formula

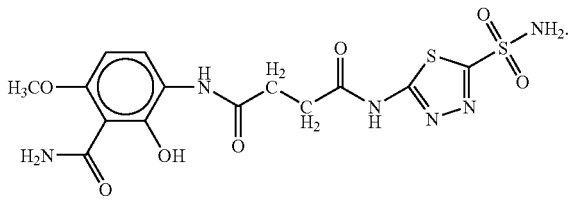

In some embodiments, $R_A$ is a bone active portion derived from an anti-cancer agent. In some embodiments, the anti-cancer agent is doxorubicin. In some embodiments, $R_A$ is a bone active portion derived from an antimicrobial agent. In some embodiments, the antimicrobial agent is vancomycin.

In some embodiments, the method for treating a bone condition in a subject in need thereof includes, administering to the subject an effective amount of a compound of the presently-disclosed subject matter. In some embodiments, the bone condition is a metabolic bone disease. In some embodiments, the metabolic bone disease is osteoporosis, and $R_A$ is a bone active portion derived from a bone active agent selected from: an androgen, a steroidal estrogenic agent, a non-steroidal estrogenic agent, a nitric-oxide-targeted agent, and a carbonic anhydrase inhibitor. In some embodiments, the subject has a primary condition associated with osteoporosis. In some embodiments, administration of the compound has an anabolic effect on the bone of the subject. In some embodiments, the bone condition is a primary or a secondary bone cancer, and wherein $R_A$ is a bone active portion derived from an anti-cancer agent. In some embodiments, the bone condition is a secondary bone cancer. In some embodiments, the subject has a primary cancer associated with a secondary bone cancer. In some embodiments, the primary cancer is breast, lung, prostate, kidney, or thyroid cancer. In some embodiments, the bone condition is a microbial infection, and wherein $R_A$ is a bone active portion derived from an antimicrobial agent. In some embodiments, the bone condition is osteomyelitis, and $R_A$ is a bone active portion derived from an antimicrobial agent. In some embodiments, the subject has a primary infection associated with osteomyelitis.

DESCRIPTION OF EXEMPLARY EMBODIMENTS

Figure 1:
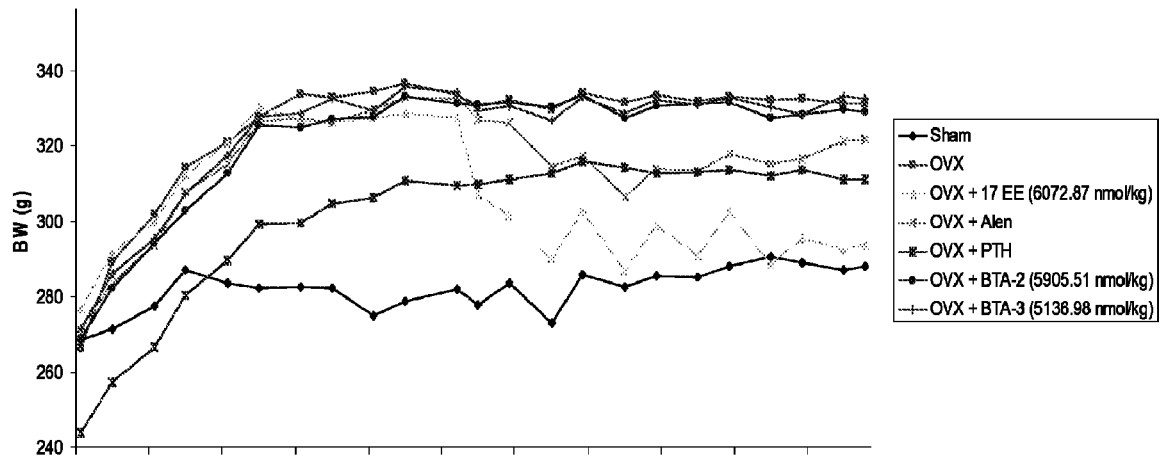
FIG. 1 is a line graph depicting body weight as a function of time for animals administered 17-ethinyl estradiol, alendronate, parathyroid hormone, the compound of Formula 161 (BTA-2), or the compound of Formula 162 (BTA-3).

The details of one or more embodiments of the presently-disclosed subject matter are set forth in this document. Modifications to embodiments described herein, and other embodiments, will be evident to those of ordinary skill in the art after a study of the information provided in this document. The information provided herein, and particularly the specific details of the described exemplary embodiments, is provided primarily for clearness of understanding and no unnecessary limitations are to be understood therefrom. In case of conflict, the specification of this document, including definitions, will control.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a," "an," and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used in the present specification, the following words and phrases are generally intended to have the meanings as set forth below, except to the extent that the context in which they are used indicates otherwise.

"Lower alkyl," refers to alkyl groups with the general formula $C_nH_{2n+1}$, where n=1 to about 6. In some embodiments, n=1 to about 3. The groups can be straight-chained or branched. Examples include methyl, ethyl, propyl, isopropyl, n-butyl, sec-butyl, t-butyl, isobutyl, n-pentyl, isopentyl, neopentyl, n-hexyl, and the like.

"Lower alkyl with heteroatoms," refers to groups with the general formula $C_nX_mH_r$, where X is a heteroatom, and n+m=2 to about 6. In some embodiments, n+m=2 to about 3. The heteroatom can be selected from: nitrogen, oxygen, sulfur, phosphorus, boron, chlorine, bromine, iodine, and other heteroatoms. In some embodiments, the heteroatom is selected from: nitrogen, oxygen, and sulfur. r=a positive whole number (integer) that is appropriate in light of n, X, and m, as will be understood by one of ordinary skill in the art. For example, if n=2, X is nitrogen, and m=1, then r=6, such that the group is $C_2H_6$. The groups can be straight-chained or branched.

"Alkyl," refers to alkyl groups with the general formula $C_nH_{2n+1}$, where n=about 6 to about 18. The groups can be straight-chained or branched.

"Alkyl with heteroatoms," when used alone or in combination with other groups, refers to groups with the general formula $C_nX_mH_r$, where X is a heteroatom, and n+m=about 6 to about 18. The heteroatom can be selected from: nitrogen, oxygen, sulfur, phosphorus, boron, chlorine, bromine, iodine, and other heteroatoms. In some embodiments, the heteroatom is selected from: nitrogen, oxygen, and sulfur. r=a positive whole number (integer) that is appropriate in light of n, X, and m, as will be understood by one of ordinary skill in the art. For example, if n=5, X is nitrogen, and m=2, then r=13, such that the group is $C_5N_2H_{13}$. The groups can be straight-chained or branched.

"Carbonyl-containing," refers to a group containing a carbonyl, for example, an aldehyde, a ketone, an ester, an amide, a carboxylic acid, or an acyl group. The groups can include 1 to about 6 carbon atoms, and at least one oxygen atom.

"Aryl," refers to an aromatic group containing ring carbon atoms and having about 5 to about 14 ring carbon atoms and up to a total of about 18 ring or pendant carbon atoms. Examples include phenyl, α-naphthyl, β3-naphthyl, tolyl, xylyl, and the like.

"Aryl lower alkyl" refers to an aryl group bonded to a bridging lower alkyl group, as defined herein. Examples include benzyl, phenethyl, naphthylethyl, and the like.

Each of the aforementioned groups could be substituted or unsubstituted. For example, "alkyl" can include substituted alkyl, substituted with hydroxyl, heteroatoms, or lower alkyl groups.

The presently-disclosed subject matter includes compounds, or pharmaceutically acceptable compositions thereof, having an affinity for bone, or "bone targeted compounds." The presently-disclosed subject matter includes bone targeted compounds and methods useful for treating conditions of interest, e.g., conditions affecting bone. The presently-disclosed subject matter further includes methods for delivering an agent of interest to bone.

The bone targeted compounds of the presently-disclosed subject matter can in some embodiments generally include three units. The three units of the compounds are: a Bone Targeting Portion, having an affinity for bone; a Linking Portion that is capable of connecting the Bone Targeting Portion to a third unit; and the third unit. In some embodiments, the third unit is a Bone Active Portion, capable of interacting with bone. For example, the Bone Active Portion could be derived from a Bone Active Agent having an effect on bone. In other embodiments, the third unit is a protecting group that assists with maintaining the stability of the bone targeted compound. In other embodiments, the third unit is a hydrogen or a hydroxyl group. In some embodiments, the compound is a salt, derived from a compound wherein the third unit is hydrogen or hydroxyl, which salt can be maintained stably.

The compounds of the presently-disclosed subject matter can be represented by the following formula:

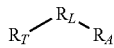

Formula 1 where, $R_T$ represents the Bone Targeting Portion, $R_L$ represents the linking portion, and $R_A$ represents the Bone Active Portion, the protecting group, or the hydrogen or hydroxyl. In some embodiments, the compounds can be provided as a salt or solvate, e.g., a pharmaceutically acceptable salt or solvate.

Bone Targeting Portion

The Bone Targeting Portion ($R_T$) of the compound has an affinity for the extracellular inorganic matrix of bone. The Bone Targeting Portion can be represented by the following formula:

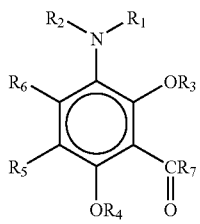

Formula 2 wherein
 $R_1$ is hydrogen, lower alkyl, alkyl, aryl lower alkyl, or aryl;
 $R_2$ is hydrogen, lower alkyl, alkyl, aryl lower alkyl, or aryl;
 $R_3$ is hydrogen, lower alkyl, alkyl, aryl lower alkyl, aryl, or carbonyl-containing;
 $R_4$ is hydrogen, lower alkyl, alkyl, aryl lower alkyl, aryl, or carbonyl-containing;

$R_5$ and $R_6$ are independently hydrogen, lower alkyl, or alkyl, or $R_5$ and $R_6$, taken together with the carbon atoms to which they are bonded, form a ring containing about 6 to about 14 ring carbon atoms and up to a total of about 18 carbon atoms, which formed ring can be monocyclic, bicyclic, or tricyclic, wherein the ring can optionally have substituents, including heteroatoms;
 $R_7$ is hydroxy, lower alkoxy, or $NR_8R_9$ and
 $R_8$ and $R_9$ are independently hydrogen, or lower alkyl.

An exemplary Bone Targeting Portion of the presently-disclosed subject matter can be represented by the following formula:

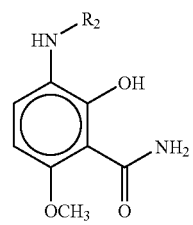

Formula 3 where $R_1$, $R_3$, $R_5$, and $R_6$ are each hydrogen; $R_4$ is methyl; and $R_7$ is amino.

Another exemplary Bone Targeting Portion of the presently-disclosed subject matter can be represented by the following formula:

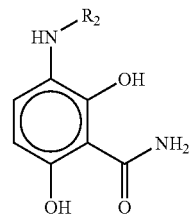

Formula 4 where $R_1$, $R_3$, $R_4$, $R_5$, and $R_6$ are each hydrogen; and $R_7$ is amino.

Another exemplary Bone Targeting Portion of the presently-disclosed subject matter can be represented by the following formula:

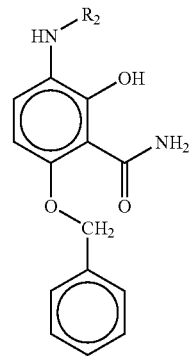

Formula 5 where $R_1$, $R_3$, $R_5$, and $R_6$ are each hydrogen; $R_4$ is benzyl; and $R_7$ is amino.

Another exemplary Bone Targeting Portion of the presently-disclosed subject matter can be represented by the following formula:

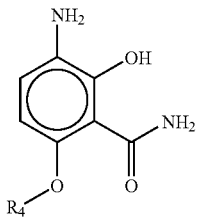

Formula 6 where $R_1$, $R_2$, $R_3$, $R_5$, and $R_6$ are each hydrogen; and $R_7$ is amino.

The linking portion is attached to the Bone Targeting Portion at $R_1$, $R_2$, or $R_4$. For example, when the linking portion is attached to the Bone Targeting Portion at $R_1$, the compound has the following formula:

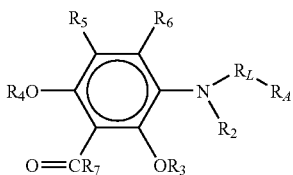

Formula 7

As another non-limiting example, when the linking portion is attached to the Bone Targeting Portion at $R_7$, the compound has the following formula:

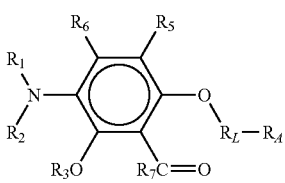

Formula 8

Bone Active Portion ($R_A$)

In some embodiments of the compounds of the presently-disclosed subject matter, $R_A$ is a Bone Active Portion of the compound. The Bone Active Portion interacts with and affects the bone. The Bone Active Portion can be derived from a Bone Active Agent, which can be selected for its efficacy in treating a condition of interest. A Bone Active Portion that is derived from a Bone Active Agent can be modified relative to the Bone Active Agent as is necessary to be connected to the remainder of the compound, while maintaining some or all of the activity associated with the Bone Active Agent, or while obtaining enhanced activity relative to the Bone Active Agent. For example, a Bone Active Portion derived from a Bone Active Agent after being linked to the compound can have the structure of the Bone Active Agent, less a leaving group (e.g., less a hydrogen, less a hydroxyl, less a covalent bond, or less another leaving group) or including a connecting group, as will be apparent to one of ordinary skill in the art.

Without wishing to be bound by theory or mechanism, once embodiments of the compound are delivered to bone for interaction therewith, the Bone Active Portion could be cleaved from the compound, becoming a free Bone Active Agent capable of interacting with adjacent bone. Alternatively, once embodiments of the compound are delivered to bone, the Bone Active Portion, as part of the bone-targeted compound, could interact with bone.

Exemplary Bone Active Portions of the compounds of the presently-disclosed subject matter can be derived from Bone Active Agents, including but not limited to steroids, including but not limited to androgens, steroidal estrogenic agents, and other sex hormones; estrogenic agents, including but not limited to steroidal estrogenic agents, estrogen precursors, estrogen analogues and metabolites, non-steroidal estrogenic agents, including plant-derived estrogens; carbonic anhydrase inhibitors; nitric oxide agents; antineoplastic or anticancer agents; antimicrobial agents; and other Bone Active Agents. Examples of Bone Active Agents from which the Bone Active Portion of the compounds of the presently-disclosed subject matter can be derived are set forth in Tables A-D.

TABLE A

Examples of Steroids from which the Bone Active Portion can be Derived
Bone Active Agent (BAA)

| androgens, including but not limited to the following: | estrogens, including but not limited to the following |
|---|---|
| testosterone | estradiol |
| dehydroepiandrosterone (DHEA) | estrone |
| 5α-dihydrotestosterone | estriol |
| androstenedione | estrogen precursors |
| etiocholanolone | estrogen analogues and metabolites |
| epiandrosterone | tibolone |
| androsterone | 2-Methoxyestradiol (2-ME) |
| 17 α-methyl testosterone | |
| fluoxymesterone | |
| 17 α-ethyl testosterone | |
| 17 α-methylandrostan -3β, 17 β-diol | |
| androstan-3a, 17 β-diol | |
| androstan- 3 α- 17 α-diol | |
| androstan- 17 β- ol 3-one | |
| androstane- 17 α-ol-3 one | |
| D5-androsten-3 α, 17 β-diol | |
| D5-androstene-3β, 17β-diol | |
| androstane-3-17-dione | |
| D4-androstenedione | |
| Selective androgen receptor modulators (SARMs) | |

TABLE B

Examples of Estrogenic Agents from which
the Bone Active Portion can be Derived
Bone Active Agent (BAA)

| steroidal estrogenic agents, including but not limited to the following: | non-steroidal estrogenic agents, including but not limited to the following: |
|---|---|
| estradiol | genistein |
| estrone | resveratrol |
| estriol | daidzein |
| estrogen precursors | glycitein |
| estrogen analogues and metabolites | formononetin |
| tibolone | biochanin A |
| 2-Methoxyestradiol (2-ME) | diethylstilbestrol |
| | hexestrol |
| | xenoestrogens |
| | phytoestrogens & mycoestrogens |
| | coumestans |
| | isoflavonoids |
| | ipriflavone |
| | lignan phytoestrogens (including but not limited to: secoisolariciresinol diglycoside) |

TABLE C

Examples of other Bone Active Portions from which the
Bone Active Portion can be Derived
Bone Active Agent (BAA)

prostaglandins, including but not limited to the following
prostaglandin D2
prostaglandin EP4 agonist ONO-4819
prostaglandin E2
prostaglandin E1
prostaglandin F2a
15-methyl-PGE2
15-methyl-11-deoxy-PGE1
cyclooxygenase products derived from eicosatetraeneoic (22:4) acid and the corresponding 22:5 and 22:6 analogs parathyroid hormones, including but not limited to the following:
intact PTH (PTH [1-84])
teriparatide (recombinant human PTH [1-34])
PTH fragment (1-31)
PTH-related protein (PTHrP)
thyroid hormones, including but not limited to the following:
thyroxine (T4)
liothyronin (T3)

HMG CoA reductase inhibitors, including but not limited to the following:
lovastatin
compactin
simvastatin
pevastatin
mevastatin
cerivastatin
fluvastatin
pitavastatin
atorvastatin
selective estrogen receptor modulators (SERMS), including but not limited to the following:
raloxifene
arzoxifene
lasofoxifene
bazedoxifene
droloxifene
ospemifene
toremifene
tamoxifen
ormeloxifene
estrens
estren-α (4-estren-3 α,17β-diol)
estren-β (4-estren-3β,17β-diol)

Src tyrosine kinase inhibitors, including but not limited to the following:
AP23451
2-(4-aminocyclohexyl)-9-ethyl-N-phenyl-9H-purin-6-amine (See Boyce, et al., Clin. Cancer Res. 12, 6291s-6925s (2006), which is incorporated herein by this reference)
(N-(5-Chloro-1,3-benzodioxol-4-yl)-7-[2-(4-methylpiperazin-1-yl)ethoxy]-5-(tetrahydro-2H-pyran-4-yloxy)quinazolin-4-amine) (a/k/a AZD0530, See Estell et al., J. Clinical Oncology, 23, 16S, p. 3041 (2005) (Abstract); and Hennequin, et al., J.

carbonic anhydrase inhibitors, including but not limited to the following
acetazolamide
2-amino-1,3,4-thiadiazole-5-sulfonamide
6-hydroxy-2-benzothiazole sulfonamide
6-ethylsuccinyloxy-2-benzothiazole sulfonamide
succinylazolamide
oxaloylazolamide
etholazolamide
methazolamide
benzolamide
carbonic anhydrase inhibitors (e.g., as described in U.S. Pat. Nos. 5,641,762; 5,242,937; 5,055,480; and 5,059,613, which are incorporated herein by this reference)

cathepsin K Inhibitors, including but not limited to the following:
OST-4077 [furan-2-carboxylic acid (1-{1-[4-fluoro-2-(2-oxo-pyrrolidin-1-yl)-phenyl]-3-oxo-piperidin-4-ylcarbamoyl}-cyclohexyl)-amide]

nitric oxide agents, including but not limited to the following:
nitroglycerine
isosorbide mononitrate
erythrityl tetranitrate
alkoxy-$(NO_2)_2$
vitamin D molecules, including but not limited to the following:
ergocalciferol, (vitamin D2)
cholecalciferol, (vitiamin D3)
25-hydroxy-ergocalciferol
1,25-dihydroxyergocalciferol
25-hydroxy-cholecalciferol
1,25-dihydroxycholecaciferol
24,25-dihydroxy vitamin D3 matrix metalloproteinase (MMP) inhibitors, including but not limited to the following:
batimastat
marimastat
prinomastat
tanomastat
trocade
interleukin-6 Receptor Antagonists, including but not limited to the following:
20S,21-epoxy-resibufogenin-3-formate (ERBF)
integrin alphavbeta3 inhibitors, including but not limited to the following:
3,4-dichloro-phenylbiguanide
3,5-dichloro-phenylbiguanide
CB1- and CB2-selective cannabinoid receptor antagonists
calcium-Sensing Receptor Antagonists
chloride channel inhibitors
non-steroidal anti-inflammatory agents (NSAIDs)
growth Factors
strontium ranelate
isotaxiresinol
clomiphene
reveromycin A
autocoids
RANK-L antagonists
thiazides TABLE C-continued Examples of other Bone Active Portions from which the
Bone Active Portion can be Derived
Bone Active Agent (BAA)

| | |
|---|---|
| Medicinal Chemistry 49, 22, 6465-6488 (2006), which is incorporated herein by this reference) | ferulic acid |
| beta-blockers | femarelle (DT56a) |

TABLE D

Examples of other Bone Active Portions from which the
Bone Active Portion can be Derived
Bone Active Agent (BAA)

anti-cancer agents, including but not limited to the following:

| | |
|---|---|
| doxorubicin | methotrexate |
| cyclophosphamide/cytoxan | capecitabine |
| ifosfamide | carboplatin |
| vincristine | 5-fluorouracil |
| cisplatin | epirubucin |
| etoposide | topotecan |
| methotrexate | irinotecan |
| taxanes, e.g., docetaxel, paclitaxel | erlotinib |
| vinorelbine | gefitinib |
| gemcitabine | bexarotene |
| capecitabine | vinblastine |
| carboplatin | free radical scavengers | antimicrobial agents, including but not limited to the following:

vancomycin

As noted above, the Bone Active Portion of some embodiments of the compounds of the presently-disclosed subject matter interacts with and affect bone, having a desired effect on bone. The desired effect can vary, for example, based on the bone condition being treated. Compounds of the presently-disclosed subject matter can affect bone to treat a variety of bone conditions, including those set forth in Tables E and F.

TABLE E

Primary Bone Conditions

| | Primary Bone Condition | Category (ies) of Bone Active Agent(s) |
|---|---|---|
| Metabolic Bone Diseases (MBD) | Osteoporosis<br>Paget's Disease<br>Osteogenesis imperfecta<br>Primary hyperparathyroidism<br>Fibrous dysplacia (McCune-Albright syndrome)<br>Osteopetrosis<br>Tumor-induced osteomalacia<br>Rickets (nutritional, genetic, drug-induced)<br>Renal osteodystrophy<br>Fanconi syndrome<br>Hypophosphatasia | Anabolic Agent and/or Anti-catabolic Agent |
| Fracture | Fracture resulting from a MBD, another disease or disorder, or an external physical force | Anabolic Agent |
| Cancer | Primary bone cancer (e.g., primary bone sarcoma) | Anti-cancer agents |

TABLE F

Primary Conditions, with which another
Secondary Bone Conditions is Associated

| Primary Condition | Secondary Bone Condition | Category (ies) of Bone Active Agent(s) |
|---|---|---|
| Alcoholism<br>Anorexia Nervosa (and other eating disorders)<br>Asthma, certain treatment programs for; and bone loss associated with rheumatoid arthritis<br>Autoimmune Diseases, e.g., lupus<br>Celiac Disease (Gluten allergy)<br>Diabetes<br>Inflammatory Bowel Diseases (Crohn's Disease, ulcerative colitis) | Osteoporosis | Anabolic Agent and/or Anti-catabolic Agent |
| Cancer (other than primary bone cancer, including: breast, lung, prostate, kidney, thyroid, and other cancers) | Bone metastasis | Anti-cancer agents |
| Infection | Osteomyelitis | Antimicrobial agents |

With reference to Table E, in some embodiments, compounds wherein the Bone Active Portion is derived from a Bone Active Agent set forth in Tables A-C can be used to treat bone conditions including metabolic bone diseases. In some embodiments, when a metabolic bone disease is being treated, an anti-catabolic effect, an anabolic effect, or a combination thereof is desired. In some embodiments, compounds wherein the Bone Active Portion is derived from a Bone Active Agent set forth in Tables A-C can be used to treat bone conditions including bone fracture. In some embodiments, when a bone fracture is being treated, an anabolic effect is desired. In some embodiments, compounds wherein the Bone Active Portion is derived from a Bone Active Agent that is a nitric oxide agent (e.g., a nitric oxide agent as set forth in Table C) can be used to treat bone conditions including bone fracture. In some embodiments, compounds wherein the Bone Active Portion is derived from a Bone Active Agent that is a vasodilator can be used to treat bone conditions including bone fracture.

With continued reference to Table E, in some embodiments, compounds wherein the Bone Active Portion is derived from a Bone Active Agent that is an anti-cancer agent (e.g., anti-cancer agent set forth in Table D) can be used to treat a primary or a metastatic bone cancer, where an anti-cancer effect is desired. In some embodiments, compounds wherein the Bone Active Portion is derived from a Bone Active Agent that is an anti-microbial agent can be used to treat a bone infection. For example, compounds wherein the Bone Active Portion is derived from an antimicrobial agent (e.g., antimicrobial agent set forth in Table D) can be used to treat osteomyelitis, where an antimicrobial effect is desired.

With reference to Table F, it can sometimes be desirable to administer to a subject having a primary condition a compound useful for treating a secondary condition. In some embodiments, a subject can be identified as having one or more primary conditions associated with a secondary bone condition that is a metabolic bone disease, such as osteoporosis, as identified in Table F. The subject can then be administered a compound for treating osteoporosis. In some embodiments, such a treatment includes a prophylactic treatment, e.g., arresting or preventing the development of osteoporosis. In some embodiments, an anti-catabolic effect and/or an anabolic effect is desired. In some embodiments, a subject can be identified as having a primary cancer capable of metastasizing to bone. The subject can then be administered a compound for treating bone cancer, wherein an anti-cancer effect is desired. In this regard, in some embodiments, such a treatment includes a prophylactic treatment, e.g., arresting or preventing the development of bone cancer. In some embodiments, a subject can be identified as having a primary infection capable of leading to a secondary bone condition, osteomyelitis. The subject can then be administered a compound for treating osteomyelitis, wherein an antimicrobial effect is desired. In this regard, in some embodiments, such a treatment includes a prophylactic treatment, e.g., arresting or preventing the development of osteomyelitis.

In some embodiments, the compounds including Bone Active Portions of the presently-disclosed subject matter can have an anti-catabolic effect on bone. In some embodiments, the compounds including Bone Active Portions of the presently-disclosed subject matter can have an anabolic effect on bone. In some embodiments, the compounds including Bone Active Portions of the presently-disclosed subject matter can have an anti-catabolic effect and an anabolic effect on bone. In some embodiments, the compounds including Bone Active Portions of the presently-disclosed subject matter can have an anti-cancer effect on bone. In some embodiments, the compounds including Bone Active Portions of the presently-disclosed subject matter can have an anti-microbial effect on bone. In some embodiments, the compounds including Bone Active Portions of the presently-disclosed subject matter can have an anti-biotic effect on bone. In some embodiments, the compounds can be provided in synergistic compositions containing other compounds useful for treating a primary and/or secondary bone condition.

As used herein, a catabolic effect is an effect that results in a net reduction in bone mass, bone density, and/or bone strength. As used herein, an anti-catabolic effect is an effect that results in a decrease in the magnitude of a catabolic effect. Reduction in bone mass, density, and/or strength can be identified by comparing a first bone measurement (e.g., control or earlier time), to a second bone measurement (e.g., treated or later time). Bone mass, density, and strength can be measured using methods known to those skilled in the art.

As used herein, an anabolic effect is an effect that results in increased bone strength; or increased bone mass or density, and increased bone strength. Increases bone mass or density, and increases in bone strength provide evidence that net bone formation is being promoted. Increases in bone mass or density, and increases in bone strength can be measured by comparing a first bone measurement (e.g., control or earlier time), to a second bone measurement (e.g., treated or later time.) Bone mass or density can be measured using methods known to those skilled in the art. In some embodiments, requisite increased bone mass or density affected by treatment with a compound of interest is an increase of at least about 5%, at least about 10%, at least about 15%, at least about 20%, at least about 25%, at least about 30%, or at least about 35%, when a first bone measurement and a second bone measurement are compared.

Increased bone strength can be measured by comparing a first bone strength measurement to a second bone strength measurement. In some embodiments, the increased bone strength can be measured by comparing the bone strength of an untreated control (first bone strength measurement), to the bone strength of a bone sample after treatment with a compound of interest (second bone strength measurement). In some embodiments, increased bone strength can be measured by comparing the bone strength of a bone sample before treatment with a compound of interest (first bone strength measurement), to the bone strength of a bone sample after treatment with the compound of interest (second bone strength measurement). Mechanical competence of bone can be determined using methods known to those skilled in the art, for example, a blunt indentation force, a three point bending to failure test or a torsional analysis on bone samples from appropriate test subject, e.g., mouse, rat. Percent (%) change in bone strength can be calculated using the following formula:

$$\% \text{ change} = [(BS_2 - BS_1)/BS_1] \times 100$$

where $BS_1$ is the first bone strength measurement, and $BS_2$ is the second bone strength measurement. An increase in bone strength is identified where the change in bone strength is greater than 0, i.e., a positive % change. In some embodiments, increased bone strength affected by treatment with the compound is an increase in bone strength of at least about 1%. In other embodiments, requisite increased bone strength affected by treatment with the compound is an increase in bone strength of at least about 5%, at least about 10%, at least about 15%, at least about 20%, at least about 25%, at least about 30%, at least about 40%, at least about 50%, at least about 75%, at least about 100%, or at least about 200%, when a first bone strength measurement and a second bone strength measurement are compared.

In some embodiments, for example, where bone strength is being assessed in a human subject, fracture incidence can be recorded, and increased bone strength can be identified where there is a trend of decreased incidence of bone fracture.

Although not necessary to establish anabolic effect, additional information to establish promotion of net bone formation can be obtained. For example, assays can be conducted for certain biomarkers of bone formation (See, e.g., M J Seibel *Clin Biochem Rev* 26:97 (2005) or "The Use of Biochemical Markers of Bone Turnover in Osteoporosis" by P D Delmas et al. *Osteoporosis Int*. suppl. 6 S2-17 (2000), which are incorporated herein by these references). As another example, information can be collected as described in Riggs B L, and Parfitt A M, "Drugs Used to Treat Osteoporosis: The Critical Need for a Uniform Nomenclature Based on Their Action on Bone Remodeling," *J. Bone and Mineral Res.* 20:2 (2005), which is incorporated herein by this reference. In this regard, in some embodiments, anabolic effect can be identified where a biomarker of bone formation is found in an appropriate test sample, e.g., osteocalcin, collagen type I, as described in the Examples herein. In some embodiments, anabolic effect can be identified pursuant to an assay to evaluate stimulation of bone formation, e.g., calvarial injection, as described in the Examples herein.

As used herein, an antimicrobial effect is an effect resulting in a treatment (as defined herein) of a microbial infection, including a bacterial infection. In some embodiments, the compound can interact with and affect bone by treating a microbial infection associated with bone. In some embodiments, an anti-microbial effect includes preventing infection by a microorganism, or inhibiting the growth of a microorganism, such as a bacteria, or by exerting a direct killing effect on a microorganism.

As used herein, an anti-cancer effect is an effect resulting in a treatment (as defined herein) of a cancer. In some embodiments, an anti-cancer effect includes slowing the growth of or killing cancerous cells. In some embodiments, an anti-cancer effect includes preventing the metastasis of a primary cancer to bone. In some embodiments, an anti-cancer effect includes enhancing the killing of cancerous cells associated with the bone (e.g., acting as a chemosensitizer or radiosensitizer). With regard to cancer treatment, compounds including an anti-cancer agent can be effective against primary bone cancer, (e.g., primary bone sarcoma) and/or against secondary bone cancer, i.e., metastatic bone cancer. In the case of secondary bone cancer, breast, lung, prostate, kidney, and thyroid cancers are the types of primary cancers that most commonly metastasize to bone. It is contemplated that an anti-cancer agent from which a Bone Active Portion of a compound of the presently-disclosed subject matter is derived can be selected based on the primary tumor site. For example, when compounds of the presently-disclosed subject matter are used for treating secondary cancer, the efficacy can be enhanced by selecting a Bone Active Portion that is particularly effective against the primary cancer type that has metastasized, or has the potential to metastasize, to bone.

The foregoing paragraphs include information about certain conditions or interest and/or desired effects; however, other conditions of interest and/or desired effects are contemplated by the presently-disclosed subject matter. For example, in some embodiments, compounds of the presently-disclosed subject matter can be useful for treating muscle atrophy, or loss of muscle mass, of muscles surrounding bones of the axial skeleton. In some embodiments, compounds wherein the Bone Active Portion is derived from a steroid, such as testosterone, can be useful for treating muscle atrophy (e.g., the compound of Formula 33, set forth below, which includes a Bone Active Portion derived from testosterone, can be useful for treating muscle atrophy). For another example, in some embodiments, compounds of the presently-disclosed subject matter can be useful to facilitate delivery of a second compound of interest. For example, in some embodiments, the second compound can be administered substantially concurrently with a compound of the presently-disclosed subject matter that include a Bone Active Portion that is a vasodilator, or a Bone Active Portion that is derived from a Bone Active Agent that is a vasodilator. Without wishing to be bound by theory or mechanism, it is believed that an increased delivery of blood to bone affected by a bone-targeted vasodilator of the presently-disclosed subject matter can facilitate delivery to bone of a second compound of interest. In some embodiments, a bone-targeted vasodilator of the presently-disclosed subject matter includes a Bone Active Portion that is derived from a nitric oxide agent (NO donor), such as a nitric oxide agent as set forth in Table C.

Protecting Group ($R_A$)

With reference to Formula I, in some embodiments of the compound, $R_A$ is a protecting group. The protecting group can assist with maintaining the stability of the compound, for example, by keeping an adjacent group on the linking portion from reacting with other portions of the compound, e.g., cyclizing. Compounds including a protecting group can be stably stored until it becomes desirable to associate the compound with a Bone Active Portion. In this regard, the compounds including a protecting group are useful for preparing compounds for treating conditions associated with bone.

Exemplary protecting groups that can be used include, t-butoxycarbonyl (t-BOC) or t-butoxy, fluorenylmethoxycarbonyl (FMOC) or a fluorenylmethoxy, and other appropriate protecting groups, such as those described in Greene's Protective Groups in Organic Synthesis, 4th ed., by Peter G. M. Wuts, and Theodora W. Greene, John Wiley & Sons, inc., Hoboken, N.J., 2006, which is incorporated herein by this reference. As will be understood by those of ordinary skill in the art, appropriate protecting groups can be selected for use with the compounds disclosed herein, which will allow the compound to be stably stored, and which will allow the compound to be used to prepare compounds for treating conditions associated with bone, i.e., allow for the protecting group to be removed and for a bone targeting portion to be associated with the compound. In this regard, as will be understood by those of ordinary skill in the art, while t-butoxycarbonyl (t-BOC) or t-butoxy, or fluorenylmethoxycarbonyl (FMOC) or a fluorenylmethoxy can be appropriate protecting groups in some embodiments, they are not appropriate in other embodiments.

In some embodiments of the presently-disclosed subject matter where the protecting group is t-BOC, the compound can be represented by the following formula:

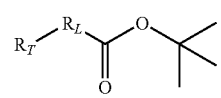

Formula 9

In some embodiments of the presently-disclosed subject matter where the protecting group is FMOC, the compound can be represented by the following formula:

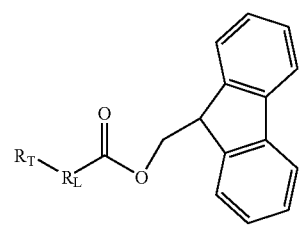

Formula 10

Hydrogen, or Hydroxyl ($R_A$)

With reference to Formula I, in some embodiments of the compound, $R_A$ is hydrogen or hydroxyl, depending on the embodiment of the Linking Portion, $R_L$, being used, as will be described below. The presently-disclosed subject matter includes salts derived from compounds where $R_A$ is hydrogen or hydroxyl, which salts can be stably stored until it becomes desirable to associate the compound with a Bone Active Portion. In this regard, the compounds in which $R_A$ is Hydrogen or Hydroxyl are useful for preparing compounds for treating conditions associated with bone.

Linking Portion

The Linking Portion ($R_L$) of the compound connects and separates the Bone Targeting Portion ($R_T$) and a Bone Active Portion, the protecting group, or the hydrogen or hydroxyl ($R_A$). Without wishing to be bound by theory, in embodiments including a Bone Active Portion, it is believed that the Linking Portion separates the Bone Targeting Portion and the Bone Active Portion to limit steric interference of Bone Active Portion when interacting with bone.

The Linking Portion can be described with reference to the following formulas:

Formula 11

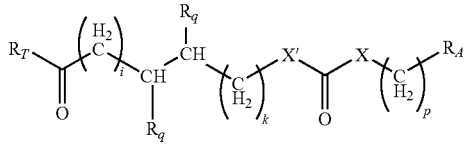

Formula 12

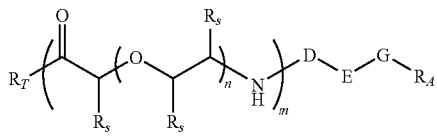

Formula 13

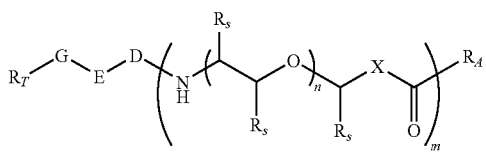

where the Linking Portion extends between $R_T$ and $R_A$.

With regard to the linking portion of Formula 11, i can be 0 to about 3, k can be 0 to about 3, and p can be 0 to about 4, where i, k, and p can vary independently of one another. For example, in an exemplary embodiment, i can be 1, k can be 2, and p can be 0, as represented by the following formulas:

Formula 14

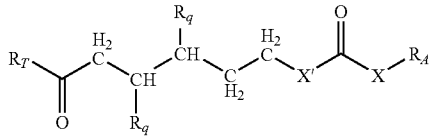

In another exemplary embodiment, i can be 2, k can be 2, and p can be 2, as represented by the following formulas:

Formula 15

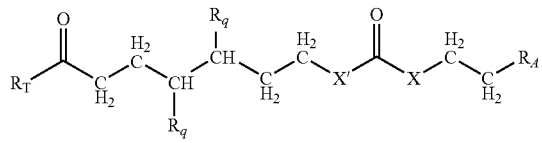

In another exemplary embodiment, i can be 3, k can be 3, and p can be 1, as represented by the following formulas:

Formula 16

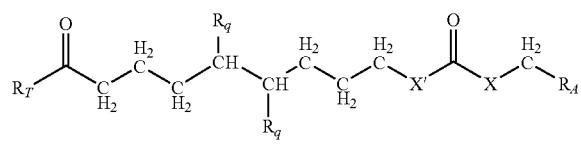

In another exemplary embodiment, i can be 0, k can be 0, and p can be 0, as represented by the following formulas:

Formula 17

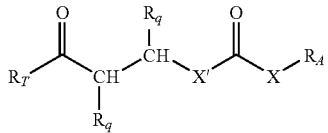

The groups of the linking portion identified as $R_q$ can be hydrogen or hydroxy, and can vary independently of one another. For example, every $R_q$ group can be hydroxy, as shown in the following formula, where i, k, and p are each 0:

Formula 18

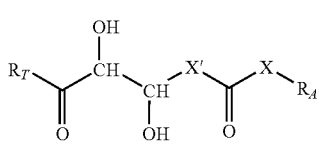

The identity of each $R_q$ group is independent. For example, one $R_q$ group can be hydrogen, while the other $R_q$ group can hydroxy, as shown in the following formula, where i, k, and p are each 0:

Formula 19

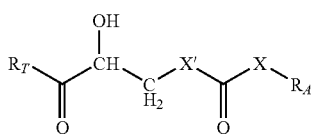

The group of the linking portion identified as X can be O, NH, S, or a covalent bond; and the group identified as X' can likewise be O, NH, S, or a covalent bond; where X and X' can vary independently of one another. In some embodiments, at least one of X' and X is a covalent bond. For example, when X is O, X' is a covalent bond, one $R_q$ group is hydrogen, the other $R_q$ group is hydroxy, and i, k, and p are each 0, then an exemplary compound can be represented by the following formula:

Formula 20

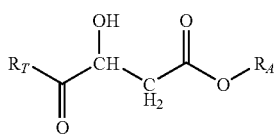

For another example, when X is a covalent bond, X' is NH, both $R_q$ groups are hydroxy, i is 2, k is 2, and p is 0, then an exemplary compound can be represented by the following formula:

Formula 21

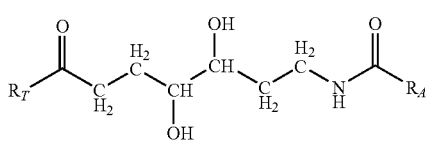

The Linking Portion can be connected to the Bone Targeting Portion ($R_T$) at $R_1$, $R_2$, or $R_4$. For example, when the Linking Portion is connected to the Bone Targeting Portion ($R_T$) at $R_1$, the compound can be represented by the following formula:

Formula 22

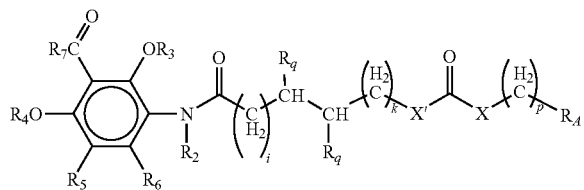

As mentioned above, a third unit $R_A$ of the compound can be selected from: a Bone Targeting Portion (See e.g., Tables A-D); a protecting group; or a hydrogen. When $R_A$ is a Bone Active Portion, it is contemplated that the Linker Portion can be bound to the Bone Active Portion to minimize the susceptibility to hydrolysis, e.g., ether linkage, to increase the bioavailability of the compound. That is to say, without wishing to be bound by theory or mechanism, if susceptibility to hydrolysis is minimized, the compound can be delivered to and affect bone.

In an exemplary embodiment, $R_A$ can be a Bone Active Portion derived from estradiol, as represented by the following formula:

Formula 23

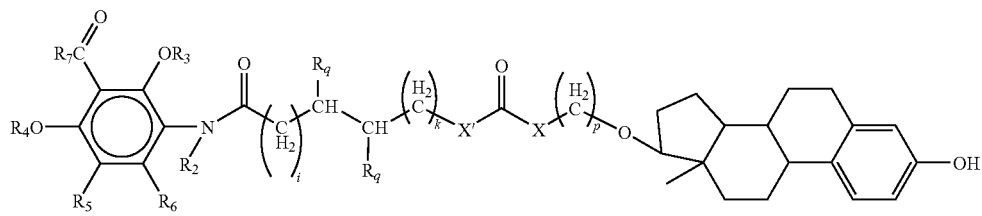

As shown in Formula 23, the Bone Active Portion derived from estradiol is estradiol less a hydrogen, allowing the Bone Active Portion to be connected to the remainder of the compound, while maintaining one or more activities generally associated with free estradiol. In some embodiments, when the Bone Active Portion of the compound is derived from estradiol, it is derived from the 17-β-enantiomer of estradiol. Without wishing to be bound by theory or mechanism, it is believed that the 17-β-enantiomer of estradiol is the active isomer.

Another exemplary compound can be represented by the following formula:

Formula 24

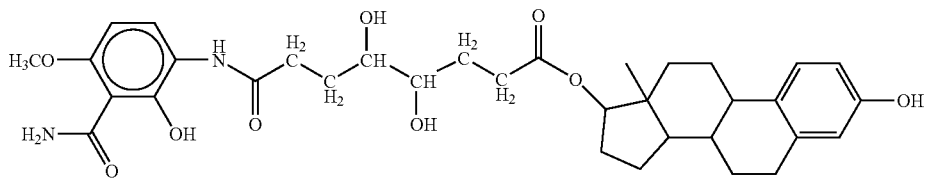

where the Linking Portion is connected to the Bone Targeting Portion ($R_T$) at $R_1$; where $R_2$, $R_3$, $R_5$, and $R_6$ are each H, $R_4$ is $CH_3$, and $R_7$ is $NH_2$; where $R_q$ are each OH, i is 2, k is 2, p is 0, and X and X' are each a covalent bond; and where $R_A$ is derived from estradiol Another exemplary compound can be represented by the following formula:

Formula 25

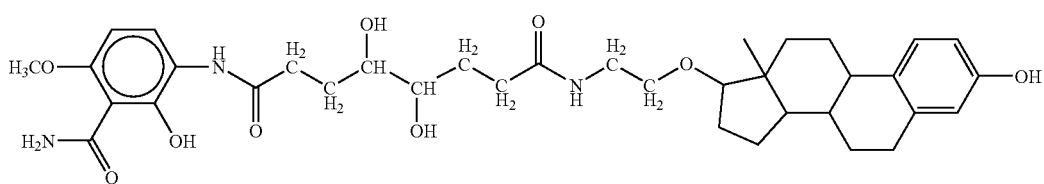

where the Linking Portion is connected to the Bone Targeting Portion ($R_T$) at $R_1$; where $R_2$, $R_3$, $R_5$, and $R_6$ are each H, $R_4$ is $CH_3$, and $R_7$ is $NH_2$; where $R_q$ are each OH, i is 2, k is 2, p is 2, X' is a covalent bond, and X is NH; and where $R_A$ is derived from Estradiol.

In some embodiments, $R_A$ can be derived from a non-steroidal estrogenic agent. In some embodiments, $R_A$ can be a Bone Active Portion derived from the non-steroidal estrogenic agent, genistein, as represented by the following formula:

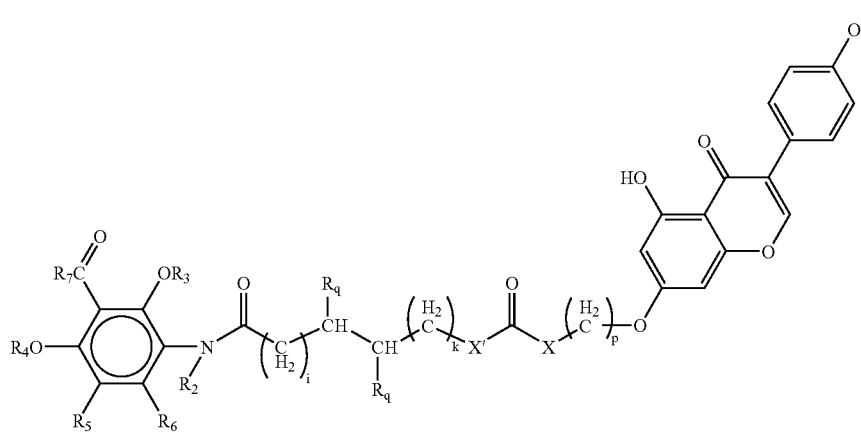

Formula 26

The Bone Active Portion derived from genistein is genistein less a hydrogen, allowing the Bone Active Portion to be connected to the remainder of the compound, while maintaining one or more activities generally associated with free genistein.

Another exemplary compound can be represented by the following formula:

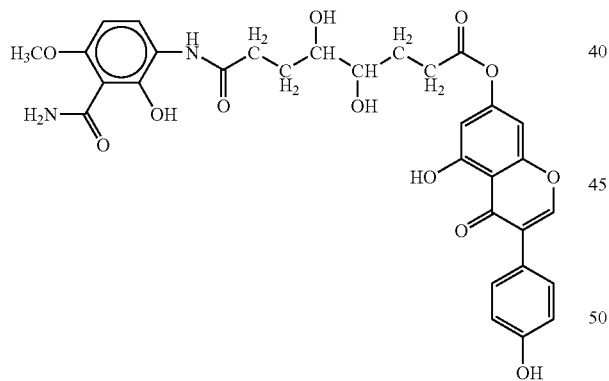

Formula 27 where the Linking Portion is connected to the Bone Targeting Portion ($R_T$) at $R_1$; where $R_2$, $R_3$, $R_5$, and $R_6$ are each H, $R_4$ is $CH_3$, and $R_7$ is $NH_2$; where $R_q$ are each OH, i is 2, k is 2, p is 0, and X' and X are each a covalent bond; and where $R_A$ is derived from genistein.

In some embodiments, $R_A$ can be derived from a nitric oxide agent. In some embodiments, $R_A$ can be a Bone Active Portion derived from the nitric oxide targeted agent, alkoxy-$NO_2$, as represented by the following formula:

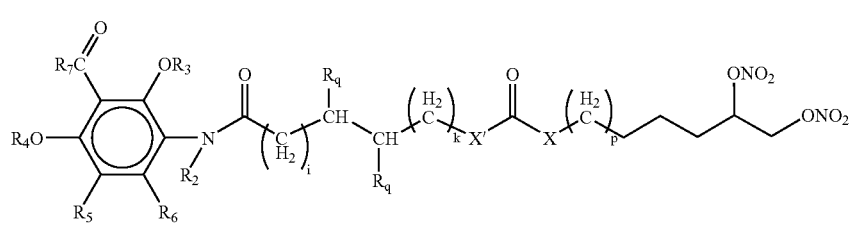

Formula 28

The Bone Active Portion derived from alkoxy-$NO_2$ is alkoxy-$NO_2$ less a hydrogen, allowing the Bone Active Portion to be connected to the remainder of the compound, while maintaining one or more activities generally associated with free alkoxy-$NO_2$.

Another exemplary compound can be represented by the following formula:

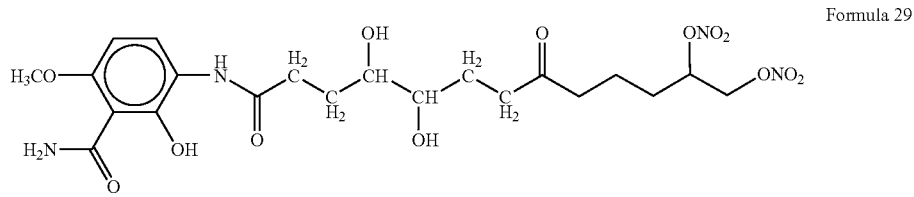

Formula 29 where the Linking Portion is connected to the Bone Targeting Portion ($R_T$) at $R_1$; where $R_2$, $R_3$, $R_5$, and $R_6$ are each H, $R_4$ is $CH_3$, and $R_7$ is $NH_2$; where $R_q$ are each OH, i is 2, k is 2, p is 0, and X' and X are each a covalent bond; and where $R_A$ is derived from alkoxy-$NO_2$.

In some embodiments, $R_A$ can be derived from an androgen. In some embodiments, $R_A$ can be a Bone Active Portion derived from the androgen, dehydroepiandrosterone (DHEA), as represented by the following formula:

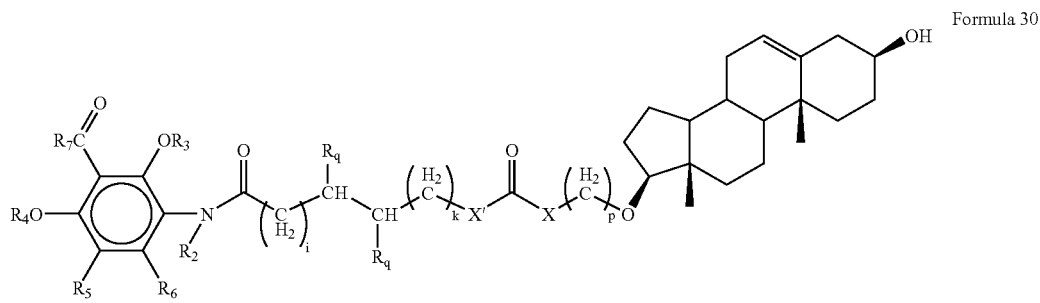

Formula 30 where the Linking Portion is connected to the Bone Targeting Portion ($R_T$) at $R_1$; where $R_2$, $R_3$, $R_5$, and $R_6$ are each H, $R_4$ is $CH_3$, and $R_7$ is $NH_2$; where $R_q$ are each OH, i is 2, k is 2, p is 2, X and X' are each a covalent bond; and where $R_A$ is derived from DHEA.

The Bone Active Portion derived from DHEA is DHEA singly bonded to oxygen at carbon 17, allowing the Bone Active Portion to be connected to the remainder of the compound, while maintaining one or more activities generally associated with free DHEA.

Another exemplary compound can be represented by the following formula:

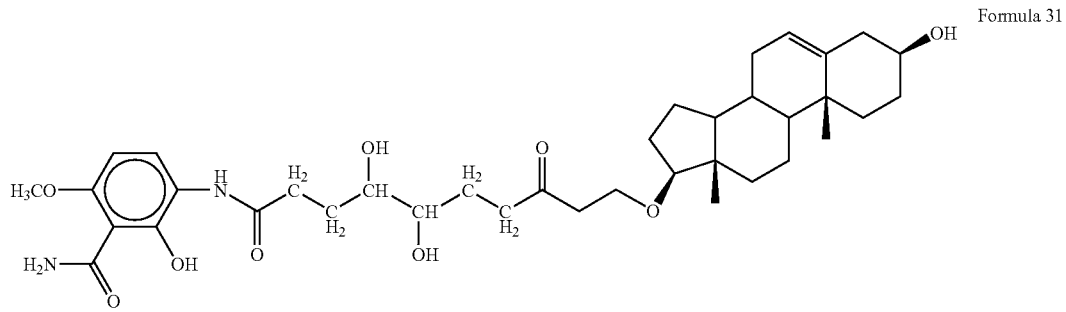

Formula 31

In some embodiments, $R_A$ can be a Bone Active Portion derived from the androgen, testosterone, as represented by the following formula:

Another exemplary compound can be represented by the following formula:

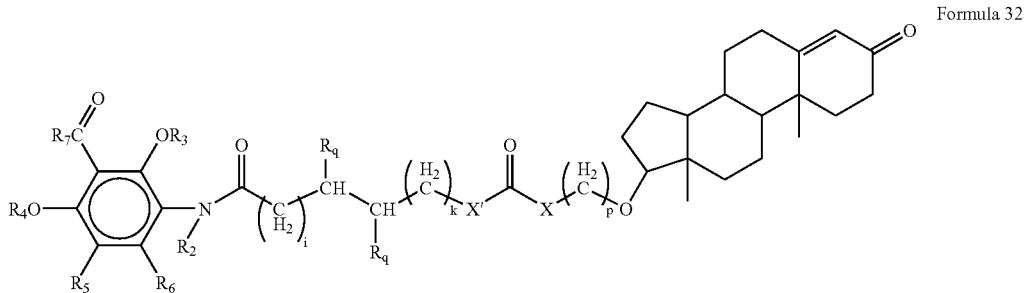

The Bone Active Portion derived from testosterone is testosterone less a hydrogen, allowing the Bone Active Portion to be connected to the remainder of the compound, while maintaining one or more activities generally associated with free testosterone.

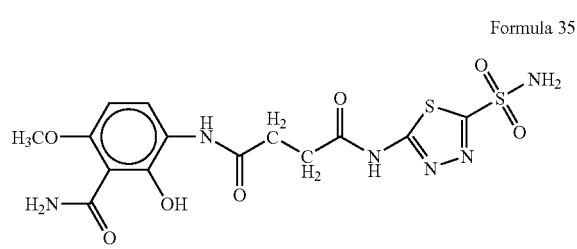

Another exemplary compound can be represented by the following formula:

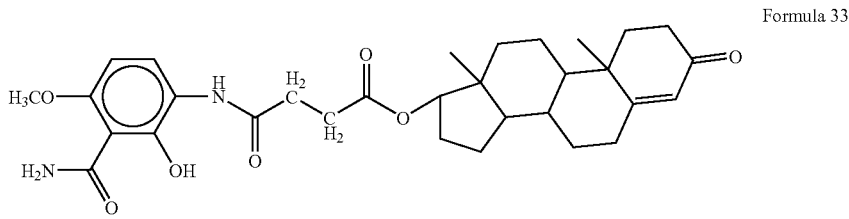

where the Linking Portion is connected to the Bone Targeting Portion ($R_T$) at $R_1$; where $R_2$, $R_3$, $R_5$, and $R_6$ are each H, $R_4$ is $CH_3$, and $R_7$ is $NH_2$; where $R_q$ are each H, i is 0, k is 0, p is 0, and X' and X are each a covalent bond; and where $R_A$ is derived from testosterone.

In some embodiments, $R_A$ can be derived from a carbonic anhydrase inhibitor. In some embodiments, $R_A$ can be a Bone Active Portion derived from the carbonic anhydrase inhibitor, 2-amino-1,3,4-thiadiazole-5-sulfonamide, as represented by the following formula:

where the Linking Portion is connected to the Bone Targeting Portion ($R_T$) at $R_1$; where $R_2$, $R_3$, $R_5$, and $R_6$ are each H, $R_4$ is $CH_3$, and $R_7$ is $NH_2$; where $R_q$ are each H, i is 0, k is 0, p is 0, and X' and X are each a covalent bond; and where $R_A$ is derived from 2-aminothiadiazole-5-sulfonamide.

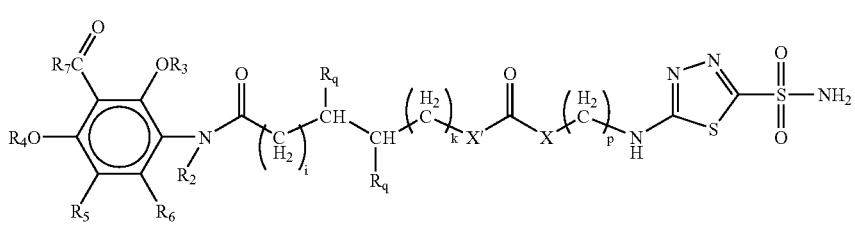

The Bone Active Portion derived from 2-amino-1,3,4-thiadiazole-5-sulfonamide less a hydrogen, allowing the Bone Active Portion to be connected to the remainder of the compound, while maintaining one or more activities generally associated with free sulfonamide.

In some embodiments, $R_A$ can be derived from an anticancer agent or an antineoplastic agent. In some embodiments, $R_A$ can be a Bone Active Portion derived from doxorubicin, as represented by the following formula:

Formula 36

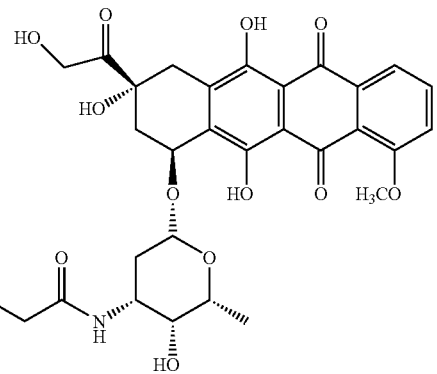
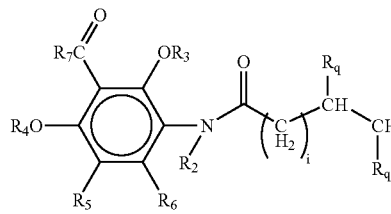

The Bone Active Portion derived from doxorubicin is doxorubicin less a hydrogen, allowing the Bone Active Portion to be connected to the remainder of the compound, while maintaining one or more activities generally associated with free doxorubicin.

Another exemplary compound can be represented by the following formula:

where the Linking Portion is connected to the Bone Targeting Portion ($R_T$) at $R_1$; where $R_2$, $R_3$, $R_5$, and $R_6$ are each H, $R_4$ is $CH_3$, and $R_7$ is $NH_2$; where $R_q$ are each OH, i is 2, k is 2, p is 0, and X' and X are each a covalent bond; and where $R_A$ is derived from doxorubicin.

In some embodiments, $R_A$ can be derived from an antimicrobial agent. In some embodiments, $R_A$ can be a Bone Active Formula 37

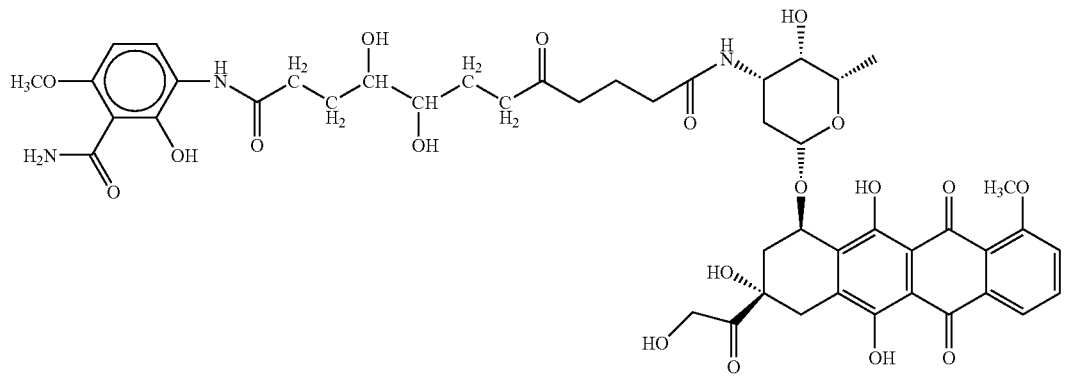

Portion derived from the antimicrobial agent, vancomycin, as represented by the following formula:

Formula 38

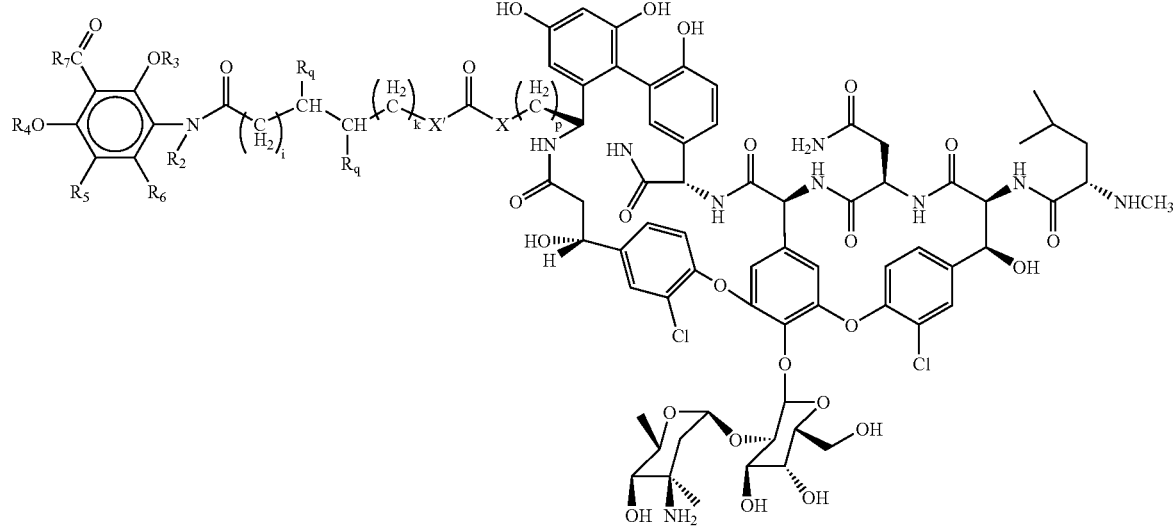

The Bone Active Portion derived from vancomycin is vancomycin less a hydroxyl, allowing the Bone Active Portion to be connected to the remainder of the compound, while maintaining one or more activities generally associated with free vancomycin.

It is noted that when some agents are joined to the compound as a Bone Active Portion, they donate an oxygen atom to an amide or ester bond of the carbonyl group between X' and X of the linking portion. Vancomycin is such an agent. When Bone Active Portions are derived from such agents, as will be understood by those of ordinary skill in the art, X' can be O, NH, or S; X is a covalent bond; and p is 0.

In this regard, an exemplary compound can be represented by the following formula:

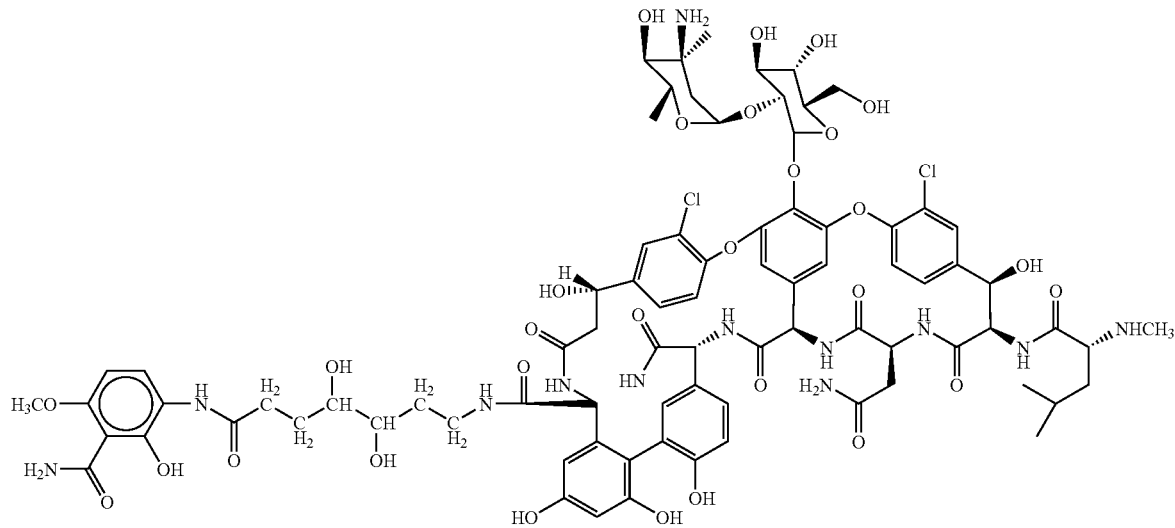

Formula 39 where the Linking Portion is connected to the Bone Targeting Portion ($R_T$) at $R_1$; where $R_2$, $R_3$, $R_5$, and $R_6$ are each H, $R_4$ is $CH_3$, and $R_7$ is $NH_2$; where $R_q$ are each OH, i is 2, k is 2, p is 0, X' is NH, and X is a covalent bond; and where $R_A$ is derived from vancomycin.

Another exemplary compound of the presently-disclosed subject matter can be represented by the following formula:

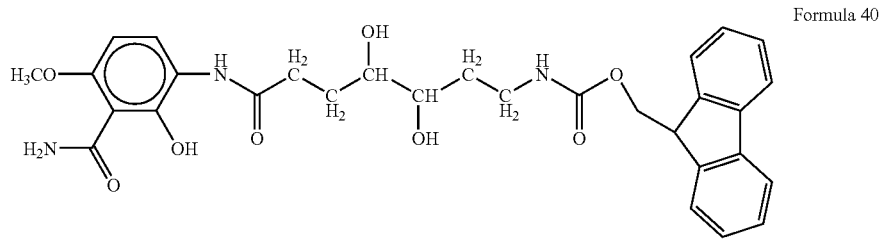

Formula 40 where $R_A$ is a protecting group, which selected protecting group is fluorenylmethoxycarbonyl (FMOC); where the Linking Portion is connected to the Bone Targeting Portion ($R_T$) at $R_1$; where $R_2$, $R_3$, $R_5$, and $R_6$ are each H, $R_4$ is $CH_3$, and $R_7$ is $NH_2$; and where $R_q$ are each OH, i is 2, k is 2, p is 0, X' is NH, and X is a covalent bond.

Another exemplary compound of the presently-disclosed subject matter can be represented by the following formula:

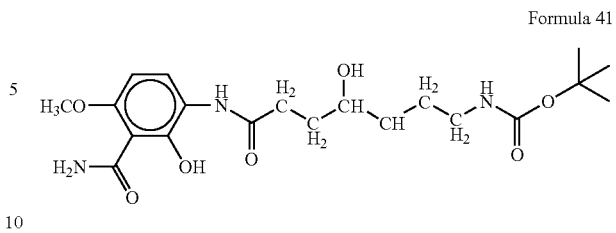

Formula 41 where $R_A$ is a protecting group, which selected protecting group is t-butoxycarbonyl (t-BOC); where the Linking Portion is connected to the Bone Targeting Portion ($R_T$) at $R_1$;

where $R_2$, $R_3$, $R_5$, and $R_6$ are each H, $R_4$ is $CH_3$, and $R_7$ is $NH_2$; and where $R_q$ are each OH, i is 2, k is 2, p is 0, X' is NH, and X is a covalent bond.

As noted above, when some agents are joined to the compound as an $R_A$ group, they donate an oxygen atom to an amide or ester bond of the carbonyl group between X' and X of the linking portion. The protecting groups FMOC and t-BOC are such agents. When $R_A$ is derived from such an agent, as will be understood by those of ordinary skill in the art, X' can be O, NH, or S; X is a covalent bond; and p is 0. As such, it is noted that, in Formulas 40 and 41, X' is NH, X is a covalent bond, and p is 0.

Another exemplary compound of the presently-disclosed subject matter can be represented by the following formula:

Formula 42

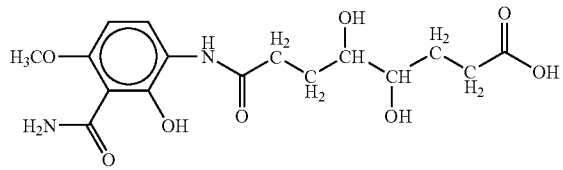

where $R_4$ is OH; where the Linking Portion is connected to the Bone Targeting Portion ($R_T$) at $R_1$; where $R_2$, $R_3$, $R_5$, and $R_6$ are each H, $R_4$ is $CH_3$, and $R_7$ is $NH_2$; and where $R_q$ are each OH, i is 2, k is 2, p is 0, and X' and X are each a covalent bond.

In some exemplary embodiments, the Linking Portion can be connected to the Bone Targeting Portion ($R_T$) at $R_4$, as shown in the following formula:

Formula 43

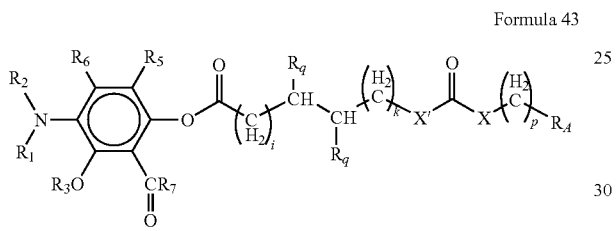

As mentioned above, a third unit $R_A$ of the compound can be selected from: a Bone Targeting Portion (See e.g., Tables A-D); a protecting group; or a hydrogen. When $R_A$ is a Bone Active Portion, it is contemplated that the Linker Portion can be bound to the Bone Active Portion to minimize the susceptibility to hydrolysis, e.g., ether linkage, to increase the bioavailability of the compound. That is to say, if susceptibility to hydrolysis is minimized, without wishing to be bound by theory or mechanism, the compound can be delivered to and affect bone, before the Bone Active Portion can be cleaved from the compound.

In an exemplary embodiment, $R_A$ can be a Bone Active Portion derived from estradiol, as represented by the following formula:

The Bone Active Portion derived from estradiol is estradiol less a hydrogen, allowing the Bone Active Portion to be connected to the remainder of the compound, while maintaining one or more activities generally associated with free estradiol. In some embodiments, when the Bone Active Portion of the compound is derived from estradiol, it is derived from the 17-β-enantiomer of estradiol. Without wishing to be bound by theory or mechanism, it is believed that the 17-β-enantiomer of estradiol is the active isomer.

Another exemplary compound can be represented by the following formula:

Formula 44

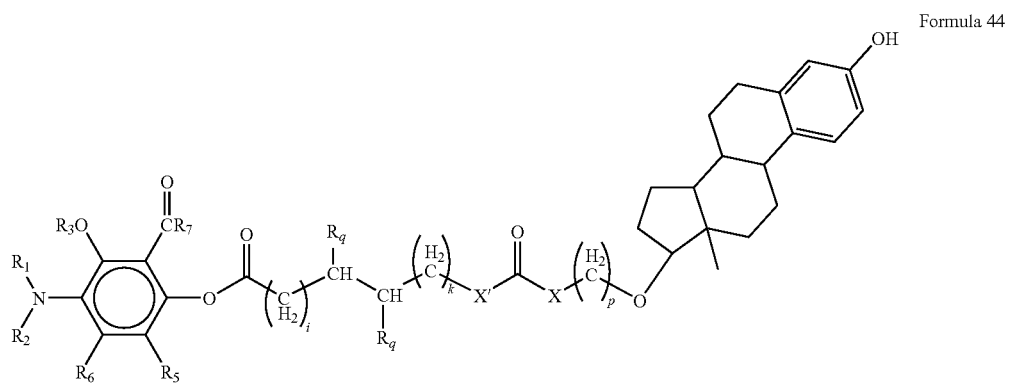

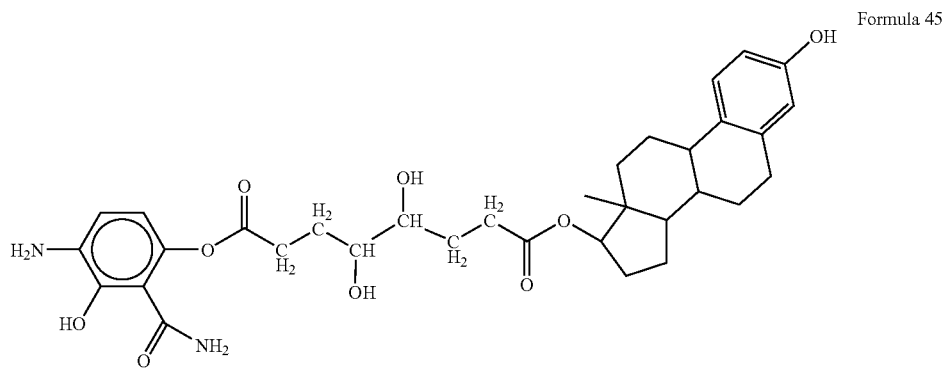

Formula 45 where the Linking Portion is connected to the Bone Targeting Portion ($R_T$) at $R_4$; where $R_1$, $R_2$, $R_3$, $R_5$, and $R_6$ are each H, and $R_7$ is $NH_2$; where $R_q$ are each OH, i is 2, k is 2, p is 0, and X' and X are each a covalent bond; and where $R_A$ is derived from estradiol Another exemplary compound can be represented by the following formula:

where the Linking Portion is connected to the Bone Targeting Portion ($R_T$) at $R_4$; where $R_1$, $R_2$, $R_3$, $R_5$, and $R_6$ are each H, and $R_7$ is $NH_2$; where $R_q$ are each OH, i is 2, k is 2, p is 2, X' is a covalent bond, and X is NH; and where $R_A$ is derived from Estradiol.

In some embodiments, $R_4$ can be a Bone Active Portion derived from a non-steroidal estrogenic agent. In some

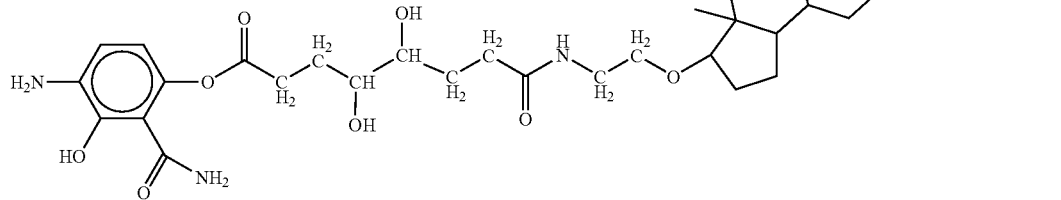

Formula 46 embodiments, $R_A$ can be a Bone Active Portion derived from the non-steroidal estrogenic agent, genistein, as represented by the following formula:

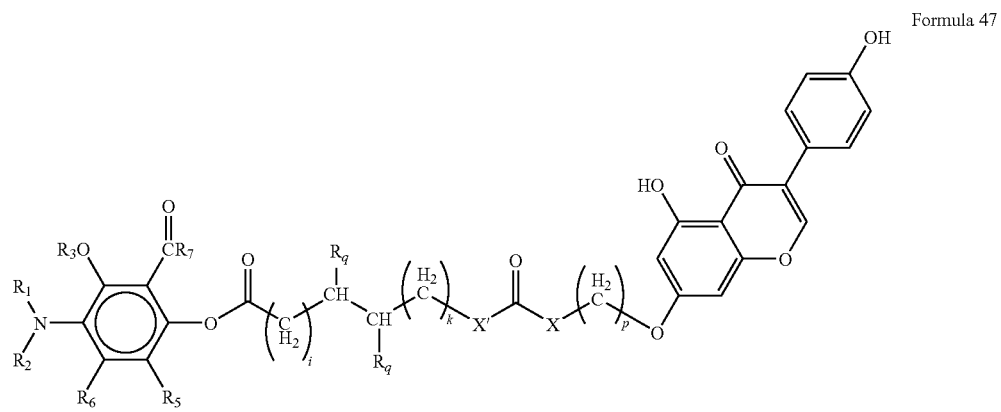

Formula 47

The Bone Active Portion derived from genistein is genistein less a hydrogen, allowing the Bone Active Portion to be connected to the remainder of the compound, while maintaining one or more activities generally associated with free genistein.

Another exemplary compound can be represented by the following formula:

Formula 48

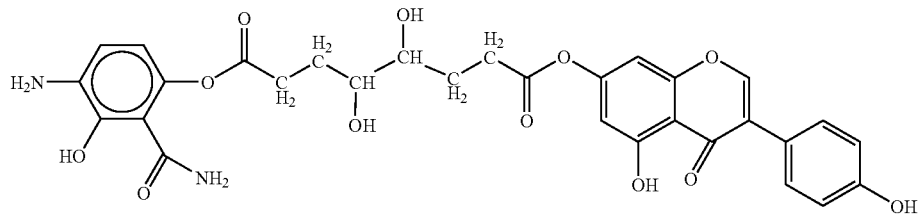

where the Linking Portion is connected to the Bone Targeting Portion ($R_T$) at $R_4$; where $R_1$, $R_2$, $R_3$, $R_5$, and $R_6$ are each H, and $R_7$ is $NH_2$; where $R_q$ are each OH, i is 2, k is 2, p is 0, and X' and X are each a covalent bond; and where $R_4$ is derived from genistein.

In some embodiments, $R_4$ can be a Bone Active Portion derived from a nitric oxide agent. In some embodiments, $R_4$ can be a Bone Active Portion derived from the nitric oxide agent, alkoxy-$NO_2$, as represented by the following formula:

Formula 49

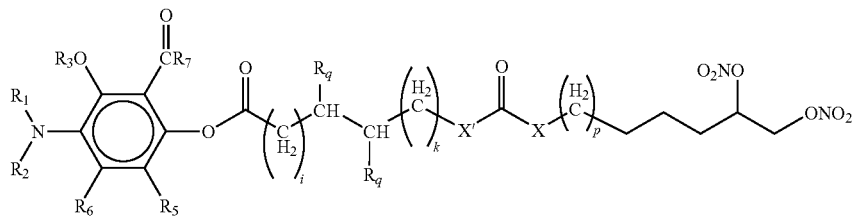

The Bone Active Portion derived from alkoxy-$NO_2$ is alkoxy-$NO_2$ less a hydrogen, allowing the Bone Active Portion to be connected to the remainder of the compound, while maintaining one or more activities generally associated with free alkoxy-$NO_2$.

Another exemplary compound can be represented by the following formula:

In some embodiments, $R_A$ can be a Bone Active Portion derived from an androgen. In some embodiments, $R_A$ can be a Bone Active Portion derived from the androgen, DHEA, as represented by the following formula:

Formula 50

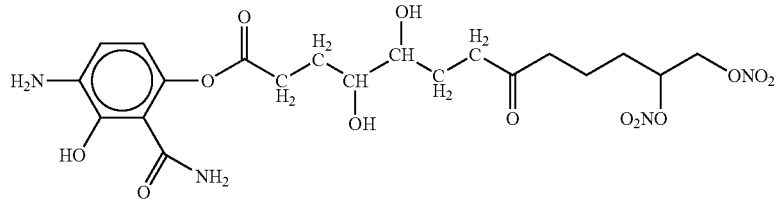

where the Linking Portion is connected to the Bone Targeting Portion ($R_T$) at $R_4$; where $R_1$, $R_2$, $R_3$, $R_5$, and $R_6$ are each H, and $R_7$ is $NH_2$; where $R_q$ are each OH, i is 2, k is 2, p is 0, and X' and X are each a covalent bond; and where $R_4$ is derived from alkoxy-$NO_2$.

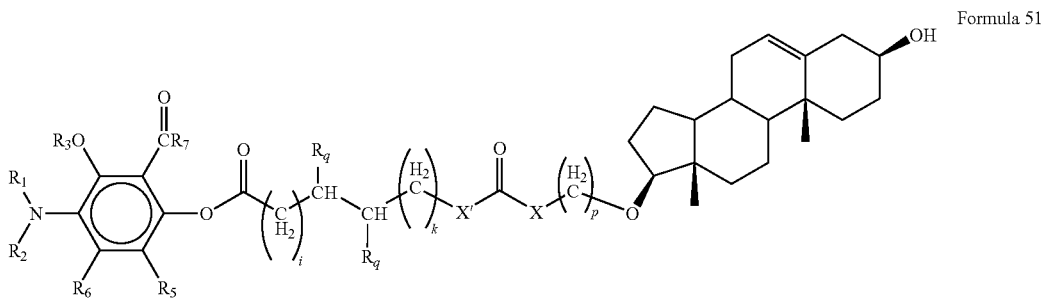

Formula 51

The Bone Active Portion derived from DHEA is DHEA singly bonded to oxygen at carbon 17, allowing the Bone Active Portion to be connected to the remainder of the compound, while maintaining one or more activities generally associated with free DHEA.

Another exemplary compound can be represented by the following formula:

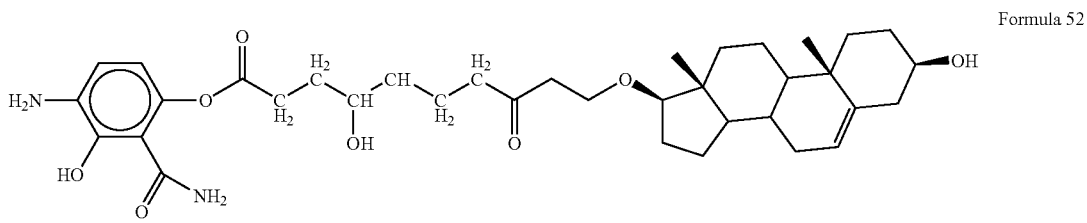

Formula 52 where the Linking Portion is connected to the Bone Targeting Portion ($R_T$) at $R_4$; where $R_1$, $R_2$, $R_3$, $R_5$, and $R_6$ are each H, and $R_7$ is $NH_2$; where $R_q$ are each OH, i is 2, k is 2, p is 2, and X' and X are each a covalent bond; and where $R_4$ is derived from DHEA.

In some embodiments, $R_4$ can be a Bone Active Portion derived from the androgen, testosterone, as represented by the following formula:

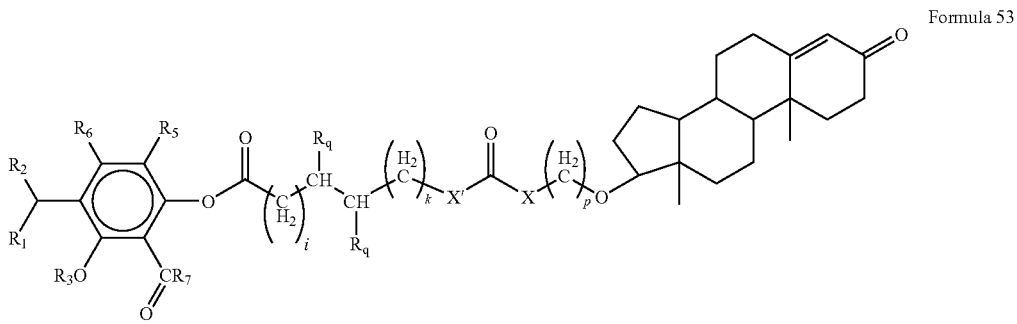

Formula 53

The Bone Active Portion derived from testosterone is testosterone less a hydrogen, allowing the Bone Active Portion to be connected to the remainder of the compound, while maintaining one or more activities generally associated with free testosterone.

Another exemplary compound can be represented by the following formula:

Formula 54

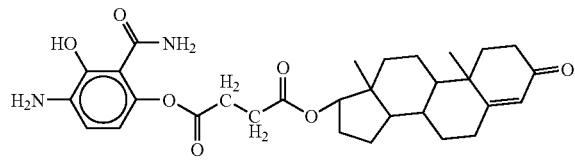

where the Linking Portion is connected to the Bone Targeting Portion ($R_T$) at $R_4$; where $R_1$, $R_2$, $R_3$, $R_5$, and $R_6$ are each H, and $R_7$ is $NH_2$; where $R_q$ are each H, i is 0, k is 0, p is 0, and X' and X are each a covalent bond; and where $R_A$ is derived from testosterone.

In some embodiments, $R_A$ can be a Bone Active Portion derived from a carbonic anhydrase inhibitor. In some embodiments, $R_A$ can be a Bone Active Portion derived from the carbonic anhydrase inhibitor, 2-aminothiadiazole-5-sulfonamide, as represented by the following formula:

Formula 56 where the Linking Portion is connected to the Bone Targeting Portion ($R_T$) at $R_4$; where $R_1$, $R_2$, $R_3$, $R_5$, and $R_6$ are each H, and $R_7$ is $NH_2$; where $R_q$ are each H, i is 0, k is 0, p is 0, and X' and X are each a covalent bond; and where $R_A$ is derived from 2-aminothiadiazole-5-sulfonamide.

In some embodiments, $R_A$ can be a Bone Active Portion derived from an anti-cancer agent or an antineoplastic agent. In some embodiments, $R_A$ can be a Bone Active Portion derived from doxorubicin, as represented by the following formula:

Formula 55

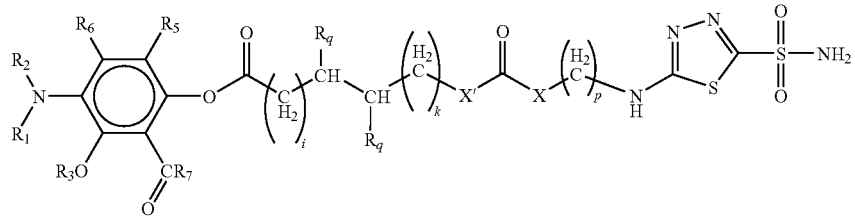

The Bone Active Portion derived from 2-amino-1,3,4-thiadiazole-5-sulfonamide less a hydrogen, allowing the Bone Active Portion to be connected to the remainder of the compound, while maintaining one or more activities generally associated with free sulfonamide.

Another exemplary compound can be represented by the following formula:

Formula 57

The Bone Active Portion derived from doxorubicin is doxorubicin less a hydrogen, allowing the Bone Active Portion to be connected to the remainder of the compound, while maintaining one or more activities generally associated with free doxorubicin.

Another exemplary compound can be represented by the following formula:

The Bone Active Portion derived from vancomycin is vancomycin less a hydroxyl, allowing the Bone Active Portion to be connected to the remainder of the compound, while maintaining one or more activities generally associated with free vancomycin.

As noted herein, when some agents are joined to the compound as a Bone Active Portion, they donate an oxygen atom

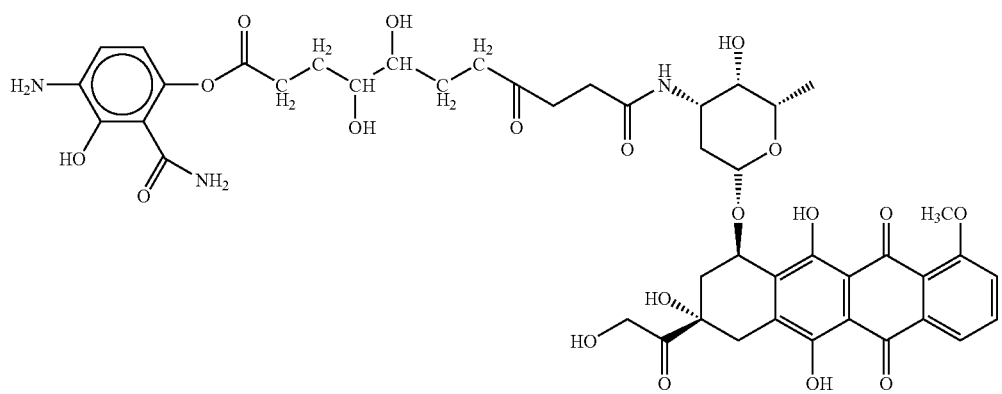

Formula 58 where the Linking Portion is connected to the Bone Targeting Portion ($R_T$) at $R_4$; where $R_1$, $R_2$, $R_3$, $R_5$, and $R_6$ are each H, and $R_7$ is $NH_2$; where $R_q$ are each OH, i is 2, k is 2, p is 0, and X' and X are each a covalent bond; and where $R_4$ is derived from doxorubicin.

In some embodiments, $R_4$ can be a Bone Active Portion derived from an antimicrobial agent. In some embodiments, $R_4$ can be a Bone Active Portion derived from the antimicrobial agent, vancomycin, as represented by the following formula:

to an amide or ester bond of the carbonyl group between X' and X of the linking portion. Vancomycin is such an agent. When Bone Active Portions are derived from such agents, as will be understood by those of ordinary skill in the art, X' can be O, NH, or S; X is a covalent bond; and p is 0.

In this regard, an exemplary compound can be represented by the following formula:

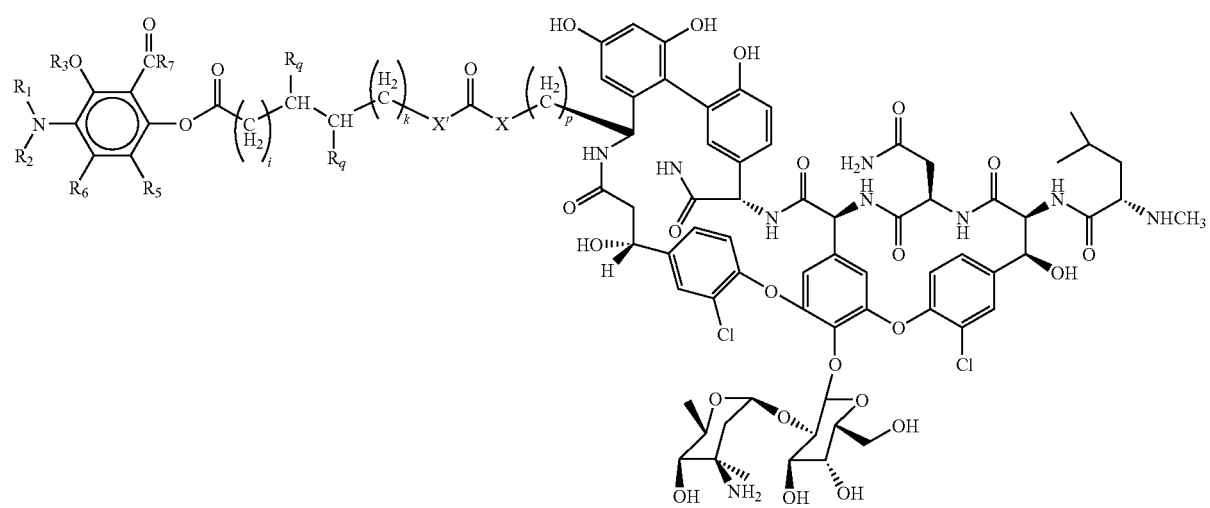

Formula 59

Formula 60

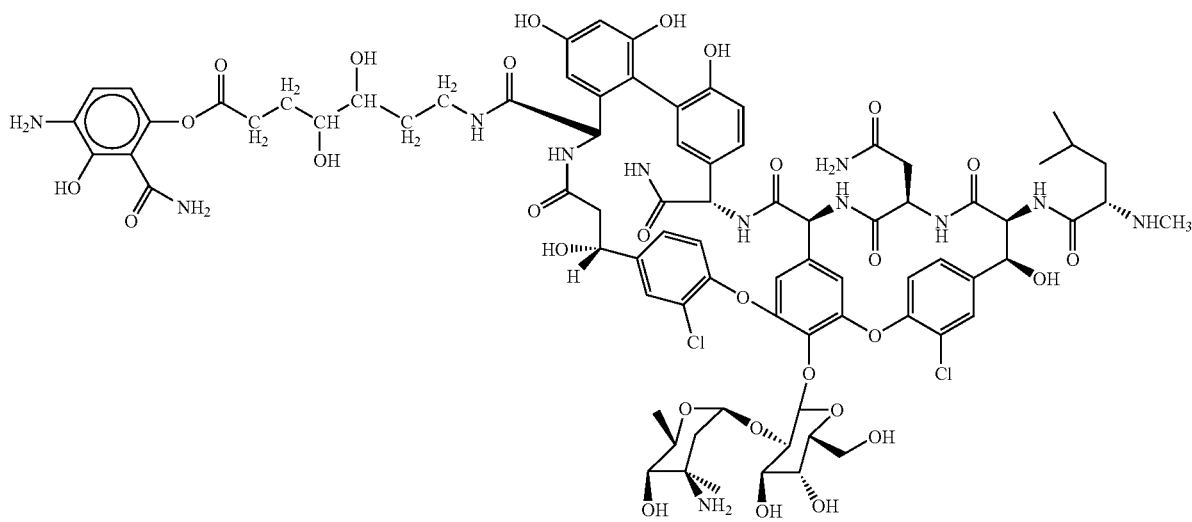

where the Linking Portion is connected to the Bone Targeting Portion ($R_T$) at $R_4$; where $R_1$, $R_2$, $R_3$, $R_5$, and $R_6$ are each H, and $R_7$ is $NH_2$; where $R_q$ are each OH, i is 2, k is 2, p is 0, X' is NH, and X is a covalent bond; and where $R_A$ is derived from vancomycin.

In some embodiments, $R_A$ is a protecting group. In some embodiments, the compound can be represented by the following formula:

Formula 61

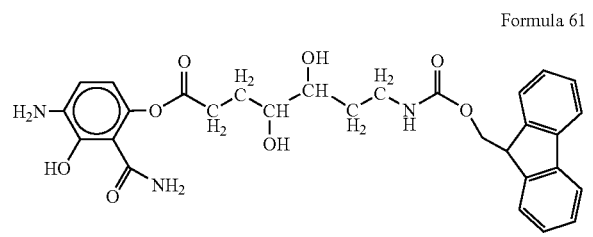

where $R_A$ is a protecting group, which selected protecting group is fluorenylmethoxycarbonyl (FMOC); where the Linking Portion is connected to the Bone Targeting Portion ($R_T$) at $R_4$; where $R_1$, $R_2$, $R_3$, $R_5$, and $R_6$ are each H, and $R_7$ is $NH_2$; where $R_q$ are each OH, i is 2, k is 2, p is 0, X' is NH, and X is a covalent bond.

In some embodiments, the compound can be represented by the following formula:

Formula 62

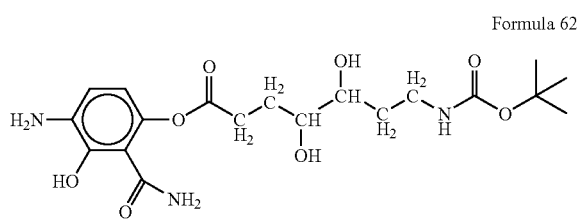

where $R_A$ is a protecting group, which selected protecting group is t-butoxycarbonyl (t-BOC); where the Linking Portion is connected to the Bone Targeting Portion ($R_T$) at $R_4$; where $R_1$, $R_2$, $R_3$, $R_5$, and $R_6$ are each H, and $R_7$ is $NH_2$; where $R_q$ are each OH, i is 2, k is 2, p is 0, X' is NH, and X is a covalent bond.

As noted above, when some agents are joined to the compound as an $R_A$ group, they donate an oxygen atom to an amide or ester bond of the carbonyl group between X' and X of the linking portion. The protecting groups FMOC and t-BOC are such agents. When $R_A$ is derived from such an agent, as will be understood by those of ordinary skill in the art, X' can be O, NH, or S; X is a covalent bond; and p is 0. As such, it is noted that, in Formulas 61 and 62, X' is NH, X is a covalent bond, and p is 0.

In some embodiments, $R_A$ can be a hydroxyl. In some embodiments, the compound can be represented by the following formula:

Formula 63

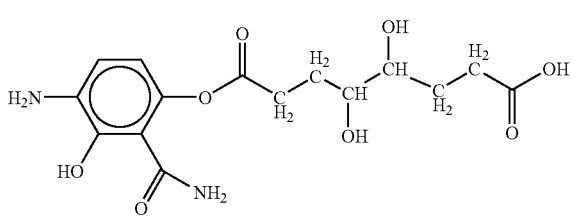

where $R_A$ is OH; where the Linking Portion is connected to the Bone Targeting Portion ($R_T$) at $R_4$; where $R_1$, $R_2$, $R_3$, $R_5$, and $R_6$ are each H, and $R_7$ is $NH_2$; where $R_q$ are each OH, i is 2, k is 2, p is 0, and X is a covalent bond.

Embodiments of the linking portion of Formula 12 and Formula 13 will now be described. The length of the linking portion can vary, depending on the embodiment of the presently-disclosed subject matter. With regard to the embodiments of the linking portion of Formula 12 and Formula 13, m can be 1 to about 3, and n can be 1 to about 4. For example, when m=1 and n=2, the compounds can be represented by the following formulas:

For another example, when m=1 and n=3, the compounds can be represented by the following formulas:

When m>1, multiple n-groups are provided. When multiple n-groups are provided, each n is independently 1 to about 4. For example, when m=3, three n-groups are provided, n', n", and n'", which are each independently 1 to about 4. With regard to the linking portion of Formula 12, when m=2, two n-groups are provided, n' and n", as shown in the following formula:

In the compound of Formula 68, n' and n" can each independently be 1 to about 4. For example, when m=2, n'=1, and n"=2, a compound according to the following formula is provided:

With regard to the linking portion of Formula 13, X can be O, NH, S, or covalent bond. When m>1, there will be more than one X; however, in such cases, only the X of the m-group adjacent $R_A$ can be something other than a covalent bond. In the following formula where m=2, two n-groups are provided, n' and n", and two X are provided, X' and X":

Each n-group, n' and n", of Formula 70 is independently 1 to about 4. However, only the X of the m-group adjacent $R_A$ can be something other than a covalent bond. As such, X' must be a covalent bond, but X", which is the X of the m-group adjacent $R_A$, can be O, NH, S, or covalent bond. For example, in the compound of the following formula, m=2, n'=1, and n"=2, X' is a covalent bond, and X" is NH:

The groups of the linking portion identified as $R_S$ can be hydrogen, hydroxy, or lower alkyl. For example, every $R_S$ group could be hydrogen, as shown in the following formulas, where m is 1, and n is 2:

The identity of each $R_S$ group is independent. For example, certain of the $R_S$ groups could be hydrogen, while others could be hydroxy, as shown in the following formula, where m is 1 and n is 2; and where X is a covalent bond for Formula 75:

Formula 74

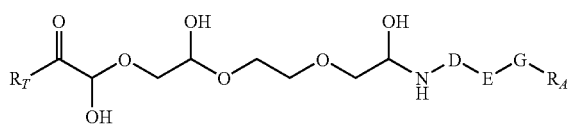

Formula 75

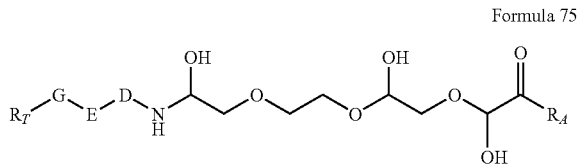

Other exemplary compounds of the presently-disclosed subject matter can be represented by the following formulas:

Formula 76

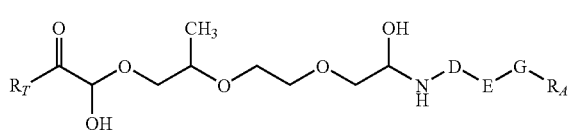

Formula 77

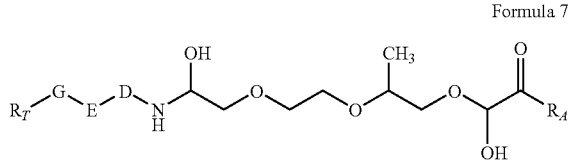

where certain of the $R_S$ groups are hydrogen, other $R_S$ groups are hydroxy, another of the $R_S$ groups is methyl, m is 1, and n is 2; and where X is a covalent bond for Formula 77.

The groups of the linking portion identified as D, E, and G are as follows.

D and G are independently selected from: covalent bond;

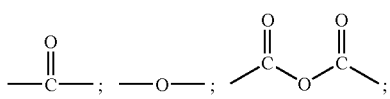

other functional groups capable of reacting with an amine, less a leaving group. That is to say, for example, an acyl halide (Y—C=O) is a functional group capable of reacting with an amine, and a carbonyl

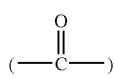

is an acyl halide, less a halogen atom (Y).

E is selected from: covalent bond; —(CT$_2$)$_r$-, where T is H, OH, or lower alkyl, and r=1 to about 8; and —(C)$_r$—, where r=2 to about 8, and where the carbons are unsaturated or partially saturated with H.

Exemplary compounds of the presently-disclosed subject matter can be represented by the following formulas:

Formula 78

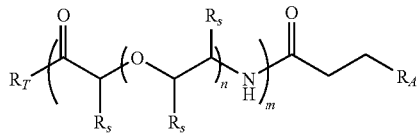

Formula 79

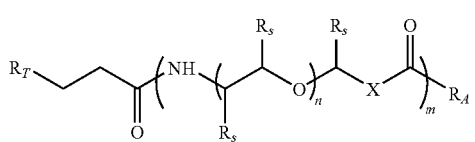

where D is

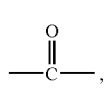

E is —(CH$_2$)$_2$—, and G is a covalent bond.

D, E, and G can be selected, for example, based on the portion of the compound to which the linking group will be bound. For example, when the Linking Portion of Formula 13 is used, the -D-E-G- segment of the Linking Portion is adjacent the Bone Targeting Portion of the compound. The Linking Portion can be connected to the Bone Targeting Portion ($R_T$) at $R_1$, as shown in the following formula:

Formula 80

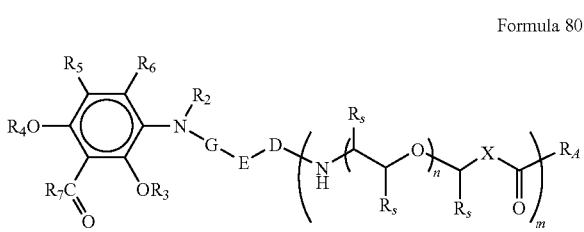

When the Linking Portion of Formula 13 is connected to the Bone Targeting Portion ($R_T$) at $R_1$, as will be understood by those skilled in the art, it can be beneficial for G to be selected to be a functional group capable of reacting with an amine, less a leaving group, for example,

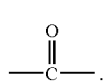

In this regard, an exemplary compound of the presently-disclosed subject matter can be represented by the following formula:

Formula 81

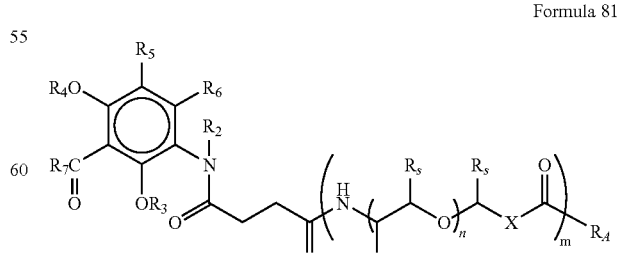

where the Linking Portion of Formula 13 is connected to the Bone Targeting Portion ($R_T$) at $R_1$;

where D and G are each

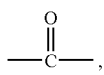

and where E is —(CH$_2$)$_2$—.

As mentioned above, a third unit R$_A$ of the compound can be selected from: a Bone Targeting Portion (See e.g., Tables A-D); a protecting group; or a hydroxyl, when Linking Portion of Formula 13 is selected.

In some embodiments, R$_A$ can be a Bone Active Portion derived from a steroidal estrogenic agent. In some embodiments, R$_A$ can be a Bone Active Portion derived from the estradiol, as represented by the following formula, where D and G are each

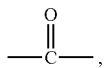

E is —(CH$_2$)$_2$—, and X is a covalent bond:

where the Linking Portion is connected to the Bone Targeting Portion (R$_T$) at R$_1$; D and G are each

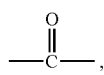

E is —(CH$_2$)$_2$—; m is 1; n is 2; X is a covalent bond; each R$_S$ is hydrogen; R$_2$, R$_3$, R$_5$, R$_6$ are each H; R$_4$ is methyl; R$_7$ is amino; and where R$_A$ is derived from estradiol.

In some embodiments, R$_A$ can be a Bone Active Portion derived from a non-steroidal estrogenic agent. In some embodiments, R$_A$ can be a Bone Active Portion derived from the non-steroidal estrogenic agent, genistein, as represented by the following formula, where D and G are each

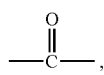

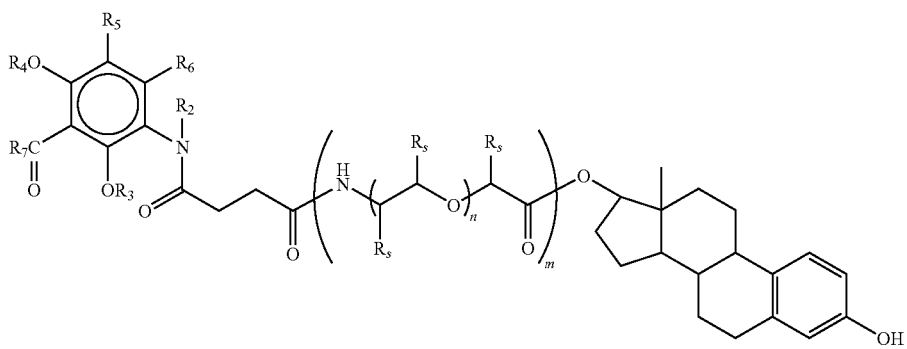

Formula 82

The Bone Active Portion derived from estradiol is estradiol less a hydrogen, allowing the Bone Active Portion to be connected to the remainder of the compound, while maintaining one or more activities generally associated with free estradiol. In some embodiments, when the Bone Active Portion of the compound is derived from estradiol, it is derived from the 17-β-enantiomer of estradiol. Without wishing to be bound by theory or mechanism, it is believed that the 17-β-enantiomer of estradiol is the active isomer.

Another exemplary compound of the presently-disclosed subject matter can be represented by the following formula:

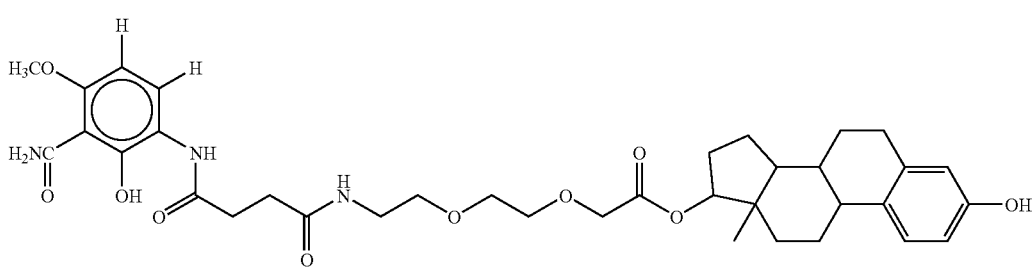

Formula 83

E is —(CH$_2$)$_2$—, and X is a covalent bond:

Formula 84

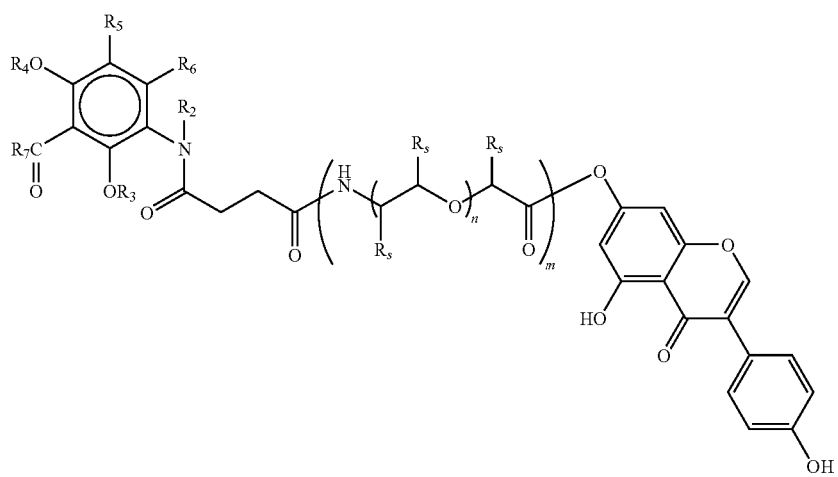

The Bone Active Portion derived from genistein is genistein less a hydrogen, allowing the Bone Active Portion to be connected to the remainder of the compound, while maintaining one or more activities generally associated with free genistein.

Another exemplary compound of the presently-disclosed subject matter can be represented by the following formula:

E is —(CH$_2$)$_2$—; m is 1; n is 2; X is a covalent bond; each $R_S$ is hydrogen; $R_2$, $R_3$, $R_5$, $R_6$ are each H; $R_4$ is methyl; $R_7$ is amino; and where $R_A$ is derived from genistein.

In some embodiments, $R_A$ can be a Bone Active Portion derived from a nitric oxide agent. In some embodiments, $R_A$ can be a Bone Active Portion derived from the nitric oxide Formula 85

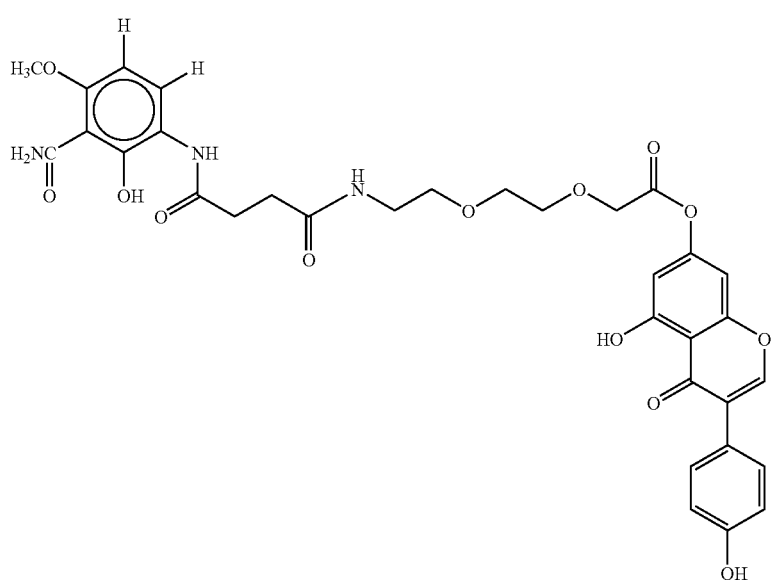

where the Linking Portion is connected to the Bone Targeting Portion ($R_T$) at $R_1$; D and G are each agent, alkoxy-NO$_2$, as represented by the following formula, where D and G are each

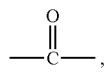,

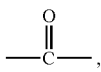,

E is —$(CH_2)_2$—, and X is a covalent bond:

Formula 86

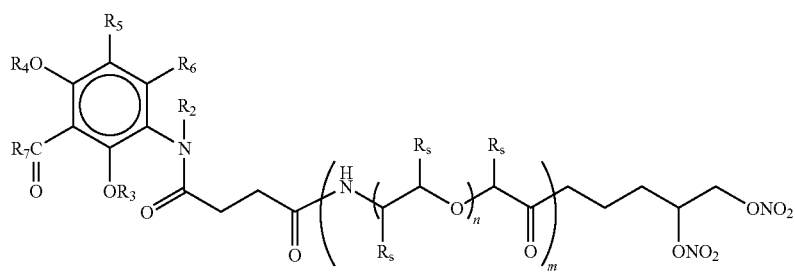

The Bone Active Portion derived from alkoxy-$NO_2$ is alkoxy-$NO_2$ less a hydrogen, allowing the Bone Active Portion to be connected to the remainder of the compound, while maintaining one or more activities generally associated with free alkoxy-$NO_2$.

Another exemplary compound of the presently-disclosed subject matter can be represented by the following formula:

E is —$(CH_2)_2$—; m is 1; n is 2; X is a covalent bond; each $R_S$ is hydrogen; $R_2$, $R_3$, $R_5$, $R_6$ are each H; $R_4$ is methyl; $R_7$ is amino; and where $R_A$ is derived from alkoxy-$NO_2$.

In some embodiments, $R_A$ can be a Bone Active Portion derived from an androgen. In some embodiments, $R_A$ can be a Bone Active Portion derived from the androgen, DHEA, as represented by the following formula, where D and G are each Formula 87

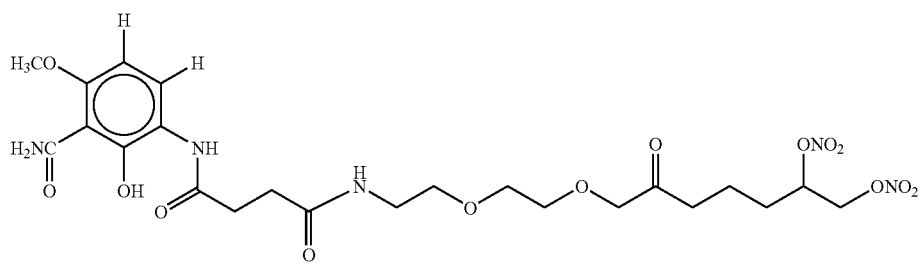

E is —$(CH_2)_2$—, and X is a covalent bond:

Formula 88

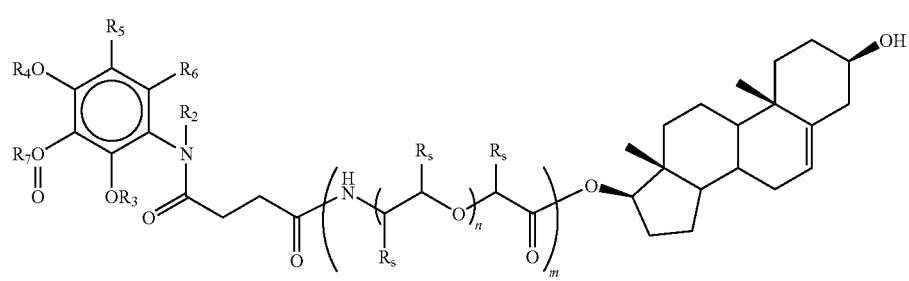

where the Linking Portion is connected to the Bone Targeting Portion ($R_T$) at $R_1$; D and G are each

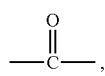

The Bone Active Portion derived from DHEA is DHEA singly bonded to oxygen at carbon 17, allowing the Bone Active Portion to be connected to the remainder of the compound, while maintaining one or more activities generally associated with free DHEA.

Another exemplary compound of the presently-disclosed subject matter can be represented by the following formula:

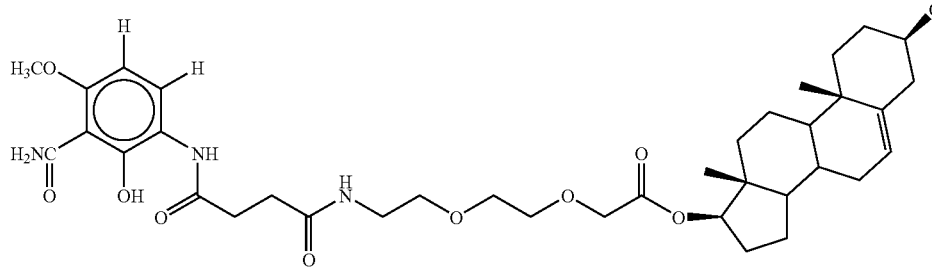

Formula 89 where the Linking Portion is connected to the Bone Targeting Portion ($R_T$) at $R_1$; D and G are each

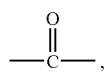

E is —$(CH_2)_2$—; m is 1; n is 2; X is a covalent bond; each $R_S$ is hydrogen; $R_2$, $R_3$, $R_5$, $R_6$ are each H; $R_4$ is methyl; $R_7$ is amino; and where $R_4$ is derived from DHEA.

In some embodiments, $R_4$ can be a Bone Active Portion derived from the androgen, testosterone, as represented by the following formula, where D and G are each

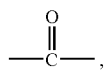

E is —$(CH_2)_2$—, and X is a covalent bond:

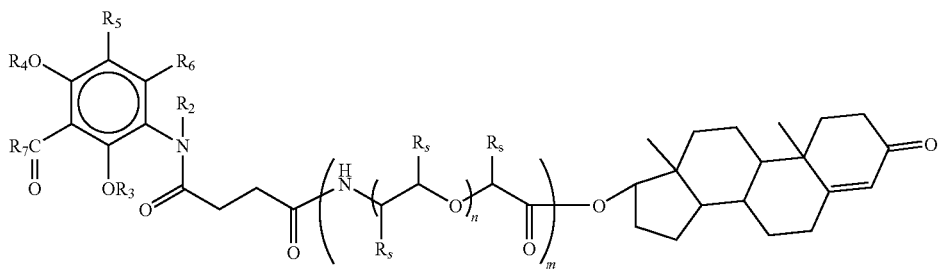

Formula 90

The Bone Active Portion derived from testosterone is testosterone less a hydrogen, allowing the Bone Active Portion to be connected to the remainder of the compound, while maintaining one or more activities generally associated with free testosterone.

Another exemplary compound of the presently-disclosed subject matter can be represented by the following formula:

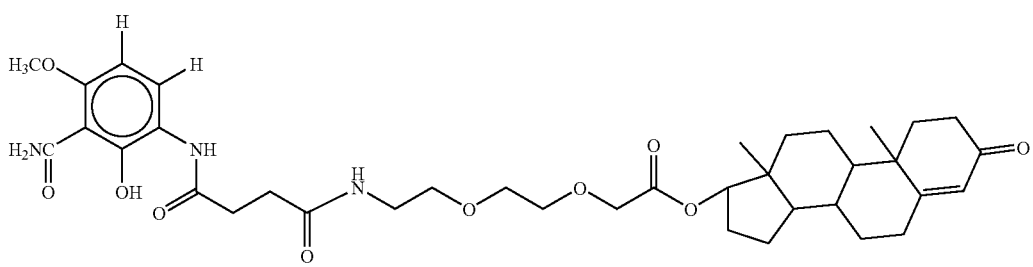

Formula 91 where the Linking Portion is connected to the Bone Targeting Portion ($R_T$) at $R_1$; where: D and G are each

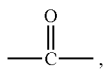

E is —(CH$_2$)$_2$—; m is 1; n is 2; X is a covalent bond; each R$_S$ is hydrogen; R$_2$, R$_3$, R$_5$, R$_6$ are each H; R$_4$ is methyl; R$_7$ is amino; and where R$_A$ is derived from testosterone.

In some embodiments, R$_A$ can be a Bone Active Portion derived from a carbonic anhydrase inhibitor. In some embodiments, R$_A$ can be a Bone Active Portion derived from the carbonic anhydrase inhibitor, 2-aminothiadiazole-5-sulfonamide, as represented by the following formula, where D and G are each

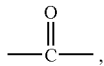

E is —(CH$_2$)$_2$—, and X is a covalent bond:

where the Linking Portion is connected to the Bone Targeting Portion (R$_T$) at R$_1$; where: D and G are each

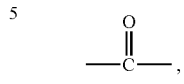

E is —(CH$_2$)$_2$—; m is 1; n is 2; X is a covalent bond; each R$_S$ is hydrogen; R$_2$, R$_3$, R$_5$, R$_6$ are each H; R$_4$ is methyl; R$_7$ is amino; and where R$_A$ is derived from 2-aminothiadiazole-5-sulfonamide.

In some embodiments, R$_A$ can be a Bone Active Portion derived from an anti-cancer agent or an antineoplastic agent. In some embodiments, R$_A$ can be a Bone Active Portion derived from doxorubicin, as represented by the following formula, where D and G are each

Formula 92

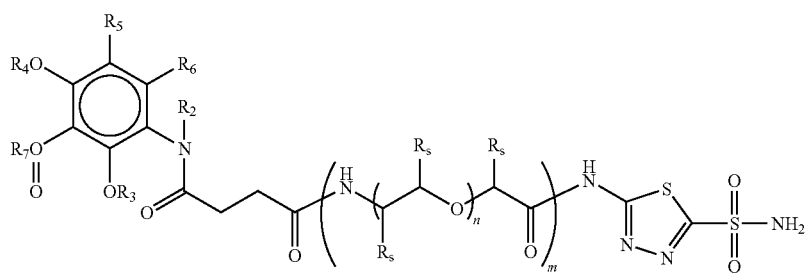

The Bone Active Portion derived from 2-amino-1,3,4-thiadiazole-5-sulfonamide is 2-amino-1,3,4-thiadiazole-5-sulfonamide less a hydrogen, allowing the Bone Active Portion to be connected to the remainder of the compound, while maintaining one or more activities generally associated with free sulfonamide.

Another exemplary compound of the presently-disclosed subject matter can be represented by the following formula:

Formula 93

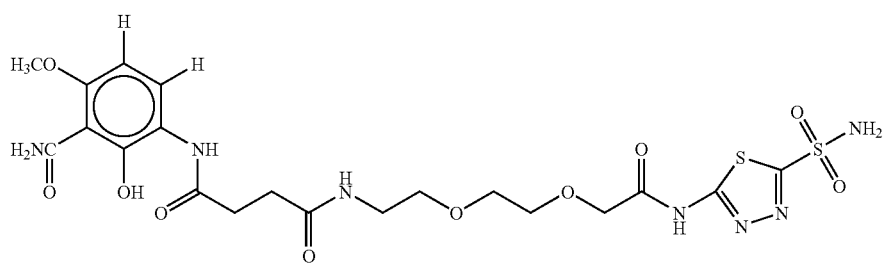

E is —(CH$_2$)$_2$—, and X is a covalent bond:

Formula 94

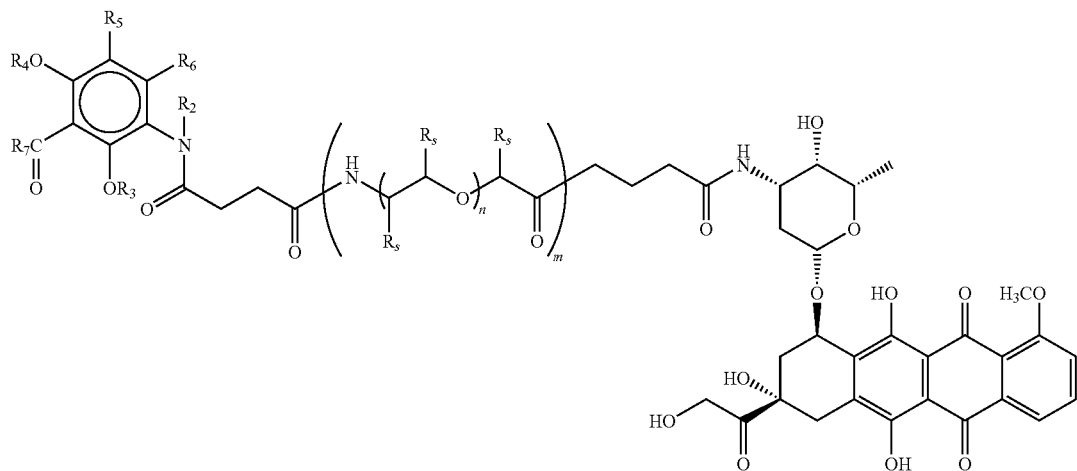

The Bone Active Portion derived from doxorubicin is doxorubicin less a hydrogen, allowing the Bone Active Portion to be connected to the remainder of the compound, while maintaining one or more activities generally associated with free doxorubicin.

Another exemplary compound of the presently-disclosed subject matter can be represented by the following formula:

E is —(CH$_2$)$_2$—; m is 1; n is 2; X is a covalent bond; each $R_S$ is hydrogen; $R_2$, $R_3$, $R_5$, $R_6$ are each H; $R_4$ is methyl; $R_7$ is amino; and where $R_A$ is derived from doxorubicin.

In some embodiments, $R_A$ can be a Bone Active Portion derived from an antimicrobial agent. In some embodiments, $R_A$ can be a Bone Active Portion derived from the antimicrobial agent, vancomycin, as represented by the following formula, where D and G are each Formula 95

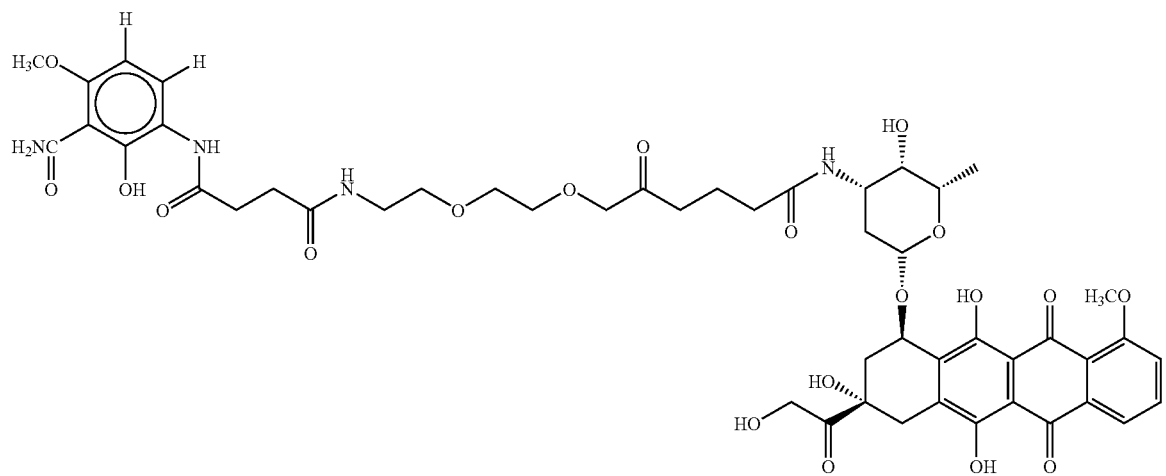

where the Linking Portion is connected to the Bone Targeting Portion ($R_T$) at $R_1$; where: D and G are each

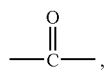, 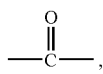, and E is —$(CH_2)_2$—:

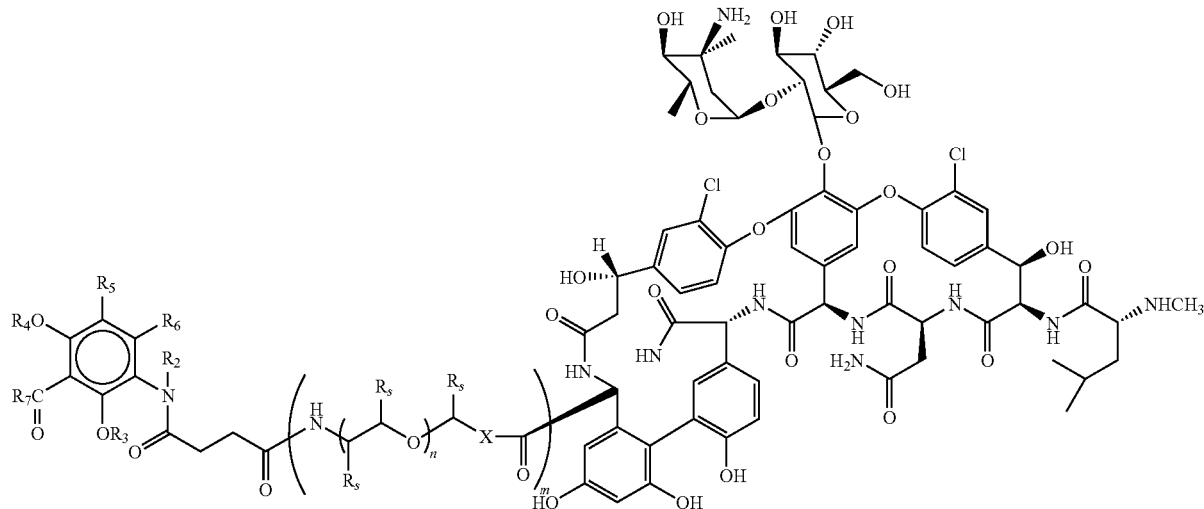

Formula 96

The Bone Active Portion derived from vancomycin is vancomycin less a hydroxyl, allowing the Bone Active Portion to be connected to the remainder of the compound, while maintaining one or more activities generally associated with free vancomycin.

It is noted that, when some agents are joined to the compound as a Bone Active Portion, they donate an oxygen atom to an amide or ester bond of the carbonyl group adjacent X of the linking portion. Vancomycin is such an agent. When Bone Active Portions are derived from such agents, as will be understood by those of ordinary skill in the art, the X of the m-group adjacent $R_A$ is something other than a covalent bond, i.e., O, NH, or S. As noted above with reference to Formula 70, when m>1, there will be more than one X; however only the X of the m-group adjacent $R_A$ can be something other than a covalent bond, any other X must be covalent bond.

As such, in some embodiments, the compound of the presently-disclosed subject matter can be represented by the following formula:

where the Linking Portion is connected to the Bone Targeting Portion ($R_T$) at $R_1$; where: D and G are each

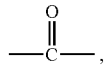

E is —$(CH_2)_2$—; m is 1; n is 2; X is NH; each $R_S$ is hydrogen; $R_2$, $R_3$, $R_5$, $R_6$ are each H; $R_4$ is methyl; $R_7$ is amino; and where $R_A$ is derived from vancomycin.

In some embodiments, $R_A$ is a protecting group. In some embodiments, the compound can be represented by the following formula:

Formula 97

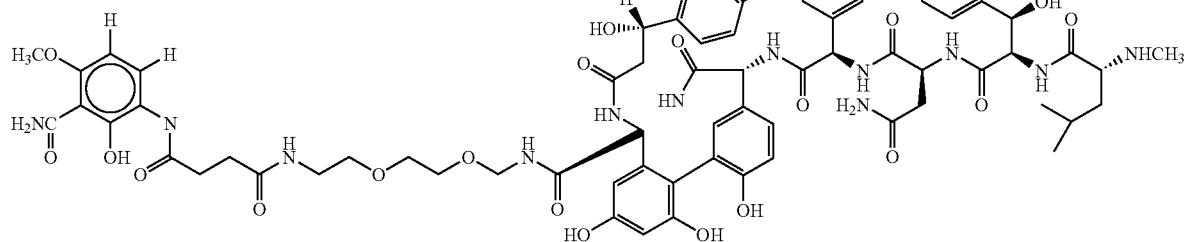

Formula 98

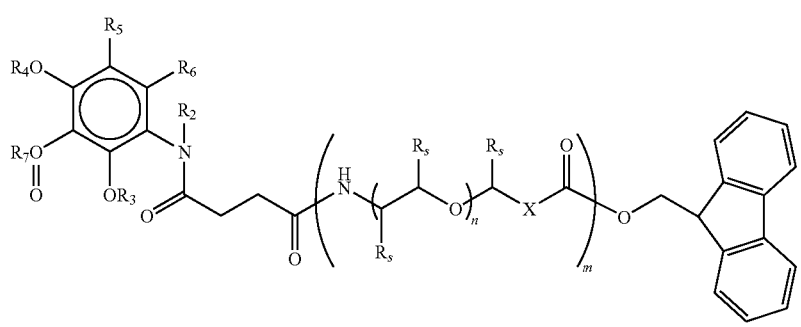

where D and G are each

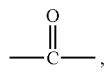

E is —(CH$_2$)$_2$—, and R$_A$ is a protecting group, which selected protecting group is fluorenylmethoxycarbonyl (FMOC). As noted above, when some agents are joined to the compound as an R$_A$ group, they donate an oxygen atom to an amide or ester bond of the carbonyl group adjacent X of the linking portion. The protecting group FMOC is such an agent. When R$_A$ is derived from such an agent, as will be understood by those of ordinary skill in the art, the X of the m-group adjacent R$_A$ is something other than a covalent bond, i.e., O, NH, or S, while any other X must be covalent bond.

In some embodiments, R$_A$ can be a hydroxyl, as represented by the following formula, where D and G are each

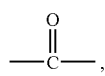

E is —(CH$_2$)$_2$—, and X is a covalent bond:

Formula 99

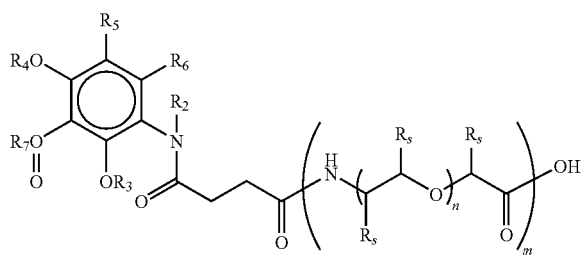

When the Linking Portion of Formula 13 is used, it can also be connected to the Bone Targeting Portion (R$_T$) at R$_4$, as shown in the following formula:

Formula 100

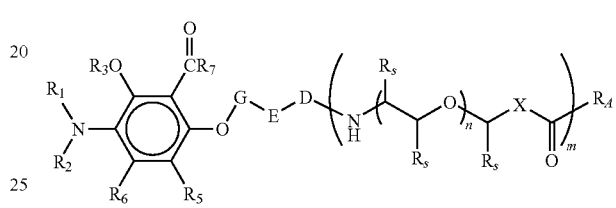

When the Linking Portion of Formula 13 is connected to the Bone Targeting Portion (R$_T$) at R$_4$, as will be understood by those skilled in the art, the following can be beneficial: G is a covalent bond; and D is a functional group capable of reacting with an amine, less a leaving group. An exemplary compound of the presently-disclosed subject matter can be represented by the following formula, where D and E are each a covalent bond, and G is

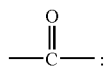

Formula 101

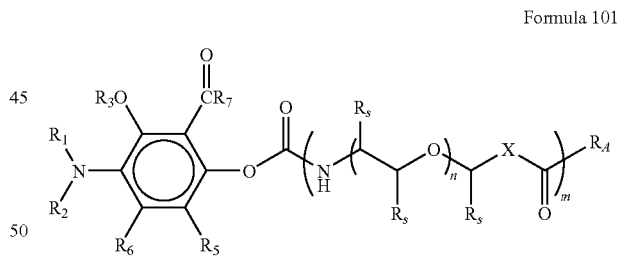

As mentioned above, the third unit R$_A$ of the compound can be selected from: a Bone Targeting Portion (See e.g., Tables A-D); a protecting group; or a hydroxyl, when Linking Portion of Formula 13 is selected.

In some embodiments, R$_A$ can be a Bone Active Portion derived from a steroidal estrogenic agent. In some embodiments, R$_A$ can be a Bone Active Portion derived from the steroidal estrogenic agent, estradiol, as represented by the following formula, where D and E are each a covalent bond, G is

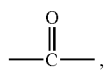

and X is a covalent bond:

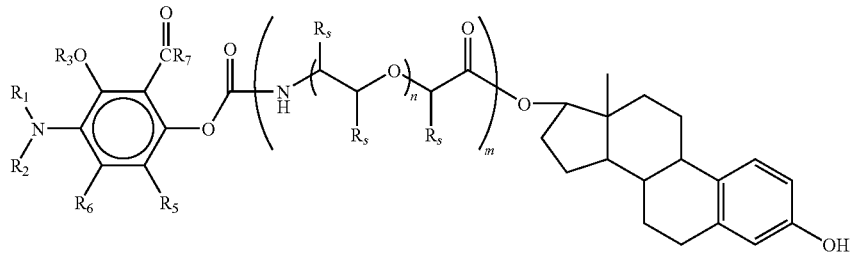

Formula 102

The Bone Active Portion derived from estradiol is estradiol less a hydrogen, allowing the Bone Active Portion to be connected to the remainder of the compound, while maintaining one or more activities generally associated with free estradiol. In some embodiments, when the Bone Active Portion of the compound is derived from estradiol, it is derived from the 17-β-enantiomer of estradiol. Without wishing to be bound by theory or mechanism, it is believed that the 17-β-enantiomer of estradiol is the active isomer.

Another exemplary compound of the presently-disclosed subject matter can be represented by the following formula:

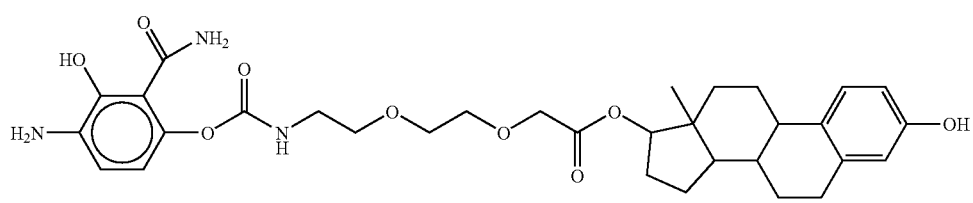

Formula 103 where the Linking Portion is connected to the Bone Targeting Portion ($R_T$) at $R_4$; where: D and E are each a covalent bond; G is

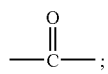

m is 1; n is 2; X is a covalent bond; each $R_S$ is hydrogen; $R_1$, $R_2$, $R_3$, $R_5$, and $R_6$ are each H; $R_7$ is $NO_2$; and where $R_A$ is derived from estradiol.

In some embodiments, $R_A$ can be a Bone Active Portion derived from a non-steroidal estrogenic agent. In some embodiments, $R_A$ can be a Bone Active Portion derived from the non-steroidal estrogenic agent, genistein, as represented by the following formula, where D and E are each a covalent bond, G is

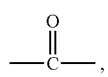

and X is a covalent bond:

Formula 104

The Bone Active Portion derived from genistein is genistein less a hydrogen, allowing the Bone Active Portion to be connected to the remainder of the compound, while maintaining one or more activities generally associated with free genistein.

Another exemplary compound of the presently-disclosed subject matter can be represented by the following formula:

Formula 105

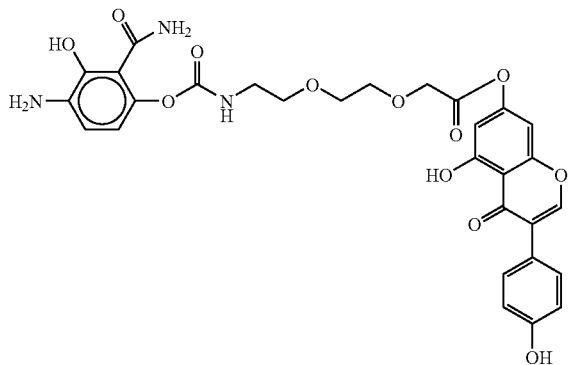

where the Linking Portion is connected to the Bone Targeting Portion ($R_T$) at $R_4$; where: D and E are each a covalent bond; G is

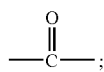

m is 1; n is 2; X is a covalent bond; each $R_S$ is hydrogen; $R_1$, $R_2$, $R_3$, $R_5$, and $R_6$ are each H; $R_7$ is $NO_2$; and where $R_A$ is derived from genistein.

In some embodiments, $R_A$ can be a Bone Active Portion derived from a nitric oxide agent. In some embodiments, $R_A$ can be a Bone Active Portion derived from the nitric oxide agent, alkoxy-$NO_2$, as represented by the following formula, where D and E are each a covalent bond, G is

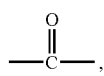

and X is a covalent bond:

Formula 106

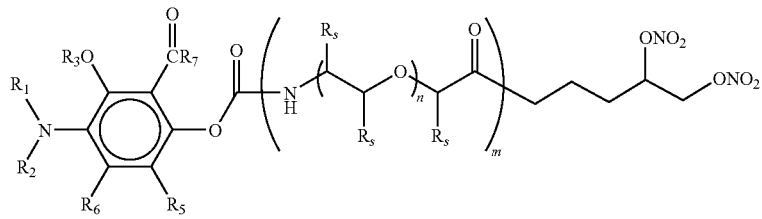

The Bone Active Portion derived from alkoxy-$NO_2$ is alkoxy-$NO_2$ less a hydrogen, allowing the Bone Active Portion to be connected to the remainder of the compound, while maintaining one or more activities generally associated with free alkoxy-$NO_2$.

Another exemplary compound of the presently-disclosed subject matter can be represented by the following formula:

Formula 107

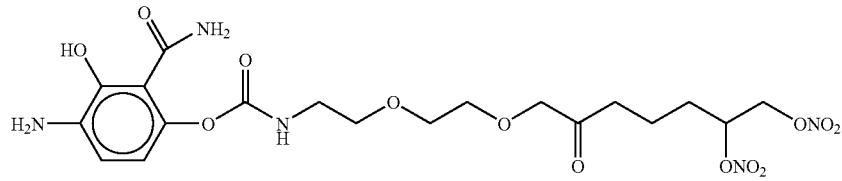

where the Linking Portion is connected to the Bone Targeting Portion ($R_T$) at $R_4$; where: D and E are each a covalent bond; G is

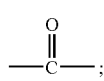

m is 1; n is 2; X is a covalent bond; each $R_S$ is hydrogen; $R_1$, $R_2$, $R_3$, $R_5$, and $R_6$ are each H; $R_7$ is $NO_2$; and where $R_A$ is derived from alkoxy-$NO_2$.

In some embodiments, $R_A$ can be a Bone Active Portion derived from an androgen agent. In some embodiments, $R_A$ can be a Bone Active Portion derived from the androgen, DHEA, as represented by the following formula, where D and E are each a covalent bond, G is

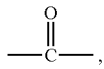

and X is a covalent bond:

Formula 108

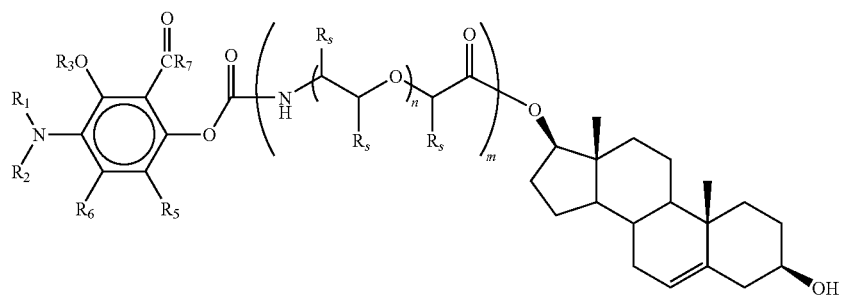

The Bone Active Portion derived from DHEA is DHEA singly bonded to oxygen at carbon 17, allowing the Bone Active Portion to be connected to the remainder of the compound, while maintaining one or more activities generally associated with free DHEA.

Another exemplary compound of the presently-disclosed subject matter can be represented by the following formula:

Formula 109

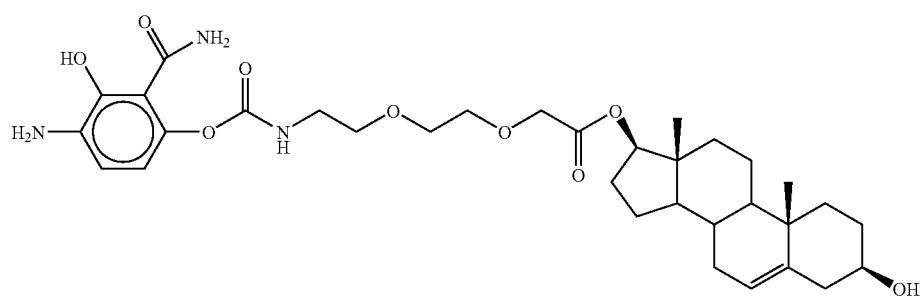

where the Linking Portion is connected to the Bone Targeting Portion ($R_T$) at $R_4$; where: D and E are each a covalent bond; G is

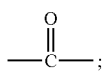

m is 1; n is 2; X is a covalent bond; each $R_S$ is hydrogen; $R_1$, $R_2$, $R_3$, $R_5$, and $R_6$ are each H; $R_7$ is $NO_2$; and where $R_A$ is derived from DHEA.

In some embodiments, $R_A$ can be a Bone Active Portion derived from the androgen, testosterone, as represented by the following formula, where D and E are each a covalent bond, G is

and X is a covalent bond:

Formula 110

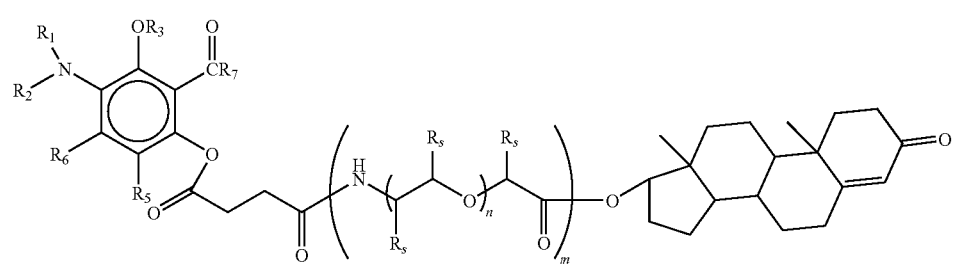

The Bone Active Portion derived from testosterone is testosterone less a hydrogen, allowing the Bone Active Portion to be connected to the remainder of the compound, while maintaining one or more activities generally associated with free testosterone.

Another exemplary compound of the presently-disclosed subject matter can be represented by the following formula:

The Bone Active Portion derived from 2-amino-1,3,4-thiadiazole-5-sulfonamide is 2-amino-1,3,4-thiadiazole-5-sulfonamide less a hydrogen, allowing the Bone Active Portion to be connected to the remainder of the compound, while maintaining one or more activities generally associated with free sulfonamide.

Another exemplary compound of the presently-disclosed subject matter can be represented by the following formula:

Formula 111

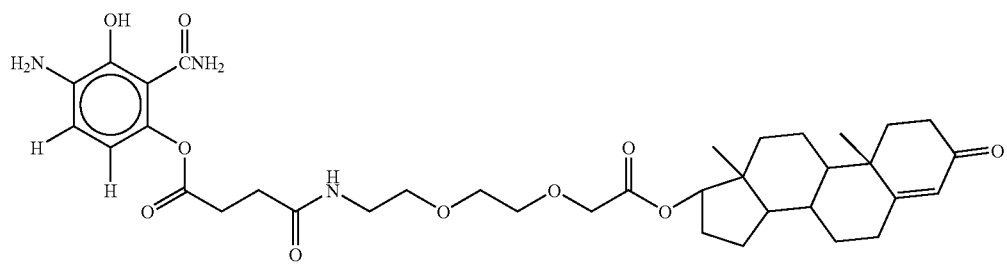

where the Linking Portion is connected to the Bone Targeting Portion ($R_T$) at $R_4$; where: D and E are each a covalent bond; G is

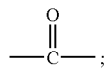

m is 1; n is 2; X is a covalent bond; each $R_S$ is hydrogen; $R_1$, $R_2$, $R_3$, $R_5$, and $R_6$ are each H; $R_7$ is $NO_2$; and where $R_4$ is derived from testosterone.

In some embodiments, $R_4$ can be a Bone Active Portion derived from a carbonic anhydrase inhibitor. In some embodiments, $R_4$ can be a Bone Active Portion derived from the carbonic anhydrase inhibitor, 2-aminothiadiazole-5-sulfonamide, as represented by the following formula, where D and E are each a covalent bond, G is

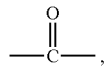

and X is a covalent bond:

Formula 112

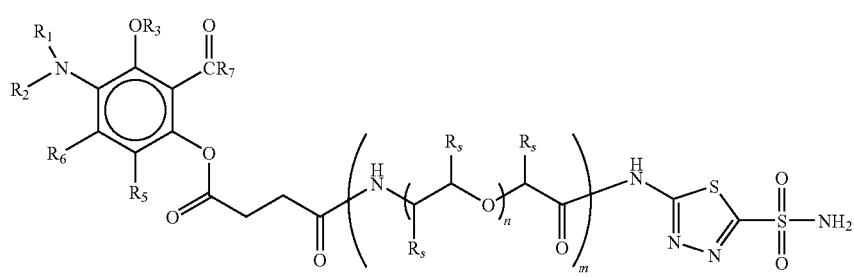

Formula 113

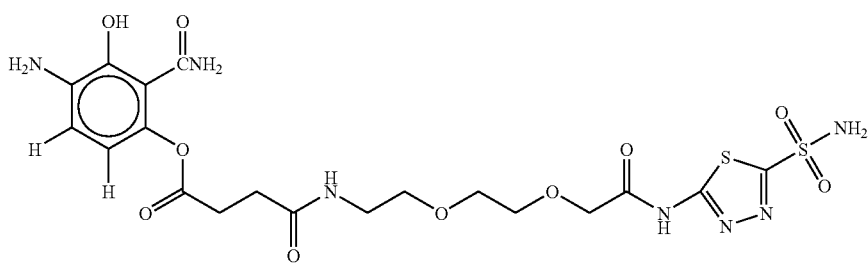

where the Linking Portion is connected to the Bone Targeting Portion ($R_T$) at $R_4$; where: D and E are each a covalent bond; G is

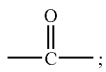

m is 1; n is 2; X is a covalent bond; each $R_S$ is hydrogen; $R_1$, $R_2$, $R_3$, $R_5$, and $R_6$ are each H; $R_7$ is $NO_2$; and where $R_A$ is derived from 2-aminothiadiazole-5-sulfonamide.

In some embodiments, $R_A$ can be a Bone Active Portion derived from an anti-cancer agent or an antineoplastic agent. In some embodiments, $R_A$ can be a Bone Active Portion derived from doxorubicin, as represented by the following formula, where D and E are each a covalent bond, G is

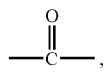

and X is a covalent bond:

Formula 114

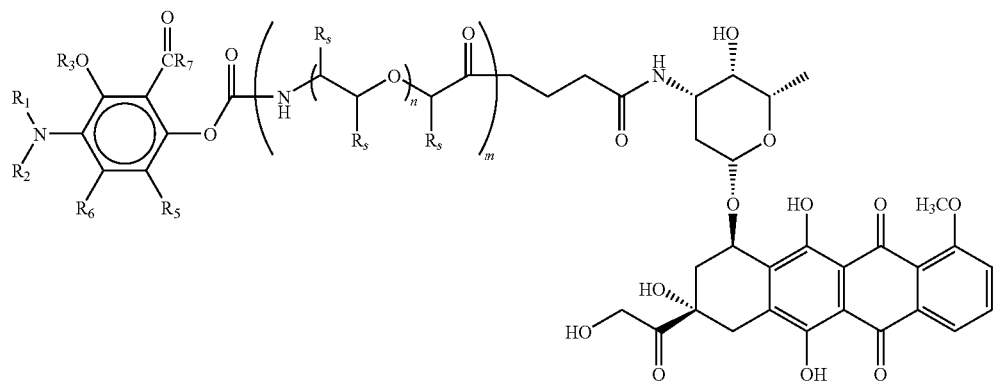

The Bone Active Portion derived from doxorubicin is doxorubicin less a hydrogen, allowing the Bone Active Portion to be connected to the remainder of the compound, while maintaining one or more activities generally associated with free doxorubicin.

Another exemplary compound of the presently-disclosed subject matter can be represented by the following formula:

Formula 115

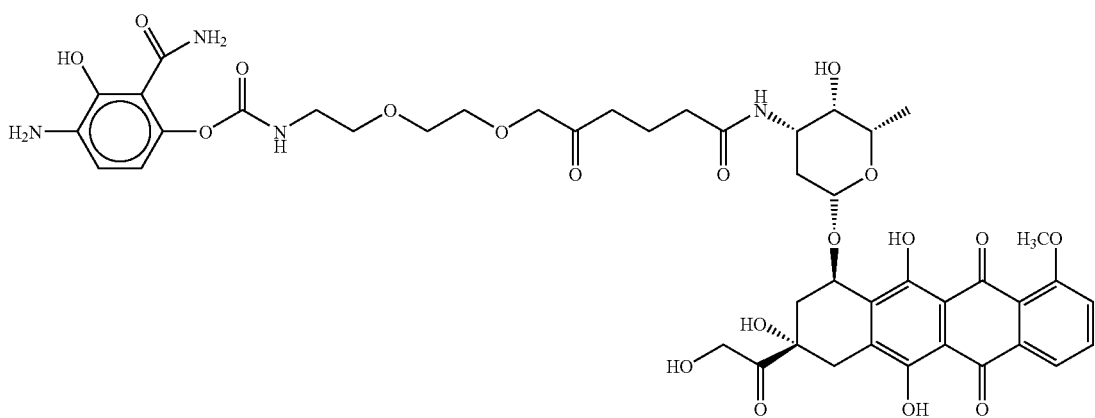

where the Linking Portion is connected to the Bone Targeting Portion ($R_T$) at $R_4$; where: D and E are each a covalent bond; G is

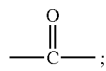

m is 1; n is 2; X is a covalent bond; each $R_S$ is hydrogen; $R_1$, $R_2$, $R_3$, $R_5$, and $R_6$ are each H; $R_7$ is $NO_2$; and where $R_A$ is derived from doxorubicin.

In some embodiments, $R_A$ can be a Bone Active Portion derived from an antimicrobial agent. In some embodiments, $R_A$ can be a Bone Active Portion derived from the antimicrobial agent, vancomycin, as represented by the following formula, where D and E are each a covalent bond, and G is

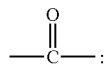

The Bone Active Portion derived from vancomycin is vancomycin less a hydroxyl, allowing the Bone Active Portion to be connected to the remainder of the compound, while maintaining one or more activities generally associated with free vancomycin.

As noted above, when some agents are joined to the compound as a Bone Active Portion, they donate an oxygen atom to an amide or ester bond of the carbonyl group adjacent X of the linking portion. Vancomycin is such an agent. When Bone Active Portions are derived from such agents, as will be understood by those of ordinary skill in the art, the X of the m-group adjacent $R_A$ is something other than a covalent bond, i.e., O, NH, or S. As noted above with reference to Formula 70, when m>1, there will be more than one X; however only the X of the m-group adjacent $R_A$ can be something other than a covalent bond, any other X must be covalent bond.

Formula 116

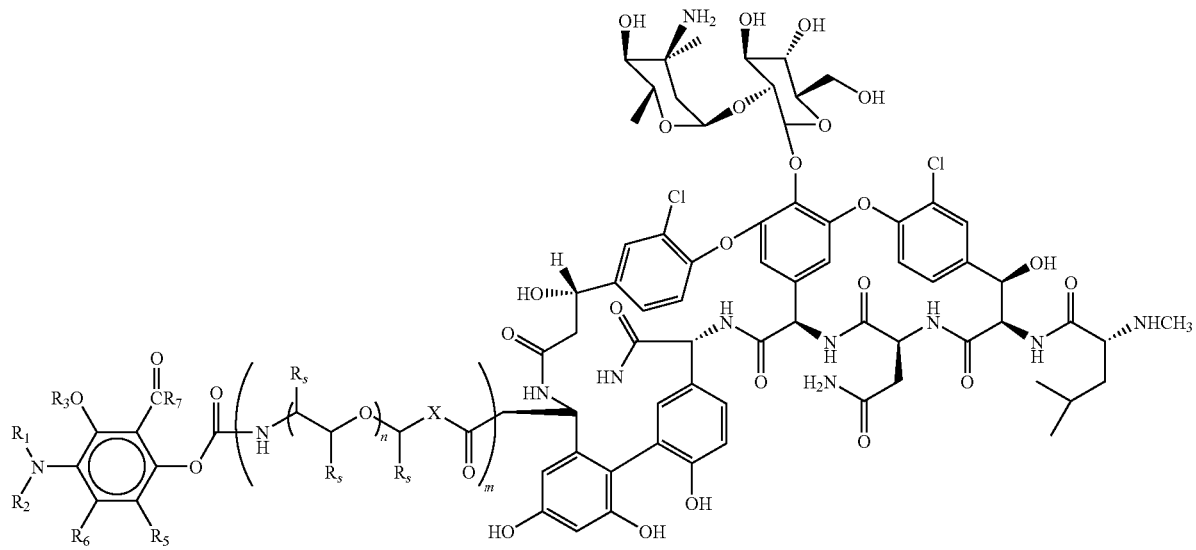

Another exemplary compound of the presently-disclosed subject matter can be represented by the following formula:

Formula 117

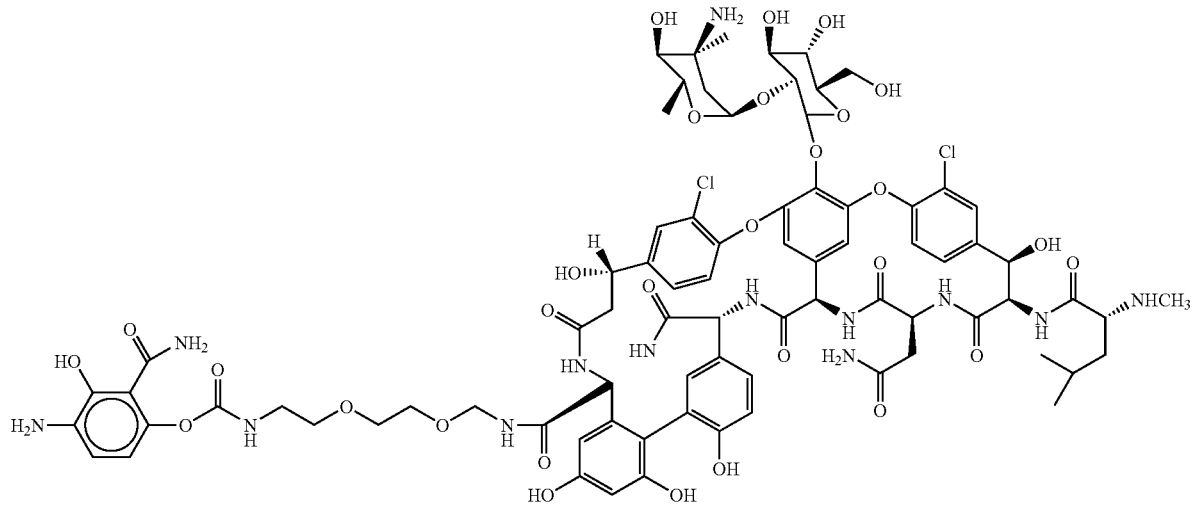

where the Linking Portion is connected to the Bone Targeting Portion ($R_T$) at $R_4$; where: D and E are each a covalent bond; G is

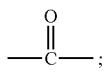

m is 1; n is 2; X is NH; each $R_S$ is hydrogen; $R_1$, $R_2$, $R_3$, $R_5$, and $R_6$ are each H; $R_7$ is $NO_2$; and where $R_A$ is derived from vancomycin.

In some embodiments, $R_A$ is a protecting group. In some embodiments, the compound can be represented by the following formula:

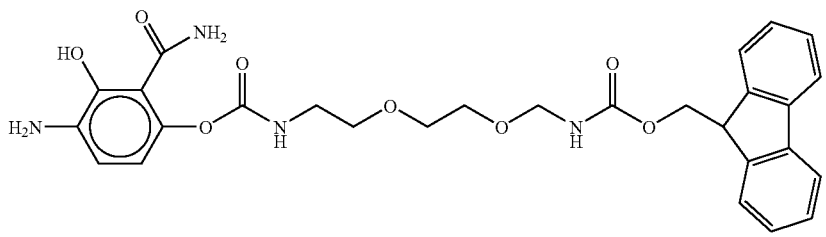

Formula 118

Where D and E are each a covalent bond; G is

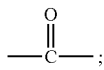

m is 1; n is 2; X is NH; each $R_S$ is hydrogen; and $R_1$, $R_2$, $R_3$, $R_5$, and $R_6$ are each H; $R_7$ is $NO_2$; and $R_A$ is a protecting group, which selected protecting group is fluorenylmethoxycarbonyl (FMOC). As noted above, when some agents are joined to the compound as an $R_A$ group, they donate an oxygen atom to an amide or ester bond of the carbonyl group adjacent X of the linking portion. The protecting group FMOC is such an agent. When $R_A$ is derived from such an agent, as will be understood by those of ordinary skill in the art, the X of the m-group adjacent $R_A$ is something other than a covalent bond, i.e., O, NH, or S, while any other X must be covalent bond.

In some embodiments, $R_A$ can be a hydroxyl. In some embodiments, the compound can be represented by the following formula:

Formula 119

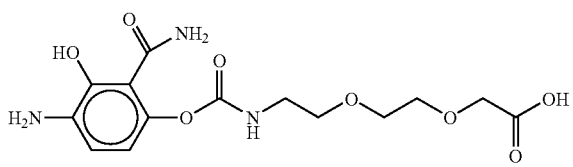

where D and E are each a covalent bond, G is

and X is a covalent bond; each $R_S$ is hydrogen; and $R_1$, $R_2$, $R_3$, $R_5$, and $R_6$ are each H; $R_7$ is $NO_2$; and $R_A$ is hydroxyl.

With reference again to the -D-E-G- segment of the Linking Portion, when the Linking Portion of Formula 12 is used, the -D-E-G- segment of the Linking Portion is adjacent the $R_A$ portion of the compounds, as shown in the following formula, where the Linking Portion is connected to the Bone Targeting Portion at $R_1$:

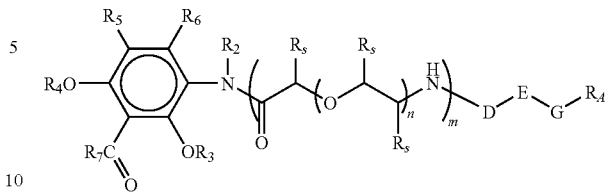

Formula 119

Because the -D-E-G- segment is positioned adjacent the third unit, $R_A$, it can be beneficial to select -D-E-G- based on the selected third unit, $R_A$. For example, when $R_A$ is a Bone Active Portion, it is contemplated that the Linker Portion can be bound to the Bone Active Portion to minimize the susceptibility to hydrolysis, e.g., ester, urido, ether, linkage, to increase the bioavailablity of the compound. That is to say, if susceptibility to hydrolysis is minimized, without wishing to be bound by theory or mechanism, the compound can be delivered to and affect bone.

As mentioned above, the third unit $R_A$ of the compound can be selected from: a protecting group; a hydrogen when the Linking Portion of Formula 12 ($R_L$ Option 1) is selected; or a Bone Targeting Portion (See e.g., Tables A-D).

When the protecting group t-butoxycarbonyl (t-BOC) is used, as will be understood by those skilled in the art, it can be beneficial in some embodiments for D, E, and G to be a covalent bond. In this regard, in some embodiments, the compound of the presently-disclosed subject matter can be represented by the following formula:

Formula 120

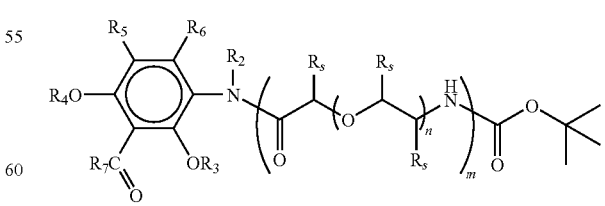

where D, E, and G are covalent bonds, and $R_A$ is t-BOC.

In some embodiments, the compound of the presently-disclosed subject matter can be represented by the following formula:

Formula 121

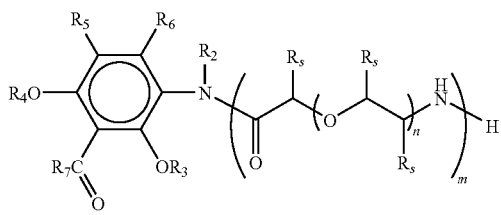

where D, E, and G are a covalent bond, and $R_A$ is H.

In some embodiments, $R_A$ can be derived from a bone active agent. In some embodiments, $R_A$ can be a Bone Active Portion derived from a steroidal estrogenic agent. In some embodiments, $R_A$ can be a Bone Active Portion derived from the a steroidal estrogenic agent, estradiol. As will be understood by those skilled in the art, in such cases, it can be beneficial in some embodiments for D to be

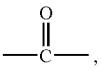

for E to be a group other than a covalent bond, and for G to be a covalent bond. In this regard, in some embodiments, the compound can be represented by the following formula, where D is $$\overset{O}{\underset{\|}{-C-}},$$

E is —(CH$_2$)$_2$—, and G is a covalent bond, and $R_A$ is derived from estradiol:

Formula 122

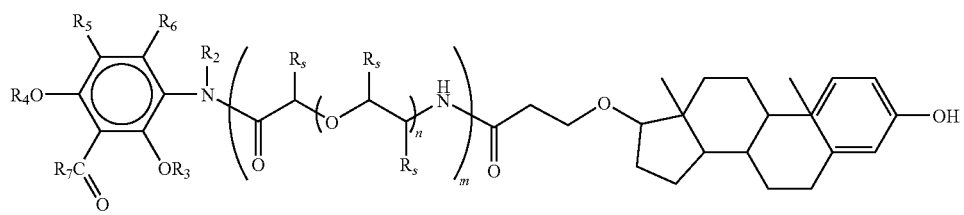

The Bone Active Portion derived from estradiol is estradiol less a hydrogen, allowing the Bone Active Portion to be connected to the remainder of the compound, while maintaining one or more activities generally associated with free estradiol. In some embodiments, when the Bone Active Portion of the compound is derived from estradiol, it is derived from the 17-β-enantiomer of estradiol. Without wishing to be bound by theory or mechanism, it is believed that the 17-β-enantiomer of estradiol is the active isomer.

Another exemplary compound of the presently-disclosed subject matter can be represented by the following formula:

Formula 123

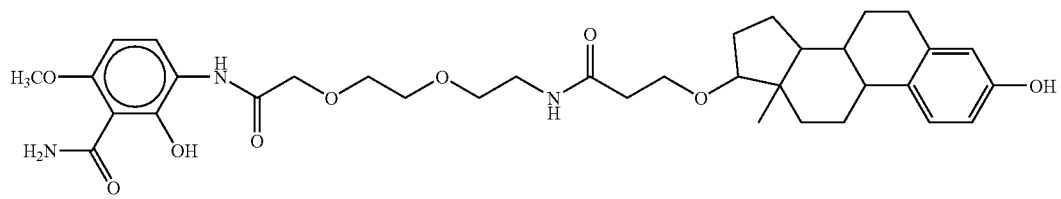

where D is

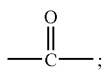

E is —$(CH_2)_2$—; G is a covalent bond; m is 1; n is 2; each $R_S$ is hydrogen; $R_2$, $R_3$, $R_5$, $R_6$ are each H; $R_4$ is methyl; $R_7$ is amino; and where $R_A$ is derived from estradiol.

Another exemplary compound of the presently-disclosed subject matter can be represented by the following formula:

Formula 124

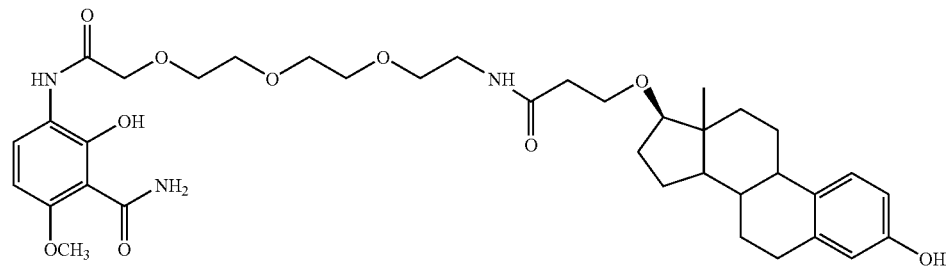

where D is

E is —$(CH_2)_2$—; G is a covalent bond; m is 1; n is 3; each $R_S$ is hydrogen; $R_2$, $R_3$, $R_5$, $R_6$ are each H; $R_4$ is methyl; $R_7$ is amino; and where $R_A$ is derived from estradiol.

Another exemplary compound of the presently-disclosed subject matter can be represented by the following formula:

Formula 125

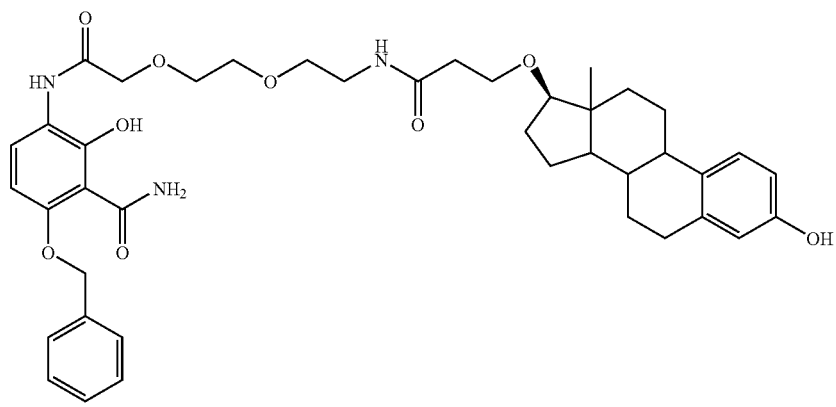

where D is

E is —$(CH_2)_2$—; G is a covalent bond; m is 1; n is 2; each $R_S$ is hydrogen; $R_2$, $R_3$, $R_5$, $R_6$ are each H; $R_4$ is benzyl; $R_7$ is amino; and where $R_A$ is derived from estradiol.

Another exemplary compound of the presently-disclosed subject matter can be represented by the following formula:

Formula 126

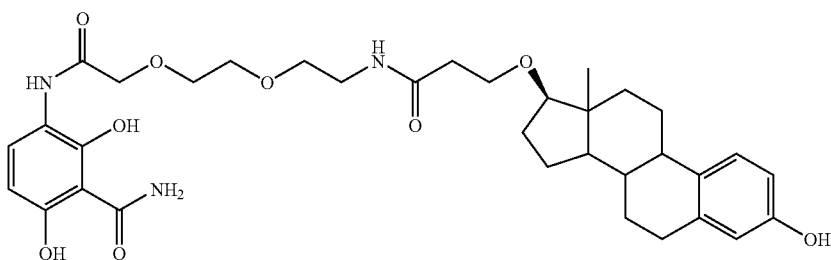

where D is

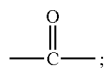

E is —(CH$_2$)$_2$—; G is a covalent bond; m is 1; n is 2; each R$_S$ is hydrogen; R$_2$, R$_3$, R$_5$, R$_4$, R$_6$ are each H; R$_7$ is amino; and where R$_A$ is derived from estradiol.

In some embodiments, R$_A$ can be a Bone Active Portion derived from an non-steroidal estrogenic agent. In some embodiments, R$_A$ can be a Bone Active Portion derived from the non-steroidal estrogenic agent, genistein, as represented by the following formulas:

The Bone Active Portion derived from genistein is genistein less a hydrogen, allowing the Bone Active Portion to be connected to the remainder of the compound, while maintaining one or more activities generally associated with free genistein.

Another exemplary compound of the presently-disclosed subject matter can be represented by the following formulas:

Formula 127A

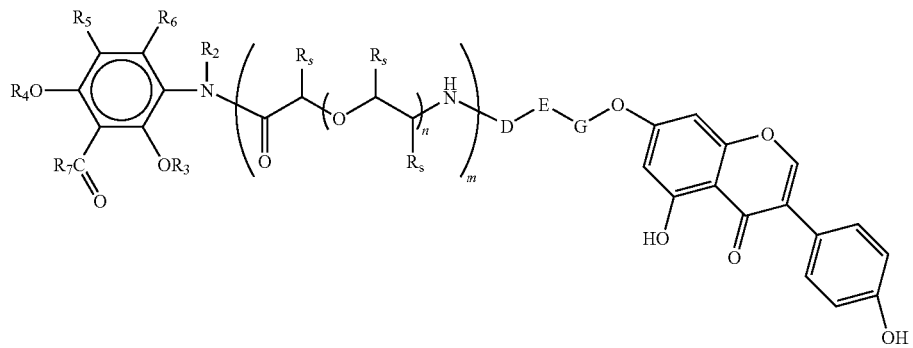

Formula 127B

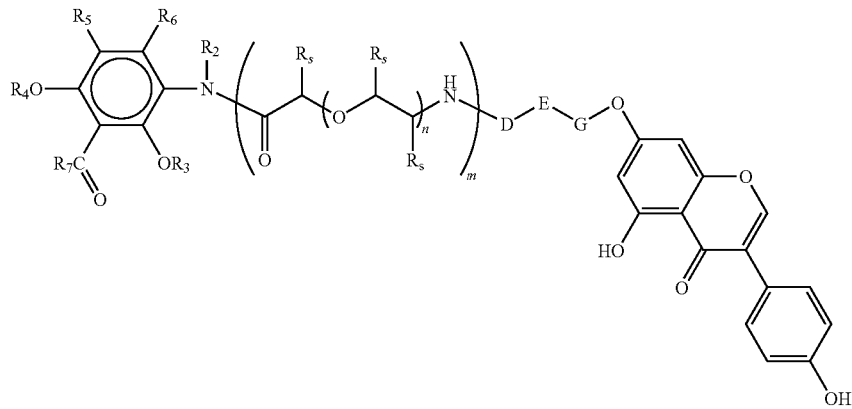

Formula 128A

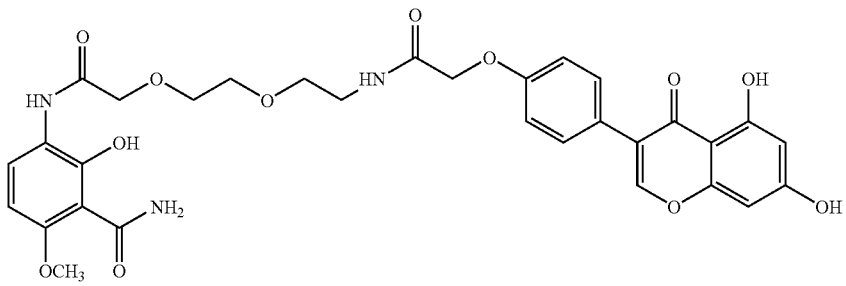

where the Linking Portion is connected to the Bone Targeting Portion ($R_T$) at $R_1$; where: D is

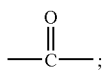

E is —($CH_2$)—; G is a covalent bond; m is 1; n is 2; each $R_S$ is hydrogen; $R_2$, $R_3$, $R_5$, $R_6$ are each H; $R_4$ is methyl; $R_7$ is amino; and where $R_A$ is derived from genistein; and E is —($CH_2$)$_3$—; m is 1; n is 2; each $R_S$ is hydrogen; $R_2$, $R_3$, $R_5$, $R_6$ are each H; $R_4$ is methyl; $R_7$ is amino; and where $R_A$ is derived from genistein.

In some embodiments, $R_A$ can be a Bone Active Portion derived from a nitric oxide agent. In some embodiments, $R_A$ can be a Bone Active Portion derived from the nitric oxide agent, alkoxy-$NO_2$, as represented by the following formula, where D is Formula 128B

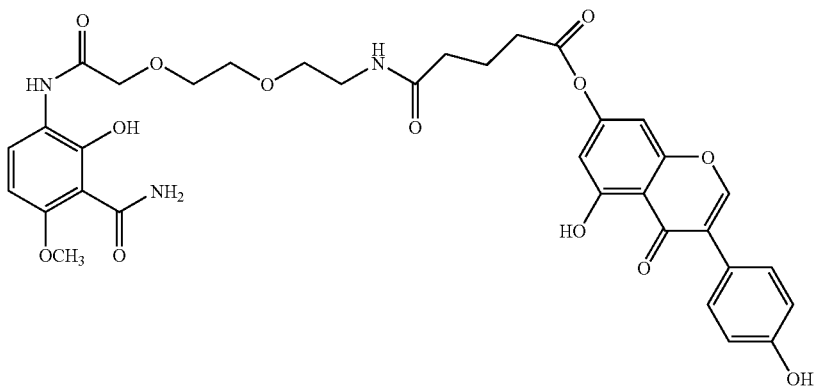

where the Linking Portion is connected to the Bone Targeting Portion ($R_T$) at $R_1$; where: D and G are each

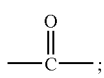

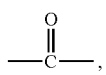

and E and G are covalent bonds:

Formula 129

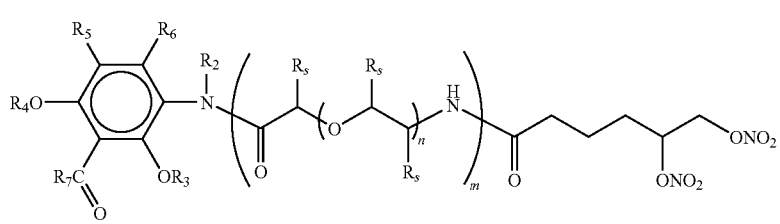

The Bone Active Portion derived from alkoxy-NO$_2$ is alkoxy-NO$_2$ less a hydrogen, allowing the Bone Active Portion to be connected to the remainder of the compound, while maintaining one or more activities generally associated with free alkoxy-NO$_2$.

Another exemplary compound of the presently-disclosed subject matter can be represented by the following formula:

Formula 130

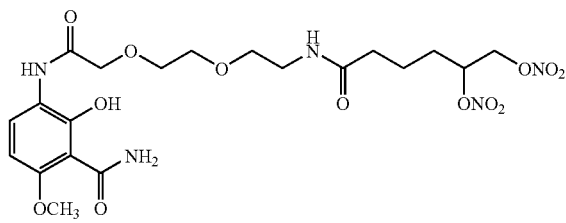

where the Linking Portion is connected to the Bone Targeting Portion (R$_T$) at R$_1$; where: D is

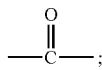

and E and G are covalent bonds; m is 1; n is 2; each R$_S$ is hydrogen; R$_2$, R$_3$, R$_5$, R$_6$ are each H; R$_4$ is methyl; R$_7$ is amino; and where R$_A$ is derived from alkoxy-NO$_2$.

In some embodiments, R$_A$ can be a Bone Active Portion derived from an androgen. In some embodiments, R$_A$ can be a Bone Active Portion derived from the androgen, DHEA, as represented by the following formula, where D is

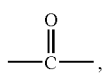

E is —(CH$_2$)$_2$—, and G is a covalent bond:

Formula 131

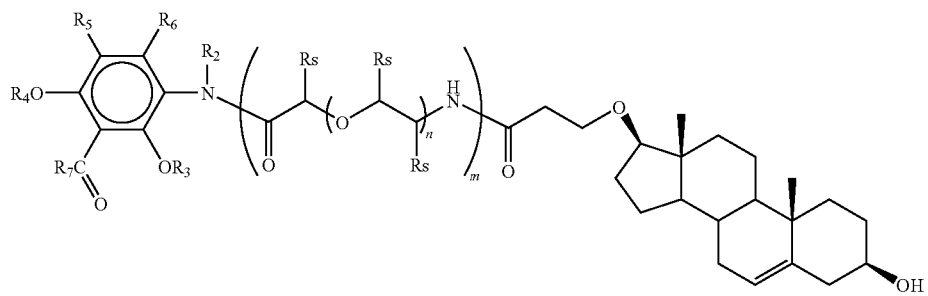

The Bone Active Portion derived from DHEA is DHEA singly bonded to oxygen at carbon 17, allowing the Bone Active Portion to be connected to the remainder of the compound, while maintaining one or more activities generally associated with free DHEA.

Another exemplary compound of the presently-disclosed subject matter can be represented by the following formula:

Formula 132

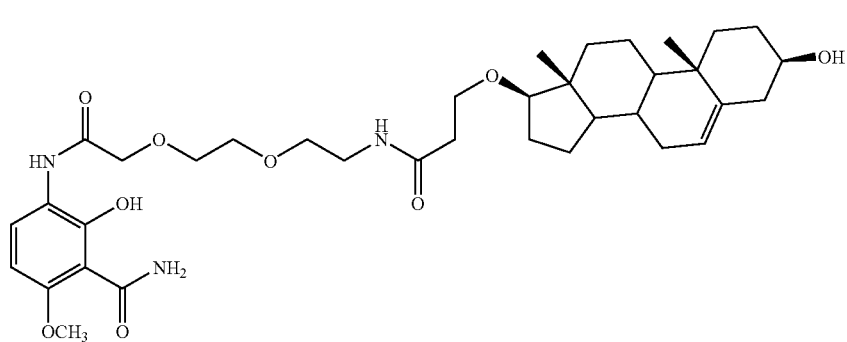

where the Linking Portion is connected to the Bone Targeting Portion ($R_T$) at $R_1$; where: D is

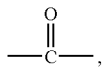

E is —$(CH_2)_2$—, and G is a covalent bond; m is 1; n is 2; each $R_S$ is hydrogen; $R_2$, $R_3$, $R_5$, $R_6$ are each H; $R_4$ is methyl; $R_7$ is amino; and where $R_A$ is derived from DHEA.

In some embodiments, $R_A$ can be a Bone Active Portion derived from the androgen, testosterone, as represented by the following formula, where D is

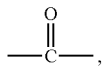

E is —$(CH_2)_2$—, and G is a covalent bond:

where the Linking Portion is connected to the Bone Targeting Portion ($R_T$) at $R_1$; where: D is

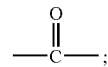

E is —$(CH_2)_2$—; G is a covalent bond; m is 1; n is 2; each $R_S$ is hydrogen; $R_2$, $R_3$, $R_5$, $R_6$ are each H; $R_4$ is methyl; $R_7$ is amino; and where $R_A$ is derived from testosterone.

In some embodiments, $R_A$ can be a Bone Active Portion derived from a carbonic anhydrase inhibitor. In some embodiments, $R_A$ can be a Bone Active Portion derived from the carbonic anhydrase inhibitor, 2-aminothiadiazole-5-sulfonamide, as represented by the following formula, where D and G are

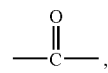

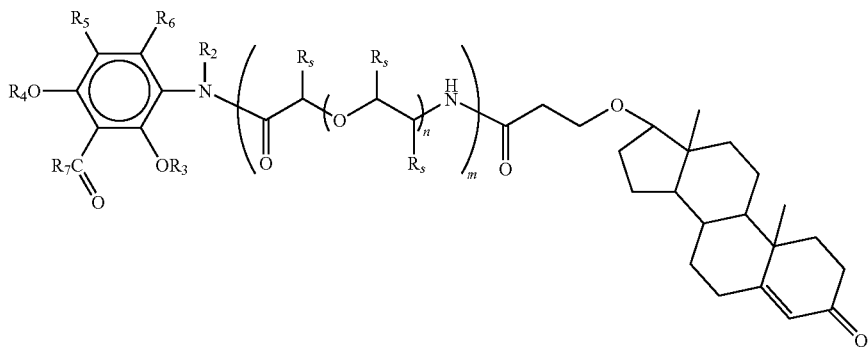

Formula 133

The Bone Active Portion derived from testosterone can be testosterone less a hydrogen, allowing the Bone Active Portion to be connected to the remainder of the compound, while maintaining one or more activities generally associated with free testosterone.

Another exemplary compound of the presently-disclosed subject matter can be represented by the following formula:

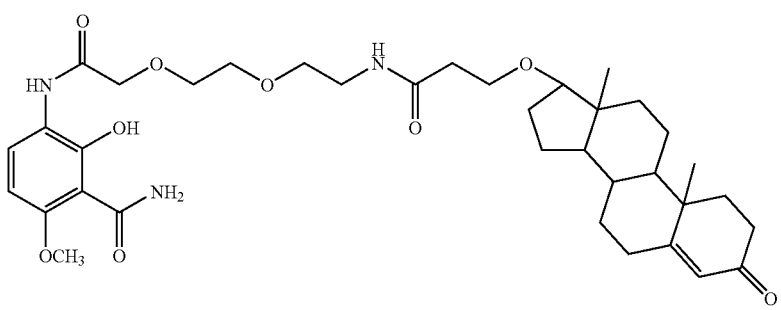

Formula 134 and E is —(CH$_2$)$_3$—:

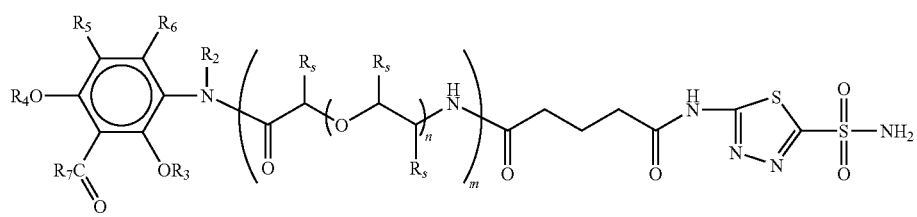

Formula 135

The Bone Active Portion derived from 2-amino-1,3,4-thiadiazole-5-sulfonamide is 2-amino-1,3,4-thiadiazole-5-sulfonamide less a hydrogen, allowing the Bone Active Portion to be connected to the remainder of the compound, while maintaining one or more activities generally associated with free sulfonamide.

Another exemplary compound of the presently-disclosed subject matter can be represented by the following formula:

and E is —(CH$_2$)$_3$—; m is 1; n is 2; each $R_S$ is hydrogen; $R_2$, $R_3$, $R_5$, $R_6$ are each H; $R_4$ is methyl; $R_7$ is amino; and where $R_A$ is derived from 2-aminothiadiazole-5-sulfonamide.

In some embodiments, $R_A$ can be a Bone Active Portion derived from an anti-cancer agent or an antineoplastic agent.

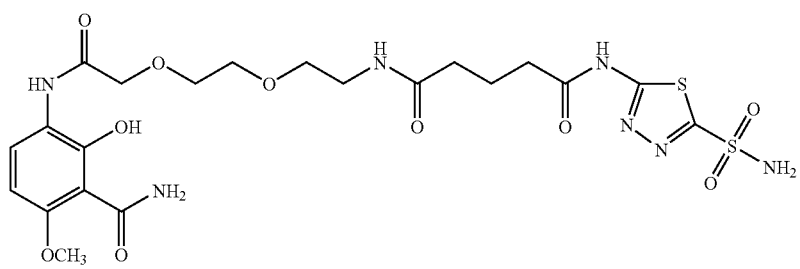

Formula 136 where the Linking Portion is connected to the Bone Targeting Portion ($R_T$) at $R_1$; where: D and G are

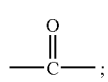

In some embodiments, $R_A$ can be a Bone Active Portion derived from doxorubicin, as represented by the following formula, where D and G ar

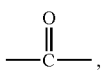

and e E is —(CH$_2$)$_3$—:

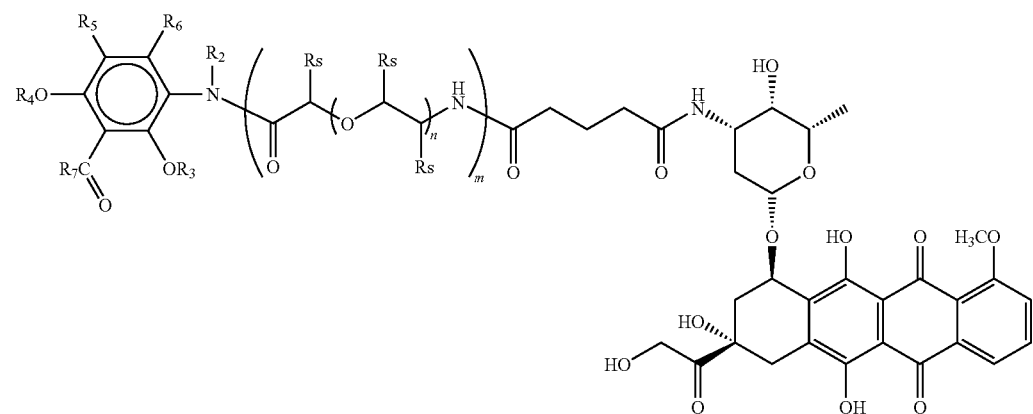

Formula 137

The Bone Active Portion derived from doxorubicin is doxorubicin less a hydrogen, allowing the Bone Active Portion to be connected to the remainder of the compound, while maintaining one or more activities generally associated with free doxorubicin.

Another exemplary compound of the presently-disclosed subject matter can be represented by the following formula:

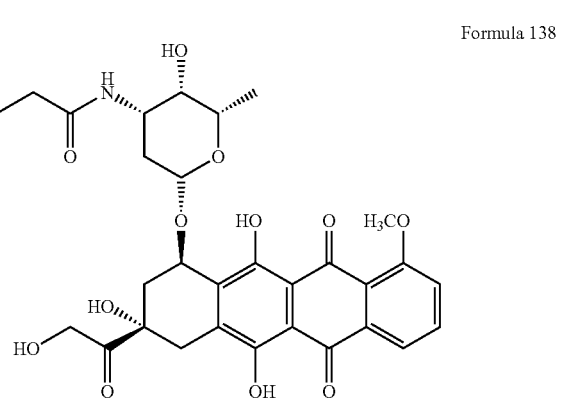

Formula 138 where the Linking Portion is connected to the Bone Targeting Portion ($R_T$) at $R_1$; where: D and G are

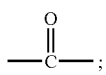

E is —$(CH_2)_3$—; m is 1; n is 2; each $R_S$ is hydrogen; $R_2$, $R_3$, $R_5$, $R_6$ are each H; $R_4$ is methyl; $R_7$ is amino; and where $R_4$ is derived from doxorubicin.

In some embodiments, $R_A$ can be a Bone Active Portion derived from an antimicrobial agent. In some embodiments, $R_A$ can be a Bone Active Portion derived from the antimicrobial agent, vancomycin, as represented by the following formula, where D is

and E and G are a covalent bond:

Formula 139

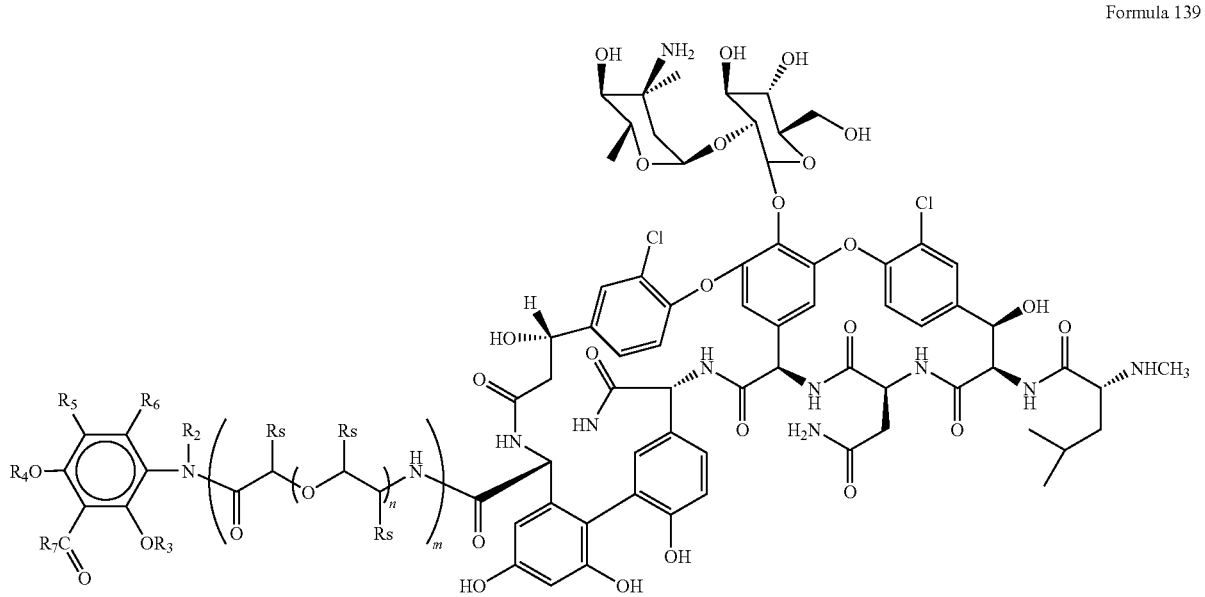

The Bone Active Portion derived from vancomycin can be vancomycin less a hydroxyl, allowing the Bone Active Portion to be connected to the remainder of the compound, while maintaining one or more activities generally associated with free vancomycin.

Another exemplary compound of the presently-disclosed subject matter can be represented by the following formula:

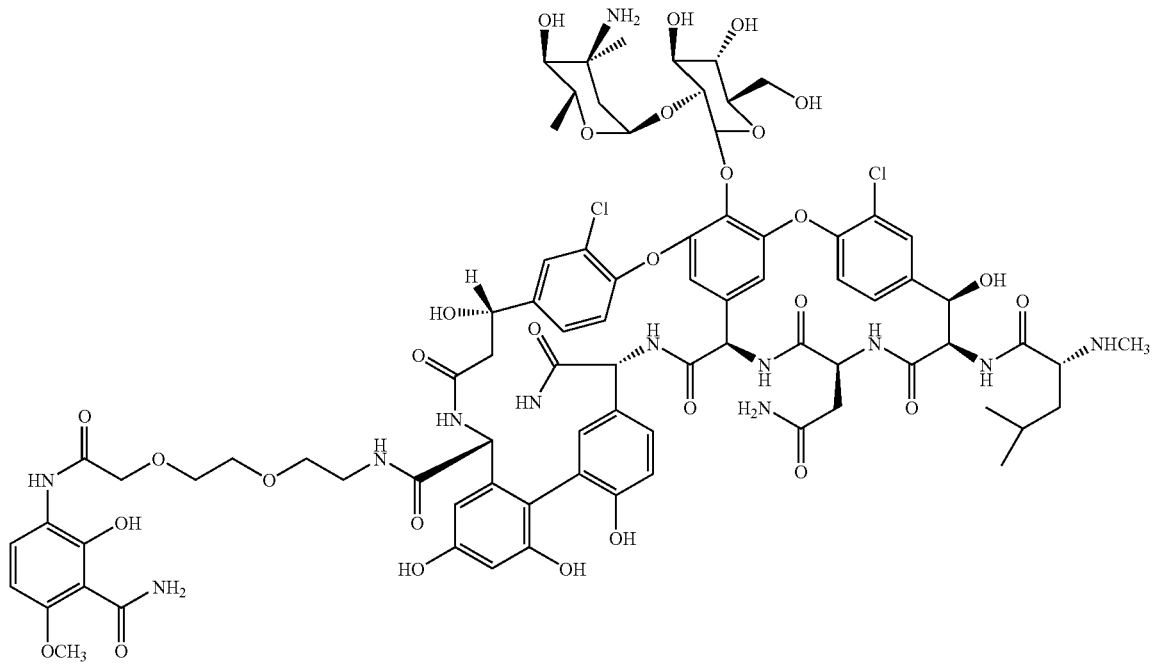

Formula 140 where the Linking Portion is connected to the Bone Targeting Portion ($R_T$) at $R_1$; where: D is

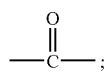

E and G are a covalent bond; m is 1; n is 2; each $R_S$ is hydrogen; $R_2$, $R_3$, $R_5$, $R_6$ are each H; $R_4$ is methyl; $R_7$ is amino; and where $R_A$ is derived from vancomycin.

In some embodiments of the compounds of the presently-disclosed subject matter, the Linker Portion of Formula 12 is used and the Linker Portion is connected to the Bone Targeting Portion at $R_4$, as represented by the following formula:

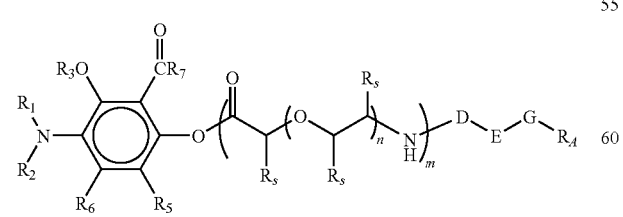

Formula 141

Because the -D-E-G- segment is positioned adjacent the third unit, $R_A$, it is beneficial to select -D-E-G- based on the selected third unit, $R_A$. For example, when $R_A$ is a Bone Active Portion, it is contemplated that the Linker Portion can be bound to the Bone Active Portion to minimize the susceptibility to hydrolysis, e.g., ester, urido, ether, linkage, to increase the bioavailability of the compound. That is to say, if susceptibility to hydrolysis is minimized, without wishing to be bound by theory or mechanism, the compound can be delivered to and affect bone.

As mentioned above, the third unit $R_A$ of the compound can be selected from: a protecting group; a hydrogen when the Linking Portion of Formula 12 is selected; or a Bone Targeting Portion (See e.g., Tables A-D).

When the protecting group t-butoxycarbonyl (t-BOC) is used, as will be understood by those skilled in the art, it can be beneficial in some embodiments for D, E, and G to be a covalent bond. In this regard, an exemplary compound of the presently-disclosed subject matter can be represented by the following formula:

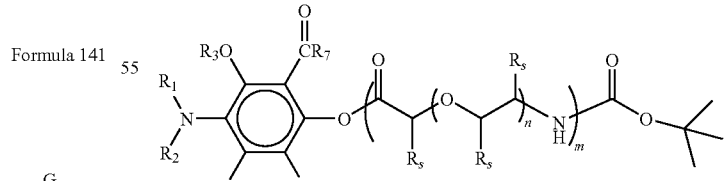

Formula 142 which is the exemplary compound of Formula 141, where D, E, and G are covalent bonds, and $R_A$ is t-BOC.

Another exemplary compound of the presently-disclosed subject matter can be represented by the following formula:

Formula 143

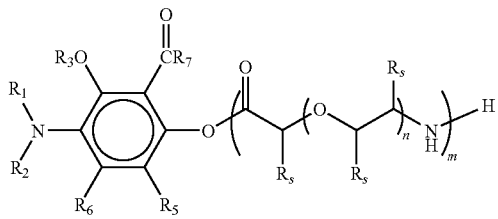

which is the exemplary compound of Formula 141, where D, E, and G are a covalent bond, and $R_A$ is H.

In some embodiments, $R_A$ can be derived from a bone active agent. In some embodiments, $R_A$ can be a Bone Active Portion derived from a steroidal estrogenic agent. In some embodiments, $R_A$ can be a Bone Active Portion derived from the a steroidal estrogenic agent, estradiol. As will be understood by those skilled in the art, in such cases, it can be beneficial in some embodiments for D to be

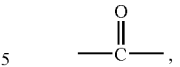

for E to be a group other than a covalent bond, and for G to be a covalent bond. In this regard, in some embodiments, the compound can be represented by the following formula, where D is

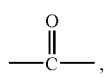

E is —$(CH_2)_2$—, and G is a covalent bond, and $R_A$ is derived from estradiol:

Formula 144

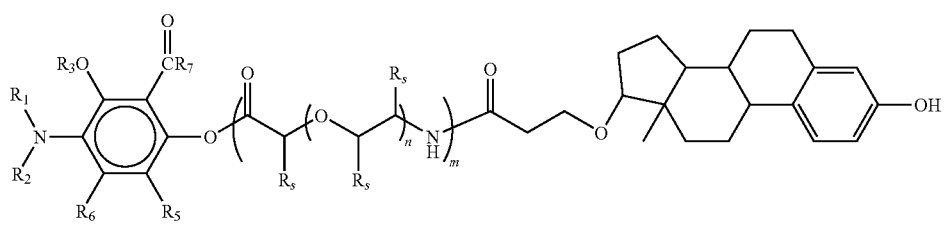

The Bone Active Portion derived from estradiol is estradiol less a hydrogen, allowing the Bone Active Portion to be connected to the remainder of the compound, while maintaining one or more activities generally associated with free estradiol. In some embodiments, when the Bone Active Portion of the compound is derived from estradiol, it is derived from the 17-β-enantiomer of estradiol. Without wishing to be bound by theory or mechanism, it is believed that the 17-β-enantiomer of estradiol is the active isomer.

Another exemplary compound of the presently-disclosed subject matter can be represented by the following formula:

Formula 145

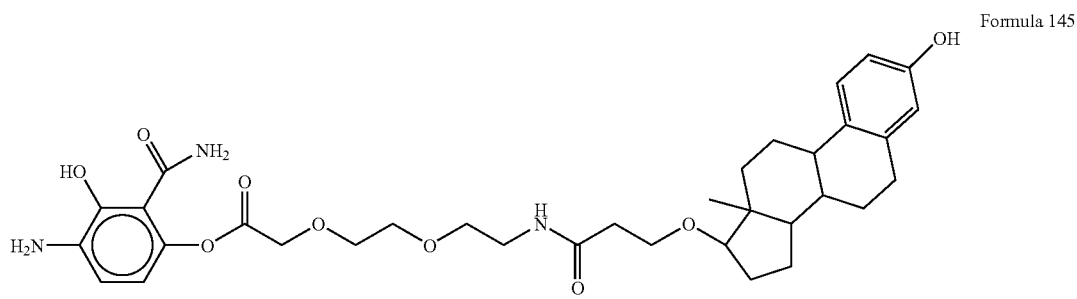

where D is

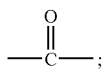

E is —(CH$_2$)$_2$—; G is a covalent bond; m is 1; n is 2; each R$_S$ is H; R$_1$, R$_2$, R$_3$, R$_5$, and R$_6$ are each H; R$_7$ is NO$_2$; and where R$_A$ is derived from estradiol.

In some embodiments, R$_A$ can be a Bone Active Portion derived from a non-steroidal estrogenic agent. In some embodiments, R$_A$ can be a Bone Active Portion derived from the non-steroidal estrogenic agent, genistein, as represented by the following formula

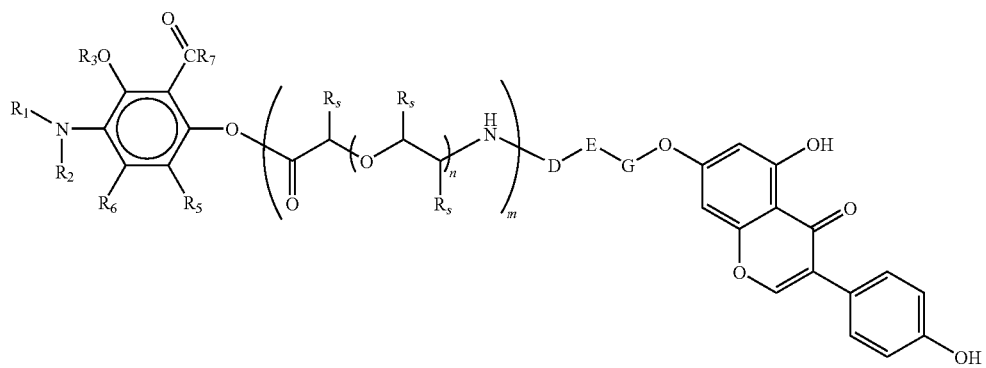

The Bone Active Portion derived from genistein is genistein less a hydrogen, allowing the Bone Active Portion to be connected to the remainder of the compound, while maintaining one or more activities generally associated with free genistein.

Another exemplary compound of the presently-disclosed subject matter can be represented by the following formula:

Formula 147

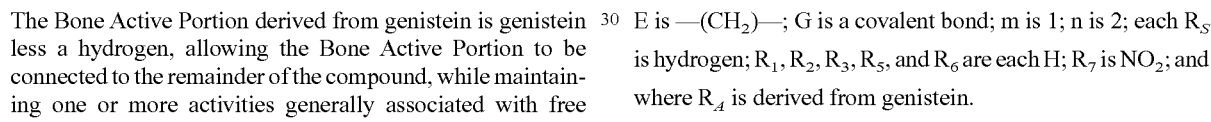

where the Linking Portion is connected to the Bone Targeting Portion (R$_T$) at R$_4$; where: D is

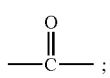

Formula 146

E is —(CH$_2$)—; G is a covalent bond; m is 1; n is 2; each R$_S$ is hydrogen; R$_1$, R$_2$, R$_3$, R$_5$, and R$_6$ are each H; R$_7$ is NO$_2$; and where R$_A$ is derived from genistein.

In some embodiments, R$_A$ can be a Bone Active Portion derived from a nitric oxide agent. In some embodiments, R$_A$ can be a Bone Active Portion derived from the nitric oxide agent, alkoxy-NO$_2$, as represented by the following formula, where D is $$\overset{O}{\underset{\phantom{C}}{-C-}},$$

and E and G are covalent bonds:

Formula 148

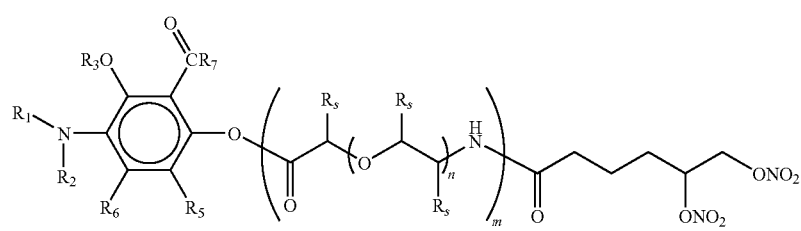

The Bone Active Portion derived from alkoxy-$NO_2$ is alkoxy-$NO_2$ less a hydrogen, allowing the Bone Active Portion to be connected to the remainder of the compound, while maintaining one or more activities generally associated with free alkoxy-$NO_2$.

Another exemplary compound of the presently-disclosed subject matter can be represented by the following formula:

Formula 149

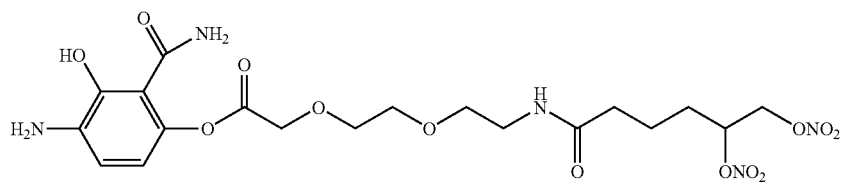

where the Linking Portion is connected to the Bone Targeting Portion ($R_T$) at $R_4$; where: D is

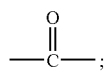

and E and G are covalent bonds; m is 1; n is 2; each $R_S$ is hydrogen; $R_1$, $R_2$, $R_3$, $R_5$, and $R_6$ are each H; $R_7$ is $NO_2$; and where $R_4$ is derived from alkoxy-$NO_2$.

In some embodiments, $R_A$ can be a Bone Active Portion derived from an androgen. In some embodiments, $R_A$ can be a Bone Active Portion derived from the androgen, DHEA, as represented by the following formula, where D is

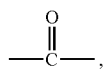

E is —$(CH_2)_2$—, and G is a covalent bond:

Formula 150

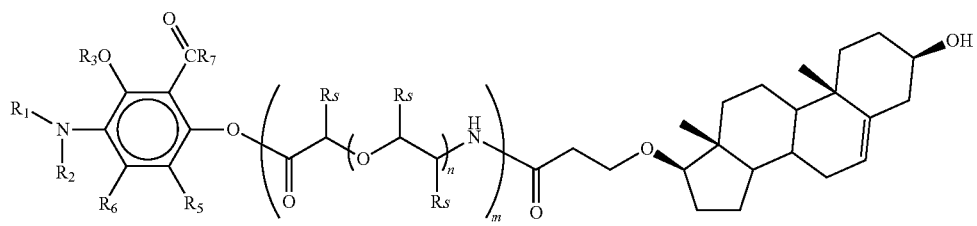

The Bone Active Portion derived from DHEA is DHEA singly bonded to oxygen at carbon 17, allowing the Bone Active Portion to be connected to the remainder of the compound, while maintaining one or more activities generally associated with free DHEA.

Another exemplary compound of the presently-disclosed subject matter can be represented by the following formula:

Formula 151

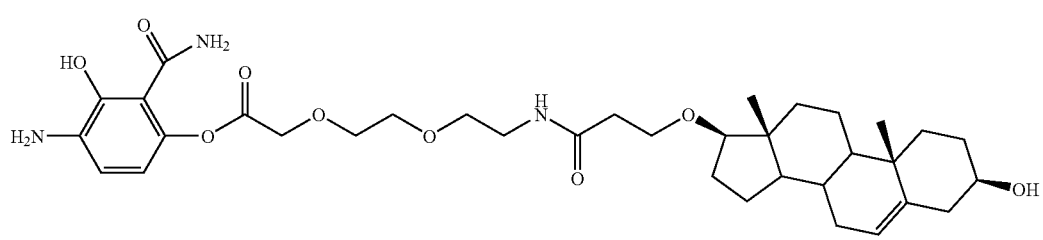

where the Linking Portion is connected to the Bone Targeting Portion ($R_T$) at $R_4$; where: D is

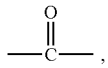

E is —$(CH_2)_2$—, and G is a covalent bond; m is 1; n is 2; each $R_S$ is hydrogen; $R_1$, $R_2$, $R_3$, $R_5$, and $R_6$ are each H; $R_7$ is $NO_2$; and where $R_A$ is derived from DHEA.

In some embodiments, $R_A$ can be a Bone Active Portion derived from the androgen, testosterone, as represented by the following formula, where D is

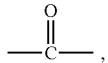

E is —$(CH_2)_2$—, and G is a covalent bond:

where the Linking Portion is connected to the Bone Targeting Portion ($R_T$) at $R_4$; where: D is $$-\overset{O}{\underset{\|}{C}}-\ ;$$

E is —$(CH_2)_2$—; G is a covalent bond; m is 1; n is 2; each $R_S$ is hydrogen; $R_1$, $R_2$, $R_3$, $R_5$, and $R_6$ are each H; $R_7$ is $NO_2$; and where $R_A$ is derived from testosterone.

In some embodiments, $R_A$ can be a Bone Active Portion derived from a carbonic anhydrase inhibitor. In some embodiments, $R_A$ can be a Bone Active Portion derived from the carbonic anhydrase inhibitor, 2-aminothiadiazole-5-sulfonamide, as represented by the following formula, where D and G are $$-\overset{O}{\underset{\|}{C}}-\ ,$$

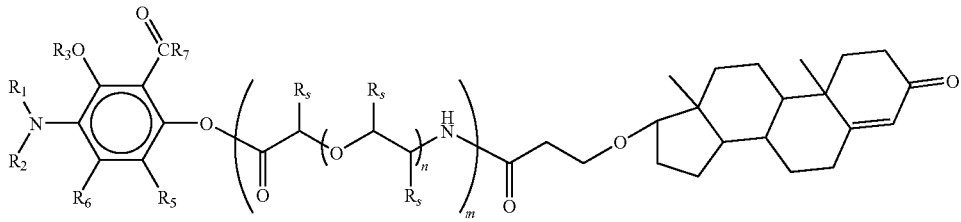

Formula 152

The Bone Active Portion derived from testosterone is testosterone less a hydrogen, allowing the Bone Active Portion to be connected to the remainder of the compound, while maintaining one or more activities generally associated with free testosterone.

Another exemplary compound of the presently-disclosed subject matter can be represented by the following formula:

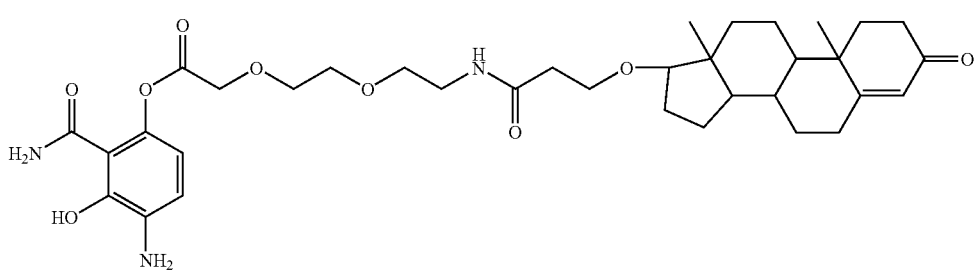

Formula 153 and E is —(CH$_2$)$_3$—:

Formula 154

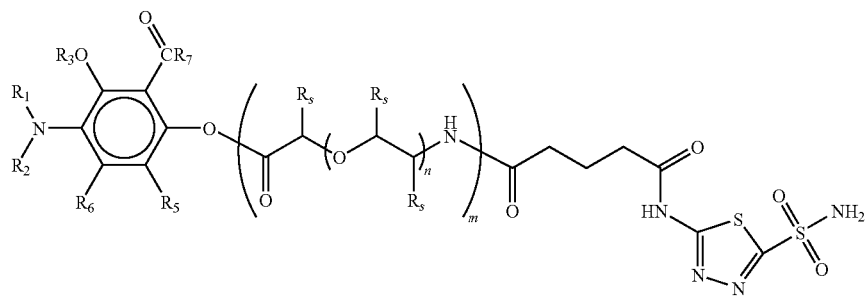

The Bone Active Portion derived from 2-amino-1,3,4-thiadiazole-5-sulfonamide is 2-amino-1,3,4-thiadiazole-5-sulfonamide less a hydrogen, allowing the Bone Active Portion to be connected to the remainder of the compound, while maintaining one or more activities generally associated with free sulfonamide.

Another exemplary compound of the presently-disclosed subject matter can be represented by the following formula:

and E is —(CH$_2$)$_3$—; m is 1; n is 2; each R$_S$ is hydrogen; R$_1$, R$_2$, R$_3$, R$_5$, and R$_6$ are each H; R$_7$ is NO$_2$; and where R$_A$ is derived from 2-aminothiadiazole-5-sulfonamide.

In some embodiments, R$_A$ can be a Bone Active Portion derived from an anti-cancer agent or an antineoplastic agent.

Formula 155

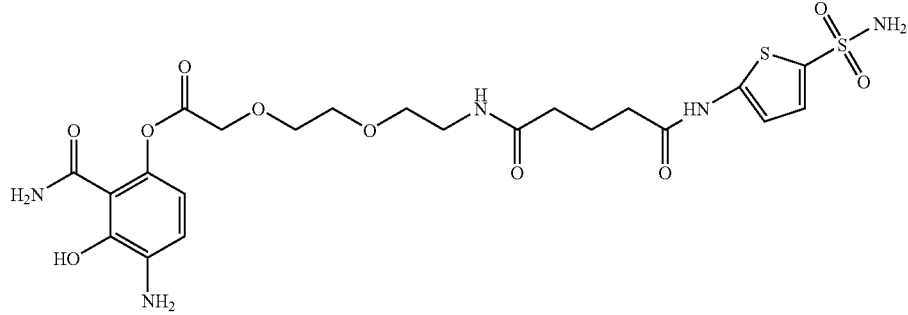

where the Linking Portion is connected to the Bone Targeting Portion (R$_T$) at R$_4$; where: D and G are

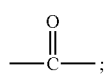;

In some embodiments, R$_A$ can be a Bone Active Portion derived from doxorubicin, as represented by the following formula, where D and G are

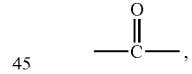, and E is —(CH$_2$)$_3$—:

Formula 156

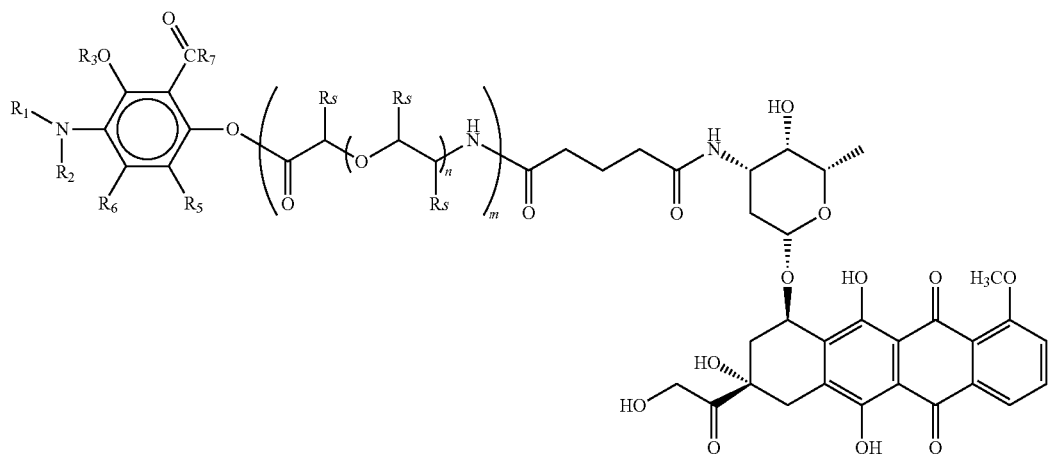

The Bone Active Portion derived from doxorubicin is doxorubicin less a hydrogen, allowing the Bone Active Portion to be connected to the remainder of the compound, while maintaining one or more activities generally associated with free doxorubicin.

Another exemplary compound of the presently-disclosed subject matter can be represented by the following formula:

In some embodiments, $R_4$ can be a Bone Active Portion derived from an antimicrobial agent. In some embodiments, $R_4$ can be a Bone Active Portion derived from the antimicrobial agent, vancomycin, as represented by the following formula, where D is Formula 157

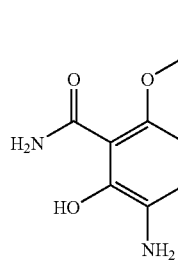
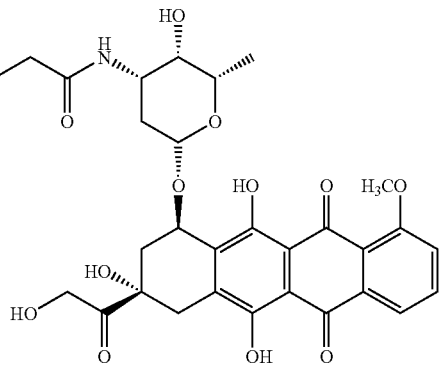

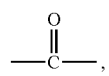

and E and G are a covalent bond:

Formula 158

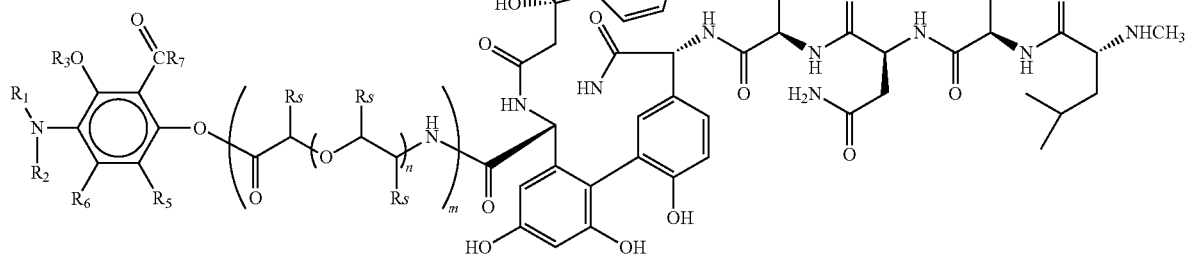

where the Linking Portion is connected to the Bone Targeting Portion ($R_T$) at $R_4$; where: D and G are

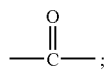

E is —(CH$_2$)$_3$—; m is 1; n is 2; each $R_S$ is hydrogen; $R_1$, $R_2$, $R_3$, $R_5$, and $R_6$ are each H; $R_7$ is NO$_2$; and where $R_4$ is derived from doxorubicin.

The Bone Active Portion derived from vancomycin can be vancomycin less a hydroxyl, allowing the Bone Active Portion to be connected to the remainder of the compound, while maintaining one or more activities generally associated with free vancomycin.

Another exemplary compound of the presently-disclosed subject matter can be represented by the following formula:

Formula 159

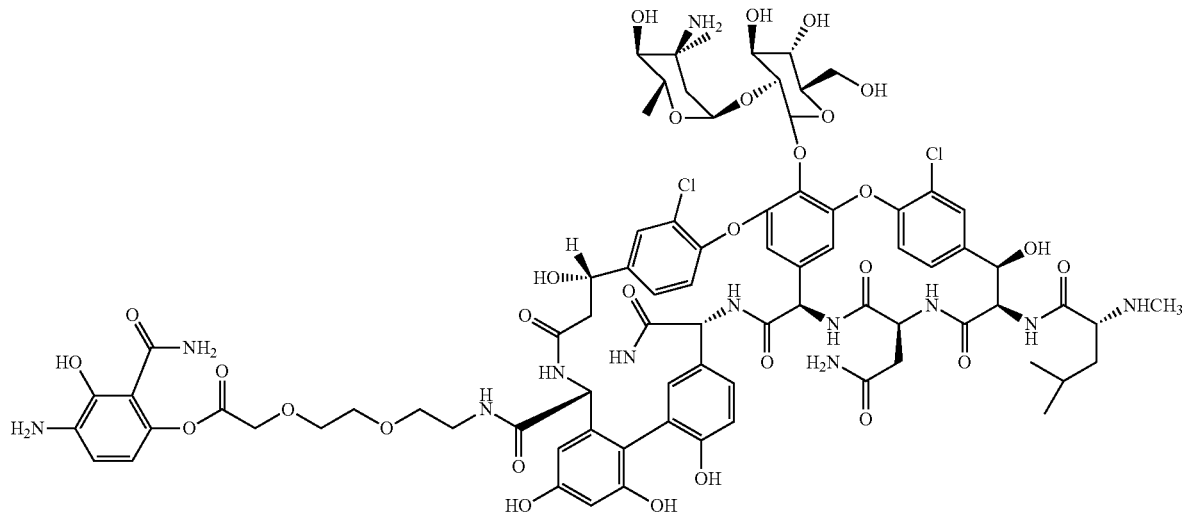

where the Linking Portion is connected to the Bone Targeting Portion ($R_T$) at $R_4$; where: D is

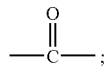

E and G are a covalent bond; m is 1; n is 2; each $R_S$ is hydrogen; $R_1$, $R_2$, $R_3$, $R_5$, and $R_6$ are each H; $R_7$ is $NO_2$; and where $R_A$ is derived from vancomycin.

As described above, in some embodiments the compounds of the presently-disclosed subject matter are characterized by at least one active portion. The Bone Targeting Portion ($R_T$) has the ability to bind to calcium with a tendency to accumulate in bone and to incorporate into its crystal lattice. In some embodiments, the compounds include an additional active portion. The Bone Active Portion ($R_A$) can be derived from a bone active agent, which interacts with bone and affects bone metabolism. For example, if the Bone Active Portion ($R_A$) is derived from vitamin D, then its interaction with bone tends to strengthen and increase bone formation. On the other hand, the steroids contemplated by the presently-disclosed subject matter exhibit bone activity and can both inhibit bone resorption and stimulate bone formation. In addition, the carbonic anhydrase inhibitors contemplated by the presently-disclosed subject matter inhibit the enzyme carbonic anhydrase, which catalyzes the reversible hydration of carbon dioxide to carbonic acid and thus it is an inhibitor of bone resorption. Other bone active agents contemplated by the presently-disclosed subject matter, e.g., listed in Tables A-D, exert their known effects in a manner relatively specific to bone.

The performance of the compounds of the presently-disclosed subject matter can be facilitated, first by the Bone Targeting Portion ($R_T$), which localizes the compound at the bone site. Once anchored at the bone site, the Bone Active Portion ($R_A$) of the molecule, i.e., the bone active domain, interacts with and affects the bone.

In some embodiments, the compounds of the presently-disclosed subject matter can be pro-drugs. In this regard, the compound can be formulated such that the Bone Active Portion ($R_A$) exhibits no initial activity; however, when subjected to the enzymatic or hydrolytic conditions occurring at the bone site, the Bone Active Portion ($R_A$) will become active.

Without wishing to be bound by theory or mechanism, it is believed that the compounds of the presently-disclosed subject matter interact with the calcium in the bone in the following manner, which is described using an exemplary embodiment of the presently-disclosed subject matter:

Formula 160

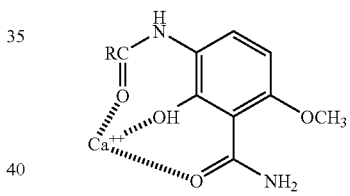

As shown by the example, in some embodiments, three positions of the Bone Targeting Portion ($R_T$) can interact with calcium, facilitating the localization of the compound to bone. In the exemplary compound of Formula 160, the $R_4$ group ($CH_3$) is not depicted as interacting with the calcium; however, it is contemplated that the $R_4$ group can affect the affinity for bone. Without wishing to be bound by theory or mechanism, it is believed that the affinity for bone can be modulated, in part, by strategically selecting the $R_4$ group based on its electron-donating properties. The greater the electron donating properties of the $R_4$ group, the greater the affinity for bone, i.e., a negative charge is directed from the side of the Bone Targeting Portion having the $R_4$ group, towards the side of the Bone Targeting Portion thought to interact with the calcium, thereby creating a stronger interaction between the Bone Targeting Portion and the positively-charged calcium.

Some embodiments of compounds of the presently-disclosed subject matter are described with reference to formulas. Some formulas include portions depicting a particular stereoisomer of one or more moieties of the compound. Such depicted stereoisomers are representative of some embodiments of the compounds; however, the formulas are intended to encompass all active stereoisomers of the depicted compounds.

The compounds of the presently-disclosed subject matter can in some embodiments contain one or more asymmetric carbon atoms and can exist in racemic and optically active forms. Depending upon the substituents, the present compounds can form addition salts as well. All of these other forms are contemplated to be within the scope of the presently-disclosed subject matter. The compounds of the presently-disclosed subject matter can exist in stereoisomeric forms and the products obtained thus can be mixtures of the isomers.

The presently-disclosed subject matter includes methods for treating bone conditions in a subject. Methods include administering to the subject an effective amount of a compound of the presently-disclosed subject matters, as described above.

As used herein, the terms treatment or treating relate to any treatment of a bone condition of interest, including but not limited to prophylactic treatment and therapeutic treatment As such, the terms treatment or treating include, but are not limited to: preventing a condition of interest or the development of a condition of interest; inhibiting the progression of a condition of interest; arresting or preventing the development of bone condition of interest; reducing the severity of condition of interest; ameliorating or relieving symptoms associated with a condition of interest; and causing a regression of the condition of interest or one or more of the symptoms associated with the condition of interest. Examples of conditions of interest are noted herein. For example, in some embodiments, the condition of interest can be a primary or secondary bone condition of interest.

As noted above, in some embodiments, the bone condition of interest is a metabolic bone disease (MBD), wherein treatment can result in an anti-catabolic effect and/or an anabolic effect. In some embodiments, the bone condition of interest is a bone fracture, wherein treatment can result in an anabolic effect. In some embodiments, the bone condition of interest is a bone cancer, wherein treatment can result in an anti-cancer effect. In some embodiments, the bone condition of interest is a bone microbial infection, wherein treatment can result in an anti-microbial effect. Other conditions of interest and/or desired effects are noted herein and/or are contemplated by the presently-disclosed subject matter.

As used herein, the term effective amount refers to a dosage sufficient to provide treatment for the bone condition of interest being treated. This can vary depending on the patient, the condition, and the treatment being effected. The exact amount that is required will vary from subject to subject, depending on the species, age, and general condition of the subject, the particular carrier or adjuvant being used, mode of administration, and the like. As such, the effective amount will vary based on the particular circumstances, and an appropriate effective amount can be determined in a particular case by one of ordinary skill in the art using only routine experimentation.

As noted above, in some embodiments, the compound can be provided as a pharmaceutically-acceptable salt or solvate. Suitable acids and/suitable bases, as will be known to those of ordinary skill in the art, are capable of forming salts of the compounds described herein, e.g., hydrochloric acid (HCl), sodium hydroxide. A solvate is a complex or aggregate formed by one or more molecules of a solute, e.g. a compound or a pharmaceutically-acceptable salt thereof, and one or more molecules of a solvent. Such solvates can be crystalline solids having a substantially fixed molar ratio of solute and solvent. Suitable solvents will be known by those of ordinary skill in the art, e.g., water, ethanol.

As will be understood by those of ordinary skill in the art, a dosage regimen can be adjusted to provide an optimum treatment effect and can be administered daily, biweekly, weekly, bimonthly, monthly, or at other appropriate time intervals. As will be understood by those of ordinary skill in the art, compounds of the presently-disclosed subject matter can be administered orally, intravenously, intramuscularly, subcutaneously, or by other art-recognized means.

For oral administration, the compositions can take the form of, for example, tablets or capsules prepared by a conventional technique with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycollate); or wetting agents (e.g., sodium lauryl sulphate). The tablets can be coated by methods known in the art. Liquid preparations for oral administration can take the form of, for example, solutions, syrups or suspensions, or they can be presented as a dry product for constitution with water or other suitable vehicle before use. Such liquid preparations can be prepared by conventional techniques with pharmaceutically acceptable additives such as suspending agents (e.g., sorbitol syrup, cellulose derivatives or hydrogenated edible fats); emulsifying agents (e.g. lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate. Preparations for oral administration can be suitably formulated to give controlled release of the active compound. For buccal administration the compositions can take the form of tablets or lozenges formulated in conventional manner.

The compounds can also be formulated as a preparation for injection. Thus, for example, the compounds can be formulated with a suitable carrier. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants.

As used herein, the term subject refers to humans and other animals. Thus, veterinary uses are provided in accordance with the presently disclosed subject matter. The presently disclosed subject matter provides for the treatment of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

The presently-disclosed subject matter includes a method of making a bone-targeted compound for the treatment of a bone condition of interest. A bone active agent is selected, from which the bone active portion of the compound will be derived. An appropriate stably-stored compound of the presently-disclosed subject matter is selected, wherein $R_A$ is a protecting group, hydrogen, or hydroxyl, as described above. The stably-stored compound and the bone active agent are used to prepare a compound, wherein $R_A$ is a bone active portion derived from the selected bone active agent. In some embodiments, the selected bone active agent has an independent ability to treat the bone condition of interest; however, the resulting compound having the bone active portion derived from the bone active agent has an enhanced ability to target bone and treat the bone condition of interest, and a reduced capacity for negative side effects. In this regard, the methods and compounds of the presently-disclosed subject matter can be used to salvage once-promising treatment compounds that were abandoned due to insufficient bioavailability, insufficient bioactivity, and/or unacceptable side effects.

The presently-disclosed subject matter is further illustrated by the following specific but non-limiting examples. The following examples may include compilations of data that are representative of data gathered at various times during the course of development and experimentation related to the presently-disclosed subject matter. The following examples include some examples that are prophetic.

EXAMPLES

Syntheses. The compounds of the presently-disclosed subject matter can be prepared in accordance with the exemplary schemes set forth in the Examples herein, and by techniques known to those of ordinary skill in the art.

Exemplary Synthesis where $R_A$ is a Protecting Group

The following is exemplary, where $R_A$ is the Protecting Group, FMOC. About 2.5 g of FMOC-8-amino-3,6-dioxaoctanoic acid (Peptides International, Inc., Louisville, Ky.), about 0.9 g of hydroxybenzatriazol (HOBt), about 2.9 g of benzotriazole-1-yl-oxy-tris-(dimethylamino)-phosphonium hyexafluorophosphate (BOP), and about 1.1 ml diisopropylethylamine (DIEA) are dissolved in about 20 ml dimethylformamide (DMF). In a separate flask, about 0.89 g of 2-hydroxy-6-methoxy-3-amino-benzamide is dissolved in about 20 ml DMF. The two solutions are mixed together and stirred at room temperature for about 24 hours. Thin layer chromatography shows no indication of remaining starting material. The DMF is removed under vacuum, and crude product appears as a brown oil. The crude product is take up in ethyl acetate, and washed with brine 2x, 5% HCl 2x, and saturated NaHCO₃ 2x, the dried over sodium sulfate. The product is then condensed via rotary evaporation, resulting in a sticky brown oil. When the resulting oil is dissolved in methanol and triturated, a brownish-white solid precipitates. The mixture is stored at about 35° F. The precipitate is collected via vacuum filtration. The yield is approximately 2 g, about 75%. $^1$H NMR data: δ3.15, m, 2 H, 6' CH₂, δ3.44, t, J 5.98 Hz, 2 H, 5' CH₂, δ3.60, br s, 2 H, 4' CH₂, δ3.69, br s, 2 H, 3' CH₂, δ3.88, s, 3 H, C6 OCH₃, δ4.09, s, 2 H, 2' CH₂, δ4.19, q, J 6.59 Hz, 1 H, 9' CH, δ4.27, d, J 6.40 Hz, 2 H, 8' CH₂, δ6.54, d, J 8.97 Hz, 1 H, C5 H, δ7.31, m, 3 H, C14' H/C6 amide H, δ7.40, m, 2 H, C12'H, δ7.67, d, J 7.87 Hz, 2 H, C13' H, δ7.88, d, J 7.32 Hz, C11' H, δ8.18, d, J 8.60 Hz, 1 H, C4 H, δ8.29, s, 1H, Cl amide H, δ8.33, s, 1 H, Cl amide H, δ8.85, s, 1H, C3 amide H.

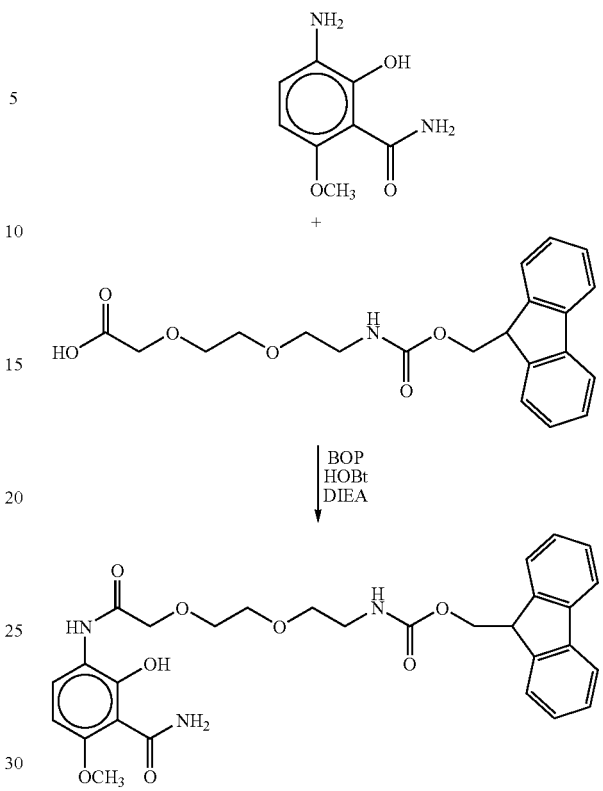

The following are exemplary for deprotection of compounds where $R_A$ is FMOC, where HCl salts are formed. About 1.8 g of FMOC-8-amino-3,6-dioxaoctanoic acid-BTA is dissolved in 20% piperidine in DMF and stirred for about 20 minutes. The solvent is removed and fresh piperidine solution is added to repeat the deprotection reaction. Deprotection is performed about three times. After the final solvent removal, a solid product appears and diethyl ether is added. The mixture is acidified with 7N HCl in methanol and decanted. After triturating in dichloromethane, an off-white precipitate is collected via vacuum filtration. The yield is about 0.94 g, about 86%. $^1$H: δ2.96, t, 2 H, 6' CH₂, δ3.65, m, 4 H, 4'/5' CH₂, δ3.73, m, 2 H, 3' CH₃, δ3.89, s, 3 H, C6 OCH₃, δ4.12, 2 H, 2' CH₂, δ6.56, d, J 8.91 Hz, 1 H, C5 H, δ8.17, d, J 9.15 Hz, 1 H, C4 H, δ8.30, s, 1 H, Cl amide H, δ8.35, s, 1 H, Cl amide H, δ8.87, s, 1 H, C3 amide H, $^{13}$C, δ39.22; C6', δ57.03, C6-OCH₃, δ67.34, C5', δ70.46, C4', δ70.93, C3', δ85.93, C2', δ99.21, C6, δ156.70, Cl', δ159.83, C4.

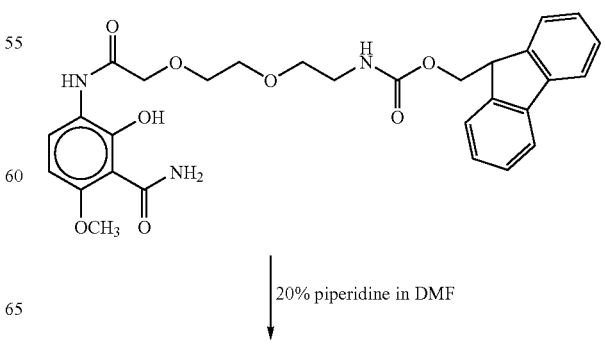

133
-continued

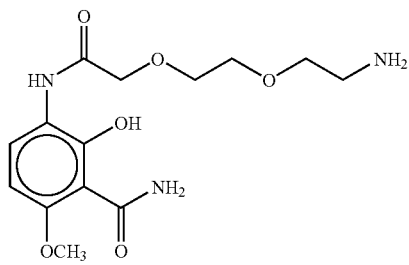

↓ 7N HCl in MeOH

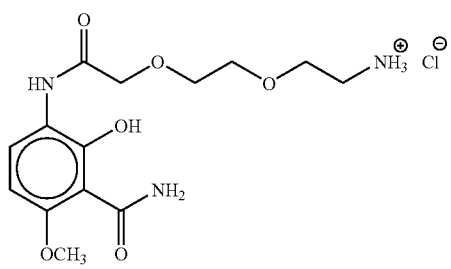

The procedures described above were used for the following transformations as well:

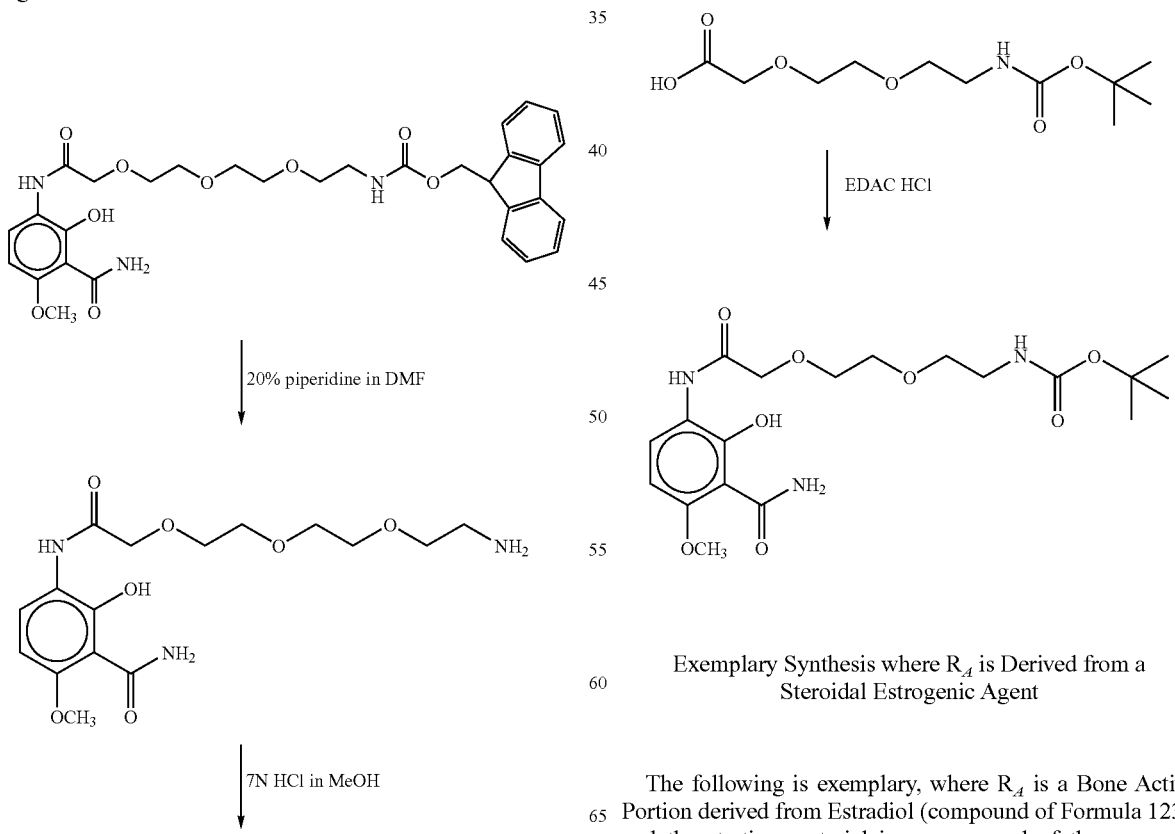

↓ 7N HCl in MeOH

134
-continued

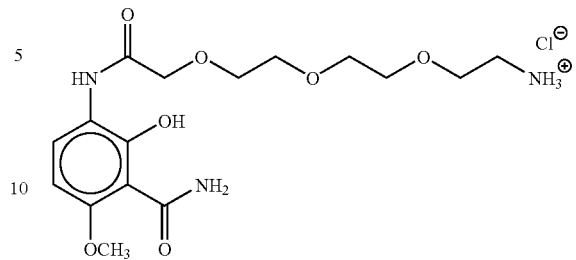

The following is exemplary, where $R_A$ is t-BOC:

[Formula 2, where $R_1$, $R_2$, $R_3$, $R_5$, and $R_6$ = H; $R_4$ = CH$_3$; and $R_2$ = NH$_2$]

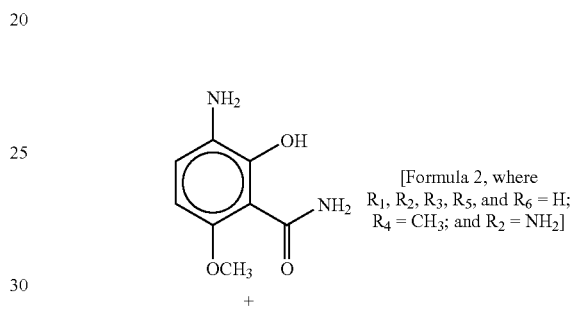

Exemplary Synthesis where $R_A$ is Derived from a Steroidal Estrogenic Agent

The following is exemplary, where $R_A$ is a Bone Active Portion derived from Estradiol (compound of Formula 123), and the starting material is a compound of the presently disclosed subject matter, where $R_A$ is a protecting group.

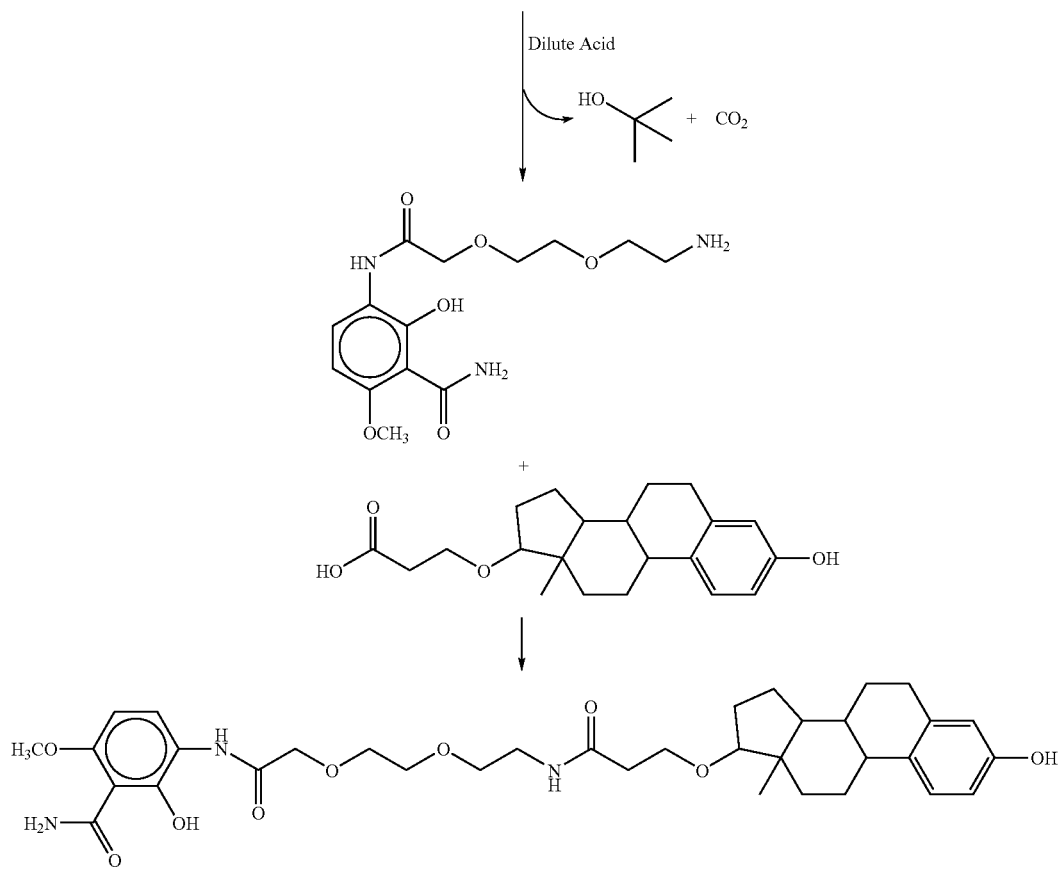
The following is another exemplary manner in which the compound of Formula 123 can be prepared.
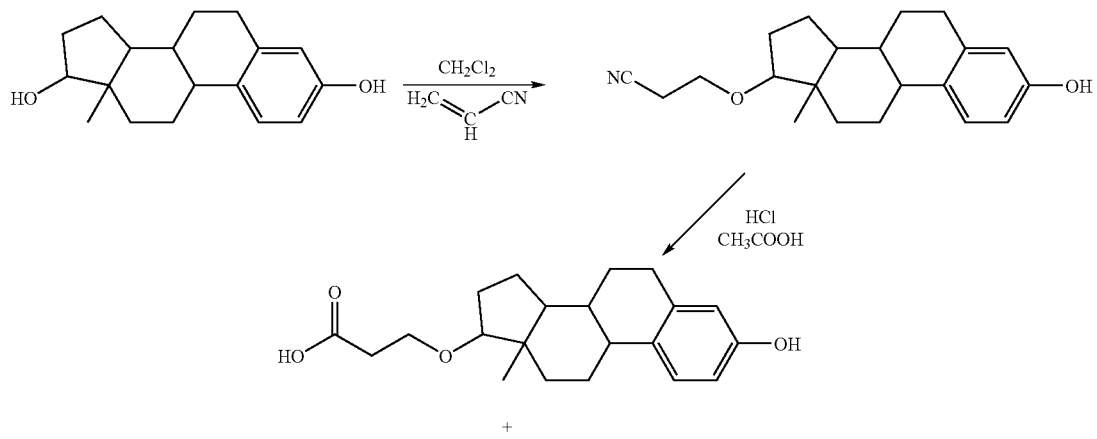

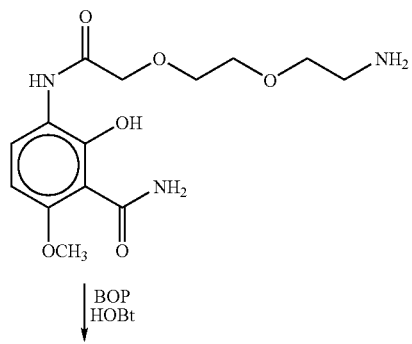

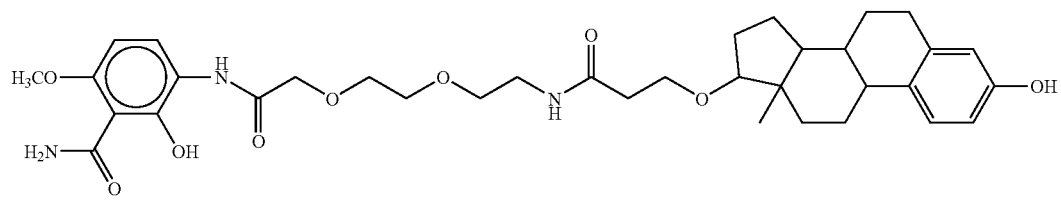

The following is exemplary for preparation of the compound of Formula 123. In a round-bottom flask about 0.48 g (1.4 mmol) 17-β-estro-O-propanoic acid, about 0.38 g (2.8 mmol) hydroxybenzotriazole (HOBt), about 1.24 g (2.8 mmol) benzotriazole-1-yl-oxy-tris-(dimethylamino)-phosphonium hexafluorophosphate (BOP), and about 0.5 g (1.4 mmol) NBR-VI-232-1 (synthesis described herein) were combined. The dry mixture was dissolved in about 20 mL dimethylformamide (DMF) then about 488 µL (2.8 mmol) of N,N-diisopropylethylamine (DIEA) was added. The reaction was allowed to stir at room temperature for about 48 hours.

The reaction solvent was removed under vacuum and the resulting yellow oil was taken up in about 50 mL ethylacetate (EtOAc). It was then washed with brine 2×, 5% HCl 2×, and saturated sodium bicarbonate 2× and dried over sodium sulfate. After gravity filtration, the filtrate was condensed via rotary evaporation to yield a sticky oil. Upon trituration of the oil in cold methanol, product NBR-VI-240-1 precipitated out as an off-white solid. The product was collected via vacuum filtration. Yield: 510 mg, 55.7%. $^1$H: δ0.66, s, 3 H, angular methyl, δ1.10, m, δ1.16-1.32, m, δ1.35, m, δ1.55, m, δ1.73, m, δ1.86-1.97, m, δ2.04, t, δ2.19, d, δ2.27, t, J 6.47 Hz, 2H, 8' $CH_2$, δ2.68, m, 2 H, δ3.21, q, J 5.61 Hz, 2 H, 6' $CH_2$, δ3.44, t, J 5.86 Hz, 2 H, 5' $CH_2$, δ3.55, m, 1 H, C9' $H_1$, δ3.60, m, 2 H, 4' $CH_2$, δ3.69, m, 2 H, 3' $CH_2$, δ3.63, m, 1 H, C9'$H_2$, δ3.87, s, 3 H, C6 $OCH_3$, δ4.09, s, 2 H, 2' $CH_2$, δ6.42, br s, 1 H, C18' H, δ6.49, dd, $J_1$ 8.54 Hz, $J_2$ 2.20 Hz, 1 H, C20' H, δ6.54, d, J 9.03 Hz, 1 H, C5 H, δ7.01, J 8.54 Hz, 1 H, C21' H, δ7.81, t, J 5.61 Hz, 1 H, C6' amide H, δ8.19, d, J 9.03 Hz, 1 H, C4 H, δ8.29, s, 1 H, Cl amide H, δ8.33, s, 1 H, Cl amide H, δ8.85, s, 1 H, C3 amide H, δ8.96, s, 1 H, C19' OH. Thin-Layer Chromatography: $R_f$=0.62 in EtOAc:Acetone:Methanol, 7:7:5.

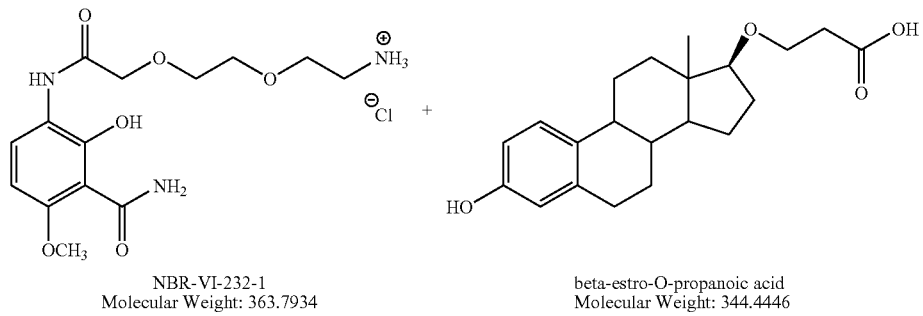

NBR-VI-232-1
Molecular Weight: 363.7934 beta-estro-O-propanoic acid
Molecular Weight: 344.4446

BOP
HOBt
DIEA

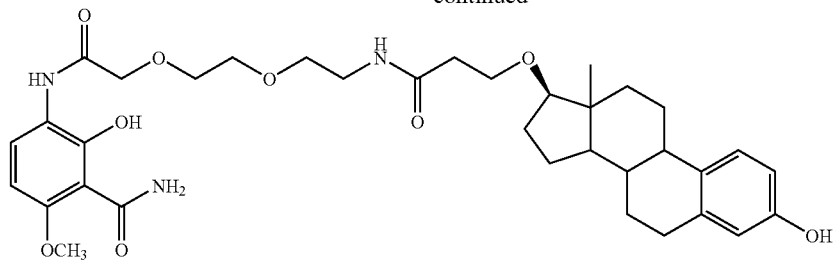

NBR-VI-240-1
Molecular Weight: 653.7624

The compound of Formula 124 can be prepared in the following manner.

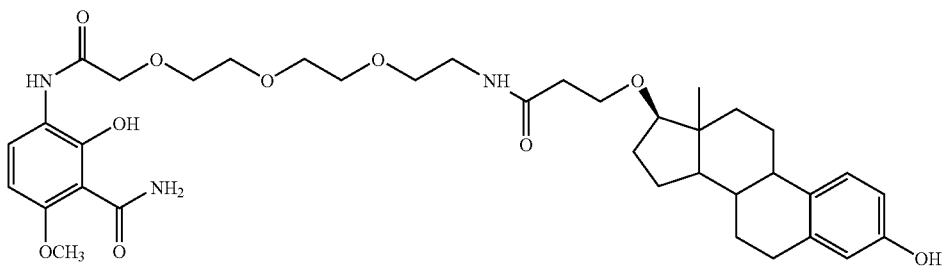

The compound of Formula 123 was formed as described in above. The product was oily, but after sitting in hexane at 4° C., a light gray precipitate could be collected via vacuum filtration. This solid was subjected to thin-layer chromatography and $^1$H NMR for characterization. TLC: $R_f$=0.64 in EtOAc:Acetone:MeOH (18:2:5) and a 1-dimensional $^1$H NMR spectrum confirms the structure. The compound begins decomposing at 93° C. and melts from 97-100°. The yield was about 50 mg, 14.4%.

Exemplary Synthesis where $R_A$ is a Protecting Group

A exemplary compound of the presently-disclosed subject matter can be prepared in the following manner.

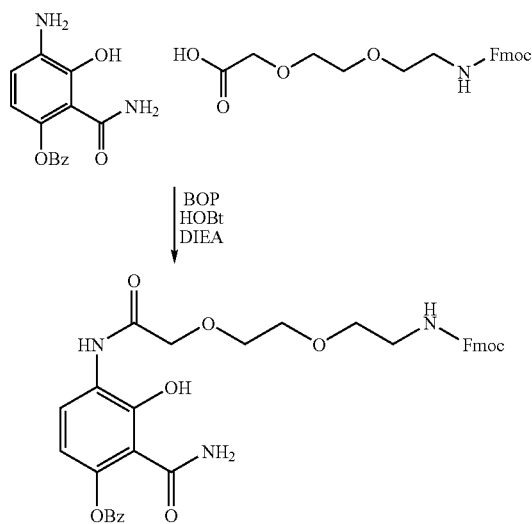

In a 200 mL round-bottom flask were dissolved 5.00 g (13 mmol) Fmoc-MiniPEG, 2.95 g (10 mmol) of 2-hydroxy-6-benzyloxy-3-amino-benzamide hydrochloride (BTA RIC-T3), 3.51 g (26 mmol) HOBt, 11.5 (26 mmol) BOP, and 4.53 mL (26 mmol) DIEA, in 70 mL of DMF. The homogeneous solution was allowed to stir at room temperature overnight.

The DMF was removed under vacuum after ~22 hours to give a dark brown oil. The oil was dissolved in 100 mL EtOAc and washed with brine 2×, 5% HCl 2×, and saturated NaHCO$_3$ 2×, then dried over sodium sulfate and concentrated via rotary evaporation to give a sticky brown residue. The residue was taken up in methanol and triturated. An off-white precipitate (NBR-VI-227-2) was collected and washed with MeOH via vacuum filtration. The yield was about 4.67 g, 70%. $^1$H: δ3.15, t, J 5.50 Hz, 2H, 6' CH$_2$, δ3.44, t, J 5.73 Hz, 2 H, 5' CH$_2$, δ3.59, br s, 2H, 4' CH$_2$, δ3.67, br s, 2H, 3' CH$_2$, δ4.19, t, J 6.71 Hz, 1 H, C9' H, 64.27, d, J 6.83 Hz, 2 H, 2' CH$_2$, δ5.27, s, 2 H, C6 CH$_2$(benzyl), δ6.64, d, J 8.78 H, 1 H, C5 H, δ7.31, m, 3H, C14' H/benzyl H$_c$, δ7.36, d, J 7.32 Hz, 1 H, 6' amide H, δ7.40, m, 4 H, C12' H/benzyl H$_b$, δ7.48, d, J 7.20 Hz, 2 H, benzyl H$_a$, δ7.67, d, J 7.20 Hz, 2H, C13' H, δ7.87, d, J 7.69 Hz, 2H, C11' H, δ8.13 Hz, d, J 4.52 Hz, 1H, C4 H, δ8.19, s, 1H, C1 amide H, δ8.36, s, 1 H, C1 amide H, δ8.86, s, 1H, C3 amide H.

The following are exemplary for deprotection of compounds where $R_A$ is FMOC, where HCl salts are formed. About 2.50 g (3.8 mmol) of NBR-VI-227-2 was dissolved and stirred in about 20 mL of 20% piperidine in DMF for 20 minutes before the solvent was removed under vacuum. The piperidine treatment and solvent removal were repeated twice more. After the final solvent removal, the mixture was taken up in ether and acidified with 7N HCl in MeOH. A white precipitate was collected via filtration, however the solid proved to be the Fmoc hydrocarbon. The remaining filtrate was concentrated and taken up in a small amount of methanol. It was then allowed to sit in MeOH at 4° C. for 48 hours. A solid/oil mixture resulted. The mixture was dried under vacuum for 1 hour, taken up in ether, then briefly exposed to dry ice-acetone bath and triturated. After some 10 minutes, a light purple precipitate was noted. This solid, NBR-VI-236-1, was collected via vacuum filtration. It was then recrystallized from methanol/ether to give off-white solid, NBR-VI-236-2. The yield was about 740 mg, 56.5%. $^1$H: $\delta$2.94, t, J 5.37 Hz, 2 H, 6' CH$_2$, $\delta$3.63, m, 4 H, 4'/5' CH$_2$, $\delta$3.71, m, 3' CH$_2$, $\delta$4.11, s, 2 H, 2' CH$_2$, $\delta$5.29, s, 2 H, benzyl CH$_2$, $\delta$6.65, d, J 9.15 Hz, 1 H, C5 H, $\delta$7.36, d, J 7.20 Hz, 1 H, benzyl H$_c$, $\delta$7.41, t, J 7.44 Hz, 2 H, benzyl H$_b$, $\delta$7.49, d, J 7.69 Hz, 2 H, benzyl H$_a$, $\delta$8.12, d, J 9.03 Hz, 1 H, C4 H, $\delta$8.20, s, 1 H, Cl amide H, $\delta$8.37, s, 1 H, Cl amide H, $\delta$8.88, s, 1 H, C3 amide H.

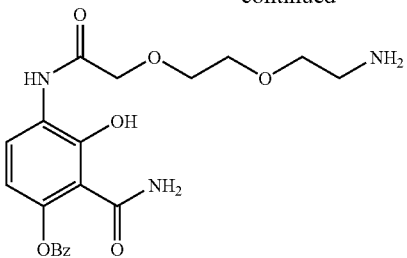

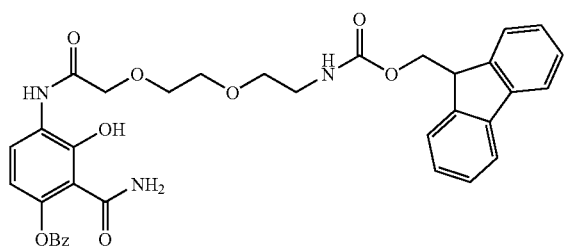

Exemplary Synthesis where R$_A$ is Derived from a Steroidal Estrogenic Agent

The compound of Formula 125 (product NBR-VI-247-2) can be prepared in the following manner.

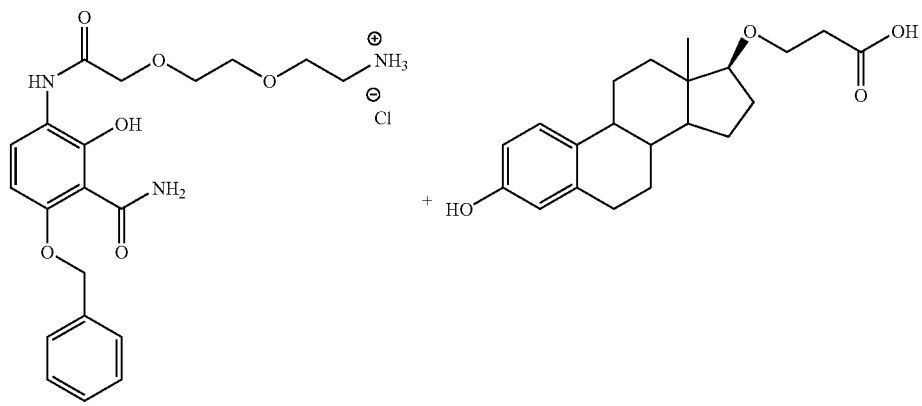

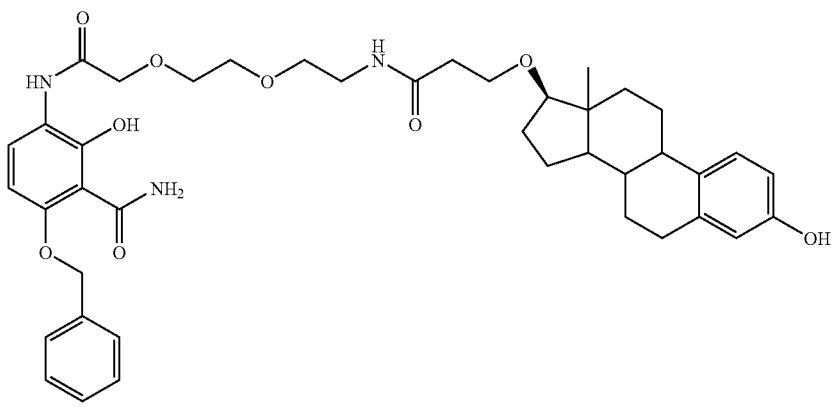

NBR-VI-247-2
Molecular Weight: 729.8583

In a 25 mL round-bottom flask was dissolved 300 mg (0.7 mmol) NBR-VI-236-2, 250 mg (0.7 mmol) β-estro-propanoic acid, 620 mg (1.4 mmol) BOP, 189 mg (1.4 mmol) HOBt, and 244 μl DIEA in 15 mL of DMF. The reaction was allowed to stir at room temperature for two days, after which time the solvent was removed under vacuum. The resulting oil was taken up in ethyl acetate and washed with brine 2×, 5% HCl 2×, and saturated NaHCO$_3$ 2×. The organic layer was then dried over Na$_2$SO$_4$, filtered, and concentrated. Product NBR-VI-2471 resulted as an oil. The product was combined with another oily product (NBR-VI-246-1) obtained from a previous experiment, then subjected to column chromatography (solvent system=EtOAc:Acetone, 9:1). After the appropriate fractions were pooled and concentrated, sticky gray oil NBR-VI-247-2 was obtained. The yield was about 365 mg, 71.4%

The following is exemplary, where R$_A$ is a Bone Active Portion derived from Estradiol.

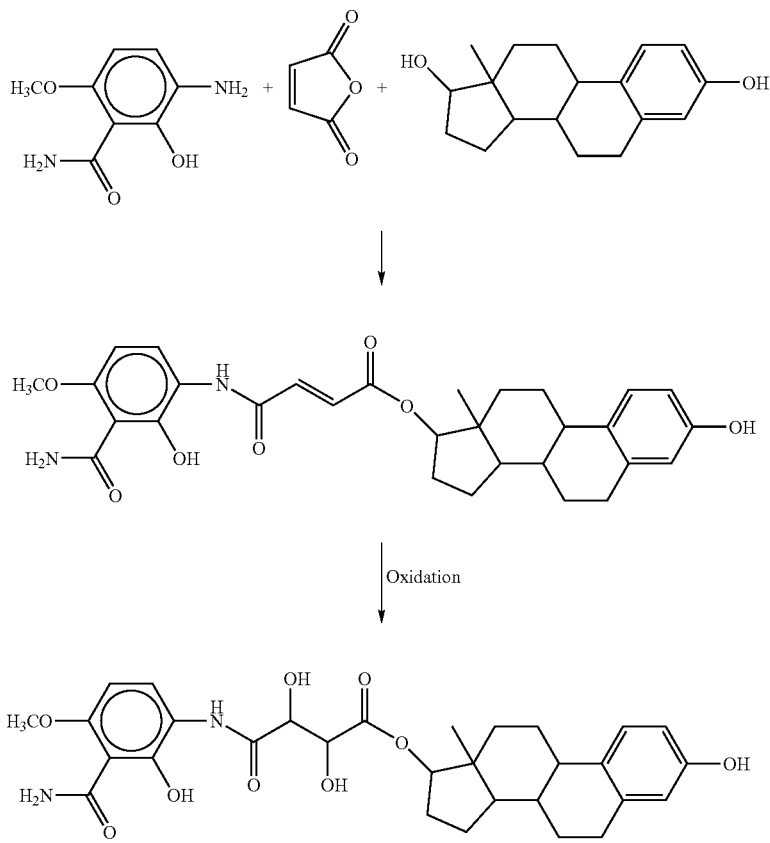

Exemplary Synthesis where $R_A$ is Derived from a Nonsteroidal Estrogenic Agent

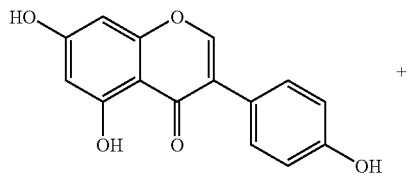

+

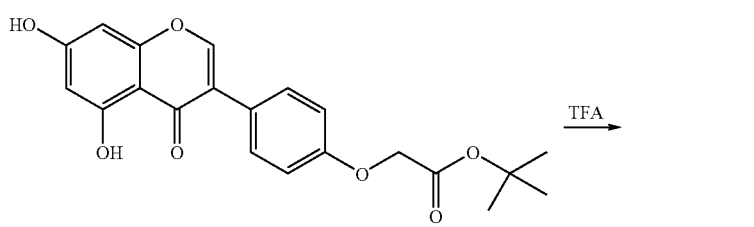

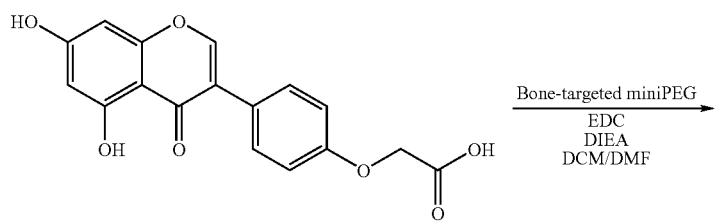

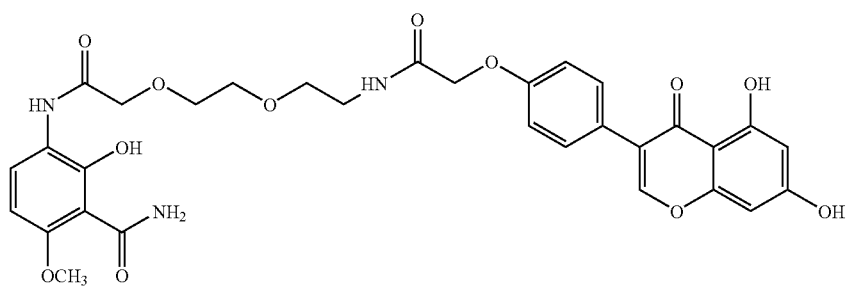

-continued

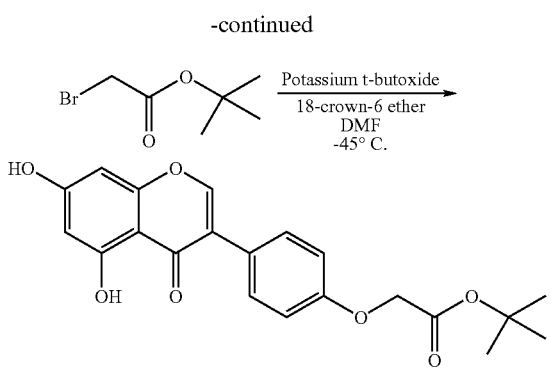

The compound wherein $R_A$ was derived from genistein was prepared as follows. Genistein (500 mg, 1.8 mmol) was stirred in 50 mL of DMF along with potassium t-butoxide (438 mg, 3.9 mmol) at ambient temperature under nitrogen for 3 hours. The reaction solution was then cooled to −45° C. in a dry ice-acetonitrile bath and t-butyl bromoacetate (274 µL, 1.8 mmol) was added. The reaction was allowed to stir for 18 hours in the dry ice bath, slowly warming to room temperature. The solvent was then removed under vacuum and the resulting residue was taken up in water and acidified with 5% HCl (aq). An off-white precipitate was collected via vacuum filtration. Both thin-layer chromatography and proton NMR were conducted to confirm that desired protect had been prepared. The off-white precipitate product was used in the following step.

The off-white precipitate product produced as described in the preceding paragraph (100 mg, 0.3 mmol) was stirred in 10 mL of dichloromethane (DCM) and 3 mL trifluoroacetic acid for 45 minutes at room temperature. The solvent was then removed in vacuo and the residue was taken up in DCM and evaporated to dryness three times to yield a light yellow product.

The bright yellow product (100 mg (est.), 0.3 mmol) was stirred in 5 mL DCM along with diisopropylethylamine (DIEA; 157 µL, 0.9 mmol) and 1-ethyl-3-(3-dimethylaminopropyl) carbodiimide (EDC; 115 mg, 0.6 mmol). After 5 minutes, a bone-targeted miniPEG compound (109 mg, 0.3 mmol) was added. DMF (7 ml) was added to assist with solubilizing the miniPEG compound. After two hours, the reaction mixture was filtered and the filtrate washed with brine 2×, 5% HCl 2×, and saterated sodium bicarbonate 2×, then dried over sodium sulfate. The organic solvent was removed under vacuum and the resulting white residue was characterized with TLC and $^1$H NMR, which indicated that the desired product had been made.

Exemplary Synthesis where $R_4$ is Derived from a Nitric-Oxide Agent

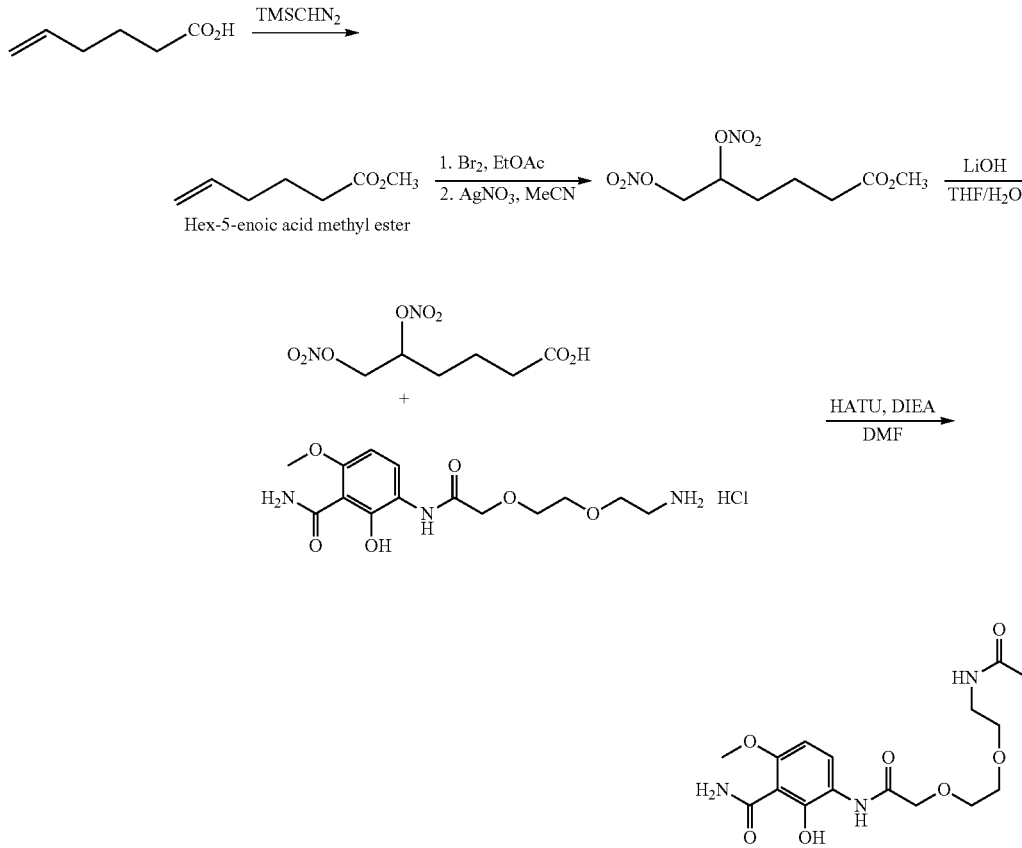

Hex-5-enoic acid methyl ester was prepared as follows. Hex-5-enoic acid (2.00 g, 17.5 mmol) was dissolved in diethyl ether (8 mL) and methanol (4 mL) and cooled to 0° C. To this solution was added 2.0 M Trimethylsilyl diazomethane (9 mL) dropwise. It was noted that a yellow TMS-diazomethane solution dissipates upon stirring with the reaction mixture, and the reaction is deemed complete when the yellow color persists. Caution should be observed, as the reaction is associated with vigorous gas evolution. When the yellow color persists in the reaction mixture, TLC analysis was conducted and confirmed consumption of the acid. The solvent was evaporated under reduced pressure carefully (product is somewhat volatile) and replaced with ethyl acetate. The solution was washed with saturated $NaHCO_3$, dried, and the filtrate was used directly in the next step. $^1H$ NMR (400 MHz) $CDCl_3$ δ 5.45 (m, 1H), δ 4.9 (m, 2H), δ 3.65 (s, 3H), δ 2.20 (t, 2H), δ 2.05 (m, 2H), δ 1.70 (m, 2H).

5,6 dinitroxyhexanoic acid was prepared as follows. A 0.37 M solution of hex-5-enoic acid methyl ester in ethyl acetate (30 mL, 11.1 mmol) was treated with $Br_2$ (1.78 g, 11.1 mmol) dropwise. The color dissipated after stirring and upon full addition a light yellow color resulted. After stirring for 1 h at room temperature, the solvent was switched to acetonitrile (40 mL) and $AgNO_3$ (7.5 g, 44.4 mmol) was added in one portion. The heterogeneous mixture was refluxed for 12 h, cooled to rt and filtered. The filtrate was concentrated and switched with ethyl acetate so that it could be washed with water three times (40 mL). The organic layer was dried, concentrated and used directly in the next step. The crude yellow oil (assume 11.1 mmol) was treated with THF (3 mL) and water (1 mL) and cooled to 0° C. LiOH monohydrate (0.50 g, 12 mmol) was added in one portion and stirred at 0° C. for 1 hour and allowed to warm to rt. TLC confirmed the disappearance of SM. The reaction mixture was concentrated to remove THF, ethyl acetate and 0.25M $KHSO_4$ was added. The organic layer was dried and concentrated to provide a light brown oil. The key structural components of the compound were confirmed and the material was used in the following step.) $^1H$ NMR (400 MHz) CDCl3 δ 5.35 (m AMX like, 1H), δ 4.65 (m AMX like, 1H), δ 4.40 (m AMX like, 1H), δ 2.40 (m, 2H), δ 2.05 (m, 4).

The dinitroxy compound was prepared as follows. The crude acid from above (about 11.1 mmol) was treated with N,Ndiisopropylethylamine (3.8 ml, 2.2 mmol), BT-2-(peg2)-$NH_3Cl$ (4.04 g, 11.1 mmol), and DMF (20 mL). The solution was cooled to 0° C. and to this solution was added HATU (4.2 g, 11.1 mmol). After stirring for 12 h, the reaction was deemed complete by LC/MS. The reaction was added to a separatory funnel already charged with 100 mL of EtOAc and 100 mL of water. The layers were separated and the organic layer was washed one time with saturated $NaHCO_3$, followed by 10% citric acid. The organic layer was then dried with $MgSO_4$, filtered and concentrated. The crude product was purified by preparative HPLC to provide 0.26 g of pure product.

Exemplary Synthesis where $R_A$ is Derived from an Androgen

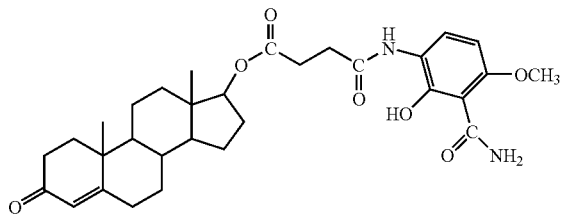

The compound wherein $R_A$ was derived from testosterone was prepared as follows. Four grams of testosterone-17-hemisuccinate was dissolved in 25 mL dimethylformanide (DMF) and 1.4512 g of N-hydroxybenzenetriazine (HOBT) was added. The mixture was cooled to 0-5° C. and was stirred for 30 minutes. Diisopropylcarbodiimide (1.354 g) was added, followed by stirring for 30 minutes at 0-5° C. A solution of 1.955 g of 3-amino-2-hydroxy-6-methyoxybenzamide in 10 mL DMF was added and the mixture was stirred for 24 hours at room temperature. The reaction was stopped by addition of 200 mL $H_2O$ and the mixture was extracted with 3×100 mL portions of ethyl acetate which was then washed with $H_2O$, then 2×25 mL portions of 10% aqueous $NaHCO_3$, then with $H_2O$ again. The ethyl acetate solution was dried over $Na_2SO_4$ and concentrated under reduced pressure.

Exemplary Synthesis where $R_A$ is Derived from a Carbonic Anhydrase Inhibitor

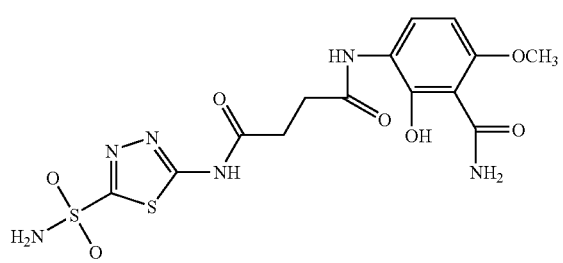

The compound wherein $R_A$ was derived from 2-amino-1,3,4-thiadiazole-5-sulfonamide was prepared as follows. 2-amino-1,3,4-thiadiazole-5-sulfonamide is reacted with succinic anhydride to form the succinamide derivative, 2-(4-carboxypropionylamino) 1,3,4-thiadiazole-5-sulfonamide. This product is reacted with 3-amino-2-hydroxy-6-methoxy-benzamide in the presence of diisopropylcarbodiimide to form the above-identified compound.

Exemplary Synthesis where $R_A$ is Derived from a Steroid

Compounds of the presently-disclosed subject matter including a Bone Active Portion derived from a steroid can be prepared in the following manner. A steroid of interest is identified. Steroids can include a substituted carbon ring system of 18 to 27 carbons, which can be saturated or partially unsaturated. With reference to the following steroid carbon ring skeleton, the ring system can be substituted at carbons 3, 10, 13, and 17 with pendant heteroatoms and/or branched chain hydrocarbons.

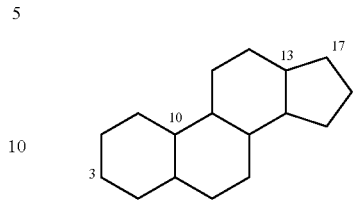

The steroid of interest can include at least one substitution at a carbon selected from 3, 10, 13, and 17. In some embodiments, the at least one substitution is at a carbon selected from 3 and 17. The at least one substitution can include between about 2 and about 20 atoms, having a terminal group such as an amino (—NH), hydroxyl (—OH), carboxyl (—COOH), sulfhydryl (—SH), or another group having an active hydrogen that will allow the steroid to undergo a condensation reaction with a compound of the presently-disclosed subject matter where $R_A$ is a protecting group, hydrogen, or hydroxyl.

As noted above, compounds in which $R_A$ is a protecting group can be stably stored until it becomes desirable to associate the compound with a Bone Active Portion. Similarly, as also noted above, salts derived from compounds in which $R_A$ is hydrogen or hydroxyl can be stably stored until it becomes desirable to associate the compound with a Bone Active Portion. For purposes of the present example, the compounds of the presently-disclosed subject matter where $R_A$ is a protecting group, hydrogen, or hydroxyl will be referred to as precursor compounds.

A precursor compound can be selected depending on the terminal group of the at least one substitution, as will be understood by those of ordinary skill in the art. For example, if the terminal group is an amino or a hydroxyl, it can be desirable to select a precursor compound including a carboxyl capable of condensing with the amino or the hydroxyl. The reaction can be conducted under amide- or ester-forming conditions, as are known to those of ordinary skill in the art.

Exemplary Synthesis where $R_A$ is Derived from an Anti-Cancer Agent

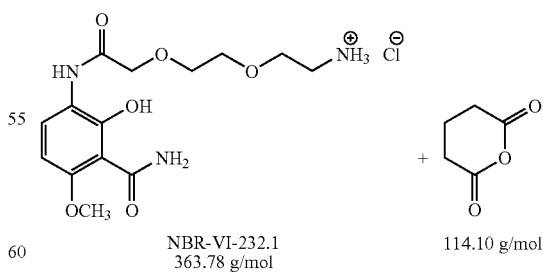

NBR-VI-232.1
363.78 g/mol 114.10 g/mol

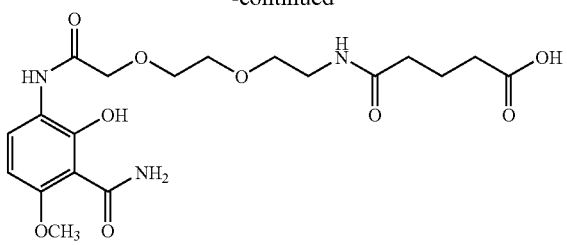

NBR-VI-262-1
Molecular Weight: 441.4324

In a 100 mL round-bottom flask was combined 500 mg (1.35 mmol) NBR-VI-232-1, 155 mg (1.35 mmol) glutaric anhydride, 590 µl DIEA, and 40 mL DMF. A homogeneous solution formed and it was stirred overnight at room temperature. Approximately 20 mL of 50% aq. MeOH was then added to the reaction solution and it was allowed to stir for 30 minutes more. The solvent was removed under vacuum to give a sticky brown solid. When triturated in methanol, off-white precipitate NBR-VI-262-1 was noted and collected via suction filtration. The yield was about 500 mg, 83%.

286 mg (0.65 mmol) of NBR-VI-262-1, along with 174 mg (1.29 mmol) of HOBt, 571 mg (1.29 mmol) BOP, and 225 µl DIEA, were dissolved in 25 mL DMF. After 5 minutes, 250 mg (0.43 mmol) of doxorubicin.HCl was added to the stirring solution. The reaction flask was wrapped in foil and purged with $N_2$. The flask was sealed and the reaction left stirring overnight.

After about 21 hours the DMF was removed under vacuum to give a red oil. The oil was taken up in EtOAc and triturated. A red solid precipitated. The mixture was centrifuged and the supernatant removed. The solid was washed with EtOAc twice more, each time removing the solvent by centrifugation/decanting. The red product, NBR-VI-269-1, was purified via reverse-phase column chromatography (Mega Bond Elut column). Product NBR-VI-274-1 was obtained after the chromatographic separation. The yield was about 120 mg, 28.8%.

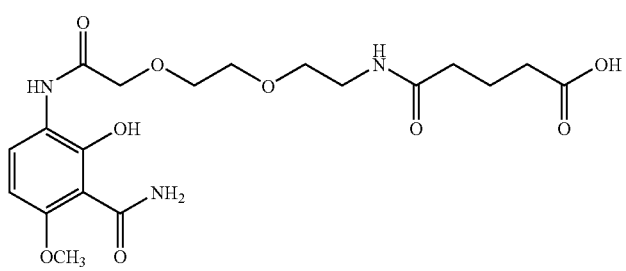

NBR-VI-262-1
Mol. Wt.: 441.43

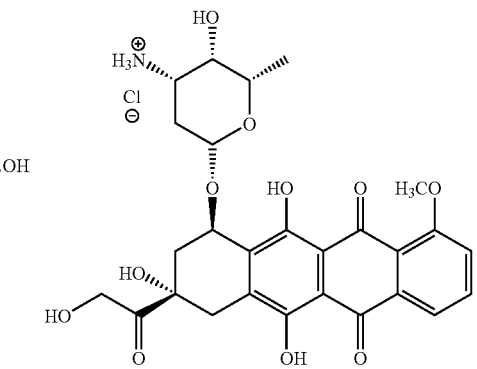

Molecular Weight: 579.9802

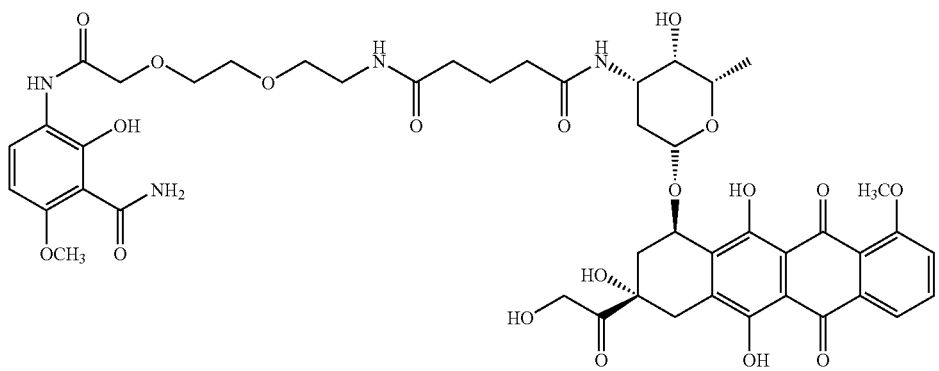

NBR-VI-274-1
Mol. Wt.: 966.94

Exemplary Synthesis where $R_A$ is Derived from an Antimicrobial Agent
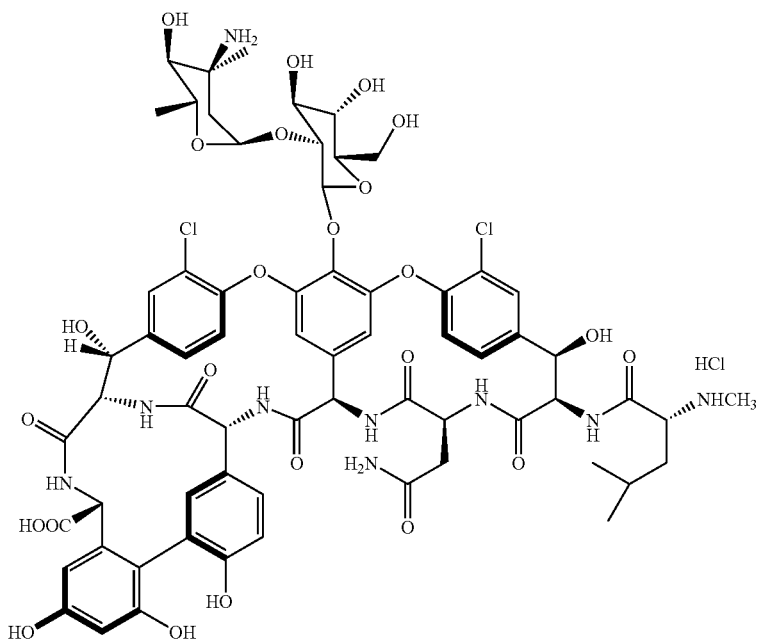
Vancomycin
$C_{66}H_{76}Cl_3N_9O_{24}$
Mol. Wt.: 1485.71
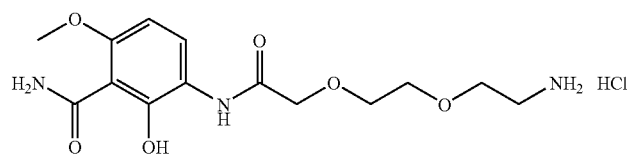
BT2-peg2-NH₃Cl
Mol. Wt.: 363.79
$\xrightarrow{\text{DIEA, HATU}}{\text{DMSO/DMF}}$
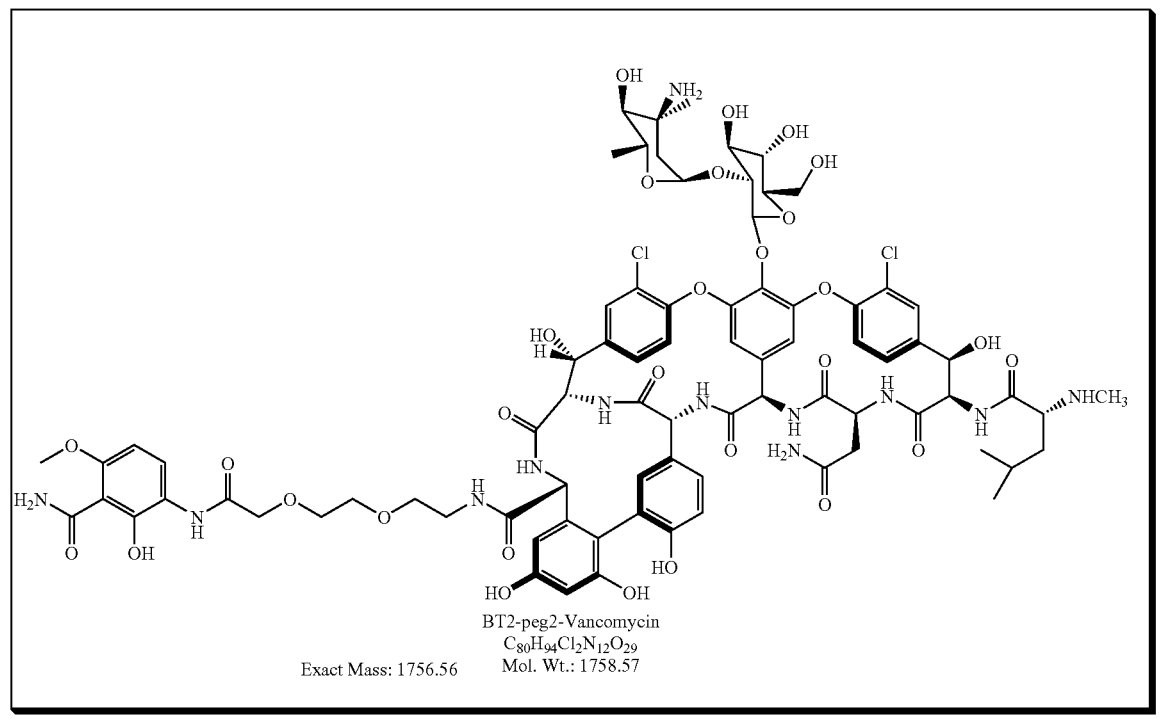
BT2-peg2-Vancomycin
$C_{80}H_{94}Cl_2N_{12}O_{29}$
Exact Mass: 1756.56    Mol. Wt.: 1758.57

The compound wherein $R_A$ was derived from vancomycin was prepared as follows. Vancomycin HCl (0.100 g, 67.3 µmol) was treated with N,Ndiisopropylethylamine (43 mg, 336 µmol), BT-2-(peg2)-NH$_3$Cl (37 mg, 101 µmol), DMSO (1 mL) and DMF (1 mL). The solution was cooled to 10° C. and to this solution was added HATU (38 mg, 101 µmol). After stirring for 12 h, the reaction was deemed complete by LC % MS. The reaction mixture was directly purified by preparative HPLC to provide 25 mg of the desired conjugate.

Targeting Bone

A Hydroxyapatite (HA) Binding Assay is used to determine whether compounds have an affinity for bone. Compounds of the presently-disclosed subject matter having a Bone Targeting Portion ($R_T$) are studied using the HA Binding Assay. A $10^{-3}$ M solution of each analyte was made in 100% dimethylsulfoxide (DMSO). A 100 fold dilution was then made to form a $10^{-5}$ M solution in 50 mM Tris-HCl buffer, pH 7.4, 1% DMSO. Tetracycline was used as a reference analyte and approximately 50% was adsorbed to HA at the concentration of $10^{-5}$ M. The HA slurry was 0.5 g/100 mL 50 mM Tris-HCl buffer, 1% DMSO.

For each analyte, two samples were prepared. For one sample, 1 mL of $10^{-5}$ M analyte and 100 µL 50 mM Tris-HCl buffer, 1% DMSO was pipetted into a microcentrifuge tube. For the second sample, 1 mL of $10^{-5}$ M analyte and 100 µL of the HA slurry was pipetted into a microcentrifuge tube. The samples were mixed gently by inversion for 4 minutes and then centrifuged at 12,000 g for 3 minutes to sediment the HA contained in those samples. The supernatant was transferred to another microcentrifuge tube.

An electronic spectral scan (ultraviolet-visible) from 220-520 nm was obtained for each analyte using a Varian Cary 300 Bio Scan. The blank was 50 mM Tris-HCl buffer, 1% DMSO. The wavelength of maximum absorbance ($\lambda_{max}$) was determined, and the extinction coefficient ($\epsilon$) was calculated using the Beer-Lambert Law.

The absorbance of the samples incubated with HA was measured at $\lambda_{max}$, and the molar concentration of the analyte was then determined using the Beer-Lambert Law and the previously calculated extinction coefficient. The fraction adsorbed to HA for each sample was subsequently calculated. Binding to Hydroxyapatite is expressed as a binding index for each compound tested, adjusted such that tetracycline had a binding index of 100. Data are set forth in the following Table.

| Binding to Hydroxyapatite | |
|---|---|
| Compound | Binding Index |
| 17, β-estradiol | −8 |
| tetracycline | 100 |
| bone targeted steroidal estrogenic agent (compound of Formula 123) | 160 |
| bone targeted steroidal estrogenic agent (compound of Formula 124) | 100 |
| bone targeted steroidal estrogenic agent (compound of Formula 125) | 160 |
| bone targeted nitric oxide agent (compound of Formula 130) | 130 |
| bone targeted androgen (compound of Formula 33) | 140 |
| bone targeted carbonic anhydrase inhibitor (compound of Formula 35) | 20 |
| bone targeted anti-cancer agent (compound of Formula 138) | 60 |
| bone targeted antimicrobial (compound of Formula 140) | 80 |

Other compounds of the presently-disclosed subject matter, including bone targeted nonsteroidal estrogenic agents (e.g., compound including a Bone Active Portion derived from genistein), and other bone targeted androgens (e.g., compound including a Bone Active Portion derived from DHEA), are tested and determined to have an affinity for bone.

Affecting Bone

Animals. Six month old, bilaterally ovariectomized (OVX) or sham operated Sprague-Dawley female rats (Harlan Laboratories, Indianapolis, Ind.) were maintained at the University of Louisville Research Resources Center at 22° C. with a 12-h light/dark cycle and ad libitum access to tap water and rodent chow (Purina Laboratory Rodent Diet 5001). All animal procedures were approved by the Institutional Animal Care and Use Committee, which is certified by the American Association for Accreditation of Laboratory Animal Care.

In vivo experiments were conducted in order to investigate the efficacy of compounds of the presently-disclosed subject matter. In all of the experiments, OVX and sham operated rats were randomly divided into groups of 5-7 animals. In all of the studies experimental groups included: i) Sham-operated control (euthanized six weeks post surgery as a pretreatment control), ii) OVX control (euthanized six weeks post surgery as a pretreatment control), iii) Sham control receiving vehicle, iv) OVX control receiving vehicle, v) OVX receiving 17-ethinyl estradiol (equimolar concentration with a selected test compound), vi) OVX receiving alendronate (1.6 mg/kg), and vii) OVX receiving parathyroid hormone 1-34 (PTH) (80 pg/kg). 17-ethinyl estradiol (17 EE) is a free estrogenic agent known to be orally active, and can serve as an example of an anti-catabolic agent. Alendronate (Alen) is a bisphosphonate that is currently used to treat osteoporosis (e.g., Fosamax®, Merck & Co., Inc,), and can serve as an example of an anti-catabolic agent. Parathyroid hormone 1-34 (PTH) is an agent that can serve as an example of an anabolic agent. All compounds and vehicle (1% DMSO in corn oil) were administered three times per week orally by gavage except for PTH which was administered via a subcutaneous injection in a volume of 0.5 ml/kg body mass thrice per week. Compound administration was initiated 6 weeks following surgery and lasted for 6 weeks (18 doses total).

Compounds of the presently-disclosed subject matter were orally administered to OVX rats at various doses. As indicated above all BTE's were administered three times per week for 6 weeks.

Following 6 weeks of treatment, blood was obtained from each animal via cardiac puncture following an overnight fast and animals were subsequently euthanized via carbon dioxide asphyxiation. Blood was centrifuged immediately and the obtained serum samples were aliquoted and stored at −70° C. prior to analysis. Uteri were removed and fresh weights were obtained. Uterine masses were normalized to body mass at the end of the experiment. The left and right femora and left and right tibiae were subsequently collected from each animal, cleaned of soft tissue, and stored in saline at 4° C. prior to analysis.

Estrogenic Effect.

Quantitative Determination of Lipid Metabolism (Total Cholesterol HDL, and LDL) in Rat Serum. Total cholesterol, high-density lipoprotein (HDL), and low-density lipoprotein (LDL) were quantitatively determined in the serum of rats in order to evaluate the extraosseous effects of estrogen treatment on lipid metabolism. Commercially available kits from Wako Diagnostics (Richmond, Va.) were used for the evaluations as recommended by the manufacturer.

Uterine Mass and Body Weight. Ovariectomized (OVX) animals generally exhibit an increase in body weight; however, upon treatment with free estrogen, animals generally exhibit a decrease in body weight to a normal body weight. As such, an assessment of whole body estrogenic effect exhibited in the animals can be made by measuring body weight of the animals following treatment. Following OVX, animals exhibit a decrease in uterine mass, and a subsequent increase in uterine mass upon treatment with free estrogen. Uterine mass can be used to as a measure of estrogenic effect occurring in a tissue outside the bone in response to treatment with a test compound or composition. Generally, a lower uterine mass can be associated with a decreased risk of adverse side effects associated with the test compound or composition. A ratio of uterine mass to body weight can be used to correct for any increase in uterine size attributable to the relative size of the individual animal. Body weight and/or uterine mass also serve as an indirect measures of toxicity of a test compound.

Bone Density.

Femoral Density via Archimedes' Principle. Right femora were submerged in distilled water and fully hydrated under a vacuum for 1 hr. Subsequently, the mass of each hydrated femur was obtained in air and when submerged in water. Densities were determined using Archimedes' Principle according to the following formula: density=[mass of hydrated femur/(mass of hydrated femur−mass of hydrated femur submerged in water)]×density of distilled water at a given temperature (See Keenan, et al. Comparison of bone density measurement techniques: DXA and Archimedes' principle. J Bone Miner Res 1997; 12:1903-7.). The obtained density measurements were associated with whole bone.

Regional Femoral Density via Archimedes' Principle. In addition to whole bone measurements, assessments of the densities at different regions of the bone were made. The proximal and distal ends of the femur are comprised primarily of cancellous/trabecular bone, whereas the femoral diaphysis contains primarily cortical bone. It is in these regions of bone that problems, for example, in osteoporosis typically occur. Evaluation of the density of each of these femoral regions can thereby increase the understanding of the effect of a compound on each of these types of bone. The left femora were separated into three regions (proximal left femur, distal left femur, and left femoral diaphysis) using an Isomet Low Speed Precision Sectioning Saw from Buehler Limited (Lake Bluff, Ill.) with a diamond blade. Briefly, each femur was measured with a Cen-Tech Digital Caliper and a cut was made from each end at 20% of the length of the femur plus half the width of the blade. Subsequently, the bone marrow was washed out of the femoral diaphysis and the Archimedes density for each of the three femoral regions was determined as described above.

Volume Fraction—Ex vivo micro-computed tomography (μCT). Volume fraction is a representative value for the amount of bone that occupies a given volume or space. High resolution image data were collected using a customized micro-CT system (ACTIS 150/225 system, BIR Inc., Lincolnshire, Ill.). The metaphysis of each right tibia was scanned over a three millimeter range and three-dimensional images were reconstructed. Data were subsequently processed to reveal the volume fraction (BV/TV) occupied by trabecular (cancellous) bone tissue, cortical bone tissue, and whole bone tissue. The resulting data provides information regarding the density of whole bone, cortical bone, and trabecular bone.

Bone Strength.

Bone Mechanical Competence Indentation Test. After sacrifice, the left tibiae were trimmed to expose the cancellous bone of the proximal tibial metaphysis and an indentation test was performed by advancing a flat-tipped cylindrical post (1.5 mm diameter) axially into the cut surface to measure the compressive strength of the cancellous bone structure.

Bone Formation and Turnover.

Rat Osteocalin EIA. Osteocalcin is a hydroxyapatite-binding protein that is synthesized by osteoblasts during bone formation. Thereby, serum osteocalcin levels are commonly used as a biochemical marker of bone formation. Rat serum osteocalcin levels were measured using the Rat Osteocalcin EIA Kit from Biomedical Technologies, Incorporated (Stoughton, Mass.) as recommended by the manufacturer.

RatLaps™ ELISA for C-Telopeptide Fragments of Collagen Type I (CTX-I). Osteoclast mediated breakdown of collagen type I in bone leads to the release of free and peptide bound fragments of the collagen type I molecule. The fragment released from the carboxy-terminal region of collagen type I is termed the C-telopeptide fragment of collagen type I (CTX-I) and is commonly used as a biochemical marker of bone resorption. Bone resorption (CTX-I) was quantitatively assessed in rat serum using the commercially available Rat-Laps™ ELISA KIT from Nordic Bioscience Diagnostics A/S (Herlev, Denmark) as recommended by the manufacturer.

Stimulation of Periosteal Bone Formation in a Mouse Calvarial Injection Model. The anabolic (bone formation) of compounds of the presently-disclosed subject matter are evaluated in the mouse calvarial injection model. Briefly, 4-week-old ICR Swiss mice are injected subcutaneously over the surface of the calvariae with compounds of the presently-disclosed subject matter at concentrations of 0, 1, 3, and 10 mg/kg/day for 5 days (twice a day). Microtubule inhibitor TN-16 (5 mg/kg/day for 2 days, twice a day) are used as a positive control. Mice are sacrificed two weeks after the injections are completed. Dissected calvarial samples are fixed in 10% phosphate-buffered formalin for 2 days, decalcified in 10% EDTA for 2 weeks and then embedded in paraffin. Histological sections are cut and stained with H&E and orange G. New woven bone formation (new bone area) is quantified by histomorphometry using the OsteoMeasure system (Osteo-Metrics Inc., Atlanta, Ga.).

Anti-Cancer Effect: Colony formation assay. The anti-cancer effect of compounds including a bone active portion ($R_A$) derived from an anti-cancer agent was tested. SUM1315 human breast cancer cells (derived from a clinical metastatic nodule) were seeded in 6 well plates at 5000 cells/well in 2 ml of medium. Cells were allowed to adhere overnight prior to drug treatment. Compounds of the presently-disclosed subject matter including a bone active portion ($R_A$) derived from an anti-cancer agent, or the free anti-cancer agent, were added to the cells at concentrations of 0.05, 0.1, 0.5, 1, 5, and 10 μM and cells were allowed to grow at 37° C. for 10 days. In addition, untreated and vehicle (0.1% DMSO) treated wells were included as controls. After 10 days of treatment, medium was removed from each well and cells were subsequently washed with water. Cells were then fixed in 10% formaldehyde for 10 minutes, washed with water and then stained with 0.5% crystal violet for 5 minutes. Colonies of cells were subsequently counted under the microscope in three separate frames. Three independent experiments were performed and the results are an average of the three experiments. Images were obtained from a representative well for each concentration.

Anti-Cancer Effect: Cell Proliferation Assay. The colorometric MTT assay is based on the cleavage of a yellow MTT tetrazolium salt to form purple formazan crystals by the mitochondria of metabolically active and viable cells. The formazan crystals are insoluble in aqueous solution but can be dissolved in acid and quantified using a spectrophotometer. The number of living and viable cells in a sample directly correlates to the amount of purple formazan crystals formed. SUM1315 human breast cancer cells were seeded in triplicate in 96 well plates at 1000 cells/well and were allowed to adhere overnight prior to drug treatment. Compounds of the presently-disclosed subject matter including a bone active portion ($R_A$) derived from an anti-cancer agent, or the free anti-cancer agent, were added to the cells at concentrations of 0.05, 0.1, 0.5, 1, 5, and 10 μM and cells were allowed to grow at 37° C. for 1, 2, 3, 4, 5, or 6 days. In addition, untreated and vehicle (0.1% DMSO) treated wells were included at each time point as controls. Following treatment the MTT assay was subsequently performed and the absorbance at 490 nm was recorded. Three independent experiments were performed and the results were averaged.

Antimicrobial Effect: Minimum Inhibitory Concentration (MIC) of a Test Compound Against Isolates of *Staphylococcus aureus*. The Minimum inhibitory concentration (MIC) of compounds of the presently-disclosed subject matter including a bone active portion ($R_A$) derived from an antimicrobial agent, and free antimicrobial agents, were determined by Ricerca Biosciences LLC (Concord, Ohio) using the standard in vitro broth microdilution assay (CLSI). Two isolates of *S. aureus*, one resistant to Methicillin (ATCC 33591) and one nonresistant to Methicillin (ATCC 49230) were used for the evaluation. ATCC 49230 is a clinical isolate from a patient with chronic osteomyelitis. Additionally, a quality control isolate (ATCC 29213) was included in the analysis. Briefly, twelve, serial, one-half dilutions of compounds of the presently-disclosed subject matter including a bone active portion ($R_A$) derived from an antimicrobial agent, and free antimicrobial agents, were prepared in 96-well plates in Mueller Hinton Broth (MHB). The highest concentration of each compound used was 64 μg/mL. Bacterial suspensions were prepared and added to each well at a concentration of approximately $5 \times 10^5$ colony-forming-units per milliliter. The inoculated plates were incubated for 16-20 h at 35±1° C. At the completion of incubation, the wells of each plate were evaluated visually for the presence of bacterial growth. All testing was completed in duplicate. The MIC is the concentration of the compound at which growth of the bacteria was not visible.

Bone Targeting Portion ($R_T$)

Animals were treated with the following compounds having an affinity for bone as assessed by HA-binding assay, including bone targeting portions ($R_T$), but lacking linking portions ($R_L$) and bone active portions ($R_A$). Samples were collected and studied as described above.

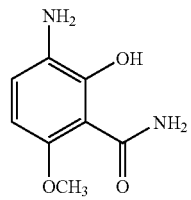

Formula 161 (BTA-2)

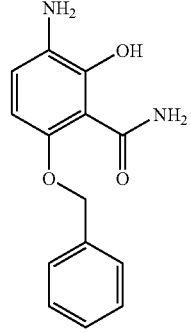

Formula 162 (BTA-3)

Figure 2:
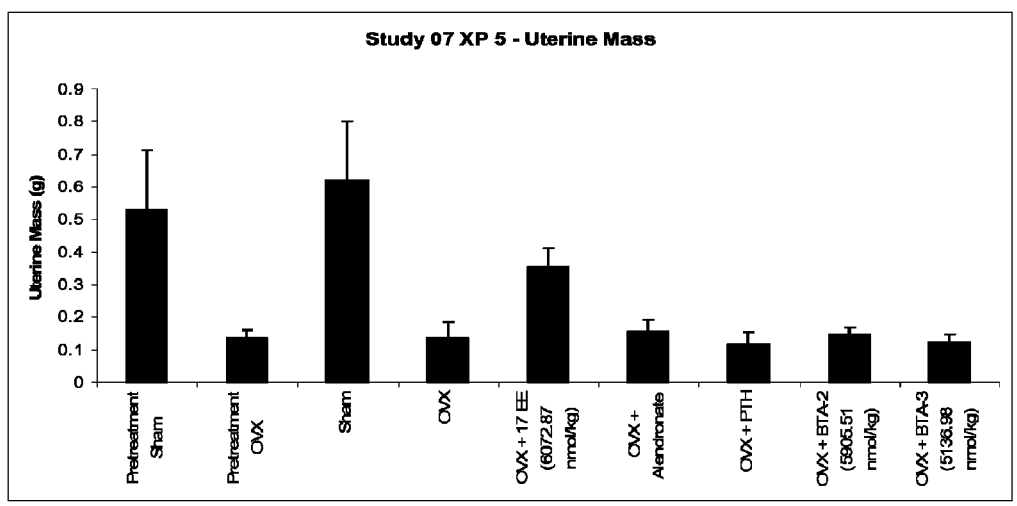
FIG. 2 is a bar graph depicting the uterine mass of animals administered 17-ethinyl estradiol, alendronate, parathyroid hormone, the compound of Formula 161 (BTA-2), or the compound of Formula 162 (BTA-3).
Figure 3:
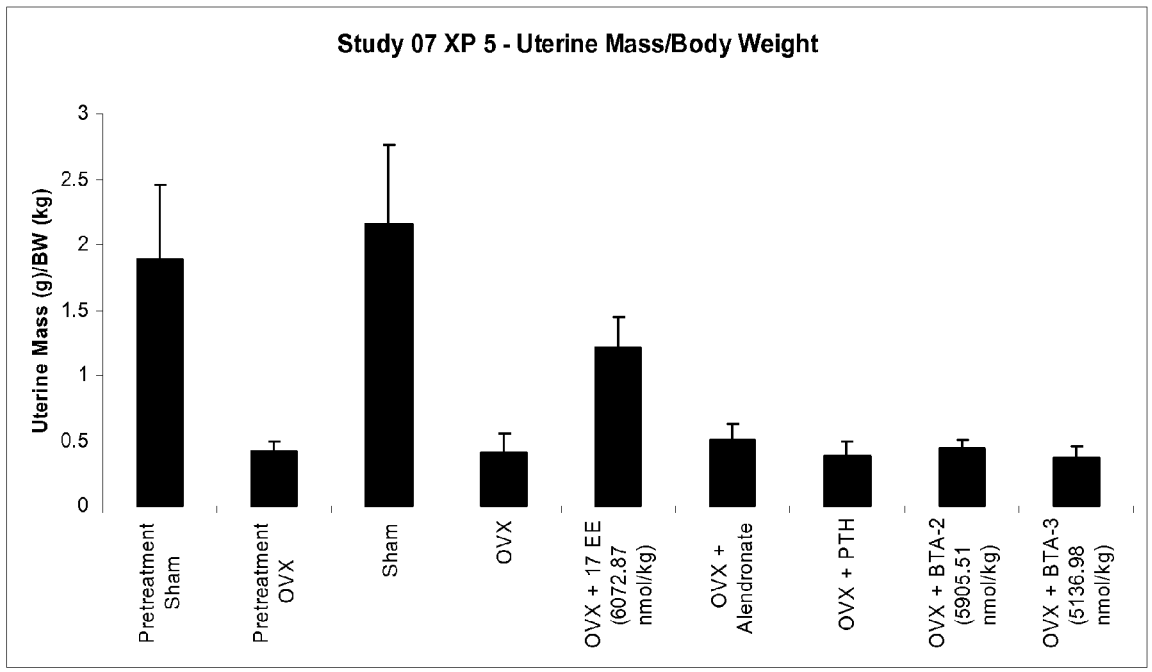
FIG. 3 is a bar graph depicting the ratio of uterine mass to body weight of animals administered 17-ethinyl estradiol, alendronate, parathyroid hormone, the compound of Formula 161 (BTA-2), or the compound of Formula 162 (BTA-3).

With reference to FIG. 1, the body weights of the animals were measured at regular time intervals and body weights were plotted as a function of time. Body weight can serve as an indirect measure of toxicity. The compounds of Formulas 161 (BTA-2) and 162 (BTA-3) are shown to have no effect on body weight. Turning now to FIGS. 2 and 3 the uterine mass of each animal was measured and expressed both independently, and as a ratio of uterine mass to body weight. The compounds of Formulas 161 (BTA-2) and 162 (BTA-3) are shown to have no effect on uterine mass, nor ratio of uterine mass to body weight.

Figure 4:
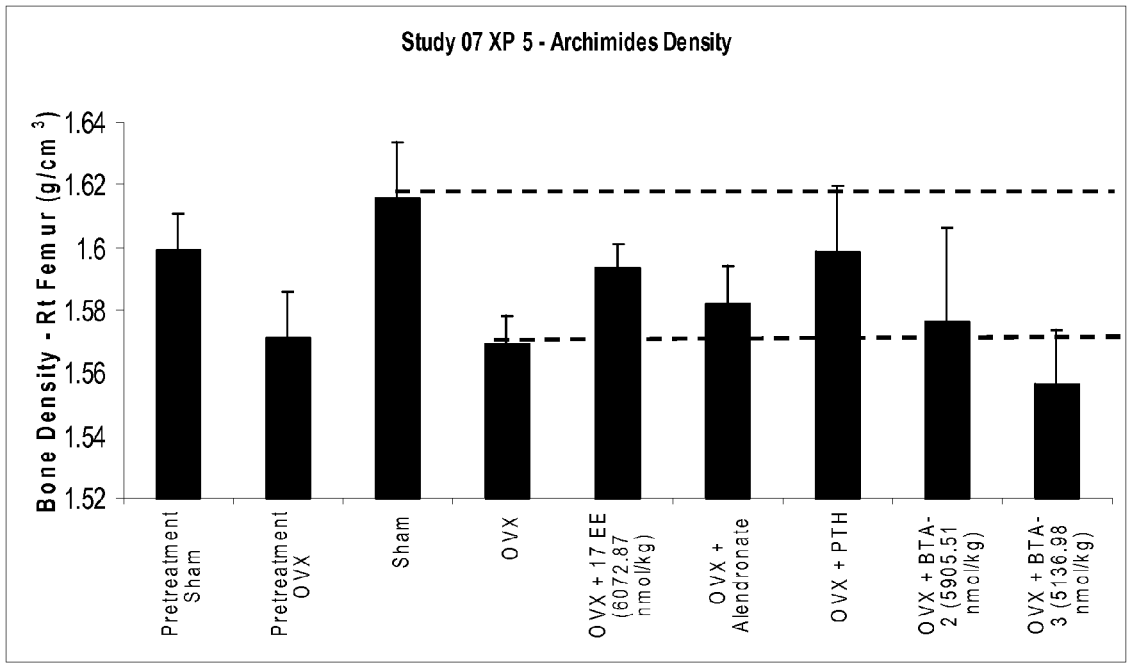
FIG. 4 is a bar graph depicting the whole bone density of animals administered 17-ethinyl estradiol, alendronate, parathyroid hormone, the compound of Formula 161 (BTA-2), or the compound of Formula 162 (BTA-3).
Figure 5:
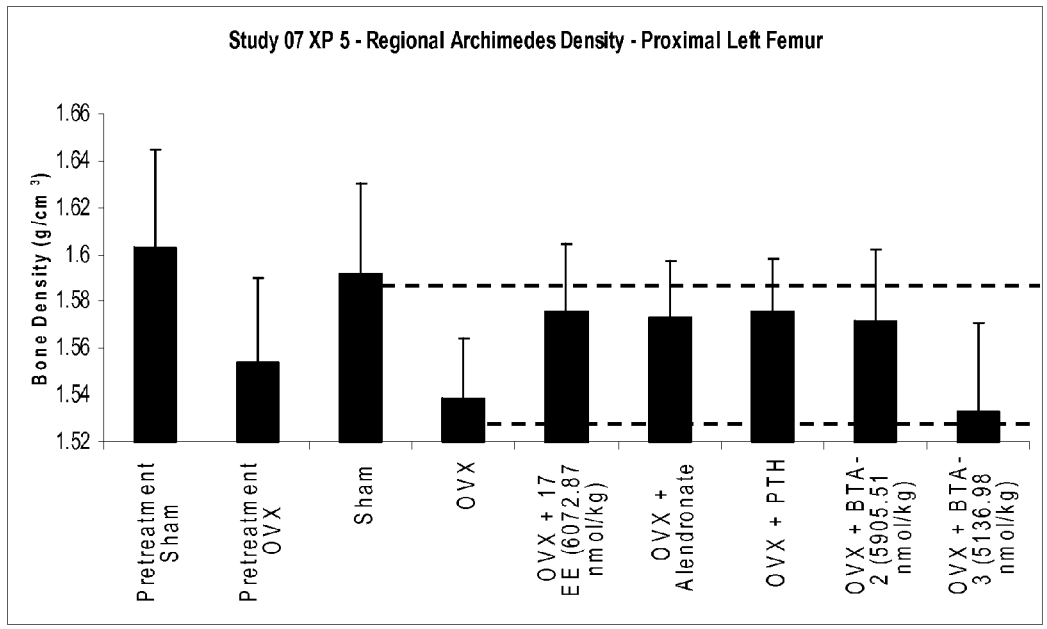
FIG. 5 is a bar graph depicting the regional bone density of the proximal left femur of animals administered 17-ethinyl estradiol, alendronate, parathyroid hormone, the compound of Formula 161 (BTA-2), or the compound of Formula 162 (BTA-3).
Figure 6:
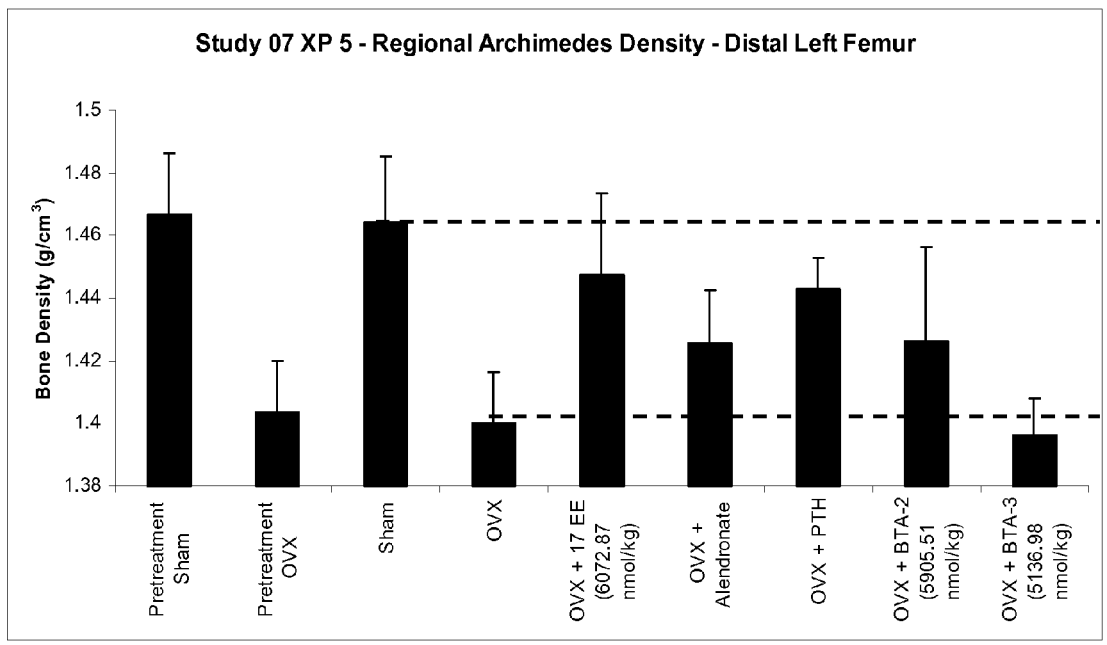
FIG. 6 is a bar graph depicting the regional bone density of the distal left femur of animals administered 17-ethinyl estradiol, alendronate, parathyroid hormone, the compound of Formula 161 (BTA-2), or the compound of Formula 162 (BTA-3).

The right femora were used to assess bone density, as described above. With reference to FIG. 4, whole bone density was not significantly effected by compounds of Formulas 161 (BTA-2) or 162 (BTA-3). Regional bone density was also assessed, as described above. With reference to FIGS. 5 and 6, regional bone density was not significantly effected by compounds of Formulas 161 (BTA-2) or 162 (BTA-3).

Compound Including Bone Active Portion ($R_A$) Derived from a Steroidal Estrogenic Agent Animals were treated with a compounds including a bone active portion ($R_A$) derived from a steroidal estrogenic agent. Compounds wherein the bone active portion was derived from estradiol were selected as examples of compounds including a bone active portion derived from a steroidal estrogenic agent. The compounds of Formulas 123, 124, and 125 were orally administered to animals at doses of 10, 100, or 1000 μg/kg.

Body Weight and Uterine Mass.

Figure 7:
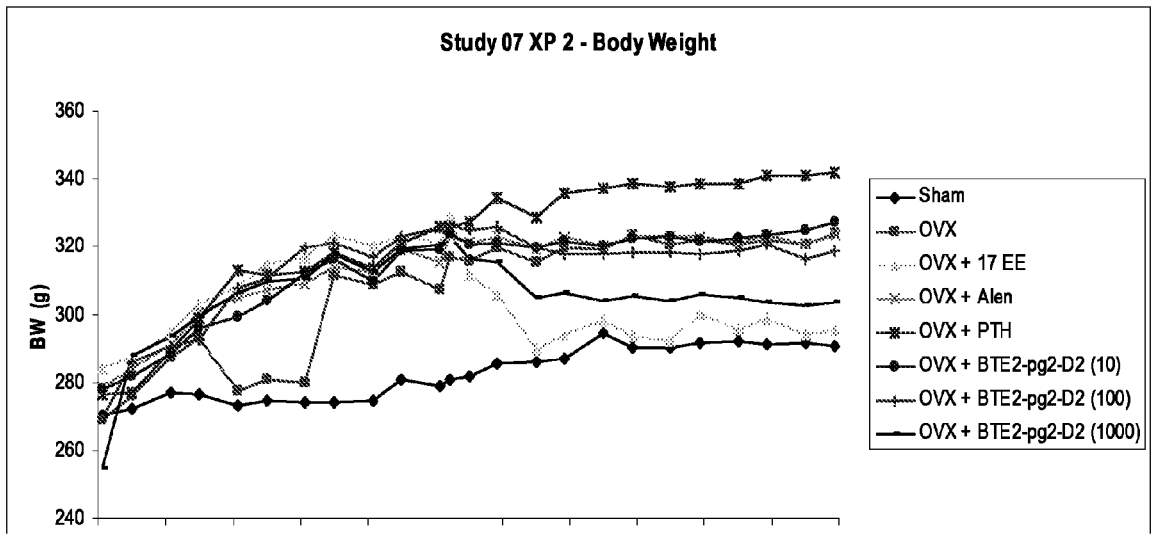
FIG. 7 is a line graph depicting body weight as a function of time for animals administered 17-ethinyl estradiol, alendronate, parathyroid hormone, or the compound of Formula 123 (BTE2-pg2-D2) at doses of 10, 100, or 1000 µg/kg.

With reference to FIG. 7, the body weights of the animals were measured at regular time intervals and body weights were plotted as a function of time. Body weight can serve as an indirect measure of toxicity. With increasing doses of the compound of Formula 123 (BTE2-pg2-D2), body weight is shown to decrease, approaching the sham animal when the compound of Formulas 123 (BTE2-pg2-D2) is administered at the highest concentration.

Figure 8:
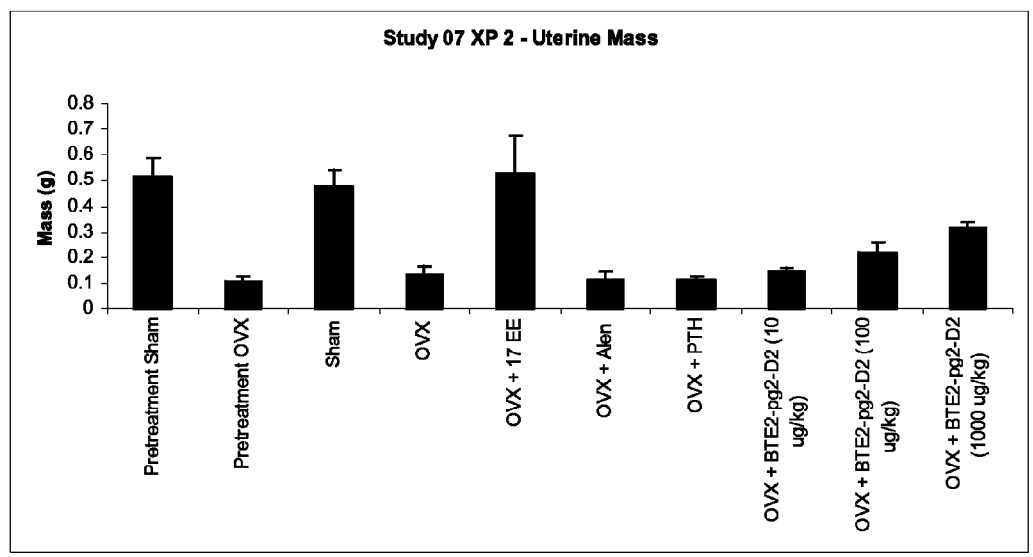
FIG. 8 is a bar graph depicting the uterine mass of animals administered 17-ethinyl estradiol, alendronate, parathyroid hormone, or the compound of Formula 123 (BTE2-pg2-D2) at doses of 10, 100, or 1000 µg/kg.
Figure 9:
FIG. 9 is a bar graph depicting the ratio of uterine mass to body weight of animals administered 17-ethinyl estradiol, alendronate, parathyroid hormone, or the compound of Formula 123 (BTE2-pg2-D2) at doses of 10, 100, or 1000 µg/kg.

Turning now to FIGS. 8 and 9 the uterine mass of each animal was measured and expressed both independently, and as a ratio of uterine mass to body weight. Animals treated with the compound of Formula 123 (BTE2-pg2-D2) had lower uterine masses, and uterine mass to body weight ratios as compared to the animals treated with the free steroidal estrogenic agent, 17-ethinyl estradiol. This is a surprising result given that the compound of Formula 123 includes a bone active portion derived from the steroidal estrogenic agent, estradiol. These results indicate that the compounds of the presently-disclosed subject matter including a bone active portion derived from a estrogenic agent do not act in the same manner as free estrogenic agents.

Lipid Metabolism.

Total cholesterol, high-density lipoprotein (HDL), and low-density lipoprotein (LDL) in collected serum samples are quantitatively determined. The compound of Formula 123 (BTE2-pg2-D2) have a limited or no effect on lipid metabolism.

Bone Density.

Femoral Density and Regional Femoral Density.

Figure 10:
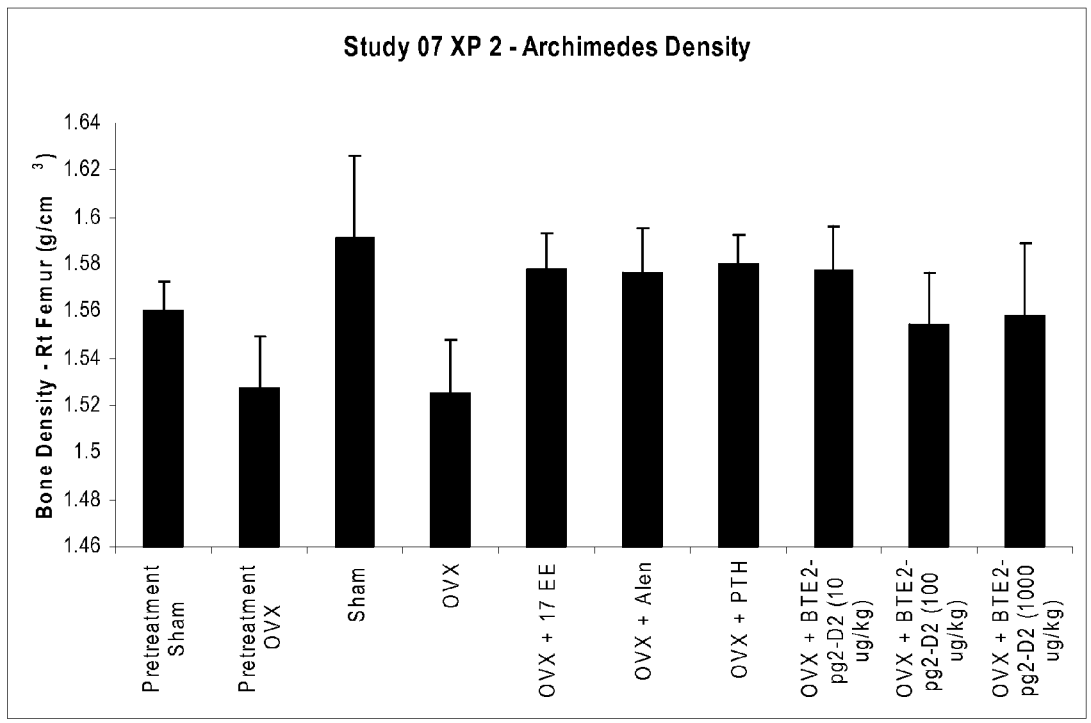
FIG. 10 is a bar graph depicting the whole bone density of animals administered 17-ethinyl estradiol, alendronate, parathyroid hormone, or the compound of Formula 123 (BTE2-pg2-D2) at doses of 10, 100, or 1000 µg/kg.

The right femora were used to assess bone density, as described above. With reference to FIG. 10, whole bone density was affected by the compound of Formula 123 (BTE2-pg2-D2). Animals receiving Formula 123 (BTE2-pg2-D2) were shown to have whole bone densities in the same ranges as those animals receiving 17-ethinyl estradiol (17 EE), Alendronate (Alen), or Parathyroid hormone 1-34 (PTH).

Figure 11:
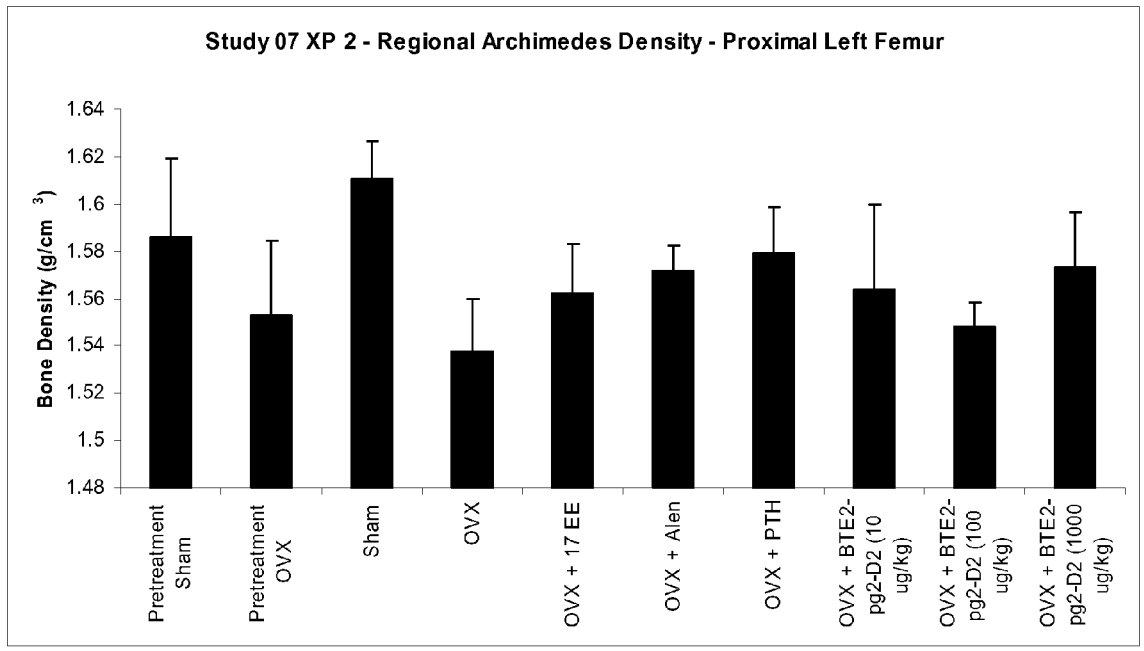
FIG. 11 is a bar graph depicting the regional bone density of the proximal left femur of animals administered 17-ethinyl estradiol, alendronate, parathyroid hormone, or the compound of Formula 123 (BTE2-pg2-D2) at doses of 10, 100, or 1000 µg/kg.
Figure 12:
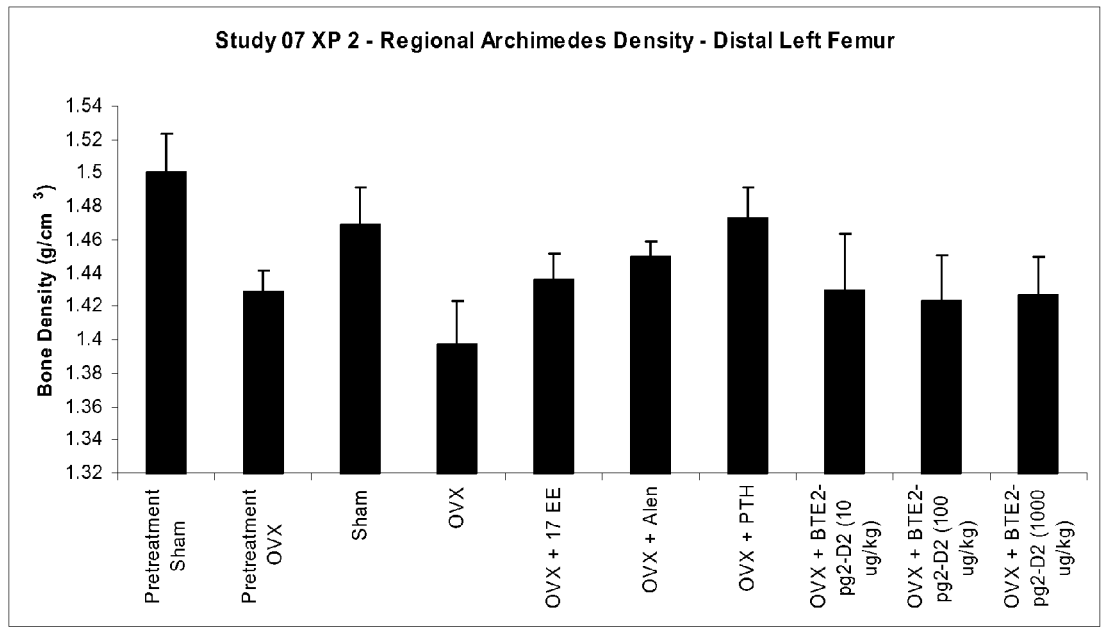
FIG. 12 is a bar graph depicting the regional bone density of the distal left femur of animals administered 17-ethinyl estradiol, alendronate, parathyroid hormone, or the compound of Formula 123 (BTE2-pg2-D2) at doses of 10, 100, or 1000 µg/kg.
Figure 13:
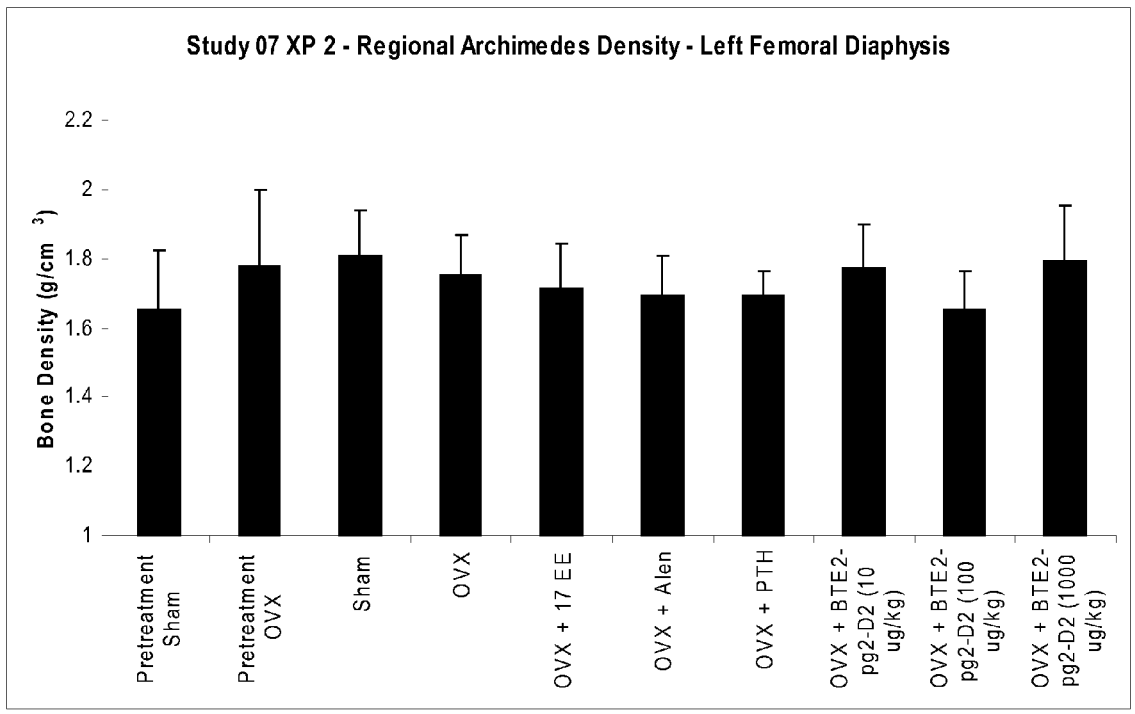
FIG. 13 is a bar graph depicting the regional bone density of the left femoral diaphysis of animals administered 17-ethinyl estradiol, alendronate, parathyroid hormone, or the compound of Formula 123 (BTE2-pg2-D2) at doses of 10, 100, or 1000 µg/kg.

Regional bone density was also assessed, as described above, with data presented in FIGS. 11, 12, and 13. With reference to FIGS. 11 and 12, treatment with the compound of Formula 123 (BTE2-pg2-D2) affected regional bone density. Animals receiving the compound Formula 123 (BTE2-pg2-D2) were shown to have increased regional bone densities, as compared to the OVX animals.

Volume Fraction—Trabecular, Cortical, and Whole Bone.

Samples are collected as described above. Data revealing the volume fraction (BV/TV) occupied by trabecular (cancellous) bone tissue, cortical bone tissue, and whole bone tissue is obtained. The compound of Formula 123 is found to increase bone density.

Bone Strength.

Mechanical Competence.

Samples are collected and an indentation test is performed as described above.

The compound of Formula 123 is found to increase bone strength.

Bone Formation and Turnover.

Osteocalcin.

Figure 14:
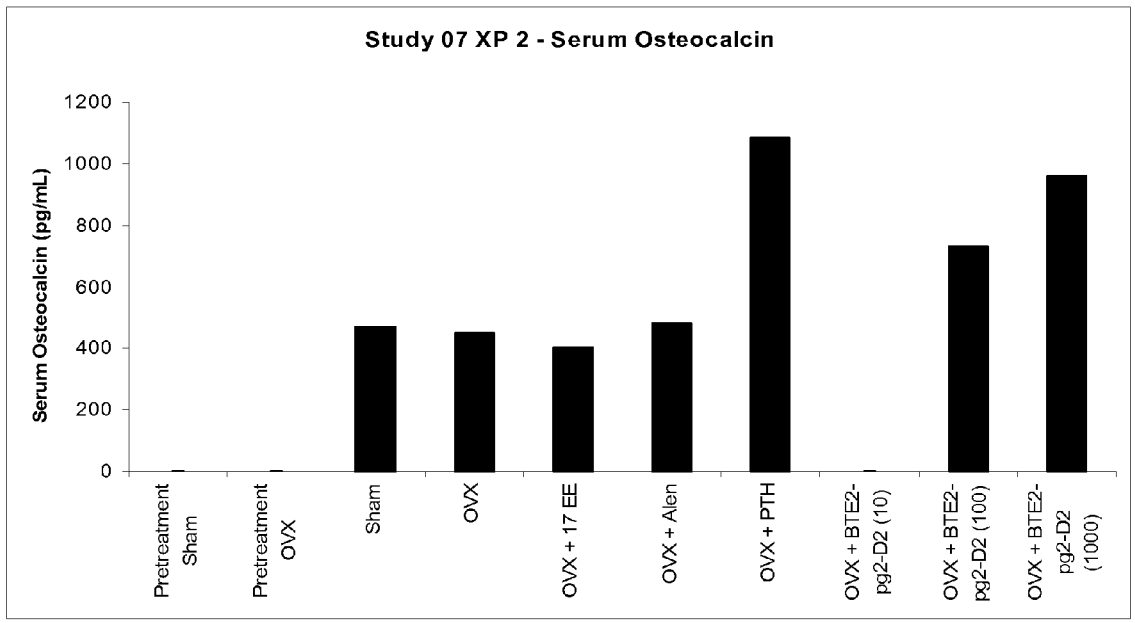
FIG. 14 is a bar graph depicting serum osteocalcin levels for animals administered 17-ethinyl estradiol, alendronate, parathyroid hormone, or the compound of Formula 123 (BTE2-pg2-D2) at doses of 100 or 1000 µg/kg.

With reference to FIG. 14, serum osteocalcin levels were measured as described above. Measurements associated with pretreatment sham, pretreatment OVX, and BTE2-pg-D2 at the 10 µg/kg dose were not made. The animals treated with the compound of Formula 123 (BTE2-pg2-D2) received either 100 or 1000 µg/kg doses. These data show that the compound of Formula 123 (BTE2-pg2-D2) stimulates osteocalcin, which indicates that the compound stimulates of bone formation in a manner similar to PTH.

Calvarial Injection Model.

Animals are administered control agents and the compound, samples are collected, and data are obtained, as described above. The compound of Formula 123 is found to affect new bone area.

Body Weight and Uterine Mass.

Figure 15:
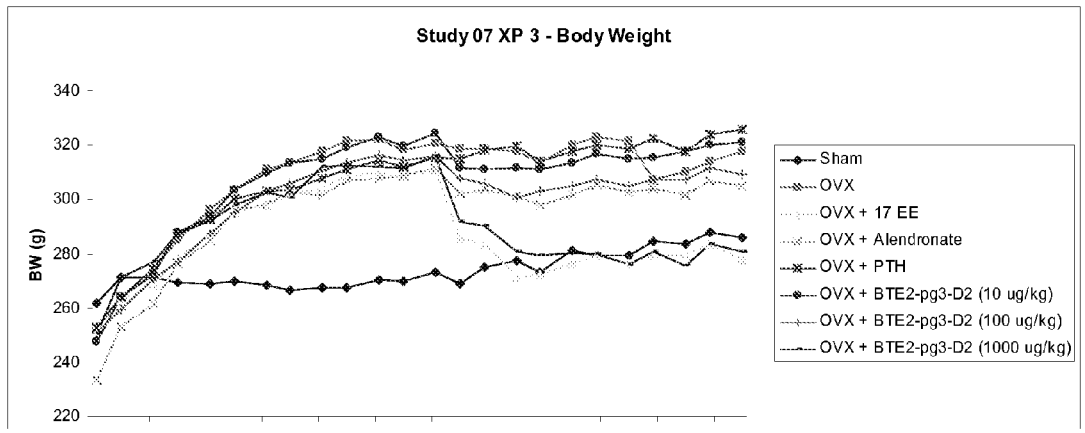
FIG. 15 is a line graph depicting body weight as a function of time for animals administered 17-ethinyl estradiol, alendronate, parathyroid hormone, or the compound of Formula 124 (BTE2-pg3-D2) at doses of 10, 100, or 1000 µg/kg.

With reference to FIG. 15, the body weights of the animals were measured at regular time intervals and body weights were plotted as a function of time. Body weight can serve as an indirect measure of toxicity. With increasing doses of the compound of Formula 124 (BTE2-pg3-D2), body weight is shown to decrease, approaching the sham animals when the compound of Formulas 124 (BTE2-pg3-D2) is administered at increasing concentrations.

Figure 16:
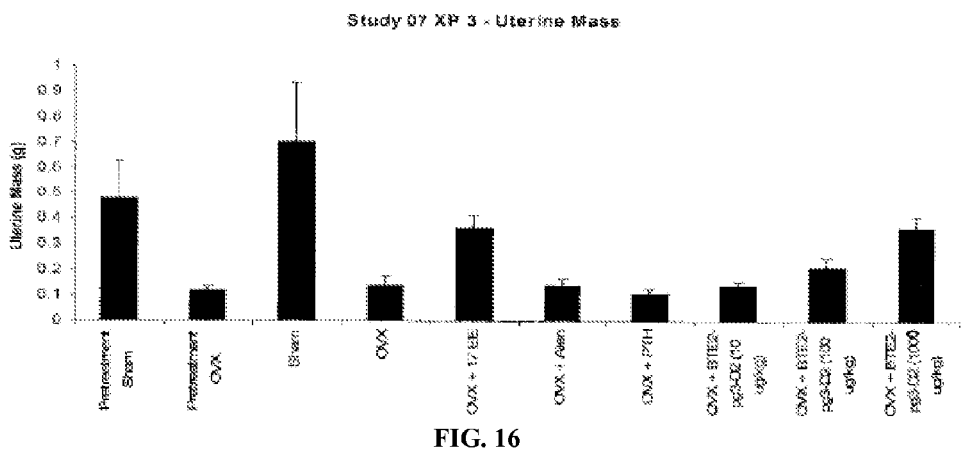
FIG. 16 is a bar graph depicting the uterine mass of animals administered 17-ethinyl estradiol, alendronate, parathyroid hormone, or the compound of Formula 124 (BTE2-pg3-D2) at doses of 10, 100, or 1000 µg/kg.
Figure 17:
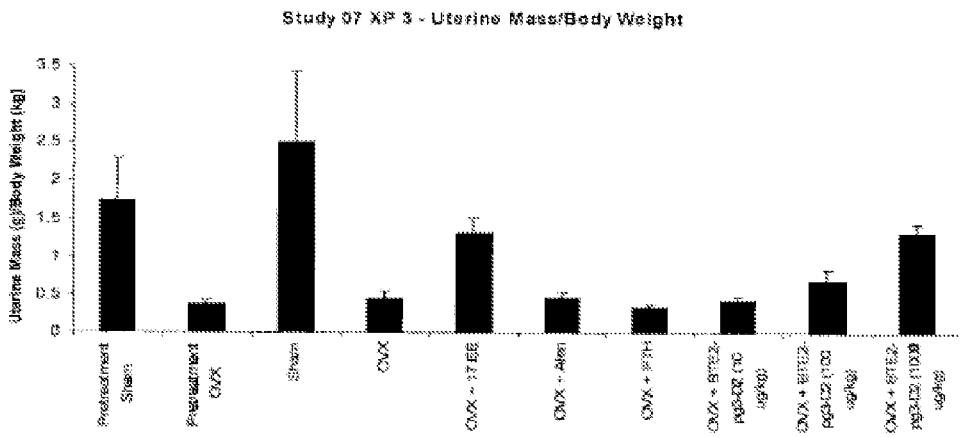
FIG. 17 is a bar graph depicting the ratio of uterine mass to body weight of animals administered 17-ethinyl estradiol, alendronate, parathyroid hormone, or the compound of Formula 124 (BTE2-pg3-D2) at doses of 10, 100, or 1000 µg/kg.

Turning now to FIGS. 16 and 17 the uterine mass of each animal was measured and expressed both independently, and as a ratio of uterine mass to body weight. Animals treated with the compound of Formula 124 (BTE2-pg3-D2) had lower uterine masses, and uterine mass to body weight ratios as compared to the animals treated with the free steroidal estrogenic agent, 17-ethinyl estradiol. This is a surprising result given that the compound of Formula 124 includes a bone active portion derived from the steroidal estrogenic agent, estradiol. These results indicate that the compounds of the presently-disclosed subject matter including a bone active portion derived from a estrogenic agent do not act in the same manner as free estrogenic agents.

Lipid Metabolism.

Total cholesterol, high-density lipoprotein (HDL), and low-density lipoprotein (LDL) in collected serum samples are quantitatively determined. The compound of Formula 124 has a limited or no effect on lipid metabolism.

Bone Density.

Femoral Density and Regional Femoral Density.

Figure 18:
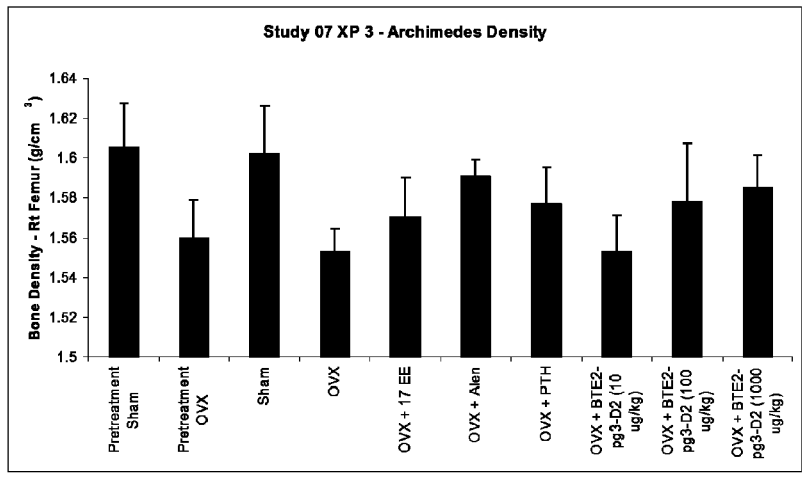
FIG. 18 is a bar graph depicting the whole bone density of animals administered 17-ethinyl estradiol, alendronate, parathyroid hormone, or the compound of Formula 124 (BTE2-pg3-D2) at doses of 10, 100, or 1000 µg/kg.

The right femora were used to assess bone density, as described above. With reference to FIG. 18, whole bone density was affected by the compound of Formula 124 (BTE2-pg3-D2). Animals receiving Formula 124 (BTE2-pg3-D2) were shown to have whole bone densities in the same ranges as those animals receiving 17-ethinyl estradiol (17 EE), Alendronate (Alen), or Parathyroid hormone 1-34 (PTH).

Figure 19:
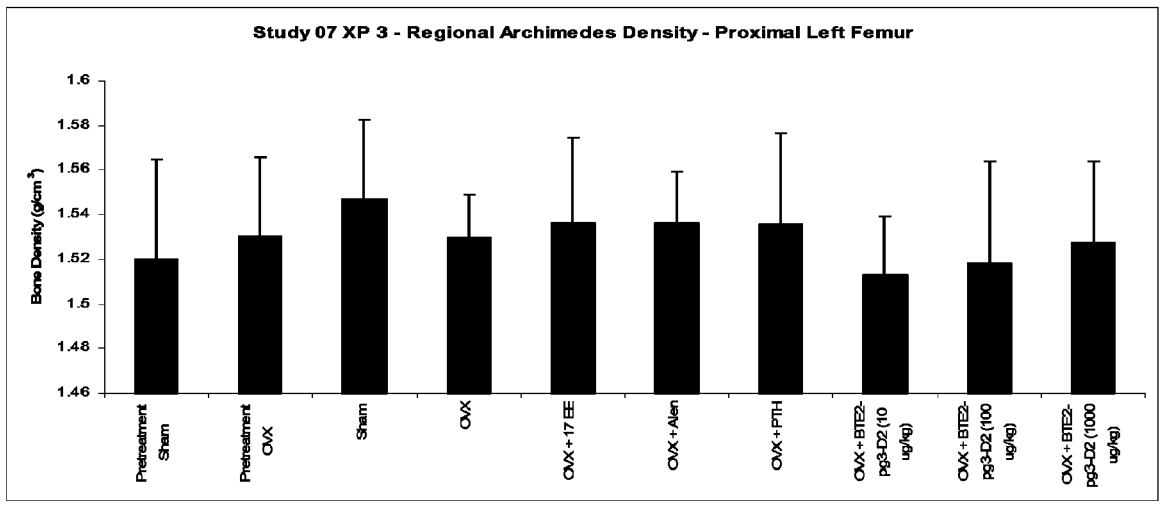
FIG. 19 is a bar graph depicting the regional bone density of the proximal left femur of animals administered 17-ethinyl estradiol, alendronate, parathyroid hormone, or the compound of Formula 124 (BTE2-pg3-D2) at doses of 10, 100, or 1000 µg/kg.
Figure 20:
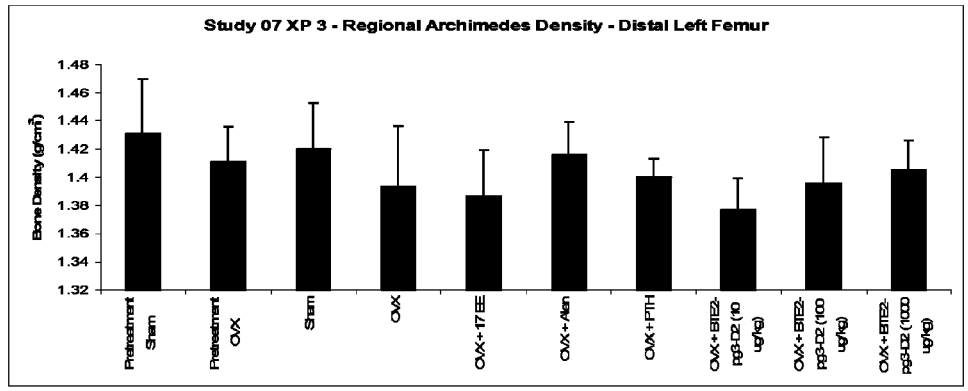
FIG. 20 is a bar graph depicting the regional bone density of the distal left femur of animals administered 17-ethinyl estradiol, alendronate, parathyroid hormone, or the compound of Formula 124 (BTE2-pg3-D2) at doses of 10, 100, or 1000 µg/kg.
Figure 21:
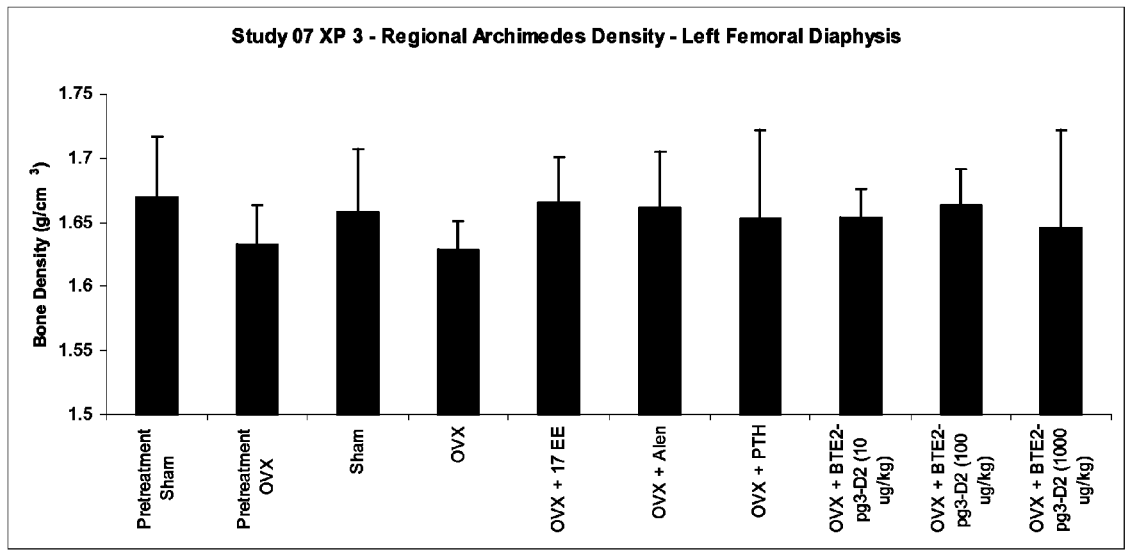
FIG. 21 is a bar graph depicting the regional bone density of the left femoral diaphysis of animals administered 17-ethinyl estradiol, alendronate, parathyroid hormone, or the compound of Formula 124 (BTE2-pg3-D2) at doses of 10, 100, or 1000 µg/kg.

Regional bone density was also assessed, as described above, with data presented in FIGS. 19, 20, and 21. Treatment with the compound of Formula 124 (BTE2-pg3-D2) affected regional bone density. Animals receiving the compound Formula 124 (BTE2-pg3-D2) were shown to have regional bone densities in the same ranges as those animals receiving 17-ethinyl estradiol (17 EE), Alendronate (Alen), or Parathyroid hormone 1-34 (PTH).

Volume Fraction—Trabecular, Cortical, and Whole Bone.

Figure 22:
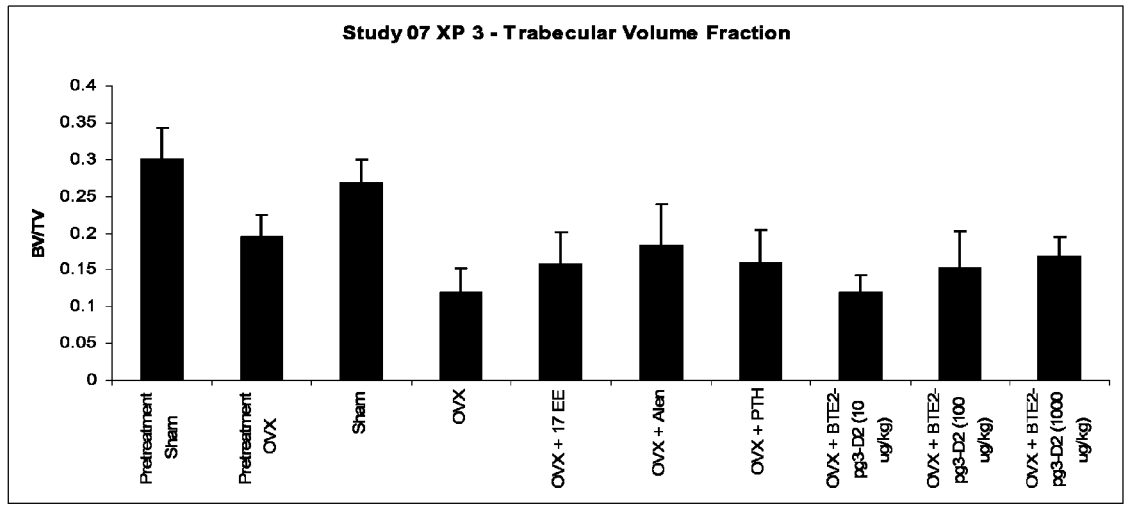
FIG. 22 is a bar graph illustrating trabecular volume fraction data for animals administered 17-ethinyl estradiol, alendronate, parathyroid hormone, or the compound of Formula 124 (BTE2-pg3-D2) at doses of 10, 100, or 1000 µg/kg.

Bone density was further assessed by measuring trabecular volume fraction using ex vivo micro-computed tomography. With reference to FIG. 22, animals receiving various doses of the compound of Formula 124 (BTE2-pg3-D2) were shown to have trabecular volume fractions in the same ranges as those animals receiving 17-ethinyl estradiol (17 EE), Alendronate (Alen), or Parathyroid hormone 1-34 (PTH). These data indicate that the compound of Formula 124 (BTE2-pg3-D2) maintains and/or stimulates trabecular bone to about the same degree as alendronate, estradiol, and PTH.

Figure 23:
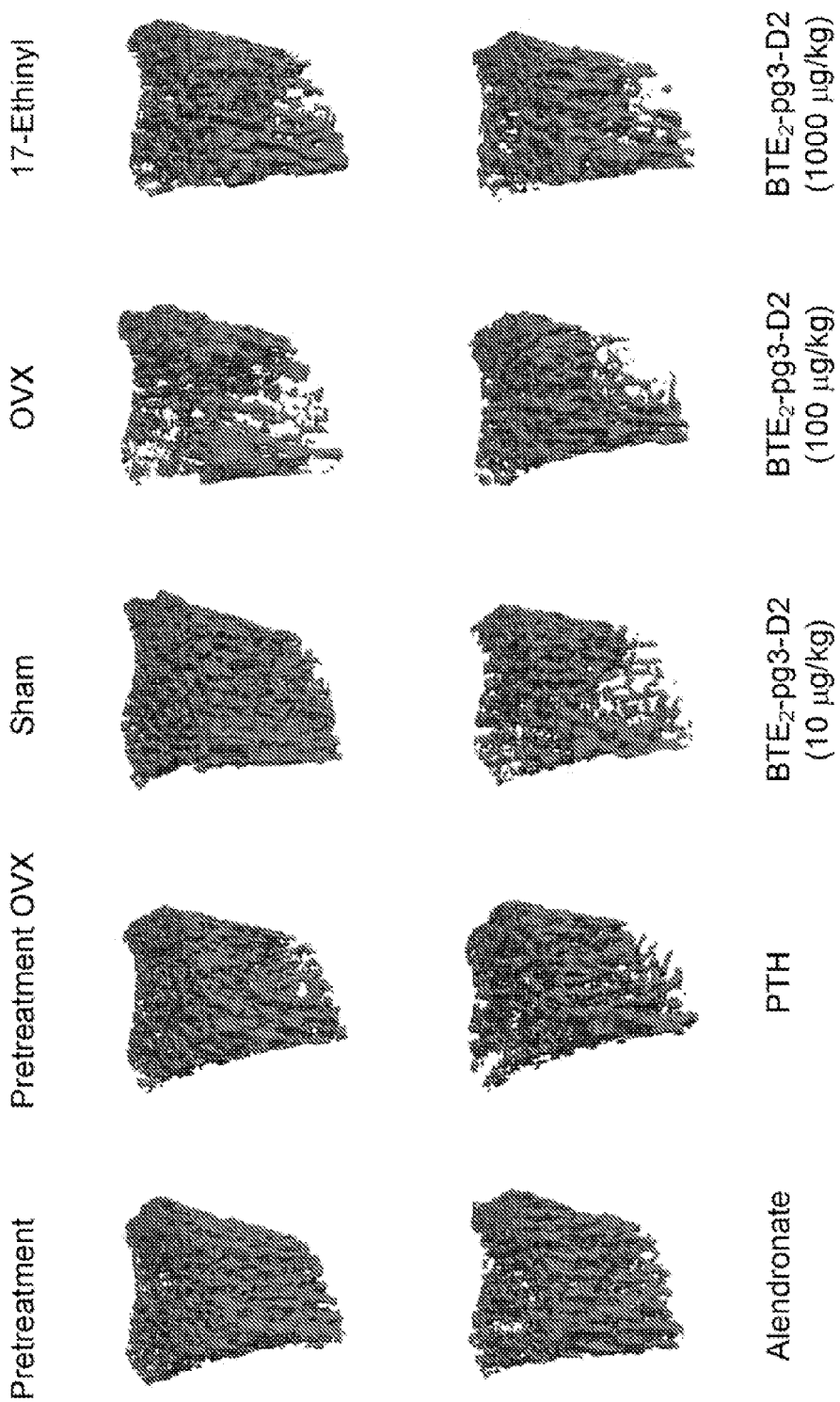
FIG. 23 includes three-dimensional images of bone that were constructed using data collected by a customized micro-CT system, for animals administered 17-ethinyl estradiol, alendronate, parathyroid hormone, or the compound of Formula 124 (BTE2-pg3-D2) at doses of 10, 100, or 1000 µg/kg.

FIG. 23 includes three-dimensional images that were reconstructed using high resolution image data collected using the customized micro-CT system described above. These data indicate that the compound of Formula 124 (BTE2-pg3-D2) affected an increase in bone density.

Bone Strength.

Mechanical Competence.

Figure 24:
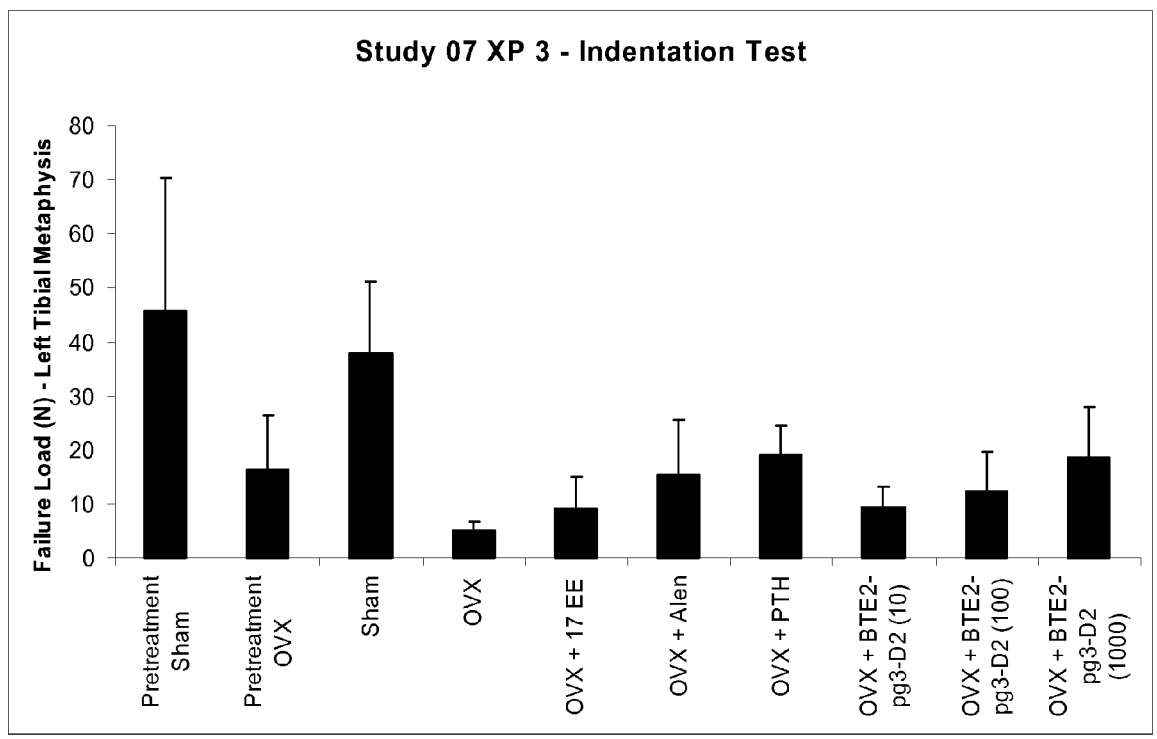
FIG. 24 is a bar graph illustrating tibial bone strength of animals administered 17-ethinyl estradiol, alendronate, parathyroid hormone, or the compound of Formula 124 (BTE2-pg3-D2) at doses of 10, 100, or 1000 µg/kg.

Bone strength was assessed using the bone mechanical competence indentation test, as described above. With reference to FIG. 24, animals receiving the compound of Formula 124 (BTE2-pg3-D2) were shown to have a dose-responsive increase in bone strength, relative to the OVX animals, with bone strength at the higher doses in the same ranges as bone strength for animals receiving alendronate or parathyroid hormone.

Bone Formation and Turnover.

Calvarial Injection Model.

Animals are administered control agents and the compound, samples are collected, and data are obtained, as described above. The compound of Formula 124 is found to increase new bone area.

Body Weight and Uterine Mass.

Figure 25:
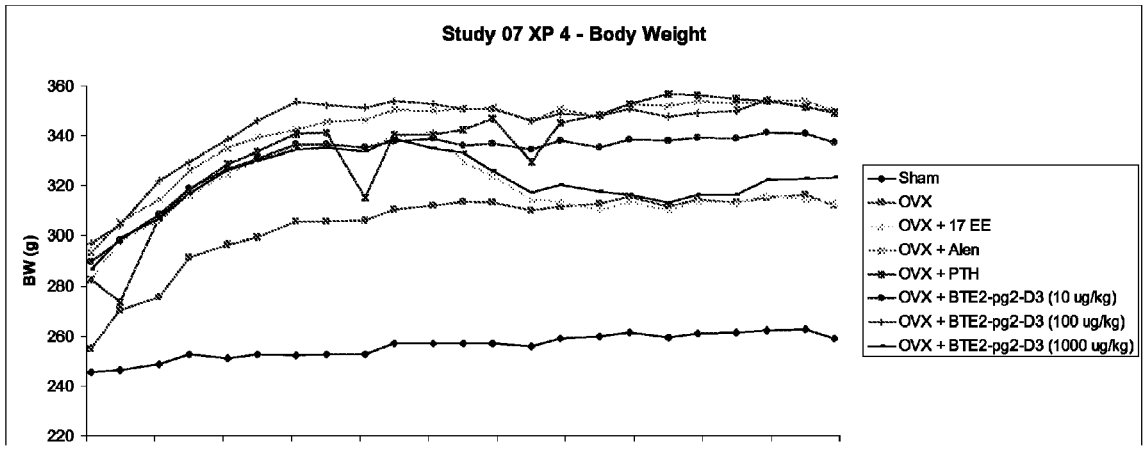
FIG. 25 is a line graph depicting body weight as a function of time for animals administered 17-ethinyl estradiol, alendronate, parathyroid hormone, or the compound of Formula 125 (BTE2-pg2-D3) at doses of 10, 100, or 1000 µg/kg.

With reference to FIG. 25, the body weights of the animals were measured at regular time intervals and body weights were plotted as a function of time. Body weight can serve as an indirect measure of toxicity. Animals receiving the compound of Formula 125 (BTE2-pg2-D3) tend to have lower body weights as compared to the animals receiving alendronate or parathyroid hormone.

Figure 26:
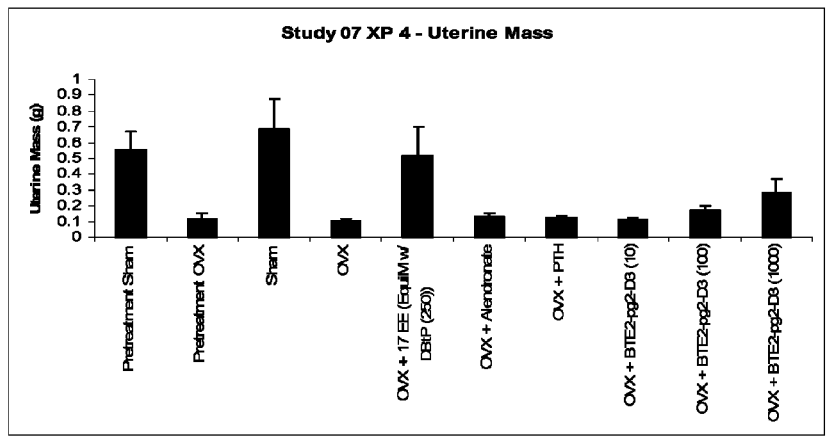
FIG. 26 is a bar graph depicting the uterine mass of animals administered 17-ethinyl estradiol, alendronate, parathyroid hormone, or the compound of Formula 125 (BTE2-pg2-D3) at doses of 10, 100, or 1000 µg/kg.
Figure 27:
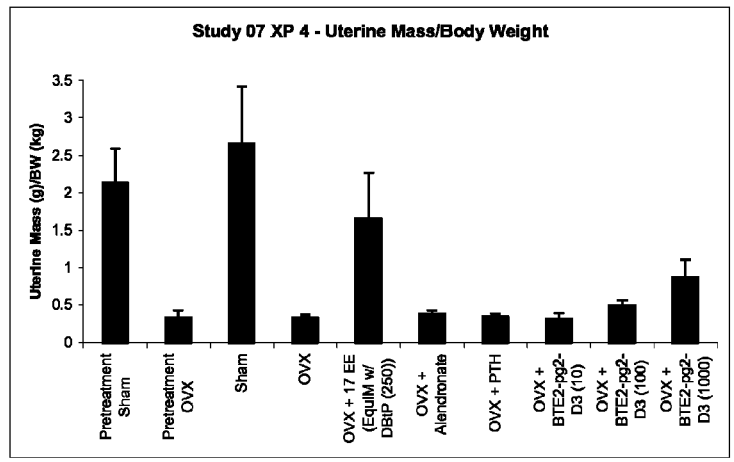
FIG. 27 is a bar graph depicting the ratio of uterine mass to body weight of animals administered 17-ethinyl estradiol, alendronate, parathyroid hormone, or the compound of Formula 125 (BTE2-pg2-D3) at doses of 10, 100, or 1000 µg/kg.
Figure 28:
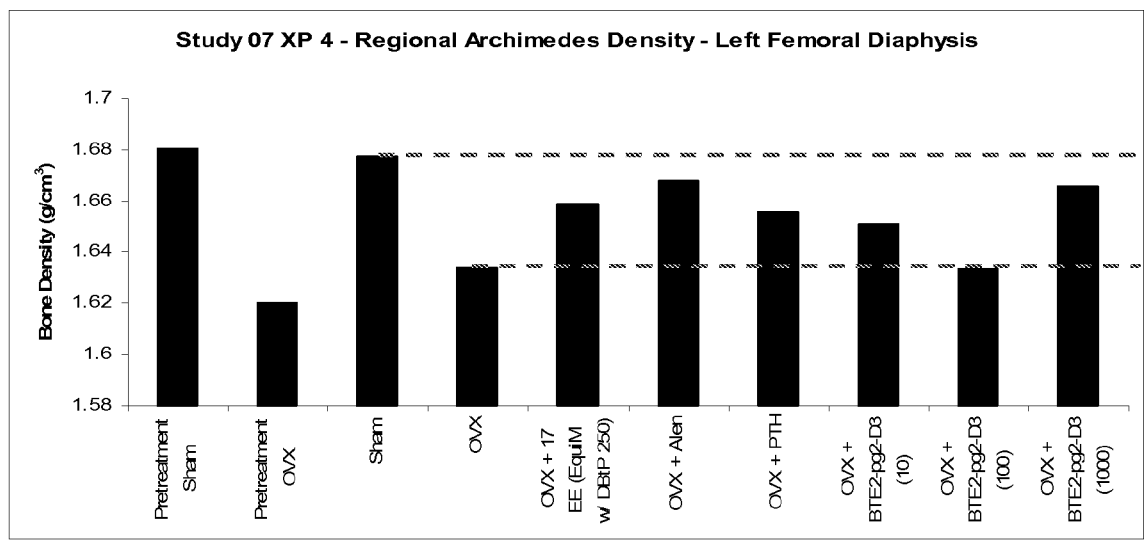
FIG. 28 is a bar graph depicting the regional bone density of animals administered 17-ethinyl estradiol, alendronate, parathyroid hormone, or the compound of Formula 125 (BTE2-pg2-D3) at doses of 10, 100, or 1000 µg/kg.
Figure 29:
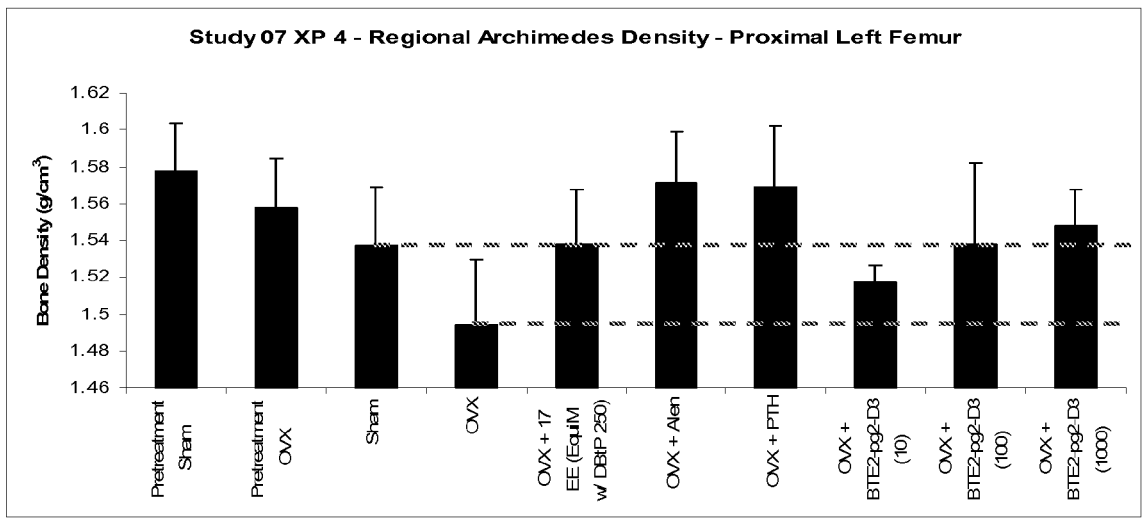
FIG. 29 is a bar graph depicting the regional bone density of the proximal left femur of animals administered 17-ethinyl estradiol, alendronate, parathyroid hormone, or the compound of Formula 125 (BTE2-pg2-D3) at doses of 10, 100, or 1000 µg/kg.
Figure 30:
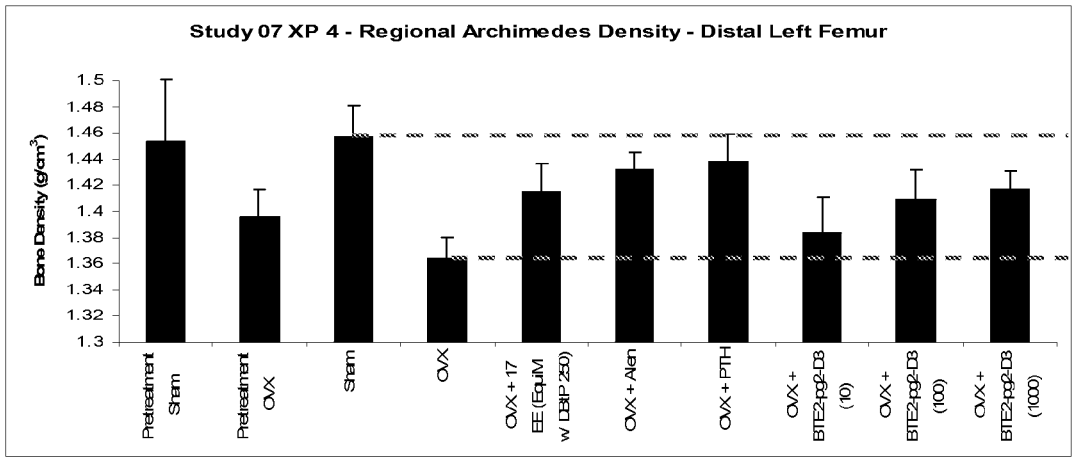
FIG. 30 is a bar graph depicting the regional bone density of the distal left femur of animals administered 17-ethinyl estradiol, alendronate, parathyroid hormone, or the compound of Formula 125 (BTE2-pg2-D3) at doses of 10, 100, or 1000 µg/kg.
Figure 31:
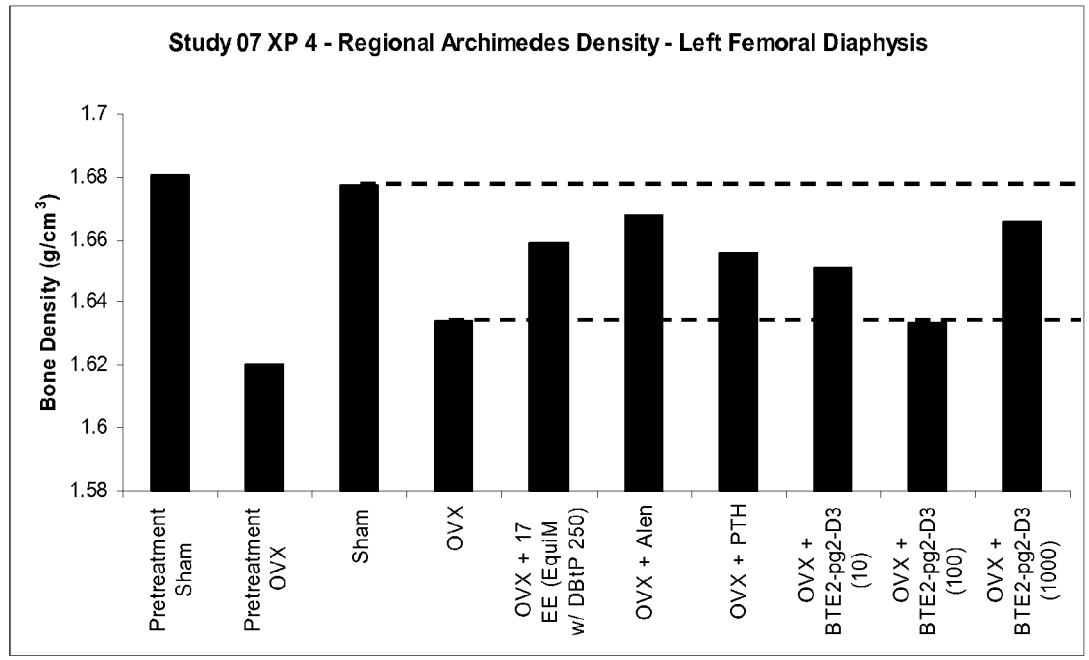
FIG. 31 is a bar graph depicting the regional bone density of the left femoral diaphysis of animals administered 17-ethinyl estradiol, alendronate, parathyroid hormone, or the compound of Formula 125 (BTE2-pg2-D3) at doses of 10, 100, or 1000 µg/kg.

Turning now to FIGS. 26 and 27 the uterine mass of each animal was measured and expressed both independently, and as a ratio of uterine mass to body weight. Animals treated with the compound of Formula 125 (BTE2-pg2-D3) had lower uterine masses, and uterine mass to body weight ratios as compared to the animals treated with the free steroidal estrogenic agent, 17-ethinyl estradiol. This is a surprising result given that the compound of Formula 125 includes a bone active portion derived from the steroidal estrogenic agent, estradiol. These results indicate that the compounds of the presently-disclosed subject matter including a bone active portion derived from a estrogenic agent do not act in the same manner as free estrogenic agents.

Lipid Metabolism.

Total cholesterol, high-density lipoprotein (HDL), and low-density lipoprotein (LDL) in collected serum samples are quantitatively determined. The compound of Formula 125 has a limited or no effect on lipid metabolism.

Bone Density.

Femoral Density and Regional Femoral Density.

Bone density was also assessed, as described above, with data presented in FIGS. 28, 29, 30, and 31. The compound of Formula 125 (BTE2-pg2-D3) affected regional bone density. Animals receiving the compound Formula 125 (BTE2-pg2-D3) were shown to have increased regional bone densities, as compared to the OVX animals. At certain doses, animals receiving the compound Formula 125 were shown to have increased regional bone densities, as compared to the Sham animals.

Volume Fraction—Trabecular, Cortical, and Whole Bone.

Figure 32:
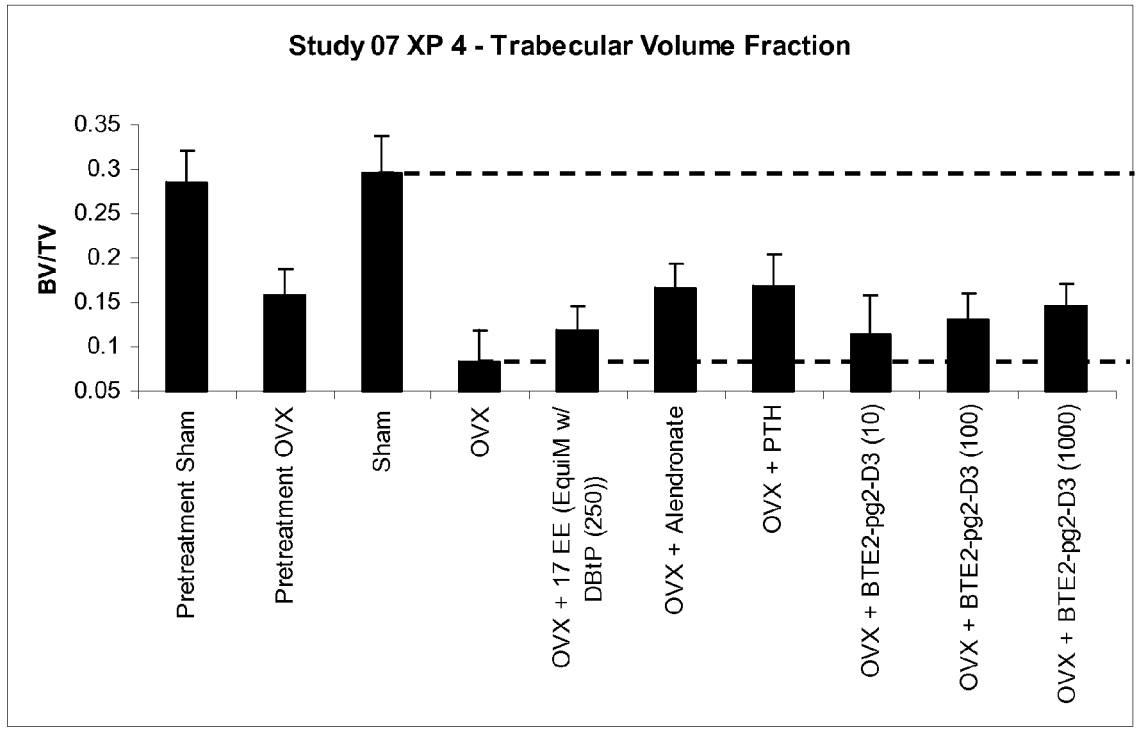
FIG. 32 is a bar graph illustrating trabecular volume fraction data for animals administered 17-ethinyl estradiol, alendronate, parathyroid hormone, or the compound of Formula 125 (BTE2-pg2-D3) at doses of 10, 100, or 1000 µg/kg.

Bone density was further assessed by measuring trabecular volume fraction using ex vivo micro-computed tomography. FIG. 32 includes the trabecular volume fraction data for control animals and animals receiving various doses of the compound of Formula 125 (BTE2-pg2-D3). These data indicate that bone density is increased, as compared to OVX animals, in animals receiving the compound of Formula 125.

Figure 33:
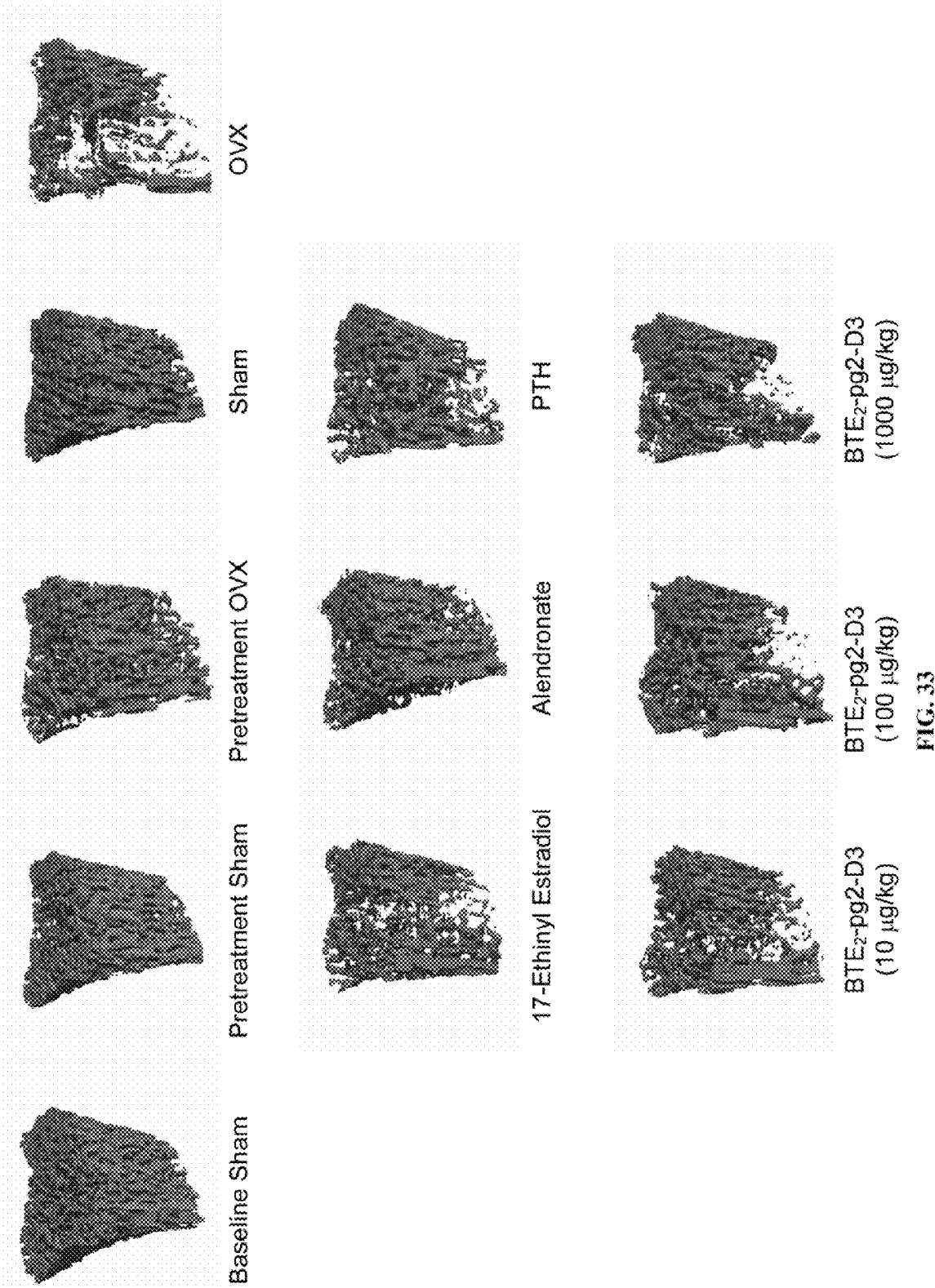
FIG. 33 includes three-dimensional images of bone that were constructed using data collected by a customized micro-CT system, for animals administered 17-ethinyl estradiol, alendronate, parathyroid hormone, or the compound of Formula 125 (BTE2-pg2-D3) at doses of 10, 100, or 1000 µg/kg.

With reference to FIG. 33, three-dimensional images were reconstructed using high resolution image data collected using the customized micro-CT system described above. These data indicate that the compound of Formula 125 (BTE2-pg2-D3) affected an increase in bone density.

Bone Strength.

Mechanical Competence.

Samples are collected and an indentation test is performed as described above.

The compound of Formula 125 is found to increase bone strength.

Bone Formation and Turnover.

Collagen Type I.

Figure 34:
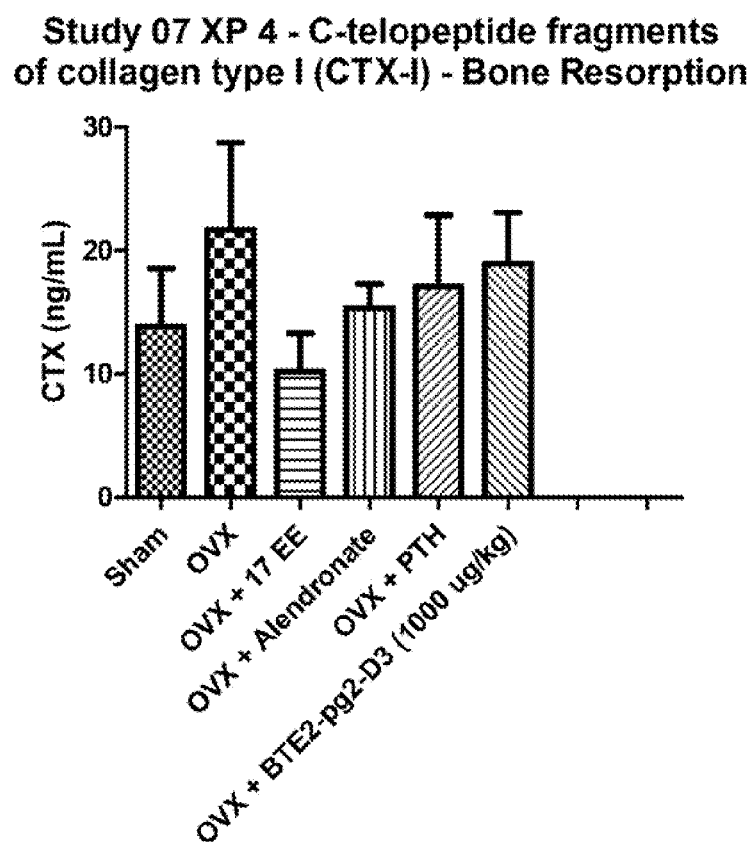
FIG. 34 is a bar graph depicting bone resorption or osteoclast-mediated breakdown of collagen type I in bone by measuring the C-telopeptide fragment of collagen type I (CTX-I) in animals administered 17-ethinyl estradiol, alendronate, parathyroid hormone, or the compound of Formula 125 (BTE2-pg2-D3) at a dose of 1000 µg/kg.

Bone resorption or osteoclast-mediated breakdown of collagen type I in bone was assessed by measuring the C-telopeptide fragment of collagen type I (CTX-I), as described above. With reference to FIG. 34, it is shown that treatment with 1000 μg/kg doses of the compound of Formula 125 (BTE2-pg2-D3) do not inhibit production of CTX-I, indicating that bone resorption is not inhibited and that the compound acts in a similar manner to known anabolic agent, parathyroid hormone 1-34 (PTH). In contrast, known anticatabolic agents, 17-ethinyl estradiol (17-EE) and alendronate (Alen), descrease the production of CTX-1 to sham levels.

Calvarial Injection Model.

Animals are administered control agents and the compound, samples are collected, and data are obtained, as described above. The compound of Formula 125 is found to increase new bone area.

Compound Including Bone Active Portion ($R_A$) Derived from an Androgen

Animals were treated with a compounds including a bone active portion ($R_A$) derived from an androgen. Compounds wherein the bone active portion was derived from testosterone were selected as examples of compounds including a bone active portion derived from an androgen. The compound of Formula 33 (BT-Testosterone) was orally administered to animals at a dose of 3000 μg/kg.

Body Weight and Uterine Mass.

Figure 35:
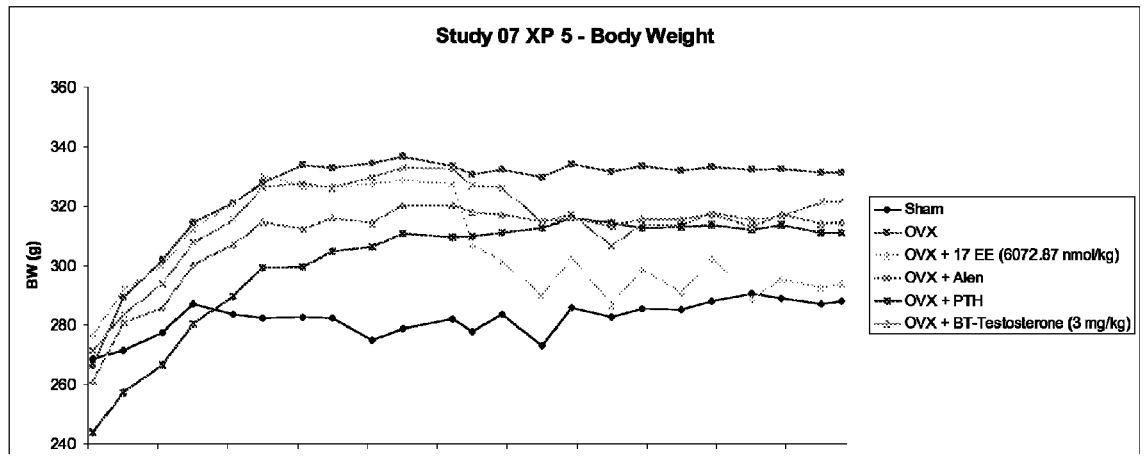
FIG. 35 is a line graph depicting body weight as a function of time for animals administered 17-ethinyl estradiol, alendronate, parathyroid hormone, or the compound of Formula 133 (BT-Testosterone) at a dose of 3 mg/kg.

With reference to FIG. 35, the body weights of the animals were measured at regular time intervals and body weights were plotted as a function of time. Body weight can serve as an indirect measure of toxicity. Animals receiving the compound of Formula 33 (BT-Testosterone) tend to have lower body weights as compared to the OVX animals.

Figure 36:
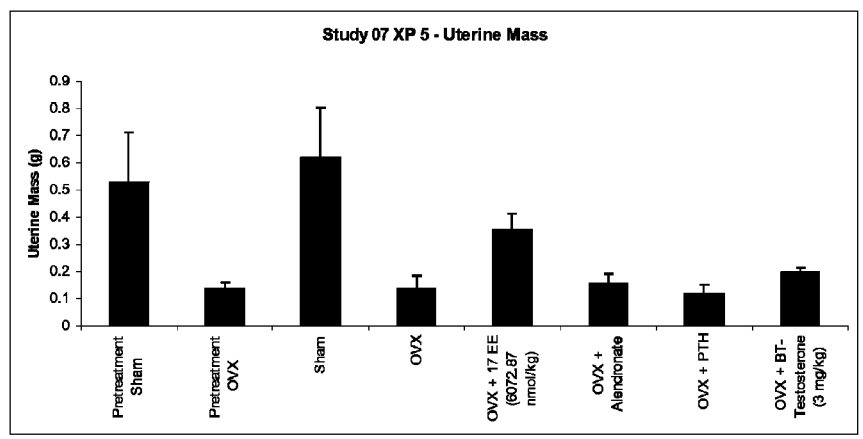
FIG. 36 is a bar graph depicting the uterine mass of animals administered 17-ethinyl estradiol, alendronate, parathyroid hormone, or the compound of Formula 133 (BT-Testosterone) at a dose of 3 mg/kg.
Figure 37:
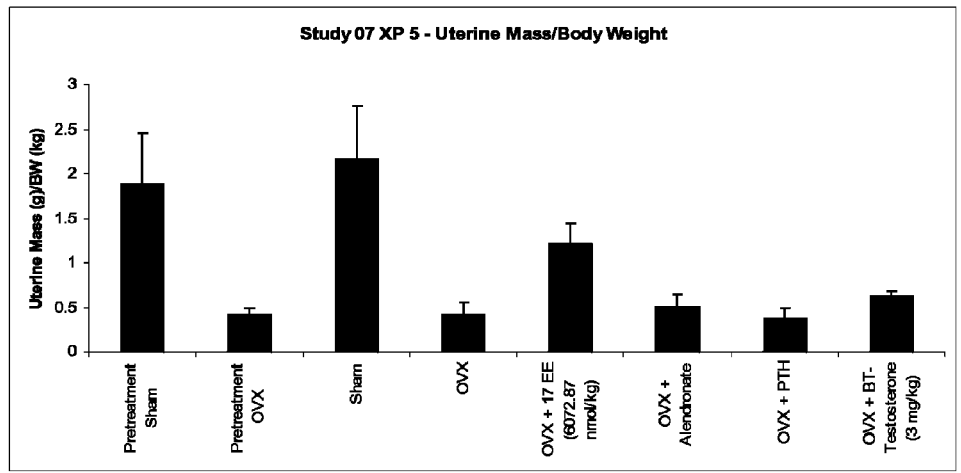
FIG. 37 is a bar graph depicting the ratio of uterine mass to body weight of animals administered 17-ethinyl estradiol, alendronate, parathyroid hormone, or the compound of Formula 133 (BT-Testosterone) at a dose of 3 mg/kg.

Turning now to FIGS. 36 and 37 the uterine mass of each animal was measured and expressed both independently, and as a ratio of uterine mass to body weight. Animals treated with the compound of Formula 33 (BT-Testosterone) had lower uterine masses, and uterine mass to body weight ratios as compared to the animals treated with the free steroidal estrogenic agent, 17-ethinyl estradiol.

Lipid Metabolism.

Total cholesterol, high-density lipoprotein (HDL), and low-density lipoprotein (LDL) in collected serum samples are quantitatively determined. The compound of Formula 33 has a limited or no effect on lipid metabolism.

Bone Density.

Femoral Density and Regional Femoral Density.

Figure 38:
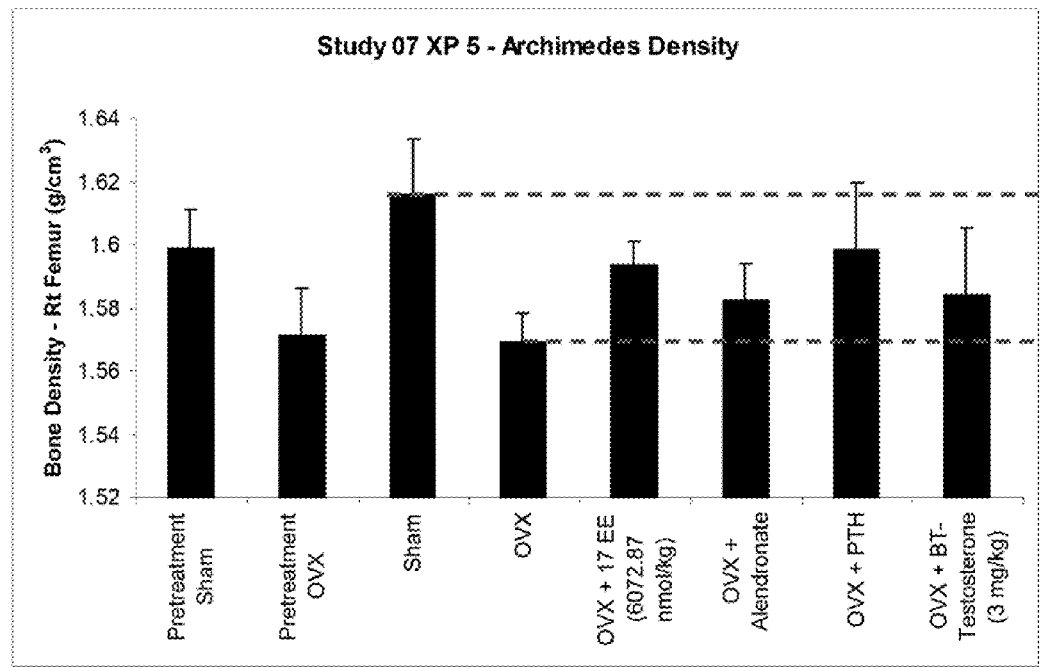
FIG. 38 is a bar graph depicting the whole bone density of animals administered 17-ethinyl estradiol, alendronate, parathyroid hormone, or the compound of Formula 133 (BT-Testosterone) at a dose of 3 mg/kg.

The right femora were used to assess bone density, as described above. With reference to FIG. 38, whole bone density was affected by the compound of Formula 33 (BT-Testosterone). Animals receiving Formula 33 (BT-Testosterone) were shown to have dose-responsive whole bone densities that were higher than that of the OVX animals, and in the same ranges as those animals receiving 17-ethinyl estradiol (17 EE), Alendronate (Alen), or Parathyroid hormone 1-34 (PTH).

Figure 39:
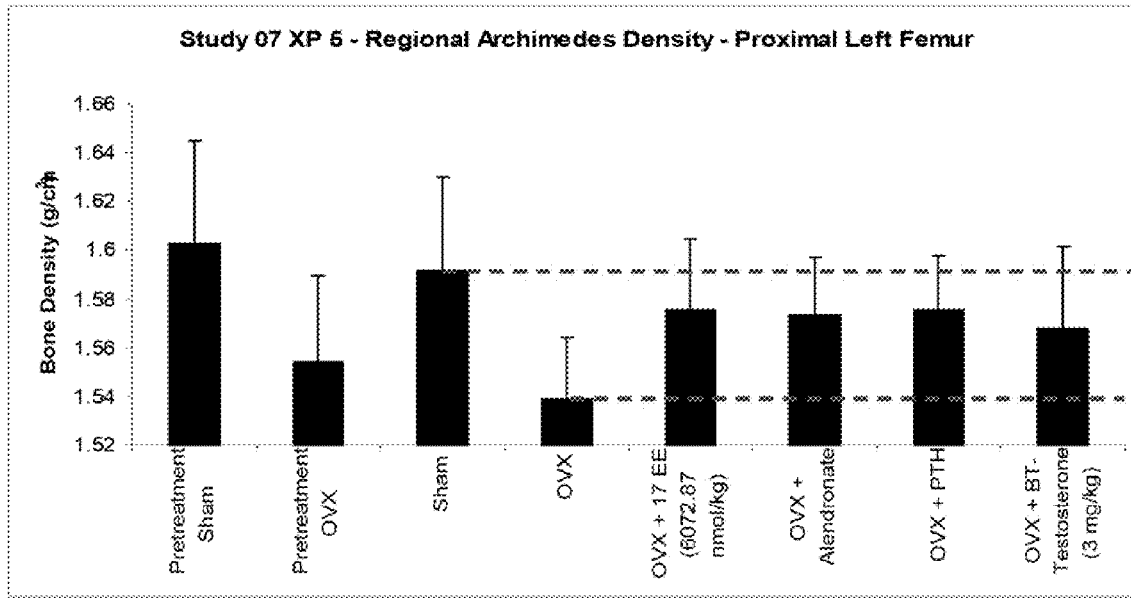
FIG. 39 is a bar graph depicting the regional bone density of the proximal left femur of animals administered 17-ethinyl estradiol, alendronate, parathyroid hormone, or the compound of Formula 133 (BT-Testosterone) at a dose of 3 mg/kg.
Figure 40:
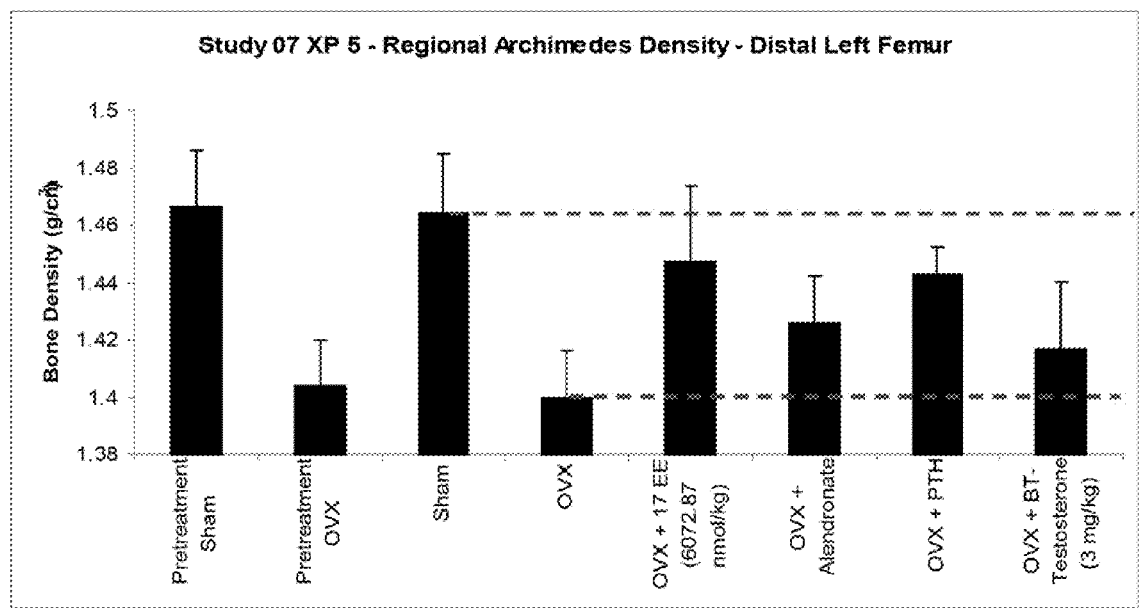
FIG. 40 is a bar graph depicting the regional bone density of the distal left femur of animals administered 17-ethinyl estradiol, alendronate, parathyroid hormone, or the compound of Formula 133 (BT-Testosterone) at a dose of 3 mg/kg.

Regional bone density was also assessed, as described above, with data presented in FIGS. 39, and 40. The compound of Formula 33 (BT-Testosterone) affected regional bone density. Animals receiving the compound Formula 33 (BT-Testosterone) were shown to have regional bone densities that were higher than that of the OVX animals, and in the same ranges as those animals receiving 17-ethinyl estradiol (17 EE), Alendronate (Alen), or Parathyroid hormone 1-34 (PTH).

Volume Fraction—Trabecular, Cortical, and Whole Bone.

Samples are collected as described above. Data revealing the volume fraction (BV/TV) occupied by trabecular (cancellous) bone tissue, cortical bone tissue, and whole bone tissue is obtained. The compound of Formula 33 is found to increase bone density.

Bone Strength.
Mechanical Competence.
Samples are collected and an indentation test is performed as described above.

The compound of Formula 33 is found to increase bone strength.

Bone Formation and Turnover.
Calvarial Injection Model.
Animals are administered control agents and the compound, samples are collected, and data are obtained, as described above. The compound of Formula 33 is found to increase new bone area.

Compound Including Bone Active Portion ($R_A$) Derived from a Non-Steroidal Estrogenic Agent Animals are administered control agents and the compound of Formula 128. A compound wherein the bone active portion was derived from genistein was selected as an example of compounds including a bone active portion derived from a non-steroidal estrogenic agent. Samples are collected and studied as described above.

Uterine Mass.
Uterine mass is obtained. The compound of Formula 128 has a limited or no effect on uterine mass.

Lipid Metabolism.
Total cholesterol, high-density lipoprotein (HDL), and low-density lipoprotein (LDL) in collected serum samples are quantitatively determined. The compound of Formula 128 has a limited or no effect on lipid metabolism.

Bone Density.
Femoral Density and Regional Femoral Density.
Samples are collected as described above. Whole bone density and regional bone density are assessed. The compound of Formula 128 is found to increase bone density.

Volume Fraction—Trabecular, Cortical, and Whole Bone.
Samples are collected as described above. Data revealing the volume fraction (BV/TV) occupied by trabecular (cancellous) bone tissue, cortical bone tissue, and whole bone tissue is obtained. The compound of Formula 128 is found to increase bone density.

Bone Strength.
Mechanical Competence.
Samples are collected and an indentation test is performed as described above.

The compound of Formula 128 is found to increase bone strength.

Bone Formation and Turnover.
Calvarial Injection Model.
Animals are administered control agents and the compound, samples are collected, and data are obtained, as described above. The compound of Formula 128 is found to increase new bone area.

Compound Including Bone Active Portion ($R_A$) Derived from a Nitric Oxide Agent Animals are administered control agents and the compound of Formula 130. A compound wherein the bone active portion was derived from alkoxy-$NO_2$ was selected as an example of compounds including a bone active portion derived from a nitric oxide agent. Samples are collected and studied as described above.

Uterine Mass.
Uterine mass is obtained. The compound of Formula 130 has a limited or no effect on uterine mass.

Lipid Metabolism.
Total cholesterol, high-density lipoprotein (HDL), and low-density lipoprotein (LDL) in collected serum samples are quantitatively determined. The compound of Formula 130 has a limited or no effect on lipid metabolism.

Bone Density.
Femoral Density and Regional Femoral Density.
Samples are collected as described above. Whole bone density and regional bone density are assessed. The compound of Formula 130 is found to increase bone density.

Volume Fraction—Trabecular, Cortical, and Whole Bone.
Samples are collected as described above. Data revealing the volume fraction (BV/TV) occupied by trabecular (cancellous) bone tissue, cortical bone tissue, and whole bone tissue is obtained. The compound of Formula 130 is found to increase bone density.

Bone Strength.
Mechanical Competence.
Samples are collected and an indentation test is performed as described above.

The compound of Formula 130 is found to increase bone strength.

Bone Formation and Turnover.
Calvarial Injection Model.
Animals are administered control agents and the compound, samples are collected, and data are obtained, as described above. The compound of Formula 130 is found to increase new bone area.

Compound Including Bone Active Portion ($R_A$) Derived from a Carbonic Anhydrase Inhibitor Animals are administered control agents and the compound of Formula 35. A compound wherein the bone active portion was derived from 2-amino-1,3,4-thiadiazole-5-sulfonamide was selected as an example of compounds including a bone active portion derived from a carbonic anhydrase inhibitor. Samples are collected and studied as described above.

Uterine Mass.
Uterine mass is obtained. The compound of Formula 35 has a limited or no effect on uterine mass.

Lipid Metabolism.
Total cholesterol, high-density lipoprotein (HDL), and low-density lipoprotein (LDL) in collected serum samples are quantitatively determined. The compound of Formula 35 has a limited or no effect on lipid metabolism.

Bone Density.
Femoral Density and Regional Femoral Density.
Samples are collected as described above. Whole bone density and regional bone density are assessed. The compound of Formula 35 is found to increase bone density.

Volume Fraction—Trabecular, Cortical, and Whole Bone.
Samples are collected as described above. Data revealing the volume fraction (BV/TV) occupied by trabecular (cancellous) bone tissue, cortical bone tissue, and whole bone tissue is obtained. The compound of Formula 35 is found to increase bone density.

Bone Strength.
Mechanical Competence.
Samples are collected and an indentation test is performed as described above.

The compound of Formula 35 is found to increase bone strength.

Bone Formation and Turnover.

Calvarial Injection Model.

Animals are administered control agents and the compound, samples are collected, and data are obtained, as described above. The compound of Formula 35 is found to increase new bone area.

Compound Including Bone Active Portion ($R_A$) Derived from an Anti-Cancer Agent Cells were treated with a compounds including a bone active portion ($R_A$) derived from an anti-cancer agent, as described above. Compounds wherein the bone active portion was derived from doxorubicin were selected as examples of compounds including a bone active portion derived from an anti-cancer agent. Cells were treated with the compound of Formula 138 (BT2-pg2-doxorubicin (Nbr-VII)), and free doxorubicin, at concentrations of 0.05, 0.1, 0.5, 1, 5, and 10 µM.

Figure 41A:
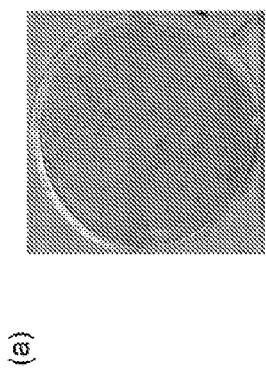
FIG. 41A includes photographs of a colony formation assay for cancer cells treated with increasing concentrations of the compound of Formula 138 (BT2-pg2-doxorubicin (Nbr-VI)) or increasing concentrations of doxorubicin.
Figure 41A:
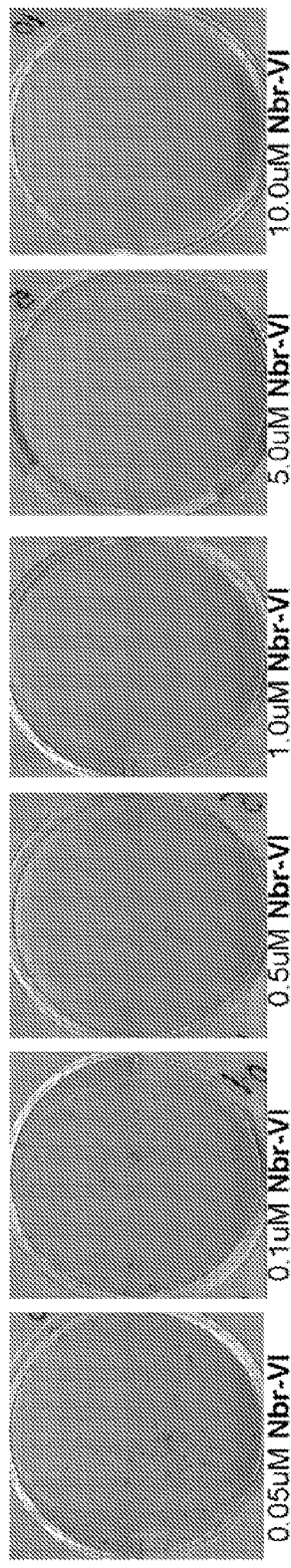
Figure 41A:
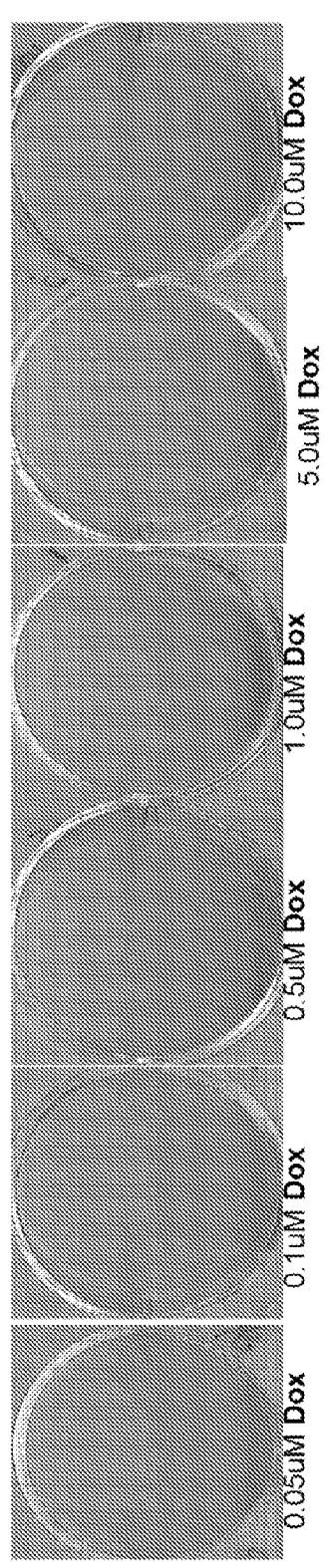
Figure 41B:
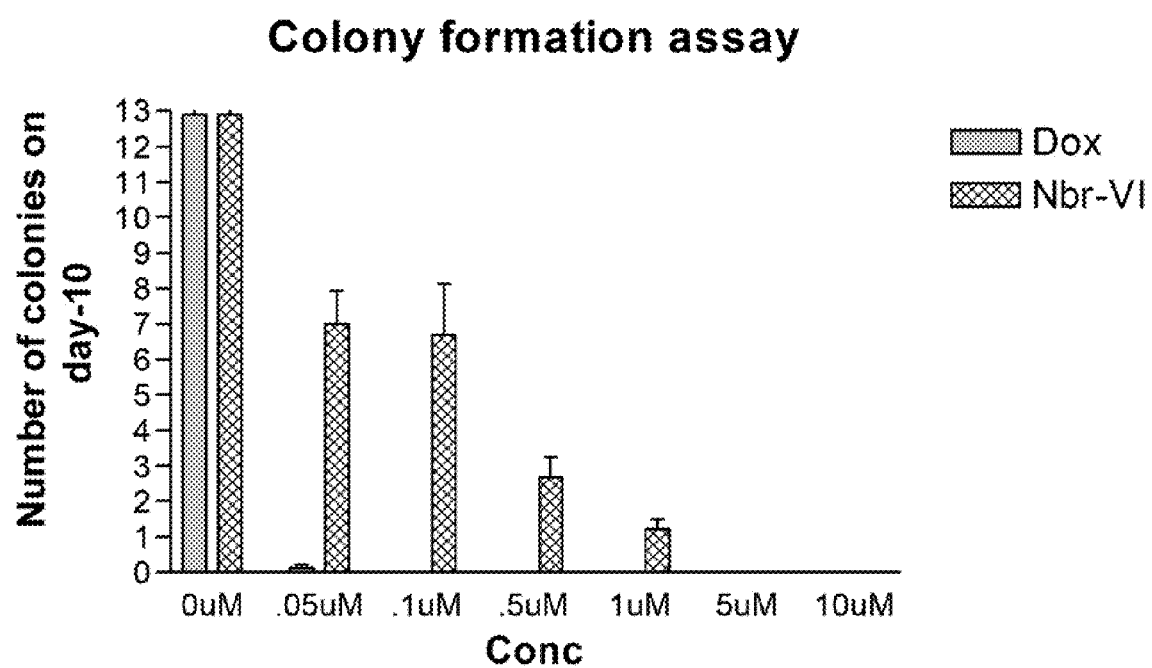
FIG. 41B is a bar graph depicting the results of a colony formation assay for cancer cells treated with increasing concentrations of the compound of Formula 138 (BT2-pg2-doxorubicin (Nbr-VI)) or increasing concentrations of doxorubicin.

With reference to FIGS. 41A and 41B, there is a dose-responsive decrease in colony formation in cells treated with the compound of Formula 138 (BT2-pg2-doxorubicin (Nbr-VI)), showing that the compound is effective against cancer cells.

Figure 42:
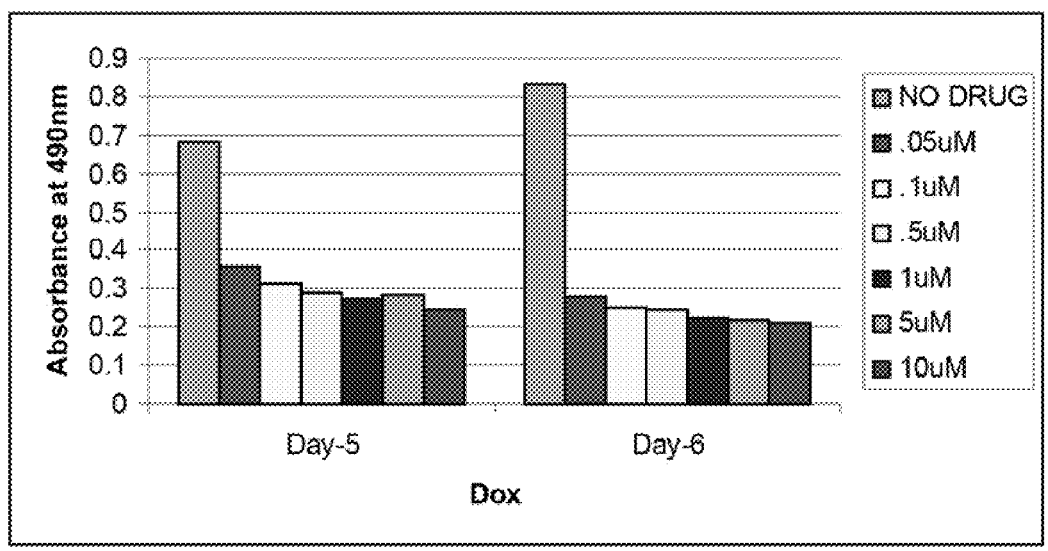
FIG. 42 is a bar graph illustrating cell proliferation data for day 5 and day 6 for cells treated with increasing concentrations of doxorubicin.
Figure 43:
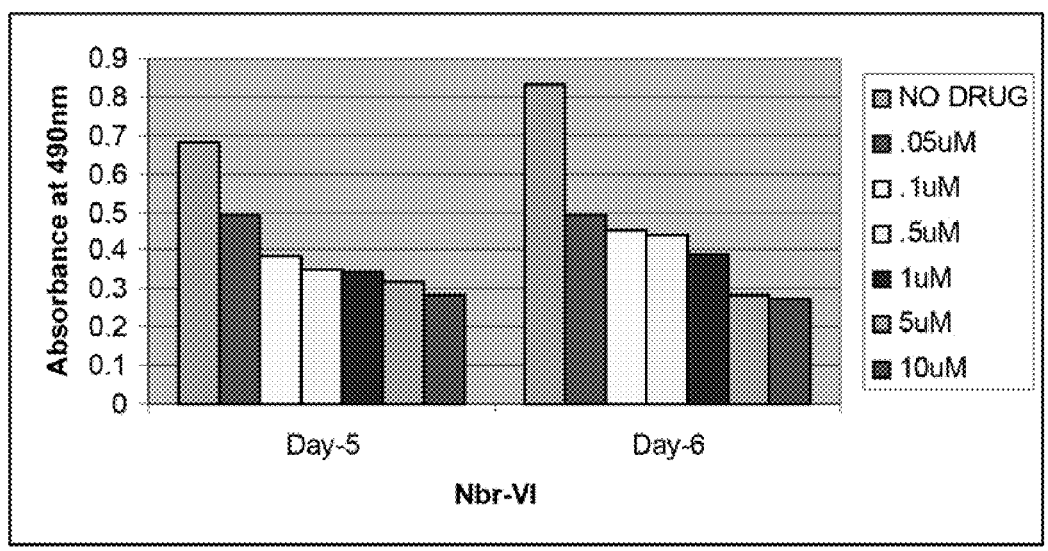
FIG. 43 is a bar graph illustrating cell proliferation data for day 5 and day 6 for cells treated with increasing concentrations of the compound of Formula 138 (BT2-pg2-doxorubicin (Nbr-VI)).
Figure 44:
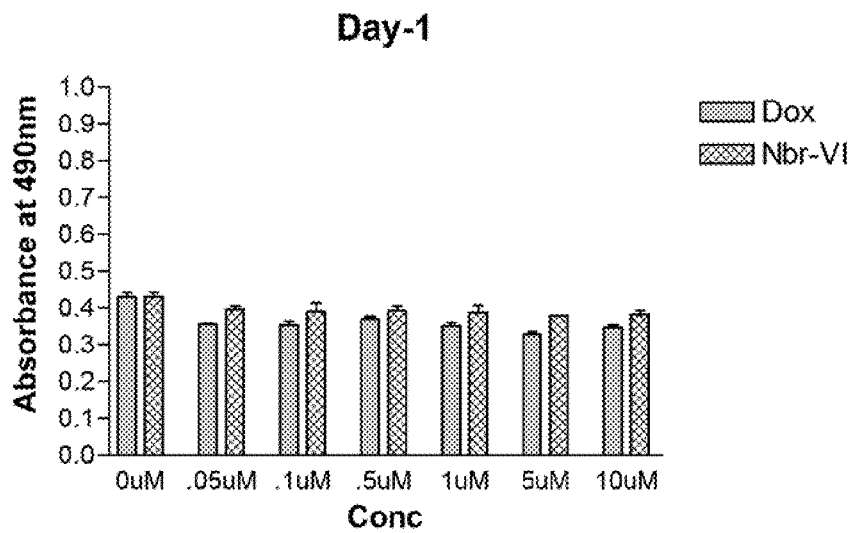
FIG. 44 is a bar graph illustrating cell proliferation data for day 1 for cells treated with increasing concentrations of the compound of Formula 138 (BT2-pg2-doxorubicin (Nbr-VI)) or increasing concentrations of doxorubicin.
Figure 45:
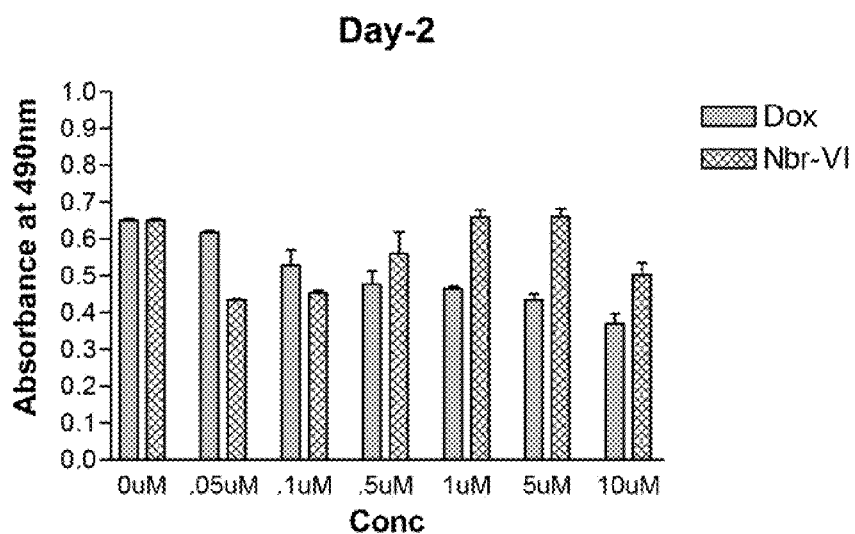
FIG. 45 is a bar graph illustrating cell proliferation data for day 2 for cells treated with increasing concentrations of the compound of Formula 138 (BT2-pg2-doxorubicin (Nbr-VI)) or increasing concentrations of doxorubicin.
Figure 46:
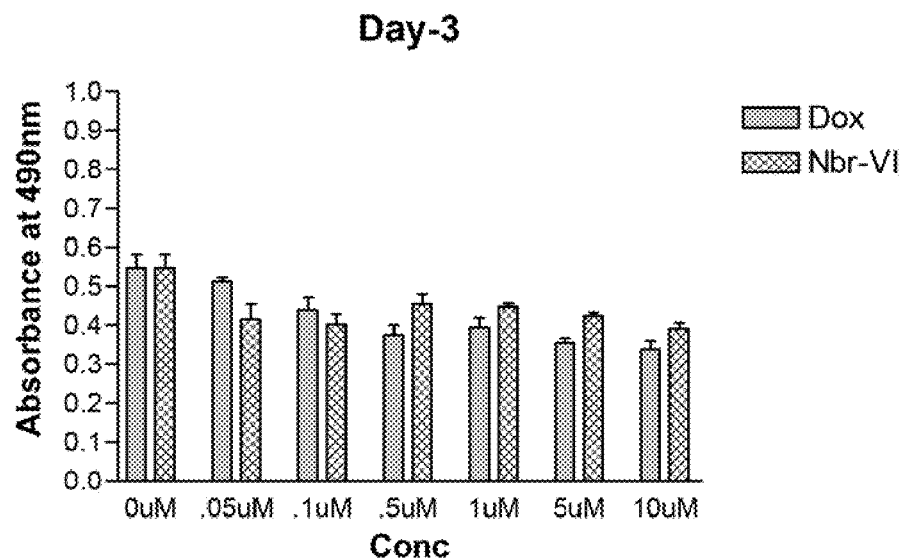
FIG. 46 is a bar graph illustrating cell proliferation data for day 3 for cells treated with increasing concentrations of the compound of Formula 138 (BT2-pg2-doxorubicin (Nbr-VI)) or increasing concentrations of doxorubicin.
Figure 47:
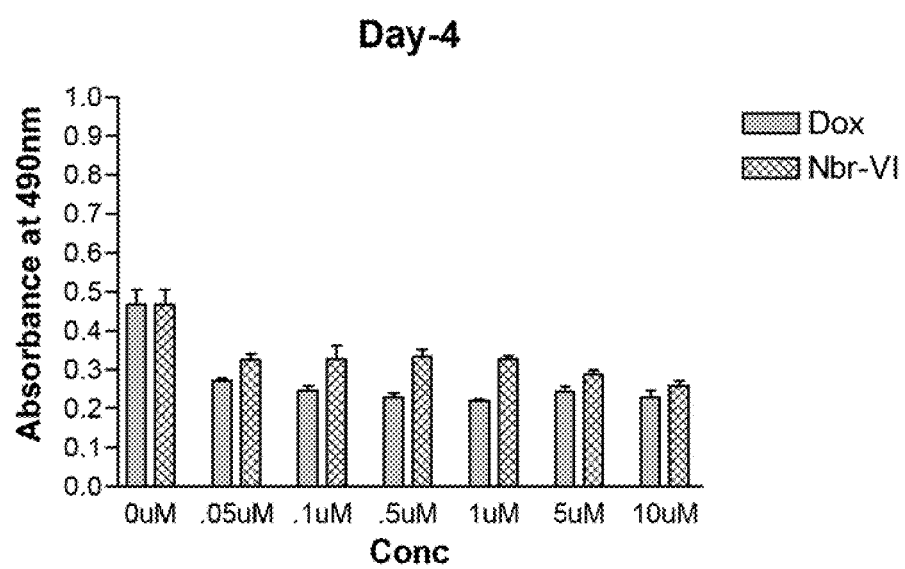
FIG. 47 is a bar graph illustrating cell proliferation data for day 4 for cells treated with increasing concentrations of the compound of Formula 138 (BT2-pg2-doxorubicin (Nbr-VI)) or increasing concentrations of doxorubicin.
Figure 48:
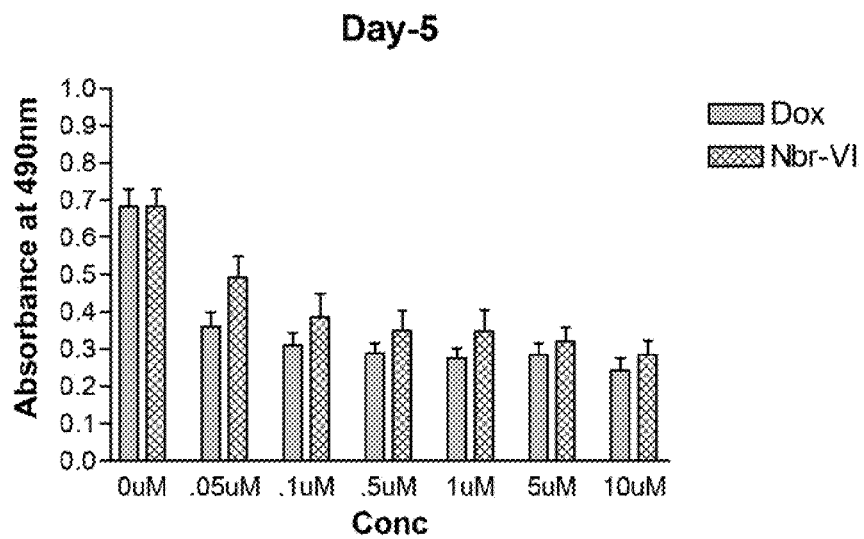
FIG. 48 is a bar graph illustrating cell proliferation data for day 5 for cells treated with increasing concentrations of the compound of Formula 138 (BT2-pg2-doxorubicin (Nbr-VI)) or increasing concentrations of doxorubicin.
Figure 49:
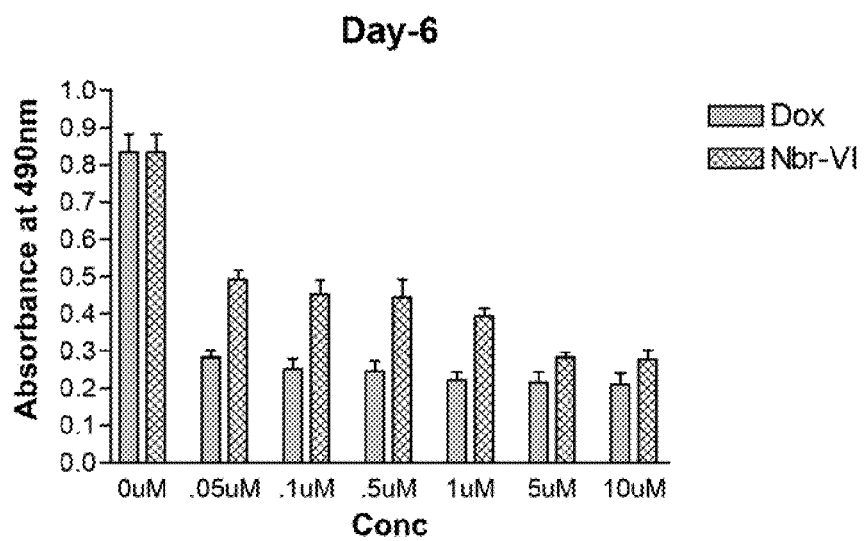
FIG. 49 is a bar graph illustrating cell proliferation data for day 6 for cells treated with increasing concentrations of the compound of Formula 138 (BT2-pg2-doxorubicin (Nbr-VI)) or increasing concentrations of doxorubicin.

FIG. 42 includes the results of treatment with doxorubicin on the cells. With reference to FIGS. 43-49, there is a dose-responsive decrease in cell proliferation in cells treated with the compound of Formula 138 (BT2-pg2-doxorubicin (Nbr-VI)), showing that the compound is effective against cancer cells, and that the efficacy is similar to that of doxorubicin.

Compound Including Bone Active Portion ($R_A$) Derived from an Antimicrobial Agent Isolates of *S. Aureus* were treated with a compounds including a bone active portion ($R_A$) derived from an antimicrobial agent, as described above. Compounds wherein the bone active portion was derived from vancomycin were selected as examples of compounds including a bone active portion derived from an antimicrobial agent. Cells were treated with the compound of Formula 140 (BT2-pg2-vancomycin), and free vancomycin. The minimum inhibitory concentrations (MIC) of the compound of Formula 140 (BT2-pg2-vancomycin) and standard (µg/mL) against strains of *Staphylococcus aureus* are set forth in the following table. These results indicate that that the compound of Formula 140 (BT2-pg2-vancomycin) is as effective as vancomycin against the tested strains of *S. aureus*.

| Compound | ATCC# | | |
|---|---|---|---|
| | 49230[a] | 33591[b] | 29213[c] |
| BT2-pg2-vancomycin | 1 | 2 | 1 |
| Vancomycin | 1 | 1 | 1 |

[a] Wild-type isolated from bone infection;
[b] MRSA;
[c] QC strain: Acceptable vancomycin MIC range: 0.5-2 µg/mL Throughout this document, various references are mentioned. All such references are incorporated herein by reference, including the references set forth in the following list:

Keenan M J, Hegsted M, Jones K L, Delany J P, Kime J C, Melancon L E, Tulley R T, Hong K D. Comparison of bone density measurement techniques: DXA and Archimedes' principle. J Bone Miner Res 1997; 12:1903-7.

Mundy G R, Garrett R, Harris S E, Chan J, Chen D, Rossini G, Boyce B, Zhao M, and Gutierrez G (1999) Stimulation of bone formation in vitro and in rodents by statins. Science 286:1946-1949.

Garrett I R, Chen D, Gutierrez G, Rossini G, Zhao M, Escobedo A, Kim K B, Hu S, Crews C M, and Mundy G R (2003) Selective inhibitors of the osteoblast proteasome stimulate bone formation in vivo and in vitro. J Clin Invest 111: 1771-1782.

Seibel M J. Biochemical Markers of Bone Turnover. Clin Biochem Rev. 2005; 26:97-122.

Delmas P D, et al. The Use of Biochemical Markers of Bone Turnover in Osteoporosis. Osteoporosis Int. suppl. 6 S2-17 (2000).

Riggs B L, and Parfitt A M, "Drugs Used to Treat Osteoporosis: The Critical Need for a Uniform Nomenclature Based on Their Action on Bone Remodeling," *J. Bone and Mineral Res.* 20:2 (2005).

U.S. patent application Ser. Nos. 11/022,024; 11/021,661; and 11/674,753, and PCT Patent Publication No. WO/0066613

What is claimed is:

1. A compound of the formula

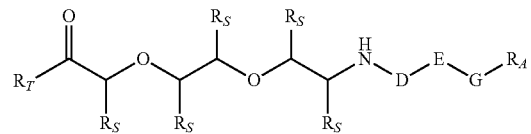

or pharmaceutically acceptable salts or solvates thereof, wherein $R_T$ is

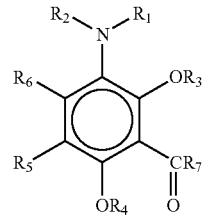

wherein $R_T$ is connected to the compound at $R_1$, $R_2$, or $R_4$;

wherein $R_1$ is hydrogen, lower alkyl, alkyl, aryl lower alkyl, aryl, or a covalent bond when $R_T$ is connected to the compound at $R_1$;

$R_2$ is hydrogen, lower alkyl, alkyl, aryl lower alkyl, aryl, or a covalent bond when $R_T$ is connected to the compound at $R_2$;

$R_3$ is hydrogen, lower alkyl, alkyl, aryl lower alkyl, aryl, or carbonyl-containing;

$R_4$ is hydrogen, lower alkyl, alkyl, aryl lower alkyl, aryl, carbonyl-containing, or a covalent bond when $R_T$ is connected to the compound at $R_4$;.

$R_5$ and $R_6$ are independently hydrogen, lower alkyl, or alkyl, or $R_5$ and $R_6$, taken together with the carbon atoms to which they are bonded, form a ring containing about 6 to about 14 ring carbon atoms and up to a total of about 18 carbon atoms, which formed ring can be monocyclic, bicyclic, or tricyclic, wherein the ring can optionally have substituents, including heteroatoms;

$R_7$ is hydroxy, lower alkoxy, or $NR_8R_9$;

$R_8$ and $R_9$ are independently hydrogen, or lower alkyl;

wherein each $R_s$ is independently hydrogen, hydroxy, lower alkyl, or lower alkyl with heteroatoms;

wherein D and G are independently covalent bond, carbonyl, epoxy, or anhydride;

wherein E is
  covalent bond,
  $(CT_2)_r$, where T is hydrogen, hydroxy, or lower alkyl, and where r is 0-8, or
  $(C)_r$, where r is 2-8, and where the carbons are unsaturated or partially saturated with hydrogen; and wherein $R_A$ is hydrogen, hydroxyl, a protecting group, or a Bone Active Portion derived from a bone active agent.

2. The compound of claim 1, according to the formula

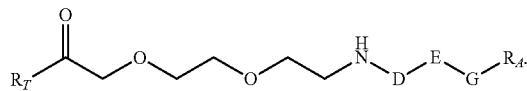

3. A compound of the formula

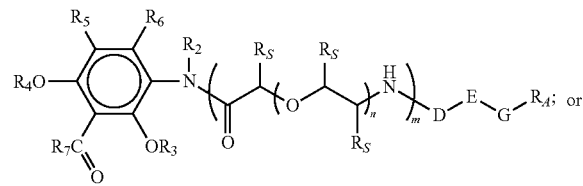

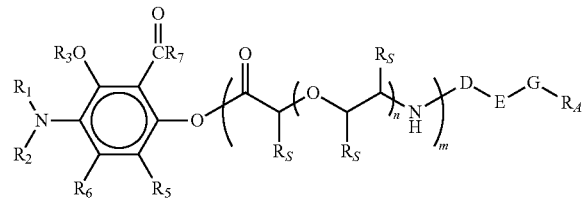

or pharmaceutically acceptable salts or solvates thereof, wherein
  $R_1$ is hydrogen, lower alkyl, alkyl, aryl lower alkyl, aryl, or a covalent bond when $R_T$ is connected to the compound at $R_1$;
  $R_2$ is hydrogen, lower alkyl, alkyl, aryl lower alkyl, aryl, or a covalent bond when $R_T$ is connected to the compound at $R_2$;
  $R_3$ is hydrogen, lower alkyl, alkyl, aryl lower alkyl, aryl, or carbonyl-containing;
  $R_4$ is hydrogen, lower alkyl, alkyl, aryl lower alkyl, aryl, carbonyl-containing, or a covalent bond when $R_T$ is connected to the compound at $R_4$;
  $R_5$ and $R_6$ are independently hydrogen, lower alkyl, or alkyl, or $R_5$ and $R_6$, taken together with the carbon atoms to which they are bonded, form a ring containing about 6 to about 14 ring carbon atoms and up to a total of about 18 carbon atoms, which formed ring can be monocyclic, bicyclic, or tricyclic, wherein the ring can optionally have substituents, including heteroatoms;
  $R_7$ is hydroxy, lower alkoxy, or $NR_8R_9$;
  $R_8$ and $R_9$ are independently hydrogen, or lower alkyl;
wherein m is 1-3, n is 1-4, and when m>1, each n is independently 1-4;
wherein each $R_s$ is independently hydrogen, hydroxy, lower alkyl, or lower alkyl with heteroatoms;
wherein D and G are independently covalent bond, carbonyl, epoxy, or anhydride;
wherein E is
  covalent bond,
  $(CT_2)_r$, where T is hydrogen, hydroxy, or lower alkyl, and where r is 0-8, or
  $(C)_r$, where r is 2-8, and where the carbons are unsaturated or partially saturated with hydrogen; and
wherein $R_A$ hydrogen, hydroxyl, a protecting group, or a Bone Active Portion derived from a bone active agent.

4. The compound of claim 3, wherein $R_A$ is hydrogen.

5. The compound of claim 3, wherein $R_A$ is a protecting group.

6. The compound of claim 3, wherein $R_A$ is a bone active portion derived from a bone active agent selected from the bone active agents set forth in Tables A-D.

7. The compound of claim 3, wherein $R_A$ is a bone active portion derived from a steroid.

8. The compound of claim 3, wherein $R_A$ is a bone active portion derived from an estrogenic agent.

9. The compound of claim 8, wherein $R_A$ is a bone active portion derived from a steroidal estrogenic agent.

10. The compound of claim 9, where the steroidal estrogenic agent is estradiol.

11. The compound of claim 10, according to the formula

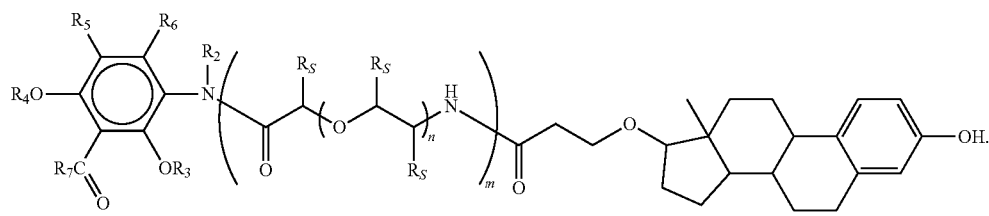

12. The compound of claim 11, according to the formula
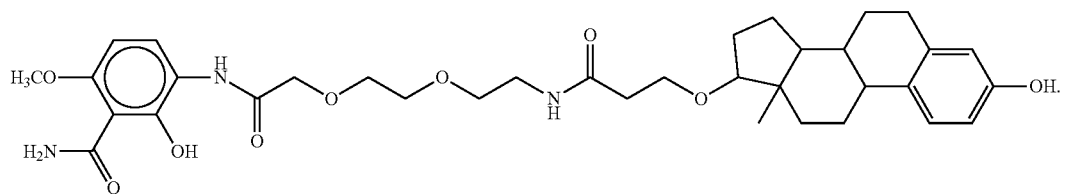
13. The compound of claim 10, according to the formula
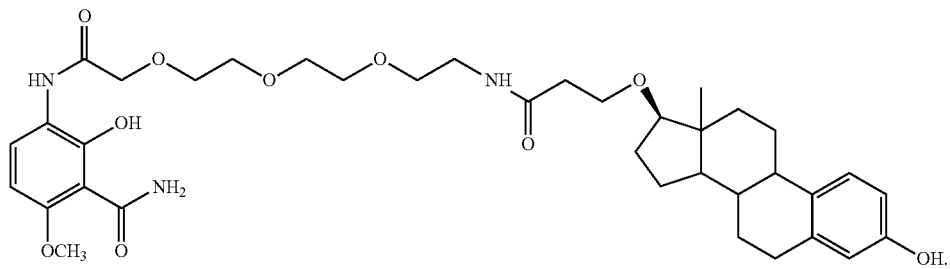
14. The compound of claim 10, according to the formula
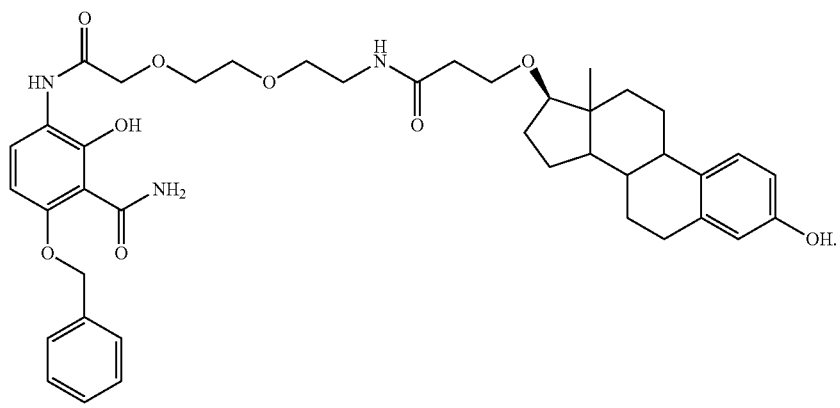
15. The compound of claim 10, according to the formula:
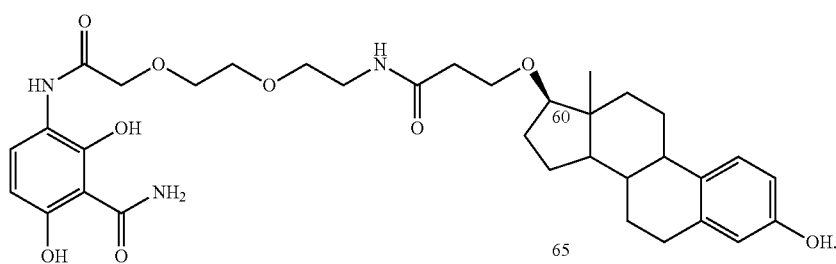

16. The compound of claim 3, wherein $R_A$ is a bone active portion derived from a non-steroidal estrogenic agent.

17. The compound of claim 16, wherein the non-steroidal estrogenic agent is genistein.

18. The compound of claim 17, according to the formula:

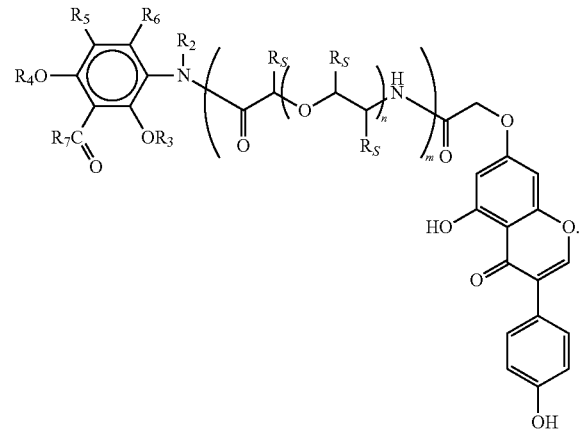

19. The compound of claim 18, according to the formula:

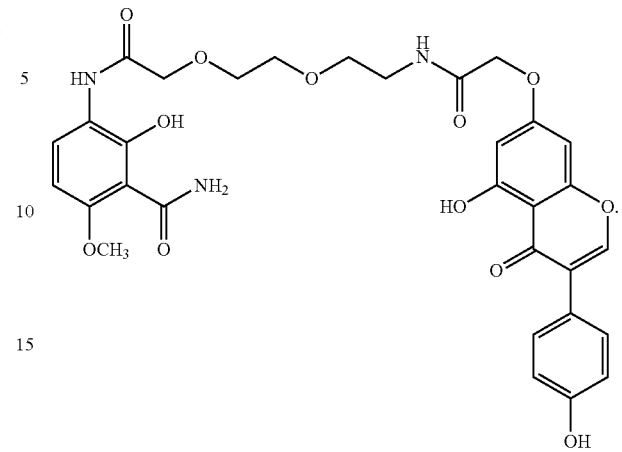

20. The compound of claim 3, wherein $R_A$ is a bone active portion derived from a nitric oxide agent.

21. The compound of claim 20, wherein the nitric oxide agent is alkoxy-$(NO_2)_2$.

22. The compound of claim 21, according to the formula:

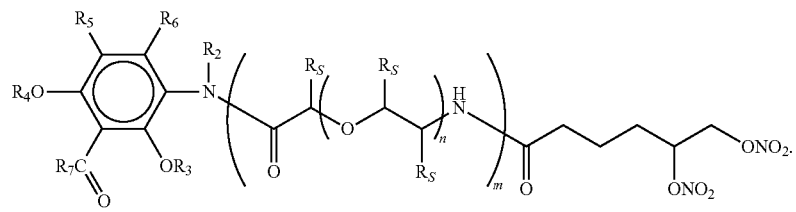

23. The compound of claim 22, according to the formula:

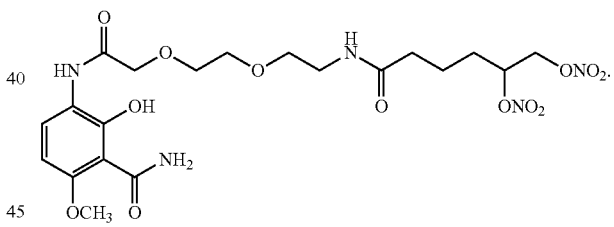

24. The compound of claim 3, wherein $R_A$ is a bone active portion derived from an androgen.

25. The compound of claim 24, wherein the androgen is DHEA.

26. The compound of claim 25, according to the formula:

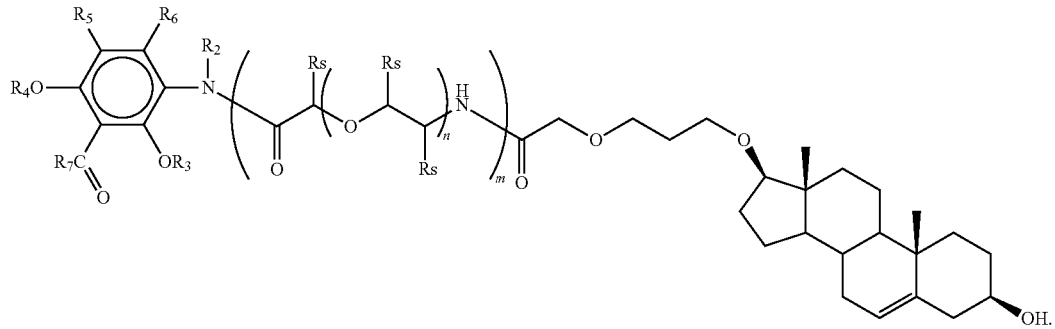

27. The compound of claim 26, according to the formula:

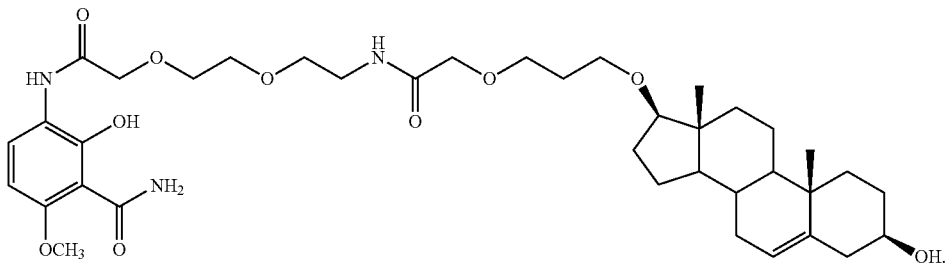

28. The compound of claim 24, wherein the androgen is Testosterone.
29. The compound of claim 3, wherein $R_A$ is a bone active portion derived from a carbonic anhydrase inhibitor.
30. The compound of claim 29, wherein $R_A$ is a bone active portion derived from a 2-amino-1,3,4-thiadiazole-5-sulfonamide.
31. The compound of claim 3, wherein $R_A$ is a bone active portion derived from an anti-cancer agent.
32. The compound of claim 31, wherein the anti-cancer agent is doxorubicin.
33. The compound of claim 32, according to the formula:

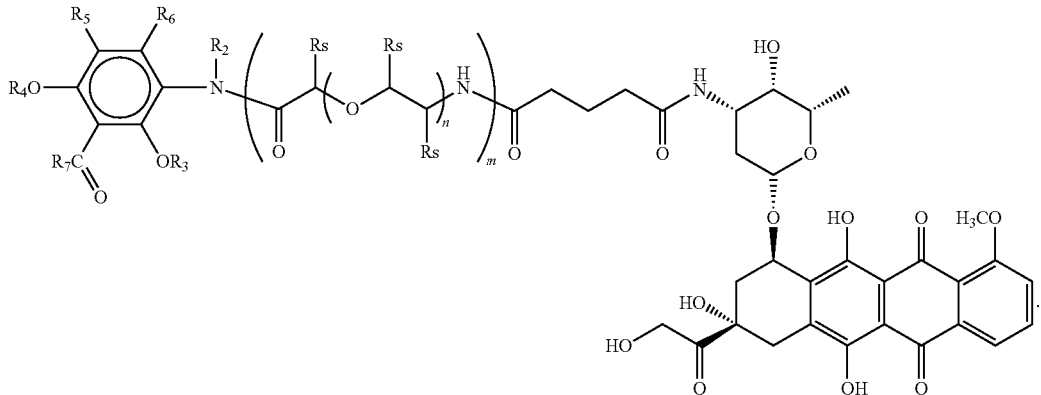

35. The compound of claim 3, wherein $R_A$ is a bone active portion derived from an antimicrobial agent.
36. The compound of claim 35, wherein the antimicrobial agent is vancomycin.

34. The compound of claim 33, according to the formula:

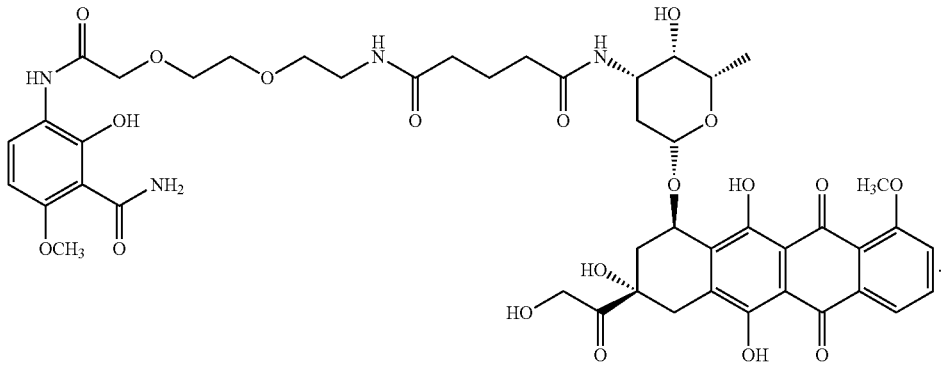

37. The compound of claim 36, according to the formula:

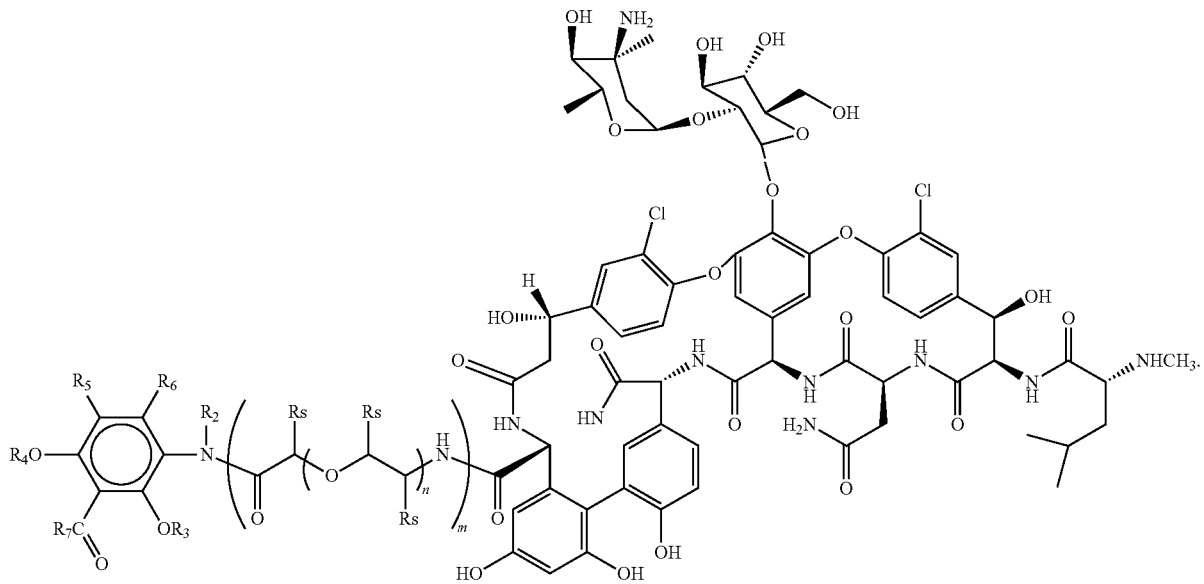

38. The compound of claim 37, according to the formula:

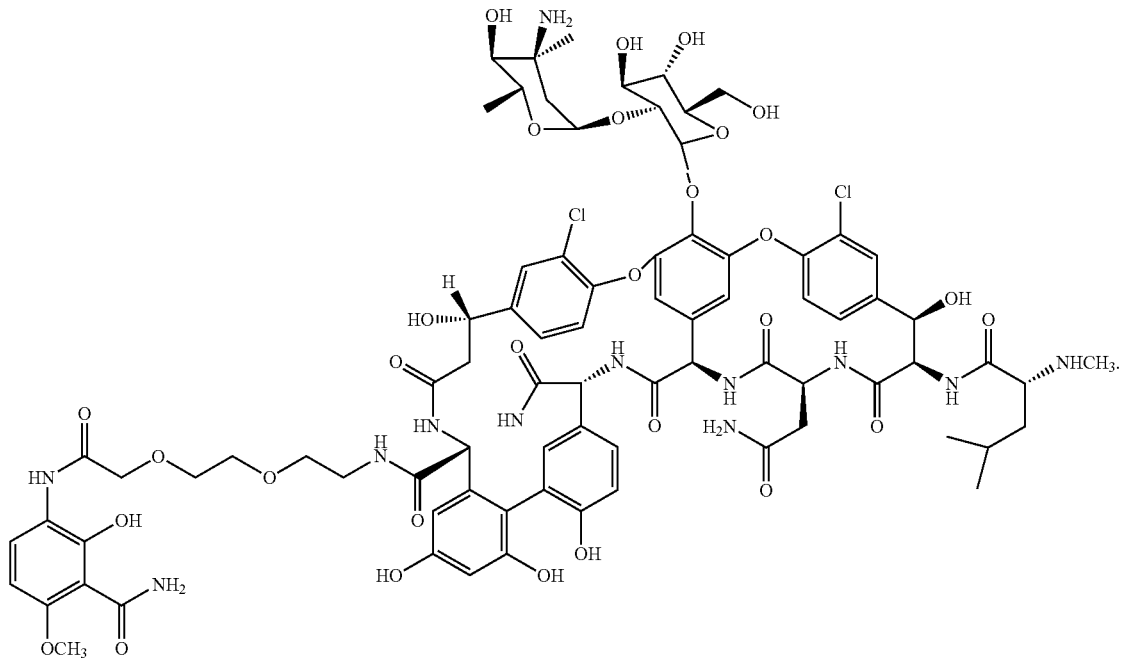

39. A method for treating a bone condition in a subject in need thereof, comprising: administering to the subject an effective amount of the compound of claim 3.

40. The method of claim 39, wherein the bone condition is a metabolic bone disease.

41. The method of claim 40, wherein the metabolic bone disease is osteoporosis, and wherein $R_A$ is a bone active portion derived from a bone active agent selected from:

an androgen, a steroidal estrogenic agent, a non-steroidal estrogenic agent, a nitric-oxide-targeted agent, and a carbonic anhydrase inhibitor.

42. The method of claim 41, wherein the subject has a primary condition associated with osteoporosis.

43. The method of claim 41, wherein administration of the compound has an anabolic effect on the bone of the subject.

44. The method of claim 39, wherein the bone condition is a primary or a secondary bone cancer, and wherein $R_A$ is a bone active portion derived from an anti-cancer agent.

45. The method of claim 44, wherein the bone condition is a secondary bone cancer.

46. The method of claim 38, wherein the subject has a primary cancer associated with a secondary bone cancer.

47. The method of claim 46, wherein the primary cancer is breast, lung, prostate, kidney, or thyroid cancer.

48. The method of claim 39, wherein the bone condition is a microbial infection, and wherein $R_A$ is a bone active portion derived from an antimicrobial agent.

49. The method of claim 48, wherein the bone condition is osteomyelitis, and wherein $R_A$ is a bone active portion derived from an antimicrobial agent.

50. The method of claim 39, wherein the subject has a primary infection associated with osteomyelitis.

* * * * *